United States Patent
Dudkin et al.

(10) Patent No.: US 8,993,779 B2
(45) Date of Patent: Mar. 31, 2015

(54) POSITIVE ALLOSTERIC MODULATORS OF MGLUR2

(75) Inventors: Vadim Y. Dudkin, Lansdale, PA (US); Mark E. Fraley, North Wales, PA (US); Kenneth L. Arrington, Revere, MA (US); Mark E. Layton, Harleysville, PA (US); Alexander J. Reif, Holland, PA (US); Kevin J. Rodzinak, Schwenksville, PA (US); Joseph E. Pero, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/814,870

(22) PCT Filed: Aug. 5, 2011

(86) PCT No.: PCT/US2011/046677
§ 371 (c)(1),
(2), (4) Date: Feb. 7, 2013

(87) PCT Pub. No.: WO2012/021382
PCT Pub. Date: Feb. 16, 2012

(65) Prior Publication Data
US 2013/0143880 A1 Jun. 6, 2013

Related U.S. Application Data

(60) Provisional application No. 61/373,050, filed on Aug. 12, 2010.

(51) Int. Cl.
| | | |
|---|---|---|
| C07D 235/26 | (2006.01) | |
| C07D 417/14 | (2006.01) | |
| C07D 403/04 | (2006.01) | |
| C07D 403/14 | (2006.01) | |
| C07D 401/04 | (2006.01) | |
| C07D 401/14 | (2006.01) | |
| C07D 401/06 | (2006.01) | |
| C07D 401/10 | (2006.01) | |
| C07D 401/12 | (2006.01) | |
| C07D 403/10 | (2006.01) | |
| C07D 405/06 | (2006.01) | |
| C07D 453/02 | (2006.01) | |
| C07D 513/14 | (2006.01) | |
| C07D 405/10 | (2006.01) | |
| C07D 409/10 | (2006.01) | |
| C07D 413/10 | (2006.01) | |
| C07D 471/04 | (2006.01) | |

(52) U.S. Cl.
CPC ............ *C07D 235/26* (2013.01); *C07D 401/04* (2013.01); *C07D 401/06* (2013.01); *C07D 401/10* (2013.01); *C07D 401/12* (2013.01); *C07D 401/14* (2013.01); *C07D 403/04* (2013.01); *C07D 403/10* (2013.01); *C07D 405/06* (2013.01); *C07D 453/02* (2013.01); *C07D 513/14* (2013.01); *C07D 405/10* (2013.01); *C07D 409/10* (2013.01); *C07D 413/10* (2013.01); *C07D 417/14* (2013.01); *C07D 471/04* (2013.01)
USPC ........ 548/306.4; 544/124; 544/139; 544/310; 544/333; 544/349; 544/354; 544/364; 544/405; 546/121; 546/113; 546/199; 546/256; 546/270.1; 546/167; 546/273.7; 548/131; 548/250; 548/247; 514/234.5; 514/252.12; 514/254.06; 514/269; 514/274; 514/300; 514/314; 514/322; 514/338; 514/378; 514/387

(58) Field of Classification Search
USPC ...................................................... 548/306.4
See application file for complete search history.

(56) References Cited

U.S. PATENT DOCUMENTS

| | | | | |
|---|---|---|---|---|
| 7,056,918 | B2 * | 6/2006 | Dombroski et al. | 514/234.5 |
| 7,687,638 | B2 * | 3/2010 | Feng et al. | 548/304.4 |
| 2003/0225127 | A1 * | 12/2003 | Bender et al. | 514/312 |
| 2007/0191447 | A1 * | 8/2007 | Kodo et al. | 514/395 |
| 2008/0293684 | A1 | 11/2008 | Pinkerton et al. | |

FOREIGN PATENT DOCUMENTS

| | | |
|---|---|---|
| JP | 03/047180 A * | 2/1991 |
| WO | 0214275 A2 | 2/2002 |
| WO | 02/072576 | 9/2002 |
| WO | 2006/002051 | 1/2006 |
| WO | 2006/030032 | 3/2006 |
| WO | 2006/091496 A2 | 8/2006 |
| WO | 2011/035124 | 3/2011 |
| WO | 2012/021382 A1 | 2/2012 |

OTHER PUBLICATIONS

Machitani et al., CA 115:92264, 1991.*
Dombroski et al., Bioorganic & Medicinal Chemistry Letters (2004), 14(4), pp. 919-923.*
Acharya et al., Tetrahedron (2002), 58(11), pp. 2095-2100.*
An English translation of JP 03/047180, 1991.*
Johnson, et al., "Discovery of Allosteric Potentiators for the Metabotropic Glutamate 2 Receptor: Synthesis and Subtype Selectivity . . . " J. Med. Chem., 2003, vol. 46, pp. 3189-3192.

(Continued)

*Primary Examiner* — Laura L. Stockton
(74) *Attorney, Agent, or Firm* — Keith D. MacMillan; John C. Todaro

(57) ABSTRACT

The present invention is directed to benzimidazolone derivatives which are positive allosteric modulators of the mGluR2 receptor, useful in the treatment or prevention of neurological and psychiatric disorders associated with glutamate dysfunction and diseases in which the mGluR2 receptor is involved. The invention is also directed to pharmaceutical compositions comprising these compounds and the use of these compounds and compositions in the prevention or treatment of such diseases in which metabotropic glutamate receptors are involved, such as schizophrenia.

9 Claims, No Drawings

(56) References Cited

OTHER PUBLICATIONS

Johnson, et al., "Allosteric modulators of metabotropic gluamate receptors: lessons learnt from MGlu1, ,Glu2 and mGlu5 potentiators and antagonists," Biochenmical Society Transactions, 2004, vol. 32, Part 5, 881-887.

Galici, et al., "A Selective Potentiator of Metabotropic Glutamate (mGlu) 2 Receptors Has Effects to an Orthosteric . . ." The Journal of Pharmacology and Eperimental Therapeutics, vol. 315, No. 3, pp. 1181-1187, 2005.

Pinkerton, et al., "Phenyl-tetrazolyl Acetophenones: Discovery of Positive Allosteric Potentiators for the Metatabotropic Glutamate 2 Receptor," J. Med. Chem., 2004, vol. 47, pp. 4595-4599.

Woolley, et al., "The mGlu2 but not the mGlu3 receptor mediates the actions of the mGluR2/3 . . ." Phychopharmacology, 2008, vol. 196, pp. 431-440.

Jullian, et al., "Agonist Selectivity of mGluR1 and mGluR2 Metabotropic Receptors: A Different Environment but Similar Recognition . . . ," J. Med. Chem., 1999, vol. 42, pp. 1546-1555.

WO12021382 Search Report, Dec. 20, 2011.

K. F. McClure et al.: "Theoretical and Experimental Design of Atypical Kinase Inhibitors: Application to p38 MAP Kinase", J. Med. Chem., vol. 48, No. 18, Aug. 5, 2005, pp. 5728-5737, XP002717434, ISSN: 0022-2623.

H.-Y. Chen et al.: "Synthesis of structurally diverse benzimidazolyl benzimidazolones by application of soluble polymer support", Tetrahedron, vol. 64, No. 27, Apr. 25, 2008, pp. 6387-6394, XP002717435, ISSN: 0040-4020.

European Search Report, International Application No. EP11816846.7-1462, PCT/US2011046677, Date of Mailing Jan. 2, 2014.

* cited by examiner

POSITIVE ALLOSTERIC MODULATORS OF MGLUR2

BACKGROUND OF THE INVENTION

The excitatory amino acid L-glutamate (sometimes referred to herein simply as glutamate) through its many receptors mediates most of the excitatory neurotransmission within the mammalian central nervous system (CNS). The excitatory amino acids, including glutamate, are of great physiological importance, playing a role in a variety of physiological processes, such as long-term potentiation (learning and memory), the development of synaptic plasticity, motor control, respiration, cardiovascular regulation, and sensory perception.

Glutamate acts via at least two distinct classes of receptors. One class is composed of the tonotropic glutamate (iGlu) receptors that act as ligand-gated ionic channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGluR) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The present invention relates to potentiators of mGlu receptors, in particular mGluR2 receptors. The mGluR receptors belong to the Type III G-protein coupled receptor (GPCR) superfamily. This superfamily of GPCR's including the calcium-sensing receptors, GABAB receptors and pheromone receptors, which are unique in that they are activated by binding of effectors to the amino-terminus portion of the receptor protein. The mGlu receptors are thought to mediate glutamate's demonstrated ability to modulate intracellular signal transduction pathways. Ozawa, Kamiya and Tsuzuski, Prog. Neurobio., 54, 581 (1998). They have been demonstrated to be localized both pre- and post-synaptically where they can regulate neurotransmitter release, either glutamate or other neurotransmitters, or modify the post-synaptic response of neurotransmitters, respectively.

At present, there are eight distinct mGlu receptors that have been positively identified, cloned, and their sequences reported. These are further subdivided based on their amino acid sequence homology, their ability to effect certain signal transduction mechanisms, and their known pharmacological properties. Ozawa, Kamiya and Tsuzuski, Prog. Neurobio., 54, 581 (1998). For instance, the Group I mGluR receptors, which include the mGlu1R and mGlu5R, are known to activate phospholipase C (PLC) via G$\alpha$g-proteins thereby resulting in the increased hydrolysis of phosphoinositides and intracellular calcium mobilization. There are several compounds that are reported to activate the Group I mGlu receptors including DHPG, (R/S)-3,5-dihydroxyphenylglycine. Schoepp, Goldworthy, Johnson, Salhoff and Baker, J. Neurochem., 63, 769 (1994); Ito, et al., keurorep., 3, 1013 (1992). The Group II mGlu receptors consist of the two distinct receptors, mGluR2 and mGluR3 receptors. Both have been found to be negatively coupled to adenylate cyclase via activation of G$\alpha$i-protein. These receptors can be activated by a selective compound such as 1S,2S,5R,6S-2 aminobicyclo [3.1.0]hexane-2,6-dicarboxylate. Monn, et al., J. Med. Chem., 40, 528 (1997); Schoepp, et al., Neuropharmacol., 36, 1 (1997). This activation leads to inhibition of glutamate release in the synapse (Cartmell et al, J Neurochem 75, 889 (2000)). Similarly, the Group III mGlu receptors, including mGluR4, mGluR6, mGluR7 and mGluR8, are negatively coupled to adenylate cyclase via G$\alpha$i and are potently activated by L-AP4 (L-(+)-2-amino-4-phosphonobutyric acid). Schoepp, Neurochem. Int., 24, 439 (1994).

Nonselective mGluR2/mGluR3 receptor agonists (Monn, et al., J. Med. Chem., 43, 4893, (2000)) have shown efficacy in numerous animal models of anxiety and psychosis as well as human clinical trials in schizophrenia patients; Patil et al, Nature Medicine, 13, 1102 (2007). Recent reports indicate that mGluR2 but not the mGluR3 receptor mediates the actions of the dual mGluR2/mGluR3 agonist LY379268 in mouse models predictive of antipsychotic activity. Woolley et al, Psycopharmacology, 196, 431 (2008). Additionally, recent animal studies demonstrate that selective potentiation of the mGluR2 receptor has similar effects to such non-selective agonists (Galici et al, Journal of Pharmacology and Experimental Therapeutics, 315, 1181 (2005)) suggesting an alternative strategy concerning the discovery of selective, positive allosteric modulators (PAMs or allosteric potentiators) of mGluR2 (Johnson et al, J. Med. Chem. 46, 3189, (2003); Pinkerton et al., J. Med. Chem., 47, 4595 (2004). These potentiators act by enabling the receptor to produce an enhanced response to endogenous glutamate. Such allosteric potentiators do not bind at the glutamate binding site also known as the "orthosteric site", and may benefit by binding to a site other than the highly conserved orthosteric site. A potential advantage to this approach includes the opportunity to have a distinct pharmacological profile by enhancing the activity of the endogenous ligand upon its binding to the orthosteric site. The pharmacological distinctions include the potential for pharmacological specificity between related receptor types that share the same endogenous ligand. In addition, positive allosteric modulators of mGluR2 have been shown to potentiate the response of mGluR2 agonists such as LY379268 (Johnson et. Al. Biochemical Soc. Trans. 32, 881 (2004) and this represents an alternative strategy for treatment using mGluR2 selective PAMs.

It has become increasingly clear that there is a link between modulation of excitatory amino acid receptors, including the glutamatergic system, through changes in glutamate release or alteration in postsynaptic receptor activation, and a variety of neurological and psychiatric disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction make the abatement of these neurological processes an important therapeutic goal.

SUMMARY OF THE INVENTION

The present invention is directed to benzimidazolone derivatives which are positive allosteric modulators of the mGluR2 receptor, useful in the treatment or prevention of neurological and psychiatric disorders associated with glutamate dysfunction and diseases in which the mGluR2 receptor is involved. The invention is also directed to pharmaceutical compositions comprising these compounds and the use of these compounds and compositions in the prevention or treatment of such diseases in which metabotropic glutamate receptors are involved, such as schizophrenia.

DETAILED DESCRIPTION OF THE INVENTION

The invention encompasses a genus of compounds of Formula I

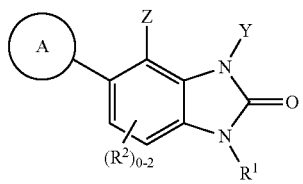

wherein:

Z is selected from H, halo, hydroxy, methyl, methoxy or CN;

Y is cyano, benzyl, $C_{1-6}$alkyl or $C_{2-6}$alkenyl, said $C_{1-6}$alkyl and $C_{2-6}$alkenyl optionally substituted with cyano;

$R^1$ is selected from the group consisting of:
(1) $C_{2-8}$alkyl,
(2) $C_{2-8}$alkenyl,
(3) $C_{2-8}$alkynyl,
(4) $C_{3-6}$cycloalkyl-$(CH_2)_p$—,
(5) aryl-$(CH_2)_p$—,
(6) heteroaryl-$(CH_2)_p$—, and
(7) heterocycle-$(CH_2)_p$—, wherein p is 0, 1, 2, 3 or 4, and groups (1) to (7) above are optionally substituted with 1 to 4 $R^2$ groups;

each $R^2$ is independently selected from the group consisting of: halo, OH, oxo, —CN, $C_{1-4}$alkyl, $C_{1-4}$alkoxy, $CF_3$, —$OCF_3$, —C(O)—O—$C_{1-4}$alkyl, —$N(R)_2$, pyrimidinyl and —CN;

ring A is selected from aryl, heteroaryl and heterocycle, wherein said heterocycle is partially aromatic and wherein said aryl, heteroaryl and heterocycle are optionally substituted with one or more $R^3$ groups up to the maximum number of substitutable positions;

each $R^3$ is independently selected from the group consisting of: halo, —CN, —$NO_2$, X, —$C(R^4)_2$—N(R)—X, —$C(R^4)_2$—N(R)C(O)—X, —$C(R^4)_2$—N(R)S(O)$_k$—X, —$C(R^4)_2$—N(R)C(O)—O—X, —C(O)—X, —C(O)—O—X, —C(O)—N(R)—X, —S(O)$_k$—X, —S(O)$_k$N(R)—X, —N(R)—X, —O—X, —N(R)C(O)—X, —N(R)S(O)$_k$—X, —N(R)C(O)—O—X, —N(R)C(O)N(R)—X and —N(R)SO$_2$N(R)—X, each X is independently selected from the group consisting of: H, $C_{1-8}$alkyl, $C_{2-6}$alkenyl, $C_{2-6}$alkynyl, $C_{3-6}$cycloalkyl, aryl, heterorayl, heterocycle, $C_{3-6}$cycloalkyl-$C(R^4)_2$—, aryl-$C(R^4)_2$—, heteroaryl-$C(R^4)_2$— and heterocycle-$C(R^4)_2$—, wherein each member of the group excluding hydrogen is optionally substituted from one up to the maximum number of substitutable positions with one or more substituents independently selected from the group consisting of: CN, halo, $R^5$, —O—$R^5$, —N(R)—$R^5$, —N(R)C(O)—$R^5$, —N(R)S(O)$_2$—$R^5$, —N(R)—C(O)—O—$R^5$, —C(O)—N(R)—$R^5$, —C(O)—O—$R^5$, —C(O)—$R^5$, —C(O)—$C(R^4)_2$—$R^5$, —C(O)—$C(R^4)_2$—S(O)$_2$—$R^5$, —$C(R^4)_2$—N(R)—$R^5$, —$SO_2$—N(R)—$R^5$, —$Si(CH_3)_2$($R^5$), —$C(R^4)_2$—$R^5$ and —$SO_2$—$R^5$;

each k is independently 0, 1 or 2;

each R is independently selected from the group consisting of: H and $C_{1-4}$alkyl;

each $R^4$ is independently selected from the group consisting of: H, OH and $C_{1-4}$alkyl;

each $R^5$ is independently selected from the group consisting of: H, $C_{1-4}$alkyl, $C_{2-4}$alkenyl, $C_{2-4}$alkynyl, $C_{3-6}$cycloalkyl, phenyl, benzyl, heterocycle and heteroaryl, wherein each member of the group excluding hydrogen is optionally substituted with 1 to 3 substituents independently selected from: halogen, cyano, hydroxy and methyl;

aryl at each occurrence is independently selected from the group consisting of: phenyl, naphthyl, anthryl and phenanthryl;

heteroaryl at each occurrence independently means a 5- or 6-membered monocyclic aromatic or 9- or 10-membered bicyclic aromatic, wherein at least one atom in the aromatic is selected from N, O and S, the sulfur optionally oxidized to sulfone or sulfoxide, and the remaining atoms are selected from C, N, O and S, the sulfur optionally oxidized to sulfone or sulfoxide;

heterocycle at each occurrence independently means a 4- to 7-membered monocyclic non-aromatic ring, an 8- to 11-membered bi-cyclic, including spiro-cyclic, non- or partially-aromatic ring or a 12- to 20-membered tri-cyclic, including spiro-cyclic portions, non- or partially-aromatic ring, each optionally substituted with 1 to 2 oxo groups, wherein at least one atom is selected from N(R), O and S, the sulfur optionally oxidized to sulfone or sulfoxide, and the remaining atoms are selected from C, N(R), O and S, the sulfur optionally oxidized to sulfone or sulfoxide;

and pharmaceutically acceptable salts thereof.

Within the genus, the invention encompasses a first sub-genus of compounds of Formula I wherein Y is methyl.

Also within the genus, the invention encompasses a second sub-genus of compounds of Formula I wherein $R^1$ is selected from the group consisting of:

cyclopropylmethyl, 2,2-difluorocyclopropylmethyl, 2,2-difluoro-1-methylcyclopropylmethyl, 1-(trifluoromethyl)cyclopropylmethyl, 4,4,4-trifluoro-2,2-dimethylbutyl, cyclobutylmethyl, 2,2-dimethylpropyl, prop-2-enyl, biphenyl and benzyl, optionally substituted with methoxy or —$OCF_3$.

Also within the genus, the invention encompasses a third sub-genus of compounds having Formula Ia

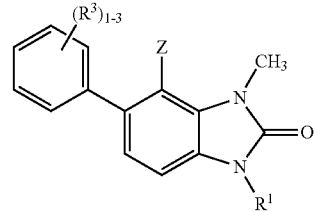

or a pharmaceutically acceptable salt thereof.

Within the third sub-genus, the invention encompasses a first class of compounds of Formula Ia wherein $R^3$ is selected from the group consisting of halo, —CN, —N(O)$_2$, amino, —N($C_{1-4}$alkyl)$_2$, —C(O)—O—$C_{1-4}$alkyl, —C(O)—$C_{1-4}$alkyl, —S(O)$_2$—$C_{1-4}$alkyl, $C_{3-6}$cycloalkyl, —C($C_{1-4}$alkyl)$_2$-NHC(O)—O—$C_{1-4}$alkyl and $C_{1-8}$alkyl optionally substituted with 1 to 4 substituents independently selected from hydroxy and halo.

Also within the genus, the invention encompasses a fourth sub-genus of compounds having Formula Ib

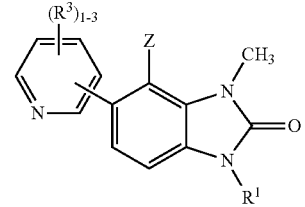

or a pharmaceutically acceptable salt thereof.

Within the fourth sub-genus, the invention encompasses a second class of compounds of Formula Ib wherein $R^3$ is selected from the group consisting of: halo, —CN, —N(O)$_2$, amino, —N(C$_{1-4}$alkyl)$_2$, —C(O)—O—C$_{1-4}$alkyl, —C(O)—C$_{1-4}$alkyl, —S(O)$_2$—C$_{1-4}$alkyl, C$_{3-6}$cycloalkyl and C$_{1-8}$alkyl optionally substituted with 1 to 4 substituents independently selected from hydroxy and halo.

Also within the genus, the invention encompasses a fifth sub-genus of compounds having Formula Ic

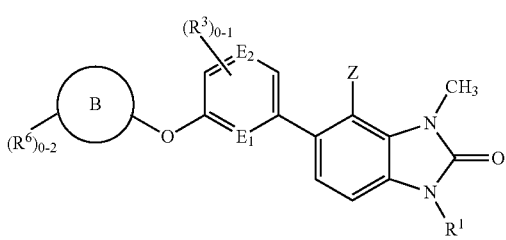

Ic or a pharmaceutically acceptable salt thereof, wherein
$E_1$ and $E_2$ are independently C or N;
ring B is phenyl or heteroaryl,
$R^3$ is CN, halo or C$_{1-4}$alkyl, optionally substituted with 1-5 halo atoms, and
each $R^6$ is independently selected from the group consisting of: CN, halo, $R^5$, —O—$R^5$, —N(R)—$R^5$, —N(R)C(O)—$R^5$, —N(R)S(O)$_2$—$R^5$, —N(R)—C(O)—O—$R^5$, —C(O)—N(R)—$R^5$, —C(O)—O—$R^5$, —C(O)—$R^5$, —C(O)—C(R$^4$)$_2$—$R^5$, —C(O)—C(R$^4$)$_2$—S(O)$_2$—$R^5$, —C(R$^4$)$_2$—N(R)—$R^5$, —SO$_2$—N(R)—$R^5$, —Si(CH$_3$)$_2$(R$^5$), —C(R$^4$)$_2$—$R^5$ and —SO$_2$—$R^5$.

Within the fifth sub-genus, the invention encompasses a third class of compounds of Formula Ic wherein ring B is phenyl. Also within the fifth sub-genus, the invention encompasses a fourth class of compounds of Formula Ic wherein ring B is pyridyl. Also within the fifth sub-genus, the invention encompasses a fifth class of compounds of Formula Ic wherein $E_1$ is C and $E_2$ is C. Also within the fifth sub-genus, the invention encompasses a sixth class of compounds of Formula Ic wherein $E_1$ is N and $E_2$ is C. Also within the fifth sub-genus, the invention encompasses a seventh class of compounds of Formula Ic wherein $E_1$ is C and $E_2$ is N.

Also within the genus, the invention encompasses an eighth sub-genus of compounds having Formula Id

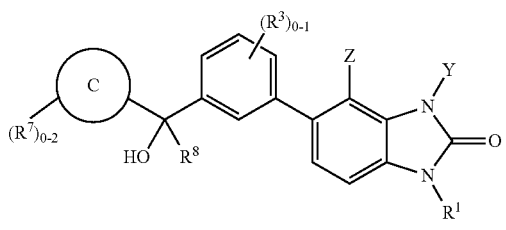

Id or a pharmaceutically acceptable salt thereof, wherein
ring C is phenyl or heteroaryl,
$R^3$ is CN, halo or C$_{1-4}$alkyl, optionally substituted with 1-5 halo atoms, and
each $R^7$ is independently selected from the group consisting of: CN, halo, $R^5$, —O—$R^5$, —N(R)—$R^5$, —N(R)C(O)—$R^5$, —N(R)S(O)$_2$—$R^5$, —N(R)—C(O)—O—$R^5$, —C(O)—N(R)—$R^5$, —C(O)—O—$R^5$, —C(O)—$R^5$, —C(O)—C(R$^4$)$_2$—$R^5$, —C(O)—C(R$^4$)$_2$—S(O)$_2$—$R^5$, —C(R$^4$)$_2$—N(R)—$R^5$, —SO$_2$—N(R)—$R^5$, —Si(CH$_3$)$_2$(R$^5$), —C(R$^4$)$_2$—$R^5$ and —SO$_2$—$R^5$;
$R^8$ is H or methyl.

The invention also encompasses the examples that follow.

The invention also encompasses a pharmaceutical composition comprising a compound of Formula I in combination with a pharmaceutically acceptable carrier.

The invention also encompasses a method for treating a neurological or psychiatric disorder associated with glutamate dysfunction in a patient in need thereof comprising administering to the patient a therapeutically effective amount of a compound of Formula I. The invention also encompasses this method wherein the neurological or psychiatric disorder associated with glutamate dysfunction is schizophrenia.

The invention also encompasses the use of a compound of Formula I for the preparation of a medicament for the treatment of a neurological or psychiatric disorder associated with glutamate dysfunction. The invention also encompasses a compound of Formula I for use in the treatment of a neurological or psychiatric disorder associated with glutamate dysfunction "Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono-, bi- or tri-cyclic structures, optionally combined with linear or branched structures, having the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

"Alkoxy" means alkoxy groups of a straight or branched having the indicated number of carbon atoms. C$_{1-6}$alkoxy, for example, includes methoxy, ethoxy, propoxy, isopropoxy, and the like.

"Cycloalkoxy" means cycloalkyl as defined above bonded to an oxygen atom, such as cyclopropyloxy.

Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Halogen" and "halo" includes fluorine, chlorine, bromine and iodine.

The point of attachment for Heterocycle may be through a carbon or nitrogen atom.

A heteroaryl group may be attached to the remainder of the molecule via a ring carbon or a ring nitrogen, provided that this is consistent with preservation of aromaticity.

The compounds of the present invention are potentiators of metabotropic glutamate (mGluR) receptor function, in particular they are potentiators of mGluR2 receptors. That is, the compounds of the present invention do not appear to bind at the glutamate recognition site on the mGluR receptor, but in the presence of glutamate or a glutamate agonist, the compounds of the present invention increase mGluR receptor response. The present potentiators are expected to have their effect at mGluR receptors by virtue of their ability to increase the response of such receptors to glutamate or glutamate agonists, enhancing the function of the receptors. It is recognized that the compounds of the present invention would be expected to increase the effectiveness of glutamate and glutamate agonists of the mGluR2 receptor. Thus, the potentiators of the present invention are expected to be useful in the treatment of various neurological and psychiatric disorders associated with glutamate dysfunction described to be treated herein and others that can be treated by such potentiators as are appreciated by those skilled in the art.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of generic formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. It will be understood that, as used herein, references to the compounds of Formula I are meant to also include a pharmaceutically acceptable salts.

Exemplifying the invention are the examples described below. The subject compounds are useful in a method of potentiating metabotropic glutamate receptor activity in a patient such as a mammal in need of such inhibition comprising the administration of an effective amount of the compound. The present invention is directed to the use of the subject compounds disclosed herein as potentiators of metabotropic glutamate receptor activity. In addition to primates, especially humans, a variety of other mammals can be treated according to the method of the present invention.

The present invention is further directed to a method for the manufacture of a medicament for potentiating metabotropic glutamate receptor activity in humans and animals comprising combining a compound of the present invention with a pharmaceutical carrier or diluent.

The subject treated in the present methods is generally a mammal, preferably a human being, male or female, in whom potentiation of metabotropic glutamate receptor activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention, As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as potentiators of metabotropic glutamate receptor activity, in particular mGluR2 activity, may be demonstrated by methodology known in the art. Activity in potentiating the mGluR2 receptor may be determined as follows. The compounds of the present invention are tested in a fluorescence laser imaging plate reader (FLIPR) based assay. This assay is a common functional assay to monitor $Ca^{2+}$ mobilization in whole cells expressing recombinant receptor coupled with a promiscuous G-protein. CHO dhfr-cells stably expressing recombinant human mGluR2 and G$\alpha$16 loaded with Fluo-4 AM (Invitrogen, Carlsbad Calif.) are treated with dose responses of compounds and the $Ca^{2+}$ response is monitored on a FLIPR384 (Molecular Devices, Sunnydale Calif.) for agonist activity. The potentiation response is monitored after a subsequent addition of an EC20 concentration of glutamate (900 nM). The maximum calcium response at each concentration of compound for agonist or potentiation are plotted as dose responses and the curves are fitted with a four parameters logistic equation giving EC50 and Hill coefficient using the iterative non linear curve fitting software program.

The compounds of the present invention may also be tested in a [$^{35}$S]-GTP$\gamma$S assay. The stimulation of [$^{35}$S]-GTP$\gamma$S binding is a common functional assay to monitor G$\alpha$i-coupled receptor in native and recombinant receptor membrane preparation. Membrane from cells stably expressing hmGlu2 CHO-K1 (50 µg) are incubated in a 96 well plate for 1 hour in the presence of GTP$\gamma$S$^{35}$ (0.05 nM), GDP (5 µM) and compounds. The reaction is stopped by rapid filtration over Unifilter GF/B plate (Packard, Bioscience, Meriden Conn.) using a 96-well cell harvester (Brandel Gaithersburg, Md.). The filter plates are counted using Topcount counter (Packard, Bioscience, Meriden Conn., USA). When compounds are evaluated as potentiators they are tested in the presence of glutamate (1 µM). The activation (agonist) or the potentiation of glutamate (potentiator) curves are fitted with a four parameters logistic equation giving $EC_{50}$ and Hill coefficient using the iterative non linear curve fitting software GraphPad (San Diego Calif., USA).

Certain compounds of the invention were tested and demonstrated activity in potentiating the mGluR2 receptor in the FLIPR assay with an EC50 of less than about 10 µM. Exs. 1-201 (12 µM), 1-202 (>30 µM), 1-203 (>30 µM), 1-205 (>30 µM) and 1-206 (20 µM) exhibited potency outside this range. Compounds within the present invention had activity in potentiating the mGluR2 receptor in the FLIPR and GTP$\gamma$S assays with an $EC_{50}$ of less than about 1 µM. Certain compounds of the invention resulted in a minimum 1.8-fold potentiation of glutamate response in the presence of an EC20 concentration of glutamate (900 nM). Such results are indicative of the intrinsic activity of the compounds in use as potentiators of mGluR2 receptor activity.

Representative FLIPR $EC_{50}$ Values

| Ex. | EC50 | N |
|---|---|---|
| 1-9 | 264 nM | 2 |
| 1-61 | 2658 nM | 1 |
| 1-94 | 41 nM | 2 |
| 1-148 | 126 nM | 2 |
| 1-187 | 182 nM | 2 |
| 2-4 | 496 nM | 3 |
| 2-38 | 41 nM | 2 |
| 3-3 | 3655 nM | 1 |
| 4-8 | 1251 nM | 1 |
| 5-12 | 3346 nM | 1 |
| 5-22 | 364 nM | 1 |
| 6-9 | 45 nM | 2 |
| 7-19 | 781 nM | 1 |
| 7-47 | 77 nM | 2 |
| 8-5 | 40 nM | 2 |
| 10-3 | 129 nM | 2 |
| 10-5 | 225 nM | 2 |

Metabotropic glutamate receptors including the mGluR2 receptor have been implicated in a wide range of biological functions. This has suggested a potential role for these receptors in a variety of disease processes in humans or other species.

The compounds of the present invention have utility in treating, preventing, ameliorating, controlling or reducing the risk of a variety of neurological and psychiatric disorders associated with glutamate dysfunction, including one or more of the following conditions or diseases: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), autism, autism spectrum disorders, attention deficit/hyperactivity disorder, and conduct disorder.

In an embodiment the present invention provides a method for treating migraine, comprising: administering to a patient in need thereof an effective amount of a compound of formula I. In another embodiment the present invention provides a method for preventing or treating anxiety, comprising: administering to a patient in need thereof an effective amount of a compound of formula I. Particular anxiety disorders of the invention are generalized anxiety disorder, panic disorder, and obsessive compulsive disorder. In another embodiment the present invention provides a method for treating schizophrenia, comprising: administering to a patient in need thereof an effective amount of a compound of formula I. In yet another embodiment the present invention provides a method for treating epilepsy, comprising: administering to a patient in need thereof an effective amount of a compound of formula I.

In an embodiment, the present invention provides a method for the treatment of schizophrenia comprising: administering to a patient in need thereof an effective amount of a compound of formula I or a pharmaceutical composition thereof. In one of the available sources of diagnostic tools, The Merck Manual (2006-2007), schizophrenia is characterized by psychosis (loss of contact with reality), hallucinations (false perceptions), delusions (false beliefs), disorganized speech and behavior, flattened affect (restricted range of emotions), cognitive deficits (impaired reasoning and problem solving), and occupational and social dysfunction. The skilled artisan will recognize that there are alternative nomenclatures, nosologies, and classification systems for neurological and psychiatric disorders, including migraine, and that these systems evolve with medical scientific progress Thus, in an embodiment the present invention provides a method for treating migraine, comprising: administering to a patient in need thereof an effective amount of a compound of formula I or a pharmaceutical composition thereof. In one of the available sources of diagnostic tools, Dorland's Medical Dictionary (23'd Ed., 1982, W. B. Saunders Company, Philidelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another embodiment the present invention provides a method for treating anxiety, comprising: administering to a patient in need thereof an effective amount of a compound of Formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another embodiment the present invention provides a method for treating depression, comprising: administering to a patient in need thereof an effective amount of a compound of Formula I or a pharmaceutical composition thereof. At present, DSM-IV provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-IV.

In another embodiment the present invention provides a method for treating epilepsy, comprising: administering to a patient in need thereof an effective amount of a compound of Formula I or a pharmaceutical composition thereof. At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepsy, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a compound of the present invention. A potentiated amount is expected to be less than the amount that is required to provided the same effect when the mGluR agonist is administered without an effective amount of a compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of formula I, a number of factors are considered by the attending diagnostician, including, but not limited to: the mGluR agonist selected to be administered, including its potency and selectivity; the compound of formula I to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form may be utilized containing such other drugs and the compound of Formula I. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be utilized. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require potentiation of metabotorpic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein. The compounds of the present invention can be prepared in a variety of fashions.

Abbreviations used in the description of the chemistry and in the Examples that follow are: Ac2O (acetic anhydride); AcOH (acetic acid); AEBSF (p-aminoethylbenzenesulfonyl fluoride); Boc (di-tert-butyl carbamate); (Boc)$_2$O (di-tert-butyl dicarbonate); BSA (bovine serum albumin); BuLi (n-Butyl lithium); CDCl3 (chloroform-d); CuI (copper iodide); CuSO4 (copper sulfate); DBU (1,8-DIAZABICYCLO[5.4.0]UNDEC-7-ENE); DCE (dichloroethane); DCM (dichloromethane); DEAD (diethyl azodicarboxylate); DIPEA (diisopropylethylamine); DMBA (1,3-dimethylbarbituric acid); DMF (N,N-dimethylformamide); DMP (Dess-Martin periodinane); DMSO (dimethyl sulfoxide); DPPA (diphenylphosphoryl azide); DTT (dithiothreitol); EDTA (ethylene-diamine-tetra-acetic acid); EGTA (ethylene-glycol-tetra-acetic acid); Et2O (diethylether); EtOAc (ethyl acetate); EtOH (ethanol); HOAc (acetic acid); HPLC (high-performance liquid chromatography); HRMS (high resolution mass spectrum); LAH (lithium aluminum hydride); LCMS (chromatograph-mass spectrometer); LHMDS (lithium bis(trimethylsilyl)amide); LRMS (low resolution mass spectrum); mCPBA (3-chloroperoxybenzoic acid); MeOH (methanol); MOM-Cl (methoxymethyl chloride); MP-B(CN)H3 (Macroporous cyanoborohydride); NaHCO3 (sodium bicarbonate); Na2SO4 (sodium sulfate); Na(OAc)3BH (sodium triacetoxyborohydride); NH4OAc (ammonium acetate); NBS (N-bromosuceinamide); NFSi (N-fluorobenzenesulfonimide); NMP (1-methyl-2-pyrrolidinone); NMR (nuclear magnetic resonance); PBS (phosphate buffered saline); PCR (polymerase chain reaction); Pd(dppf) ([1,1'-bis(diphenylphosphino)ferrocene] palladium); Pd(Ph3)4 (palladium(0) tetrakis-triphenylphosphine); POCl3 (phosphorous oxychloride); PS-DIEA (polystyrene diisopropylethylamine); PS—PPh3 (polystyrene-triphenyl phosphine); PTSA (para-toluene sulfonic acid); Pyr (pyridine); Selectfluor (1-chloromethyl-4-fluoro-1,4-diazoniabicyclo[2.2.2] octane bis(tetrafluoroborate); TBAF (tetrabutylammonium fluoride); T-BuOH (tert-butanol); THF (tetrahydrofuran); Tf (trifluoromethanesulfonyl); TFA (trifluoroacteic acid); and TMSCH2N2 (trimethylsilyldiazomethane).

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of Formula A hereinabove.

Reactions used to generate the compounds of this invention are prepared by employing reactions as shown in Reaction Schemes A-J.

Synopsis of Reaction Schemes

Reaction Scheme A: SNAr (nucleophilic aromatic substitution) displacement of the fluorine in A-1 with the an amine produces the nitro compound A-2, which can be reduced to the dianiline A-3 with Zinc and Acetic acid. A-3 can be cyclized with carbonyldiimidazole (CDT) to establish the benzimidazolinone core. Direct alkylation with an alkyl halide provides A-5, and Pd-catalyzed coupling of A-5 with a boronic acid yields the final compound, A-6.

Reaction Scheme B: The functionalized benzimidazolinone, A-5, can be cross-coupled with the phenol boronic acid to provide B-1, which can then participate in an SNAr displacement with various heterocyclic chlorides or fluorides.

Reaction Scheme C: The phenol C-1 can be treated with various benzyl alcohols via a Mitsunobu reaction to yield the series of benzyl alcohols C-2.

Reaction Scheme D: Alternatively, the phenol C-1 can undergo Cu-mediated coupling with substituted aryl halides to afford biaryl benzimidazolinones D-1.

Reaction Scheme E: Halogenated benzimidazolinone A-5 can be converted to its cooresponding pinacol borane ester, E-1, which is then cross-coupled with 6-chloro-2-bromopyridine to produce E-2. E-2 can then undergo SNAR displacement to afford the series of pyridyl biaryl benzimidazolinones, E-3.

Reaction Scheme F: Isocyanate F-1 is converted to the urea, F-2, with the appropriate amine, then cyclized via intramolecular SNAR displacement to produce benzimidazolinone F-3. F-3 can undergo Pd-catalzyed cross-coupling to produce biaryl F-4, which can substituted with various alkyl halides to provide the series F-5.

Reaction Scheme G: Difluoro nitro anisole G-1 is selectively substituted to afford G-2, which is then reduced with Fe and Acetic acid to the dianiline G-3, CDI cyclization yields benzimidazolinone G-4, followed by alkylation yields G-5. Demethylation to the phenol G-6, with subsequent conversion to the triflate G-7 allows for Pd-catalyzed cross-coupling with the appropriate boronic acid to provide biaryl G-8.

Reaction Scheme H: The phenol H-1 can participate in an $S_N$Ar displacement to produce biaryl ether H-2.

Reaction Scheme I: Alternatively, phenol H-1 can undergo a Cu-mediated coupling reaction with aryl halides to afford biaryl ethers such as I-1.

Reaction Scheme J: The addition of a Grignard reagent across the aryl acetyl J-1 can afford the tertiary alcohol J-2.

Reaction Scheme A

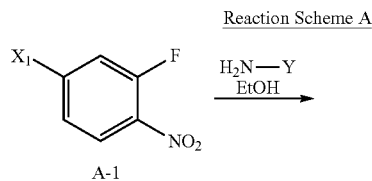

A-1

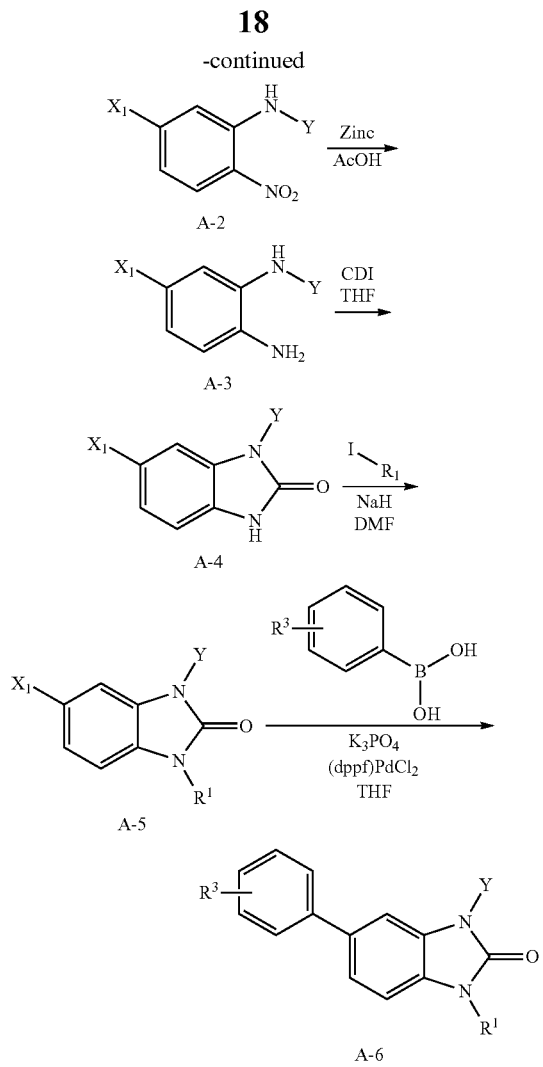

Reaction Scheme B

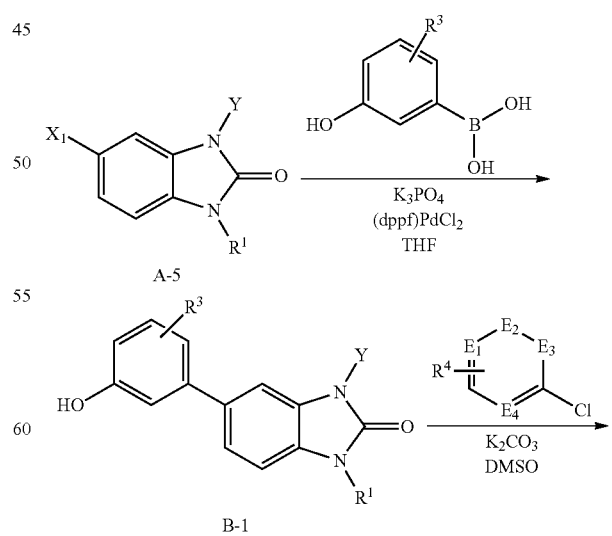

E1 through E4 = C or N

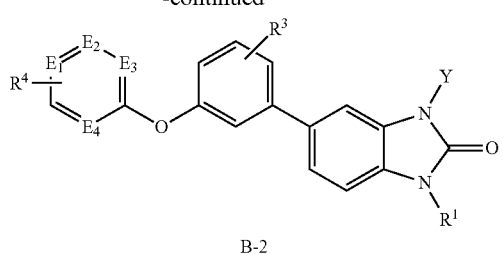
B-2
Reaction Scheme C
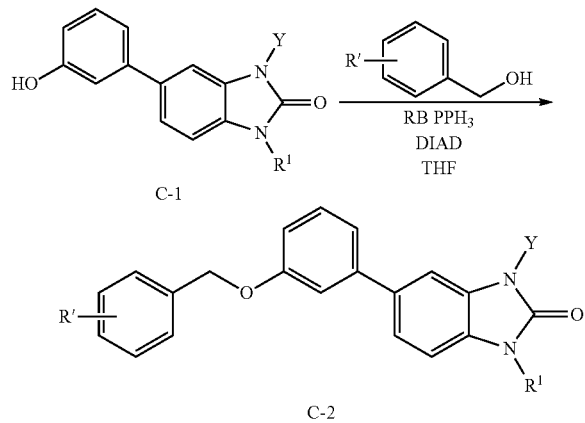
Reaction Scheme D
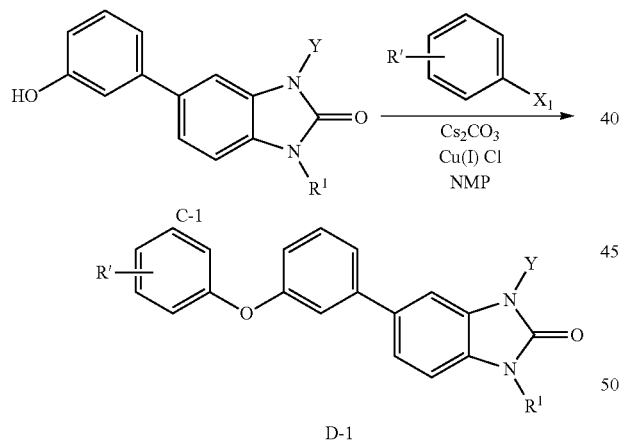
Reaction Scheme E
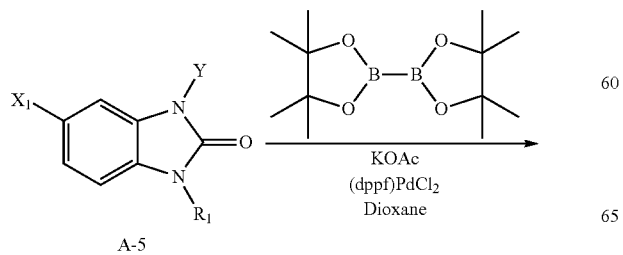
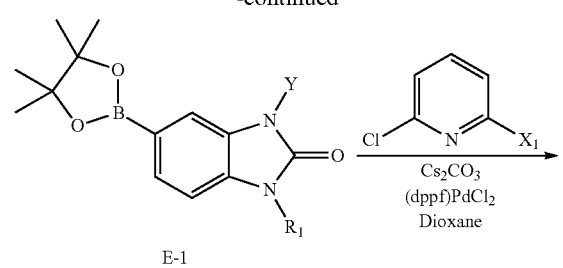
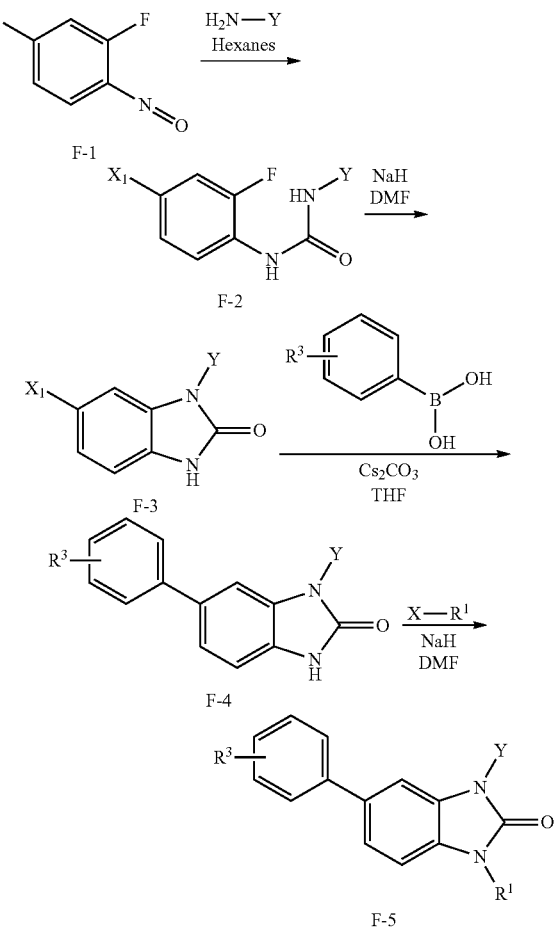
Reaction Scheme F Reaction Scheme G
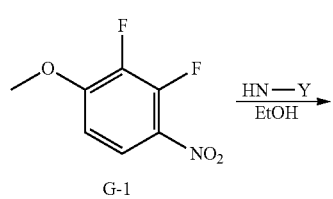
G-1
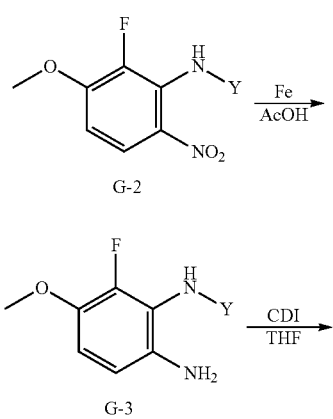
G-2
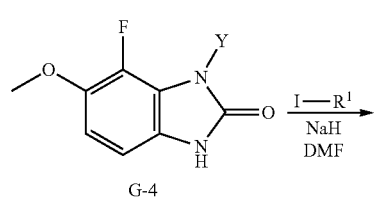
G-3
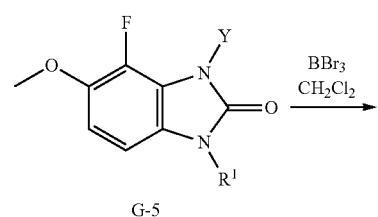
G-4
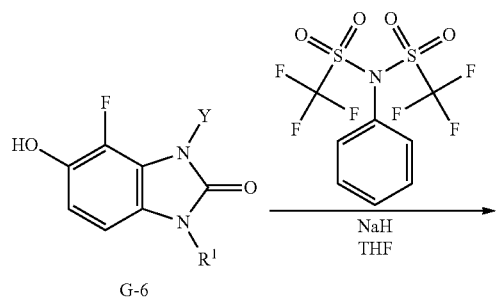
G-5
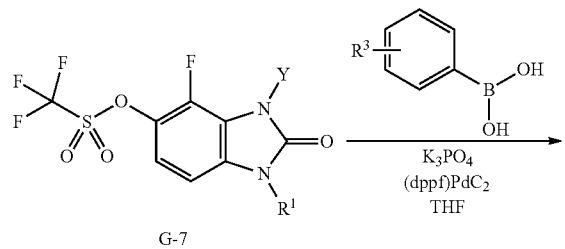
G-6
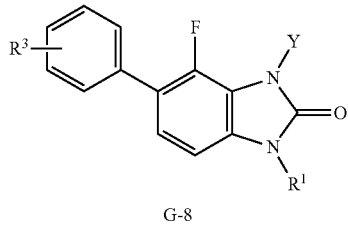
G-7
-continued
G-8
Reaction Scheme H
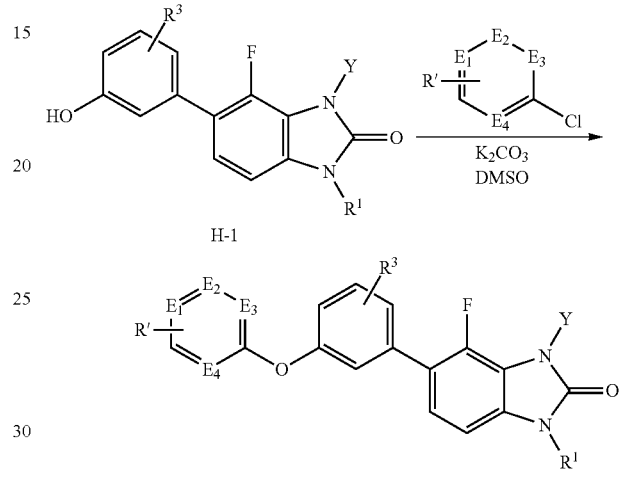
H-1
H-2
Reaction Scheme I
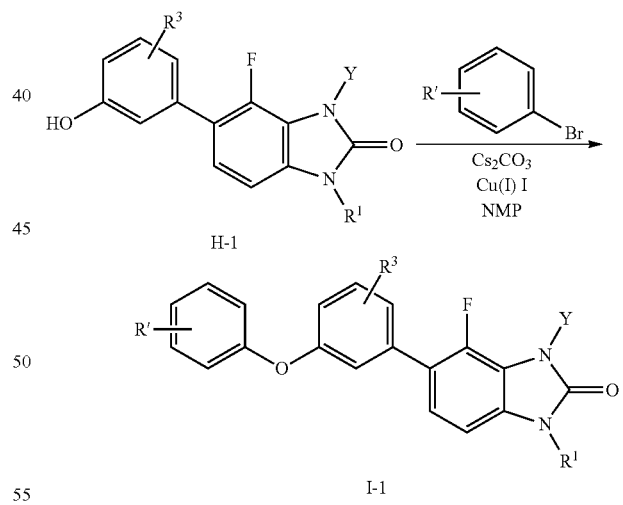
H-1
I-1
Reaction Scheme J
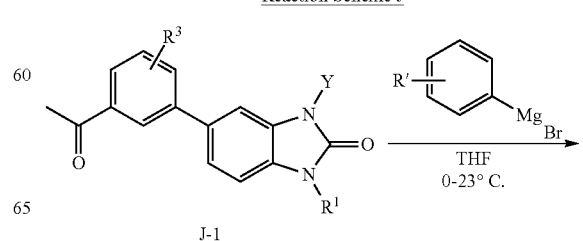
J-1

-continued

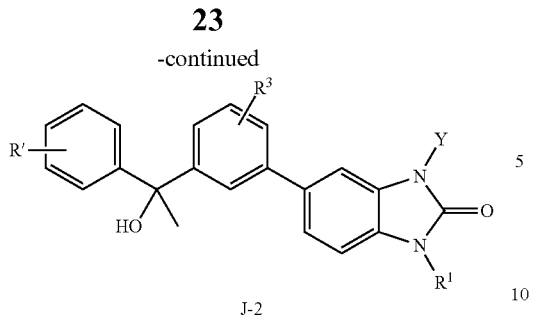

J-2

EXAMPLES

Examples provided are intended to assist in a further understanding of the invention. Particular materials employed, species and conditions are intended to be further illustrative of the invention and not limitative of the reasonable scope thereof. The reagents utilized in synthesizing the compounds depicted in the following Tables are either commercially available or are readily prepared by one of ordinary skill in the art.

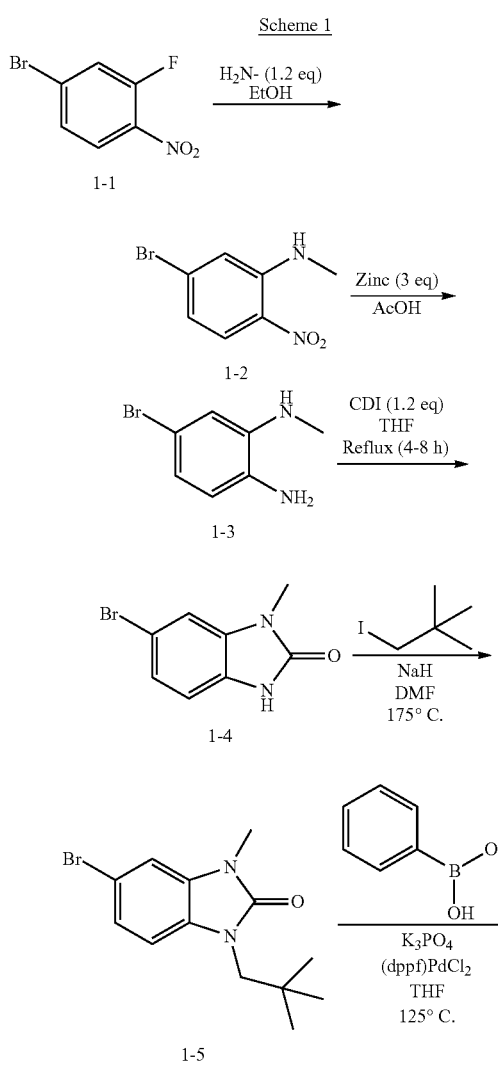

-continued

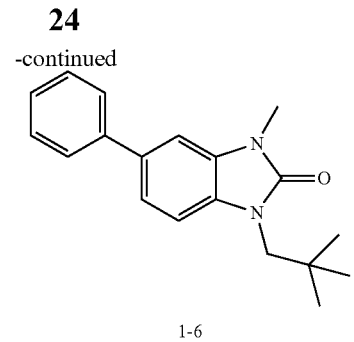

1-6

5-bromo-N-methyl-2-nitroaniline (1-2)

A solution of 4-Bromo-2-fluoronitrobenzene (1-1, 10.5 g, 47.7 mmol) in EtOH (100 ml) was treated with Methylamine (2M in MeOH, 28.6 ml, 57.3 mmol, 1.2 eq) and the resulting dark maroon solution was stirred at 23 deg C. for 13 h. The reaction was then concentrated in vacuo, and the residual yellow-orange solid was partitioned between EtOAc (2×250 ml) and water (300 ml). The combined organic layers were dried over $Na_2SO_4$ and concentrated, leaving the title compound, 5-bromo-N-methyl-2-nitroaniline (1-2), as a bright orange solid. $^1$H NMR (300 MHz, $CDCl_3$) δ 8.03 (d, 1H, J=9.15 Hz), 7.01 (sd, 1H, J=1.83 Hz), 6.77 (dd, 1H, J=7.02 Hz), 3.02 (d, 3H, J=4.88 Hz). LRMS m/z: Calc'd for $C_7H_7BrN_2O_2$ (M+H) 232.1, found 232.8.

4-bromo-$N^2$-methylbenzene-1,2-diamine (1-3)

An orange solution consisting of 5-bromo-N-methyl-2-nitroaniline (1-2, 10.5 g, 45.4 mmol) in Acetic acid (200 ml) was treated with Zinc dust (8.92 g, 136 mmol, 3.0 eq), generating a mild exotherm. The cloudy maroon reaction mixture was capped and stirred for 20 min. The reaction was >80% complete, so an additional amount of Zinc dust (1.0 g, 16 mmol, 0.35 eq) was added and the reaction was stirred for 15 min. LC/MS showed complete reduction, so the reaction mixture was filtered through Celite and washed with MeOH. The residual filtrate was concentrated in vacuo, then partitioned between EtOAc (2×300 ml) and saturated aqueous $NaHCO_3$ (350 ml). The combined organic layers were dried over $Na_2SO_4$ and concentrated, affording the title compound, 4-bromo-$N^2$-methylbenzene-1,2-diamine (1-3), as a brown solid with >90% purity. LRMS m/z: Calc'd for $C_7H_9BrN_2$ (M+H) 202.1, found 202.8.

6-bromo-1-methyl-1,3-dihydro-2H-benzimidazol-2-one (1-4)

4-bromo-$N^2$-methylbenzene-1,2-diamine (1-3, 9.31 g, 46.3 mmol) was dissolved in anhydrous THF (45 ml) and treated with CDI (9.01 g, 55.6 mmol, 1.2 eq). The resulting orange solution was stirred at reflux for 4 h, then cooled to 23 deg C. and stirred for 13 h. The cyclized product was partitioned between EtOAc (2×160 ml) and water (185 ml), and the combined organic layers were dried over $Na_2SO_4$ and concentrated.
The crude mixture contained a tan solid which was not readily soluble in EtOAc or Methylene Chloride. The material was collected via filtration and was found to only contain alittle bit of the desired product, mostly impurity. The filtrate was dried over $Na_2SO_4$, and concentrated. Obtained 6.79 g of the

5-bromo-1-(2,2-dimethylpropyl)-3-methyl-1,3-dihydro-2H-benzimidazol-2-one (1-5)

A solution of 6-bromo-1-methyl-1,3-dihydro-2H-benzimidazol-2-one (1-4, 500 mg, 2.20 mmol) in DMF (10 ml) was treated with Sodium hydride (176 mg, 4.40 mmol, 2.0 eq) followed by the 1-Iodo-2,2-Dimethylpropane (585 pt, 4.40 mmol, 2.0 eq). The reaction was irradiated at 175 deg C. for 20 min in a microwave. The reaction was complete by LC/MS, so it was partitioned between EtOAc (2×125 ml) and water (150 ml). The combined organic layers were dried over $Na_2SO_4$ and concentrated. The crude maroon-orange oil was purified via flash column chromatography ($SiO_2$: 100% Hex to 60:40 Hex:EtOAc), affording the title compound, 5-bromo-1-(2,2-dimethylpropyl)-3-methyl-1,3-dihydro-2H-benzimidazol-2-one (1-5), as a yellow solid with >95% purity. $^1$H NMR (600 MHz, CDCl$_3$) δ 7.18 (dd, 1H, J=Hz), 7.10 (s, 1H), 6.88 (d, 1H, J=Hz), 3.63 (s, 2H), 3.40 (s, 3H), 1.02 (s, 9H). LRMS m/z: Calc'd for $C_7H_7BrN_2O_2$ (M+H) 232.1, found 232.8.

1-(2,2-dimethylpropyl)-3-methyl-5-phenyl-1,3-dihydro-2H-benzimidazol-2-one (1-6)

An aqueous solution of Cesium carbonate (54.8 mg, 0.17 mmol, 5.0 eq) in water (2 mL) was charged with a solution of 5-bromo-1-(2,2-dimethylpropyl)-3-methyl-1,3-dihydro-2H-benzimidazol-2-one (1-5, 10 mg, 0.034 mmol) and phenylboronic acid (8.21 mg, 0.067 mmol, 2.0 eq), then deoxygenated. The 1,1'-Bis(diphenylphosphino)ferrocene-palladium (II)dichloride dichloromethane complex (1.37 mg, 1.68 μmol, 0.05 eq) was introduced and the mixture was irradiated in a microwave at 125 deg C. for 15 min. LC/MS showed complete conversion, so the reaction was partitioned between EtOAc (2×85 ml) and saturated aqueous NaHCO$_3$ (95 ml). The combined organic layers were dried over $Na_2SO_4$ and concentrated. The crude oil was purified via reverse-phase HPLC (Acetonitrile/Water gradient with 0.1% TFA present), affording the desired compound, 1-(2,2-dimethylpropyl)-3-methyl-5-phenyl-1,3-dihydro-2H-benzimidazol-2-one (1-6), with >95% purity. $^1$H NMR (300 MHz, CDCl$_3$) δ 7.59 (d, 2H, J=7.3 Hz), 7.45 (t, 2H, J=7.3 Hz), 7.30-7.36 (m, 2H), 7.19 (s, 1H), 7.10 (d, 1H, J=8.2 Hz), 3.70 (8, 2H), 3.49 (s, 3H), 1.07 (s, 9H). LRMS m/z: Calc'd for $C_{19}H_{22}N_2O$ (M+H) 295.4, found 295.1.

Table 1 for Scheme 1

| Cmp | Structure | Name | LRMS m/z (M + H) |
|---|---|---|---|
| 1-7 | 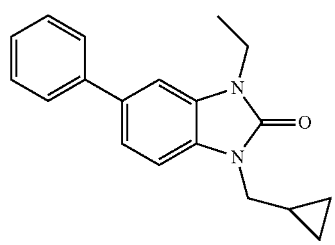 [SMILES: CCn1c(=O)n(CC2CC2)c2ccc(-c3ccccc3)cc21] | 1-(cyclopropylmethyl)-3-ethyl-5-phenyl-1,3-dihydro-2H-benzimidazol-2-one | LRMS m/z (M + H) 293.1 found, 293.4 required. |
| 1-8 | 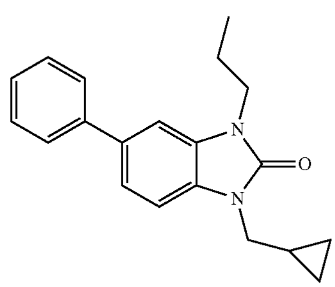 [SMILES: CCCn1c(=O)n(CC2CC2)c2ccc(-c3ccccc3)cc21] | 1-(cyclopropylmethyl)-5-phenyl-3-propyl-1,3-dihydro-2H-benzimidazol-2-one | LRMS m/z (M + H) 307.1 found, 307.4 required. |
| 1-9 | 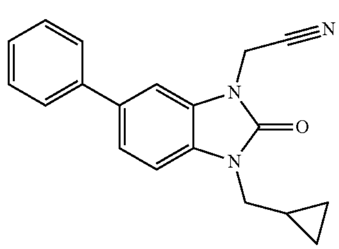 [SMILES: N#CCn1c(=O)n(CC2CC2)c2ccc(-c3ccccc3)cc21] | [3-(cyclopropylmethyl)-2-oxo-6-phenyl-2,3-dihydro-1H-benzimidazol-1-yl]acetonitrile | LRMS m/z (M + H) 304.1 found, 304.4 required. |

-continued

Table 1 for Scheme 1

| Cmp | Structure | Name | LRMS m/z (M + H) |
|---|---|---|---|
| 1-10 | 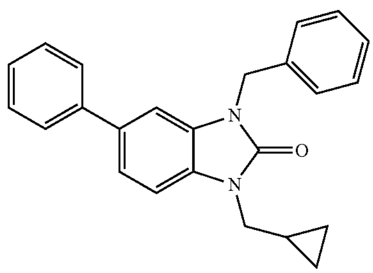 [SMILES: O=c1n(Cc2ccccc2)c2cc(-c3ccccc3)ccc2n1CC1CC1] | 3-benzyl-1-(cyclopropylmethyl)-5-phenyl-1,3-dihydro-2H-benzimidazol-2-one | LRMS m/z (M + H) 355.1 found, 355.5 required. |
| 1-11 | 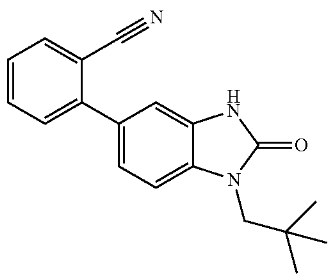 [SMILES: CC(C)(C)Cn1c(=O)[nH]c2cc(-c3ccccc3C#N)ccc21] | 2-[1-(2,2-dimethylpropyl)-2-oxo-2,3-dihydro-1H-benzimidazol-5-yl]benzonitrile | LRMS m/z (M + H) 306.1 found, 306.4 required. |
| 1-12 | 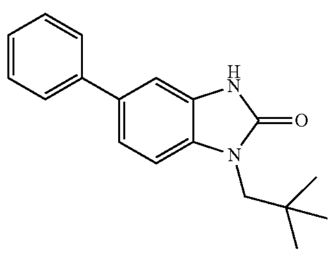 [SMILES: CC(C)(C)Cn1c(=O)[nH]c2cc(-c3ccccc3)ccc21] | 1-(2,2-dimethylpropyl)-5-phenyl-1,3-dihydro-2H-benzimidazol-2-one | LRMS m/z (M + H) 281.0 found, 281.4 required. |
| 1-13 | 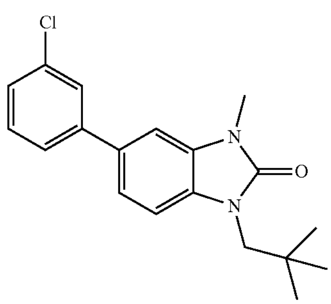 | 5-(3-chlorophenyl)-1-(2,2-dimethylpropyl)-3-methyl-1,3-dihydro-2H-benzimidazol-2-one | LRMS m/z (M + H) 329.1 found, 329.4 required. |
| 1-14 | 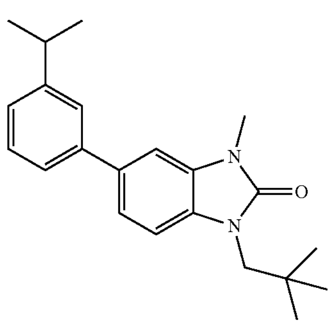 [SMILES: CC(C)c1cccc(-c2ccc3c(c2)n(C)c(=O)n3CC(C)(C)C)c1] | 1-(2,2-dimethylpropyl)-5-(3-isopropylphenyl)-3-methyl-1,3-dihydro-2H-benzimidazol-2-one | LRMS m/z (M + H) 337.2 found, 337.5 required. |

-continued

Table 1 for Scheme 1

| Cmp | Structure | Name | LRMS m/z (M + H) |
|---|---|---|---|
| 1-15 | 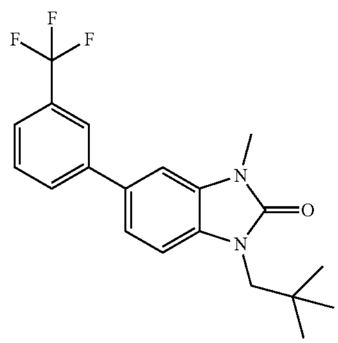 [SMILES: Cn1c(=O)n(CC(C)(C)C)c2ccc(-c3cccc(C(F)(F)F)c3)cc21] | 1-(2,2-dimethylpropyl)-3-methyl-5-[3-(trifluoromethyl)phenyl]-1,3-dihydro-2H-benzimidazol-2-one | LRMS m/z (M + H) 363.2 found, 363.4 required. |
| 1-16 | 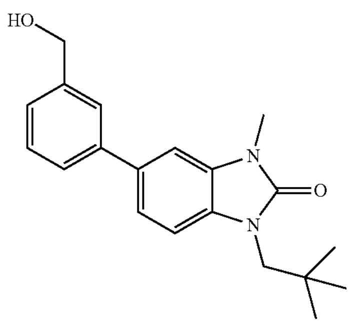 [SMILES: Cn1c(=O)n(CC(C)(C)C)c2ccc(-c3cccc(CO)c3)cc21] | 1-(2,2-dimethylpropyl)-5-[3-(hydroxymethyl)phenyl]-3-methyl-1,3-dihydro-benzimidazol-2-one | LRMS m/z (M + H) 325.2 found, 325.4 required. |
| 1-17 | 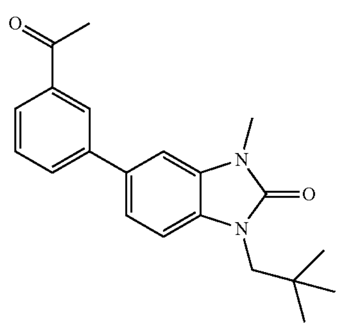 [SMILES: CC(=O)c1cccc(-c2ccc3c(c2)n(C)c(=O)n3CC(C)(C)C)c1] | 5-(3-acetylphenyl)-1-(2,2-dimethylpropyl)-3-methyl-1,3-dihydro-2H-benzimidazol-2-one | LRMS m/z (M + H) 337.2 found, 337.4 required. |
| 1-18 | 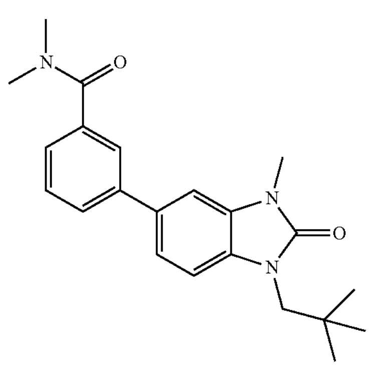 [SMILES: CN(C)C(=O)c1cccc(-c2ccc3c(c2)n(C)c(=O)n3CC(C)(C)C)c1] | 3-[2-(2,2-dimethylpropyl)-3-methyl-2-oxo-2,3-dihydro-1H-benzimidazol-5-yl]-N,N-dimethylbenzamide | LRMS m/z (M + H) 366.2 found, 366.5 required. |

-continued

Table 1 for Scheme 1

| Cmp | Structure | Name | LRMS m/z (M + H) |
|---|---|---|---|
| 1-19 | 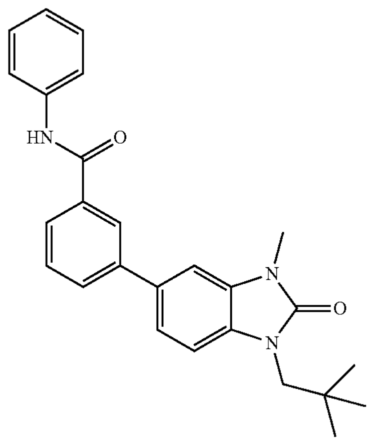 [SMILES: Cn1c(=O)n(CC(C)(C)C)c2ccc(-c3cccc(C(=O)Nc4ccccc4)c3)cc21] | 3-[1-(2,2-dimethylpropyl)-3-methyl-2-oxo-2,3-dihydro-1H-benzimidazol-5-yl]-N-phenylbenzamide | LRMS m/z (M + H) 414.2 found, 414.5 required. |
| 1-20 | 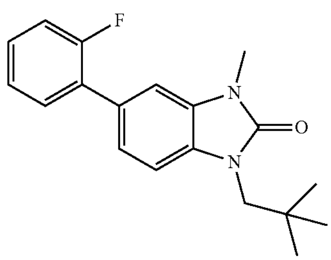 [SMILES: Cn1c(=O)n(CC(C)(C)C)c2ccc(-c3ccccc3F)cc21] | 1-(2,2-dimethylpropyl)-5-(2-fluorophenyl)-3-methyl-1,3-dihydro-2H-benzimidazol-2-one | LRMS m/z (M + H) 313.2 found, 313.4 required. |
| 1-21 | 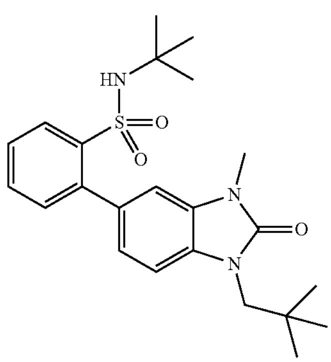 [SMILES: Cn1c(=O)n(CC(C)(C)C)c2ccc(-c3ccccc3S(=O)(=O)NC(C)(C)C)cc21] | N-(tert-butyl)-2-[1-(2,2-dimethylpropyl)-3-methyl-2-oxo-2,3-dihydro-1H-benzimidazol-5-yl]benzenesulfonamide | LRMS m/z (M + H) 430.2 found, 430.6 required. |
| 1-22 | 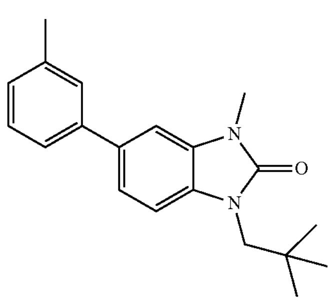 [SMILES: Cc1cccc(-c2ccc3c(c2)n(C)c(=O)n3CC(C)(C)C)c1] | 1-(2,2-dimethylpropyl)-3-methyl-5-(3-methylphenyl)-1,3-dihydro-2H-benzimidazol-2-one | LRMS m/z (M + H) 309.2 found, 309.4 required. |

-continued

Table 1 for Scheme 1

| Cmp | Structure | Name | LRMS m/z (M + H) |
|---|---|---|---|
| 1-23 | 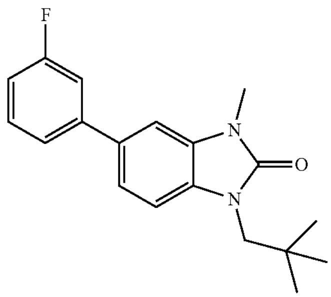 [SMILES: Cn1c(=O)n(CC(C)(C)C)c2ccc(-c3cccc(F)c3)cc21] | 1-(2,2-dimethylpropyl)-5-(3-fluorophenyl)-3-methyl-1,3-dihydro-2H-benzimidazol-2-one | LRMS m/z (M + H) 313.2 found, 313.4 required. |
| 1-24 | 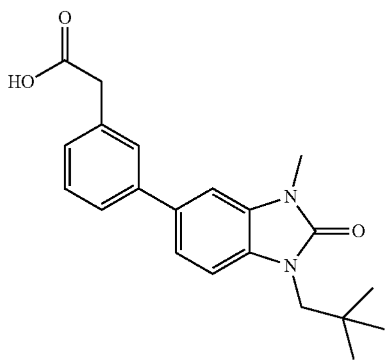 [SMILES: Cn1c(=O)n(CC(C)(C)C)c2ccc(-c3cccc(CC(=O)O)c3)cc21] | {3-[1-(2,2-dimethylpropyl)-3-methyl-2-oxo-2,3-dihydro-1H-benzimidazol-5-yl]phenyl}acetic acid | LRMS m/z (M + H) 353.2 found, 353.4 required. |
| 1-25 | 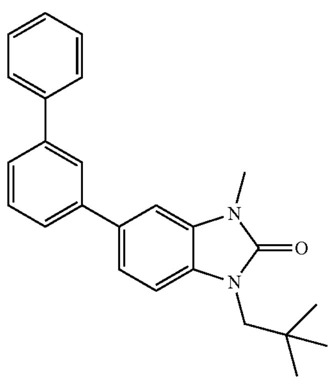 [SMILES: Cn1c(=O)n(CC(C)(C)C)c2ccc(-c3cccc(-c4ccccc4)c3)cc21] | 5-biphenyl-3-yl-1-(2,2-dimethylpropyl)-3-methyl-1,3-dihydro-2H-benzimidazol-2-one | LRMS m/z (M + H) 371.2 found, 371.5 required. |
| 1-26 | 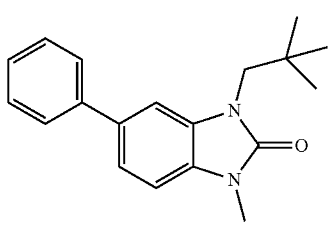 [SMILES: Cn1c(=O)n(CC(C)(C)C)c2cc(-c3ccccc3)ccc21] | 3-(2,2-dimethylpropyl)-1-methyl-5-phenyl-1,3-dihydro-2H-benzimidazol-2-one | LRMS m/z (M + H) 295.1 found, 295.4 required. |
| 1-27 | 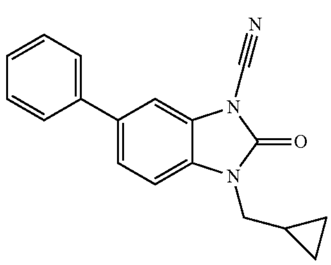 [SMILES: N#Cn1c(=O)n(CC2CC2)c2ccc(-c3ccccc3)cc21] | 3-(cyclopropylmethyl)-2-oxo-6-phenyl-2,3-dihydro-1H-benzimidazole-1-carbonitrile | LRMS m/z (M + H) 290.1 found, 290.3 required. |

TABLE 1-continued

Table 1 for Scheme 1

| Cmp | Structure | Name | LRMS m/z (M + H) |
|---|---|---|---|
| 1-28 | 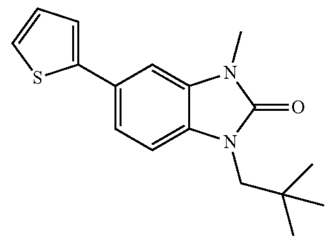 [SMILES: Cn1c(=O)n(CC(C)(C)C)c2ccc(-c3cccs3)cc21] | 1-(2,2-dimethylpropyl)-3-methyl-5-(2-thienyl)-1,3-dihydro-2H-benzimidazol-2-one | LRMS m/z (M + H) 301.1 found, 301.4 required. |
| 1-29 | 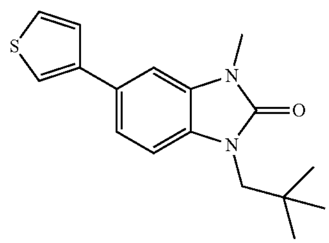 [SMILES: Cn1c(=O)n(CC(C)(C)C)c2ccc(-c3ccsc3)cc21] | 1-(2,2-dimethylpropyl)-3-methyl-5-(3-thienyl)-1,3-dihydro-2H-benzimidazol-2-one | LRMS m/z (M + H) 301.1 found, 301.4 required. |
| 1-30 | 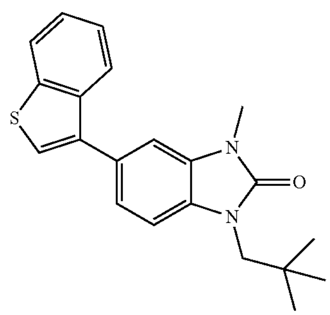 [SMILES: Cn1c(=O)n(CC(C)(C)C)c2ccc(-c3csc4ccccc34)cc21] | 5-(1-benzothien-3-yl)-1-(2,2-dimethylpropyl)-3-methyl-1,3-dihydro-2H-benzimidazol-2-one | LRMS m/z (M + H) 351.1 found, 351.5 required. |
| 1-31 | 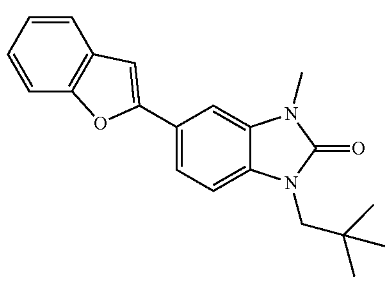 [SMILES: Cn1c(=O)n(CC(C)(C)C)c2ccc(-c3cc4ccccc4o3)cc21] | 5-(1-benzofuran-2-yl)-1-(2,2-dimethylpropyl)-3-methyl-1,3-dihydro-2H-benzimidazol-2-one | LRMS m/z (M + H) 335.2 found, 335.4 required. |
| 1-32 | 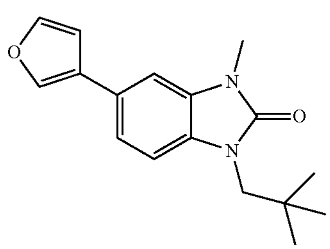 [SMILES: Cn1c(=O)n(CC(C)(C)C)c2ccc(-c3ccoc3)cc21] | 1-(2,2-dimethylpropyl)-5-(3-furyl)-3-methyl-1,3-dihydro-2H-benzimidazol-2-one | LRMS m/z (M + H) 285.1 found, 285.4 required. |

-continued

Table 1 for Scheme 1

| Cmp | Structure | Name | LRMS m/z (M + H) |
|---|---|---|---|
| 1-33 | 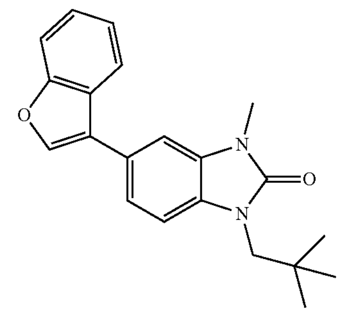 [SMILES: Cn1c(=O)n(CC(C)(C)C)c2ccc(-c3coc4ccccc34)cc21] | 5-(1-benzofuran-3-yl)-1-(2,2-dimethylpropyl)-3-methyl-1,3-dihydro-2H-benzimidazol-2-one | LRMS m/z (M + H) 335.2 found, 335.4 required. |
| 1-34 | | 5-(3,5-dimethylisoxazol-4-yl)-1-(2,2-dimethylpropyl)-3-methyl-1,3-dihydro-2H-benzimidazol-2-one | LRMS m/z (M + H) 314.2 found, 314.4 required. |
| 1-34 | | 1-(2,2-dimethylpropyl)-3-methyl-5-(5-methyl-3-phenylisoxazol-4-yl)-1,3-dihydro-2H-benzimidazol-2-one | LRMS m/z (M + H) 376.2 found, 376.5 required. |
| 1-35 | 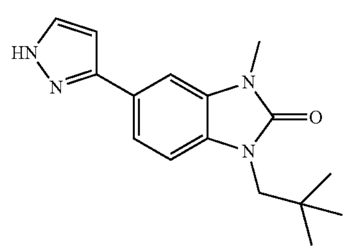 [SMILES: Cn1c(=O)n(CC(C)(C)C)c2ccc(-c3cc[nH]n3)cc21] | 1-(2,2-dimethylpropyl)-3-methyl-5-(1H-pyrazol-3-yl)-1,3-dihydro-2H-benzimidazol-2-one | LRMS m/z (M + H) 285.2 found, 285.4 required. |
| 1-36 | 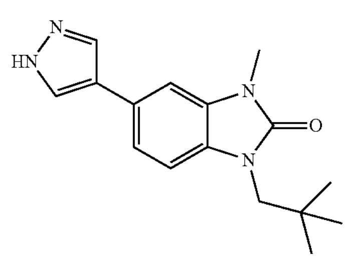 [SMILES: Cn1c(=O)n(CC(C)(C)C)c2ccc(-c3cn[nH]c3)cc21] | 1-(2,2-dimethylpropyl)-3-methyl-5-(1H-pyrazol-4-yl)-1,3-dihydro-2H-benzimidazol-2-one | LRMS m/z (M + H) 285.2 found, 285.4 required. |

Table 1 for Scheme 1

| Cmp | Structure | Name | LRMS m/z (M + H) |
|---|---|---|---|
| 1-37 | 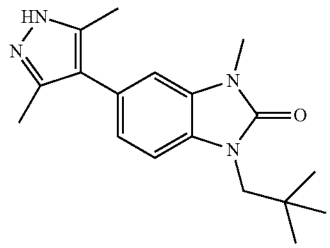 [SMILES: Cc1n[nH]c(C)c1-c1ccc2c(c1)n(C)c(=O)n2CC(C)(C)C] | 1-(2,2-dimethylpropyl)-5-(3,5-dimethyl-1H-pyrazol-4-yl)-3-methyl-1,3-dihydro-2H-benzimidazol-2-one | LRMS m/z (M + H) 313.2 found, 313.4 required. |
| 1-38 | 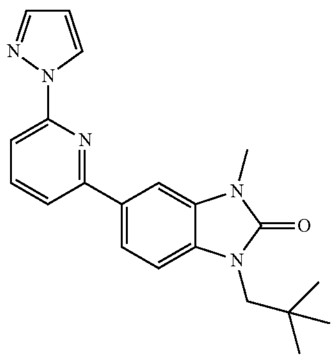 [SMILES: Cn1c(=O)n(CC(C)(C)C)c2ccc(-c3cccc(-n4cccn4)n3)cc21] | 1-(2,2-dimethylpropyl)-3-methyl-5-[6-(1H-pyrazol-1-yl)pyridin-2-yl]-1,3-dihydro-2H-benzimidazol-2-one | LRMS m/z (M + H) 362.2 found, 362.5 required. |
| 1-39 | 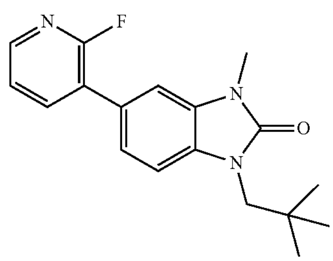 [SMILES: Cn1c(=O)n(CC(C)(C)C)c2ccc(-c3cccnc3F)cc21] | 1-(2,2-dimethylpropyl)-5-(2-fluoropyridin-3-yl)-3-methyl-1,3-dihydro-2H-benzimidazol-2-one | LRMS m/z (M + H) 314.2 found, 314.4 required. |
| 1-40 | 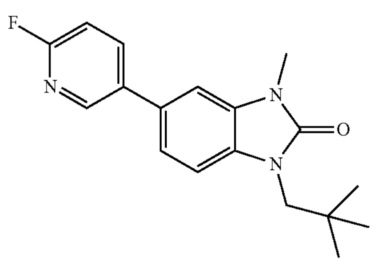 [SMILES: Cn1c(=O)n(CC(C)(C)C)c2ccc(-c3ccc(F)nc3)cc21] | 1-(2,2-dimethylpropyl)-5-(6-fluoropyridin-3-yl)-3-methyl-1,3-dihydro-2H-benzimidazol-2-one | LRMS m/z (M + H) 314.1 found, 314.4 required. |
| 1-41 | 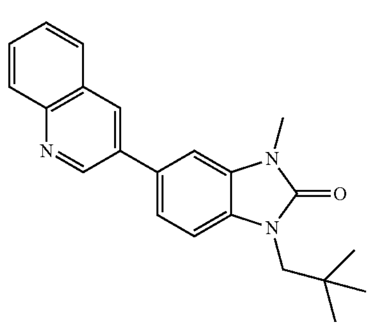 [SMILES: Cn1c(=O)n(CC(C)(C)C)c2ccc(-c3cnc4ccccc4c3)cc21] | 1-(2,2-dimethylpropyl)-3-methyl-5-quinolin-3-yl-1,3-dihydro-2H-benzimidazol-2-one | LRMS m/z (M + H) 346.2 found, 346.5 required. |

Table 1 for Scheme 1

| Cmp | Structure | Name | LRMS m/z (M + H) |
|---|---|---|---|
| 1-42 | 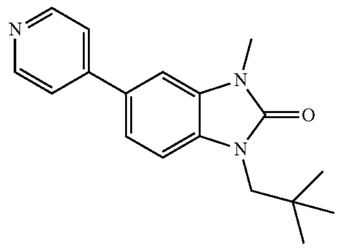 [SMILES: Cn1c(=O)n(CC(C)(C)C)c2ccc(-c3ccncc3)cc21] | 1-(2,2-dimethylpropyl)-3-methyl-5-pyridin-4-yl-1,3-dihydro-2H-benzimidazol-5-one | LRMS m/z (M + H) 296.2 found, 296.4 required. |
| 1-43 | 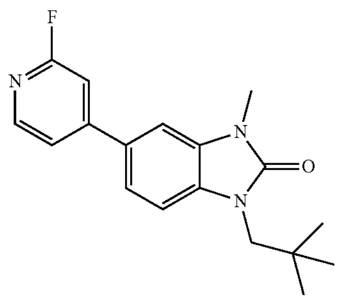 [SMILES: Cn1c(=O)n(CC(C)(C)C)c2ccc(-c3ccnc(F)c3)cc21] | 1-(2,2-dimethylpropyl)-5-(2-fluoropyridin-4-yl)-3-methyl-1,3-dihydro-2H-benzimidazol-2-one | LRMS m/z (M + H) 314.2 found, 314.4 required. |
| 1-44 | 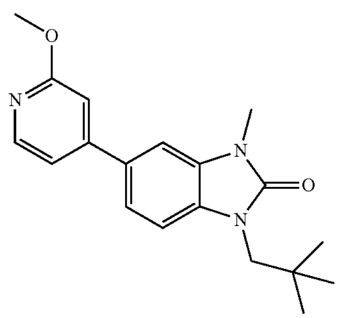 [SMILES: COc1cc(-c2ccc3c(c2)n(C)c(=O)n3CC(C)(C)C)ccn1] | 1-(2,2-dimethylpropyl)-5-(2-methoxypyridin-4-yl)-3-methyl-1,3-dihydro-2H-benzimidazol-2-one | LRMS m/z (M + H) 326.2 found, 326.4 required. |
| 1-45 | 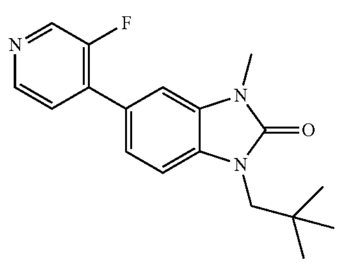 [SMILES: Cn1c(=O)n(CC(C)(C)C)c2ccc(-c3ccncc3F)cc21] | 1-(2,2-dimethylpropyl)-5-(3-fluoropyridin-4-yl)-3-methyl-1,3-dihydro-2H-benzimidazol-2-one | LRMS m/z (M + H) 314.2 found, 314.4 required. |
| 1-46 | 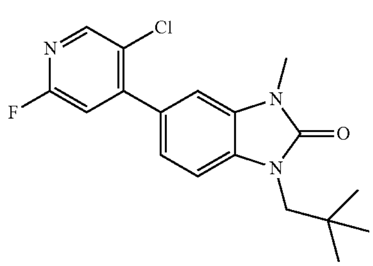 [SMILES: Cn1c(=O)n(CC(C)(C)C)c2ccc(-c3cc(F)ncc3Cl)cc21] | 5-(5-chloro-2-fluoropyridin-4-yl)-1-(2,2-dimethylpropyl)-3-methyl-1,3-dihydro-2H-benzimidazol-2-one | LRMS m/z (M + H) 348.1 found, 348.8 required. |

-continued

Table 1 for Scheme 1

| Cmp | Structure | Name | LRMS m/z (M + H) |
|---|---|---|---|
| 1-47 | 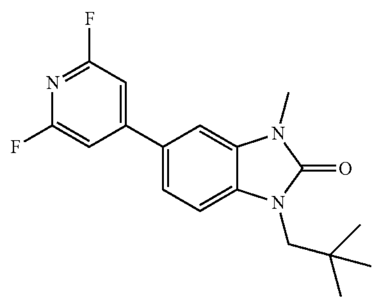 [SMILES: Cn1c(=O)n(CC(C)(C)C)c2ccc(-c3cc(F)nc(F)c3)cc21] | 5-(2,6-difluoropyridin-4-yl)-1-(2,2-dimethylpropyl)-3-methyl-1,3-dihydro-2H-benzimidazol-2-one | LRMS m/z (M + H) 332.1 found, 332.4 required. |
| 1-48 | 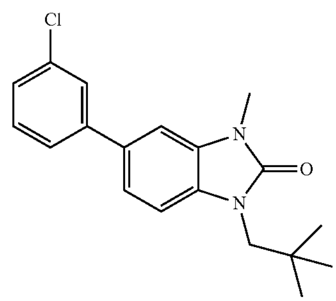 [SMILES: Cn1c(=O)n(CC(C)(C)C)c2ccc(-c3cccc(Cl)c3)cc21] | 5-(3-chlorophenyl)-1-(2,2-dimethylpropyl)-3-methyl-1,3-dihydro-2H-benzimidazol-2-one | LRMS m/z (M + H) 329.1 found, 329.9 required. |
| 1-49 | 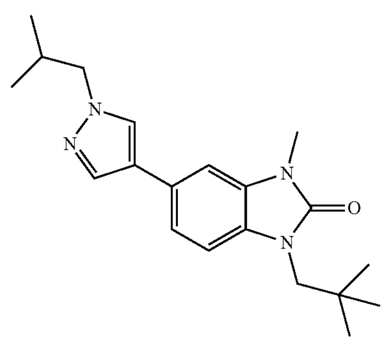 [SMILES: CC(C)Cn1cc(-c2ccc3c(c2)n(C)c(=O)n3CC(C)(C)C)cn1] | 1-(2,2-dimethylpropyl)-5-(1-isobutyl-1H-pyrazol-4-yl)-3-methyl-1,3-dihydro-2H-benzimidazol-2-one | LRMS m/z (M + H) 341.2 found, 341.5 required. |
| 1-50 | 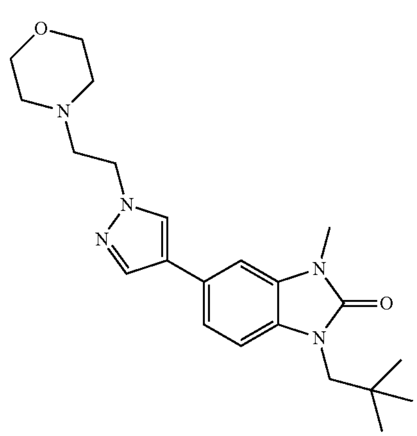 [SMILES: Cn1c(=O)n(CC(C)(C)C)c2ccc(-c3cnn(CCN4CCOCC4)c3)cc21] | 1-(2,2-dimethylpropyl)-3-methyl-5-[1-(2-morpholin-4-ylethyl)-1H-pyrazol-4-yl]-1,3-dihydro-2H-benzimidazol-2-one | LRMS m/z (M + H) 398.2 found, 398.5 required. |

-continued

Table 1 for Scheme 1

| Cmp | Structure | Name | LRMS m/z (M + H) |
|---|---|---|---|
| 1-51 | 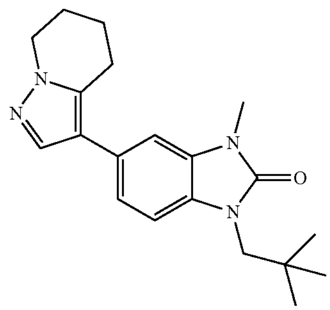 [SMILES: Cn1c(=O)n(CC(C)(C)C)c2ccc(-c3cnn4c3CCCC4)cc21] | 1-(2,2-dimethylpropyl)-3-methyl-5-(4,5,6,7-tetrahydropyrazolo[1,5-a]pyridin-3-yl)-1,3-dihydro-2H-benzimidazol-2-one | LRMS m/z (M + H) 339.2 found, 339.5 required. |
| 1-52 | 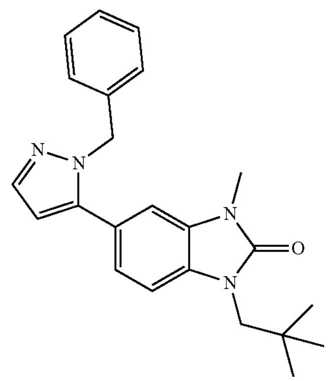 [SMILES: Cn1c(=O)n(CC(C)(C)C)c2ccc(-c3ccnn3Cc3ccccc3)cc21] | 5-(1-benzyl-1H-pyrazol-5-yl)-1-(2,2-dimethylpropyl)-3-methyl-1,3-dihydro-2H-benzimidazol-2-one | LRMS m/z (M + H) 375.2 found, 375.5 required. |
| 1-53 | 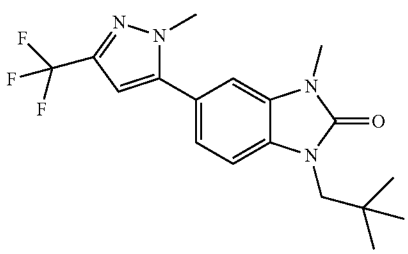 [SMILES: Cn1nc(C(F)(F)F)cc1-c1ccc2c(c1)n(C)c(=O)n2CC(C)(C)C] | 1-(2,2-dimethylpropyl)-3-methyl-5-[1-methyl-3-(trifluoromethyl)-1H-pyrazol-5-yl]-1,3-dihydro-2H-benzimidazol-2-one | LRMS m/z (M + H) 367.1 found, 367.4 required. |
| 1-54 | 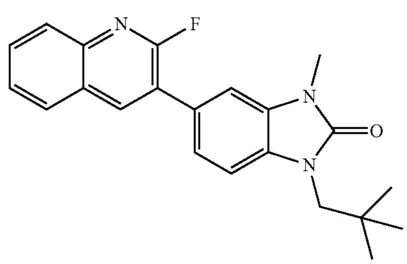 [SMILES: Cn1c(=O)n(CC(C)(C)C)c2ccc(-c3cc4ccccc4nc3F)cc21] | 1-(2,2-dimethylpropyl)-5-(2-fluoroquinolin-3-yl)-3-methyl-1,3-dihydro-2H-benzimidazol-2-one | LRMS m/z (M + H) 364.2 found, 364.4 required. |
| 1-55 | 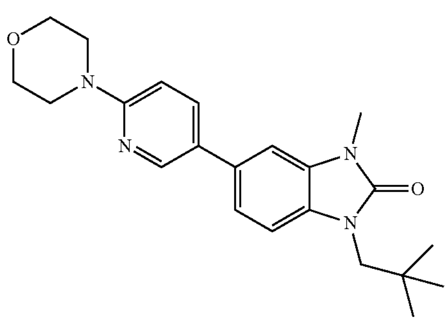 [SMILES: Cn1c(=O)n(CC(C)(C)C)c2ccc(-c3ccc(N4CCOCC4)nc3)cc21] | 1-(2,2-dimethylpropyl)-3-methyl-5-(6-morpholin-4-ylpyridin-3-yl)-1,3-dihydro-2H-benzimidazol-2-one | LRMS m/z (M + H) 381.2 found, 381.5 required. |

-continued

Table 1 for Scheme 1

| Cmp | Structure | Name | LRMS m/z (M + H) |
|---|---|---|---|
| 1-56 | 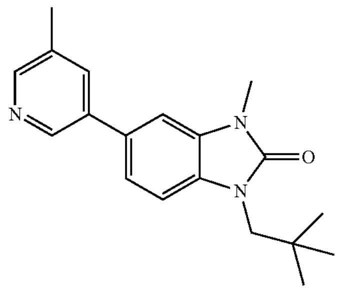 [SMILES: Cc1cncc(-c2ccc3c(c2)n(C)c(=O)n3CC(C)(C)C)c1] | 1-(2,2-dimethylpropyl)-3-methyl-5-(5-methylpyridin-3-yl)-1,3-dihydro-2H-benzimidazol-2-one | LRMS m/z (M + H) 310.2 found, 310.4 required. |
| 1-57 | 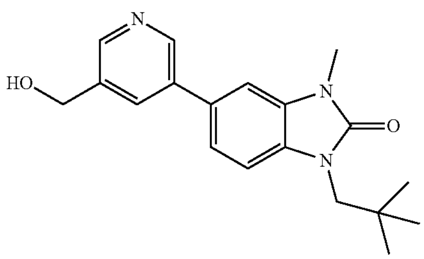 [SMILES: Cn1c(=O)n(CC(C)(C)C)c2ccc(-c3cncc(CO)c3)cc21] | 1-(2,2-dimethylpropyl)-5-[5-(hydroxymethyl)pyridin-3-yl]-3-methyl-1,3-dihydro-2H-benzimidazol-2-one | LRMS m/z (M + H) 326.2 found, 326.4 required. |
| 1-58 | 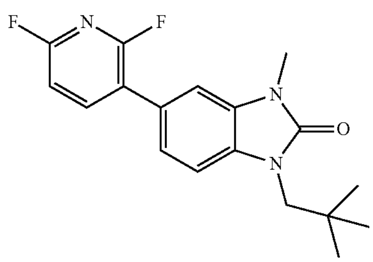 [SMILES: Cn1c(=O)n(CC(C)(C)C)c2ccc(-c3ccc(F)nc3F)cc21] | 5-(2,6-difluoropyridin-3-yl)-1-(2,2-dimethylpropyl)-3-methyl-1,3-dihydro-2H-benzimidazol-2-one | LRMS m/z (M + H) 332.1 found, 332.4 required. |
| 1-59 | 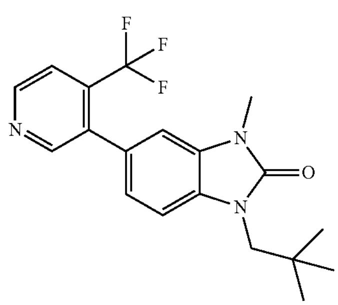 [SMILES: Cn1c(=O)n(CC(C)(C)C)c2ccc(-c3cnccc3C(F)(F)F)cc21] | 1-(2,2-dimethylpropyl)-3-methyl-5-[4-(trifluoromethyl)pyridin-3-yl]-1,3-dihydro-2H-benzimidazol-2-one | LRMS m/z (M + H) 364.1 found, 364.4 required. |
| 1-60 | 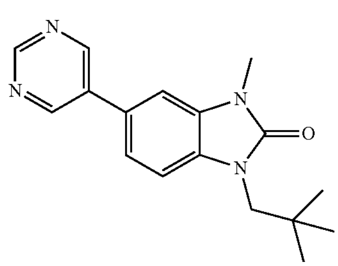 [SMILES: Cn1c(=O)n(CC(C)(C)C)c2ccc(-c3cncnc3)cc21] | 1-(2,2-dimethylpropyl)-3-methyl-5-pyrimidin-5-yl-1,3-dihydro-2H-benzimidazol-2-one | LRMS m/z (M + H) 297.2 found, 297.4 required. |

-continued

Table 1 for Scheme 1

| Cmp | Structure | Name | LRMS m/z (M + H) |
|---|---|---|---|
| 1-61 | 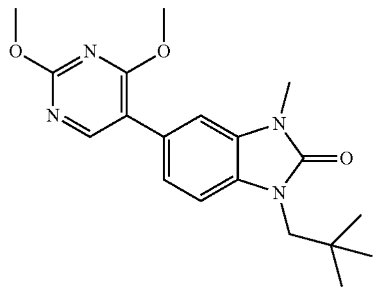 [SMILES: COc1ncc(-c2ccc3c(c2)n(C)c(=O)n3CC(C)(C)C)c(OC)n1] | 5-(2,4-dimethoxypyrimidin-5-yl)-1-(2,2-dimethylpropyl)-3-methyl-1,3-dihydro-2H--benzimidazol-2-one | LRMS m/z (M + H) 357.2 found, 357.4 required. |
| 1-62 | 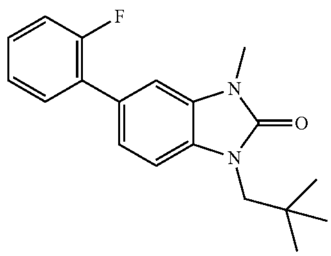 [SMILES: Cn1c(=O)n(CC(C)(C)C)c2ccc(-c3ccccc3F)cc21] | 1-(2,2-dimethylpropyl)-5-(2-fluorophenyl)-3-methyl-1,3-dihydro-2H-benzimidazol-2-one | LRMS m/z (M + H) 313.2 found, 313.4 required. |
| 1-63 | 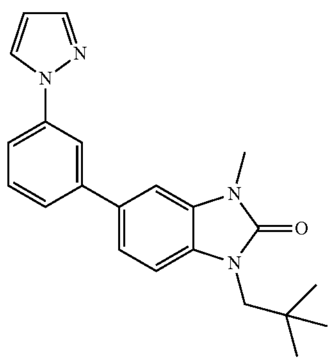 [SMILES: Cn1c(=O)n(CC(C)(C)C)c2ccc(-c3cccc(-n4cccn4)c3)cc21] | 1-(2,2-dimethylpropyl)-3-methyl-5-[3-(1H-pyrazol-1-yl)phenyl]-1,3-dihydro-2H-benzimidazol-2-one | LRMS m/z (M + H) 361.2 found, 361.5 required. |
| 1-64 | 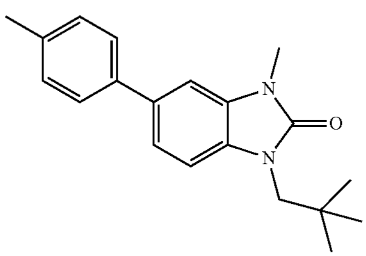 [SMILES: Cc1ccc(-c2ccc3c(c2)n(C)c(=O)n3CC(C)(C)C)cc1] | 1-(2,2-dimethylpropyl)-3-methyl-5-(4-methylphenyl)-1,3-dihydro-2H-benzimidazol-2-one | LRMS m/z (M + H) 309.2 found, 309.4 required. |
| 1-65 | 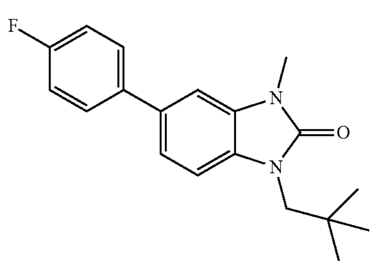 [SMILES: Cn1c(=O)n(CC(C)(C)C)c2ccc(-c3ccc(F)cc3)cc21] | 1-(2,2-dimethylpropyl)-5-(4-fluorophenyl)-3-methyl-1,3-dihydro-2H-benzimidazol-2-one | LRMS m/z (M + H) 313.2 found, 313.4 required. |

Table 1 for Scheme 1

| Cmp | Structure | Name | LRMS m/z (M + H) |
|---|---|---|---|
| 1-66 | 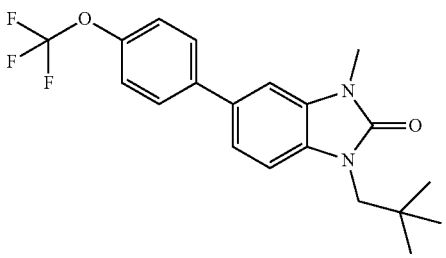 [SMILES: Cn1c(=O)n(CC(C)(C)C)c2ccc(-c3ccc(OC(F)(F)F)cc3)cc21] | 1-(2,2-dimethylpropyl)-3-methyl-5-[4-(trifluoromethoxy)phenyl]-1,3-dihydro-2H-benzimidazol-2-one | LRMS m/z (M + H) 379.1 found, 379.4 required. |
| 1-67 | 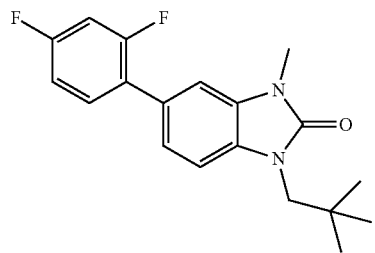 [SMILES: Cn1c(=O)n(CC(C)(C)C)c2ccc(-c3ccc(F)cc3F)cc21] | 5-(2,4-difluorophenyl)-1-(2,2-dimethylpropyl)-3-methyl-1,3-ihydro-2H-benzimidazol-2-one | LRMS m/z (M + H) 331.1 found, 331.4 required. |
| 1-68 | 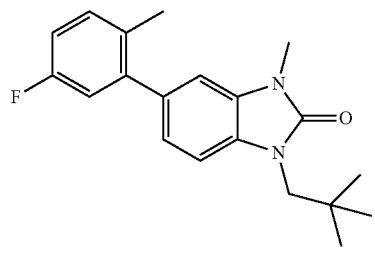 [SMILES: Cc1ccc(F)cc1-c1ccc2c(c1)n(C)c(=O)n2CC(C)(C)C] | 1-(2,2-dimethylpropyl)-5-(5-fluoro-2-methylphenyl)-3-methyl-1,3-dihydro-2H-benzimidazol-2-one | LRMS m/z (M + H) 327.2 found, 327.4 required. |
| 1-69 | 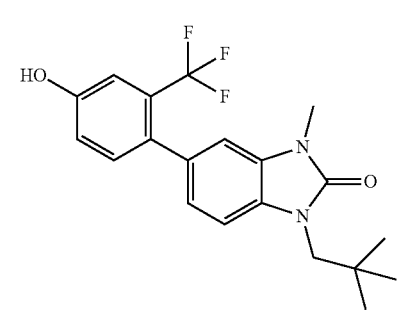 [SMILES: Cn1c(=O)n(CC(C)(C)C)c2ccc(-c3ccc(O)cc3C(F)(F)F)cc21] | 1-(2,2-dimethylpropyl)-5-[4-hydroxy-2-(trifluoromethyl)phenyl]-3-methyl-1,3-dihydro-2H-benzimidazol-2-one | LRMS m/z (M + H) 379.1 found, 379.4 required. |
| 1-70 | 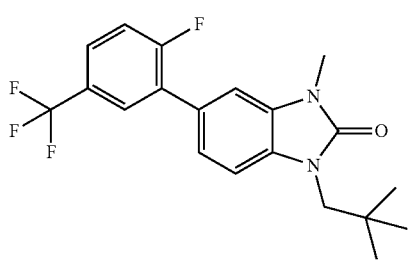 [SMILES: Cn1c(=O)n(CC(C)(C)C)c2ccc(-c3cc(C(F)(F)F)ccc3F)cc21] | 1-(2,2-dimethylpropyl)-5-[2-fluoro-5-(trifluoromethyl)phenyl]-3-methyl-1,3-dihydro-2H-benzimidazol-2-one | LRMS m/z (M + H) 381.1 found, 381.4 required. |

-continued

Table 1 for Scheme 1

| Cmp | Structure | Name | LRMS m/z (M + H) |
|---|---|---|---|
| 1-71 | 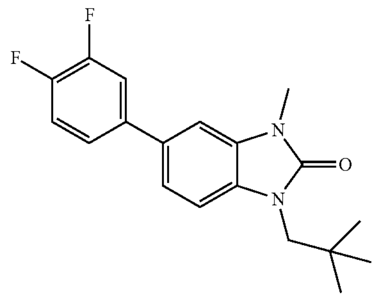 [SMILES: Cn1c(=O)n(CC(C)(C)C)c2ccc(-c3ccc(F)c(F)c3)cc21] | 5-(3,4-difluorophenyl)-1-(2,2-dimethylpropyl)-3-methyl-1,3-dihydro-2H-benzimidazol-2-one | LRMS m/z (M + H) 331.1 found, 331.4 required. |
| 1-72 | 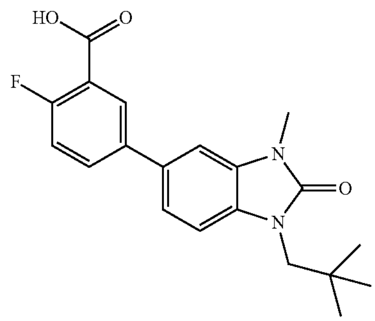 [SMILES: Cn1c(=O)n(CC(C)(C)C)c2ccc(-c3ccc(F)c(C(=O)O)c3)cc21] | 5-[1-(2,2-dimethylpropyl)-3-methyl-2-oxo-2,3-dihydro-1H-benzimidazol-5-yl]-2-fluorobenzoic acid | LRMS m/z (M + H) 357.1 found, 357.4 required. |
| 1-73 | 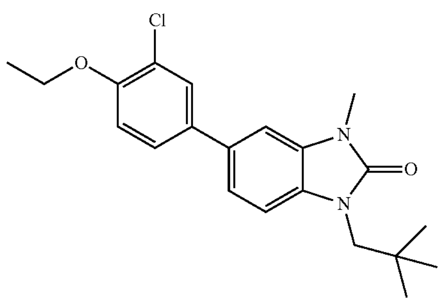 [SMILES: CCOc1ccc(-c2ccc3c(c2)n(C)c(=O)n3CC(C)(C)C)cc1Cl] | 5-(3-chloro-4-ethoxyphenyl)-1-(2,2-dimethylpropyl)-3-methyl-1,3-dihydro-2H-benzimidazol-2-one | LRMS m/z (M + H) 373.1 found, 373.9 required. |
| 1-74 | 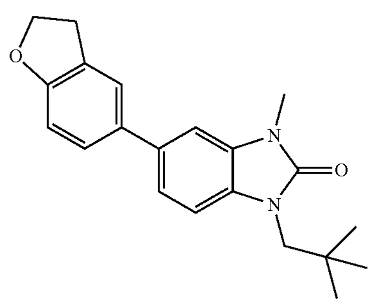 [SMILES: Cn1c(=O)n(CC(C)(C)C)c2ccc(-c3ccc4c(c3)CCO4)cc21] | 5-(2,3-dihydro-1-benzofuran-5-yl)-1-(2,2-dimethylpropyl)-3-methyl-1,3-dihydro-2H-benzimidazol-2-one | LRMS m/z (M + H) 337.2 found, 337.4 required. |
| 1-75 | 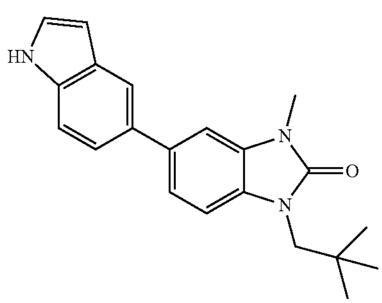 [SMILES: Cn1c(=O)n(CC(C)(C)C)c2ccc(-c3ccc4[nH]ccc4c3)cc21] | 1-(2,2-dimethylpropyl)-5-(1H-indol-5-yl)-3-methyl-1,3-dihydro-2H-benzimidazol-2-one | LRMS m/z (M + H) 334.2 found, 334.4 required. |

Table 1 for Scheme 1

| Cmp | Structure | Name | LRMS m/z (M + H) |
|---|---|---|---|
| 1-76 | 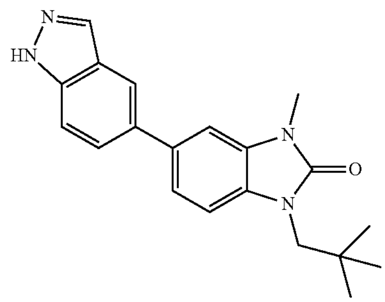 [SMILES: Cn1c(=O)n(CC(C)(C)C)c2ccc(-c3ccc4[nH]ncc4c3)cc21] | 1-(2,2-dimethylpropyl)-5-(1H-indazol-5-yl)-3-methyl-1,3-dihydro-2H-benzimidazol-2-one | LRMS m/z (M + H) 335.2 found, 335.4 required. |
| 1-77 | 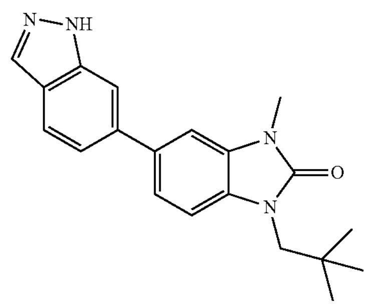 [SMILES: Cn1c(=O)n(CC(C)(C)C)c2ccc(-c3ccc4cn[nH]c4c3)cc21] | 1-(2,2-dimethylpropyl)-5-(1H-indazol-6-yl)-3-methyl-1,3-dihydro-2H-benzimidazol-2-one | LRMS m/z (M + H) 335.2 found, 335.4 required. |
| 1-78 | 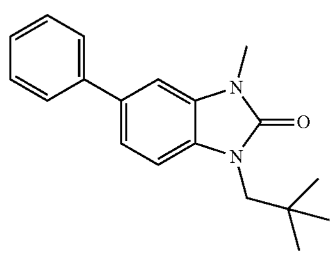 [SMILES: Cn1c(=O)n(CC(C)(C)C)c2ccc(-c3ccccc3)cc21] | 1-(2,2-dimethylpropyl)-3-methyl-5-phenyl-1,3-dihydro-2H-benzimidazol-2-one | LRMS m/z (M + H) 295.1 found, 295.4 required. |
| 1-79 | 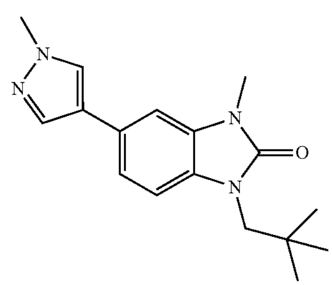 [SMILES: Cn1cc(-c2ccc3c(c2)n(C)c(=O)n3CC(C)(C)C)cn1] | 1-(2,2-dimethylpropyl)-3-methyl-5-(1-methyl-1H-pyrazol-4-yl)-1,3-dihydro-2H-benzimidazol-2-one | LRMS m/z (M + H) 299.1 found, 299.4 required. |
| 1-80 | 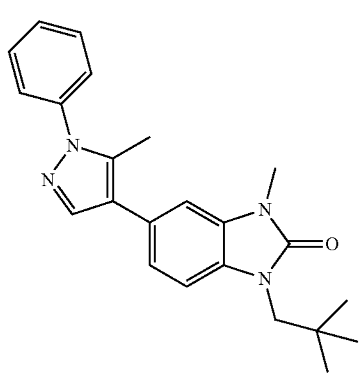 [SMILES: Cc1c(-c2ccc3c(c2)n(C)c(=O)n3CC(C)(C)C)cnn1-c1ccccc1] | 1-(2,2-dimethylpropyl)-3-methyl-5-(5-methyl-1-phenyl-1H-pyrazol-4-yl)-1,3-dihydro-2H-benzimidazol-2-one | LRMS m/z (M + H) 375.2 found, 375.5 required. |

Table 1 for Scheme 1

| Cmp | Structure | Name | LRMS m/z (M + H) |
|---|---|---|---|
| 1-81 | 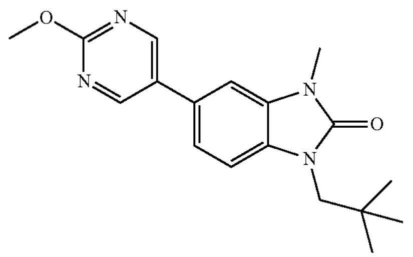 [SMILES: COc1ncc(-c2ccc3c(c2)n(C)c(=O)n3CC(C)(C)C)cn1] | 1-(2,2-dimethylpropyl)-5-(2-methoxypyrimidin-5-yl)-3-methyl-1,3-dihydro-2H-benzimidazol-2-one | LRMS m/z (M + H) 327.2 found, 327.4 required. |
| 1-82 | 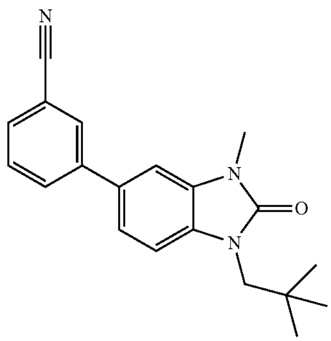 [SMILES: Cn1c(=O)n(CC(C)(C)C)c2ccc(-c3cccc(C#N)c3)cc21] | 3-[1-(2,2-dimethylpropyl)-3-methyl-2-oxo-2,3-dihydro-1H-benzimidazol-5-yl]benzonitrile | LRMS m/z (M + H) 320.2 found, 320.4 required. |
| 1-83 | 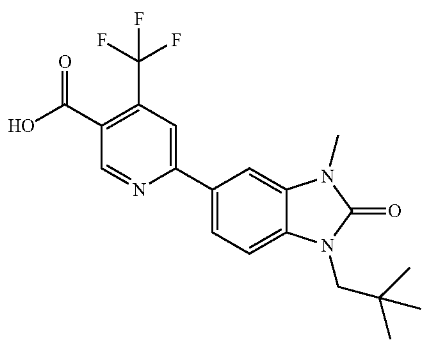 [SMILES: Cn1c(=O)n(CC(C)(C)C)c2ccc(-c3cc(C(F)(F)F)c(C(=O)O)cn3)cc21] | 6-[1-(2,2-dimethylpropyl)-3-methyl-2-oxo-2,3-dihydro-1H-benzimidazol-5-yl]-4-(trifluoromethyl)nicotinic acid | LRMS m/z (M + H) 408.2 found, 408.4 required. |
| 1-84 | 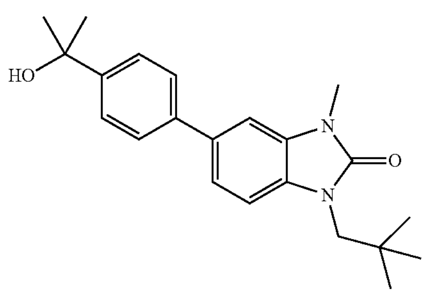 [SMILES: Cn1c(=O)n(CC(C)(C)C)c2ccc(-c3ccc(C(C)(C)O)cc3)cc21] | 1-(2,2-dimethylpropyl)-5-[4-(1-hydroxy-1-methylethyl)phenyl]-3-methyl-1,3-dihydro-2H-benzimidazol-2-one | LRMS m/z (M + H) 353.2 found, 353.5 required. |
| 1-85 | 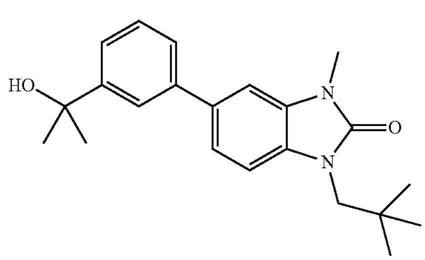 [SMILES: Cn1c(=O)n(CC(C)(C)C)c2ccc(-c3cccc(C(C)(C)O)c3)cc21] | 1-(2,2-dimethylpropyl)-5-[3-(1-hydroxy-1-methylethyl)phenyl]-3-methyl-1,3-dihydro-2H-benzimidazol-2-one | LRMS m/z (M + H) 353.2 found, 353.5 required. |

Table 1 for Scheme 1

| Cmp | Structure | Name | LRMS m/z (M + H) |
|---|---|---|---|
| 1-86 | 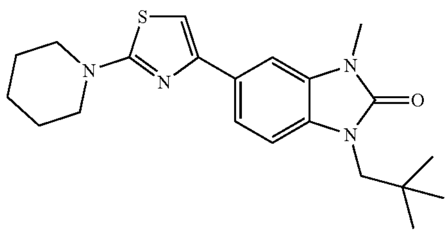 [SMILES: Cn1c(=O)n(CC(C)(C)C)c2ccc(-c3csc(N4CCCCC4)n3)cc21] | 1-(2,2-dimethylpropyl)-3-methyl-5-(2-piperidin-1-yl-1,3-thiazol-4-yl)-1,3-dihydro-2H-benzimidazol-2-one | LRMS m/z (M + H) 385.2 found, 385.5 required. |
| 1-87 | 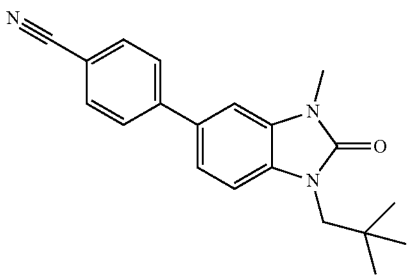 [SMILES: Cn1c(=O)n(CC(C)(C)C)c2ccc(-c3ccc(C#N)cc3)cc21] | 4-[1-(2,2-dimethylpropyl)-3-methyl-2-oxo-2,3-dihydro-1H-benzimidazol-5-yl]benzonitrile | LRMS m/z (M + H) 320.2 found, 320.4 required. |
| 1-88 | 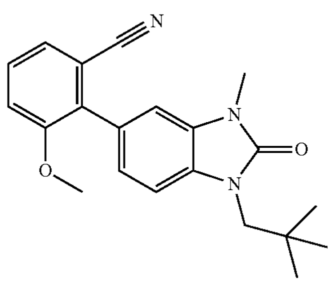 [SMILES: COc1cccc(C#N)c1-c1ccc2c(c1)n(C)c(=O)n2CC(C)(C)C] | 2-[1-(2,2-dimethylpropyl)-3-methyl-2-oxo-2,3-dihydro-1H-benzimidazol-5-yl]-3-methoxybenzonitrile | LRMS m/z (M + H) 350.1 found, 350.4 required. |
| 1-89 | 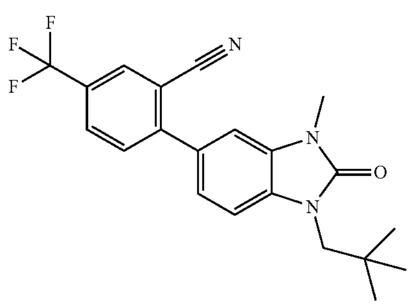 [SMILES: Cn1c(=O)n(CC(C)(C)C)c2ccc(-c3ccc(C(F)(F)F)cc3C#N)cc21] | 2-[1-(2,2-dimethylpropyl)-3-methyl-2-oxo-2,3-dihydro-1H-benzimidazol-5-yl]-5-(trifluoromethyl)benzonitrile | LRMS m/z (M + H) 388.1 found, 388.4 required. |
| 1-90 | 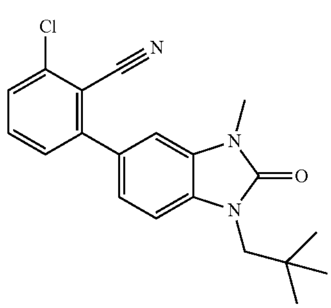 [SMILES: Cn1c(=O)n(CC(C)(C)C)c2ccc(-c3cccc(Cl)c3C#N)cc21] | 2-chloro-6-[1-(2,2-dimethylpropyl)-3-methyl-2-oxo-2,3-dihydro-1H-benzimidazol-5-yl]benzonitrile | LRMS m/z (M + H) 354.1 found, 354.9 required. |

Table 1 for Scheme 1

| Cmp | Structure | Name | LRMS m/z (M + H) |
|---|---|---|---|
| 1-91 | 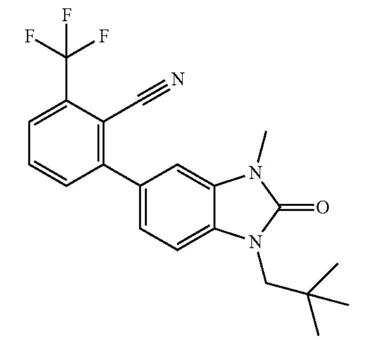 [SMILES: Cn1c(=O)n(CC(C)(C)C)c2ccc(-c3cccc(C(F)(F)F)c3C#N)cc21] | 2-[1-(2,2-dimethylpropyl)-3-methyl-2-oxo-2,3-dihydro-1H-benzimidazol-5-yl]-6-(trifluoromethyl)benzonitrile | LRMS m/z (M + H) 388.1 found, 388.4 required. |
| 1-92 | 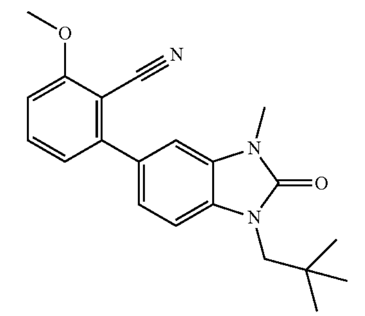 [SMILES: COc1cccc(-c2ccc3c(c2)n(C)c(=O)n3CC(C)(C)C)c1C#N] | 2-[1-(2,2-dimethylpropyl)-3-methyl-2-oxo-2,3-dihydro-1H-benzimidazol-5-yl]-6-methoxybenzonitrile | LRMS m/z (M + H) 350.1 found, 350.4 required. |
| 1-93 | 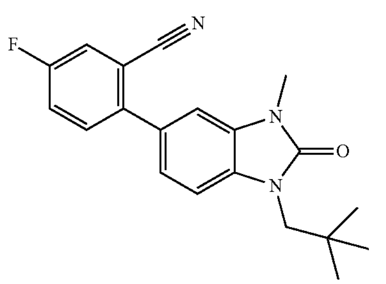 [SMILES: Cn1c(=O)n(CC(C)(C)C)c2ccc(-c3ccc(F)cc3C#N)cc21] | 2-[1-(2,2-dimethylpropyl)-3-methyl-2-oxo-2,3-dihydro-1H-benzimidazol-5-yl]-5-fluorobenzonitrile | LRMS m/z (M + H) 338.0 found, 338.4 required. |
| 1-94 | 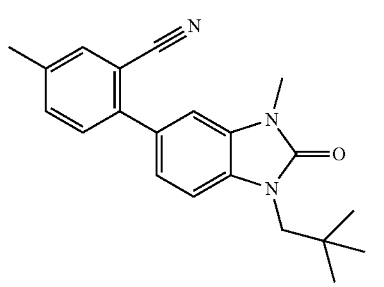 [SMILES: Cc1ccc(-c2ccc3c(c2)n(C)c(=O)n3CC(C)(C)C)c(C#N)c1] | 2-[1-(2,2-dimethylpropyl)-3-methyl-2-oxo-2,3-dihydro-1H-benzimidazol-5-yl]-5-methylbenzonitrile | LRMS m/z (M + H) 334.1 found, 334.4 required. |
| 1-95 | 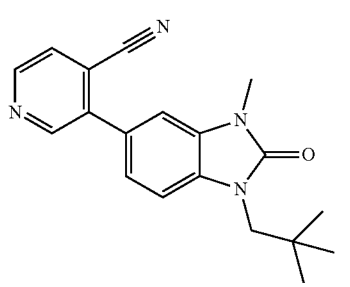 [SMILES: Cn1c(=O)n(CC(C)(C)C)c2ccc(-c3cnccc3C#N)cc21] | 3-[1-(2,2-dimethylpropyl)-3-methyl-2-oxo-2,3-dihydro-1H-benzimidazol-5-yl]isonicotinonitrile | LRMS m/z (M + H) 321.0 found, 321.4 required. |

-continued

Table 1 for Scheme 1

| Cmp | Structure | Name | LRMS m/z (M + H) |
|---|---|---|---|
| 1-96 | 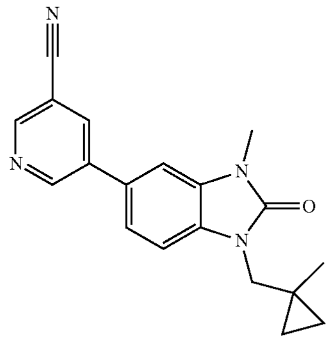 [SMILES: Cn1c(=O)n(CC2(C)CC2)c2ccc(-c3cncc(C#N)c3)cc21] | 5-{3-methyl-1-[(1-methylcyclopropyl)methyl]-2-oxo-2,3-dihydro-1H-benzimidazol-5-yl}nicotinonitrile | LRMS m/z (M + H) 319.2 found, 319.4 required. |
| 1-97 | 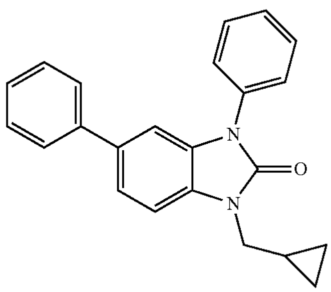 [SMILES: O=c1n(CC2CC2)c2ccc(-c3ccccc3)cc2n1-c1ccccc1] | 1-(cyclopropylmethyl)-3,5-diphenyl-1,3-dihydro-2H-benzimidazol-2-one | LRMS m/z (M + H) 341.1 found, 341.4 required. |
| 1-98 | 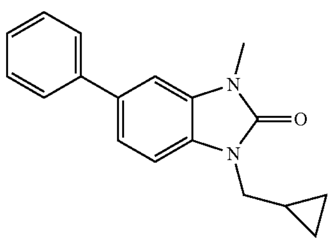 [SMILES: Cn1c(=O)n(CC2CC2)c2ccc(-c3ccccc3)cc21] | 1-(cyclopropylmethyl)-3-methyl-5-phenyl-1,3-dihydro-2H-benzimidazol-2-one | LRMS m/z (M + H) 279.1 found, 279.4 required. |
| 1-99 | 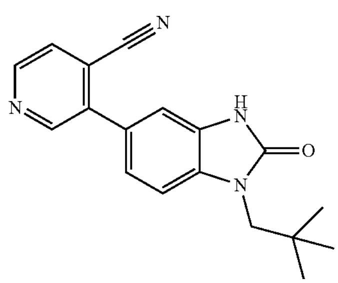 [SMILES: CC(C)(C)Cn1c(=O)[nH]c2cc(-c3cnccc3C#N)ccc21] | 3-[1-(2,2-dimethylpropyl)-2-oxo-2,3-dihydro-1H-benzimidazol-5-yl]isonicotinonitrile | LRMS m/z (M + H) 307.1549 found, 307.1553 required. |
| 1-100 | 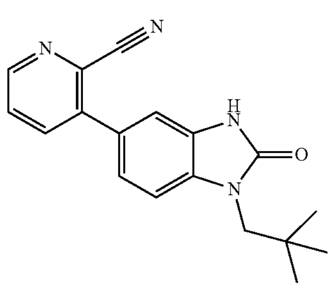 [SMILES: CC(C)(C)Cn1c(=O)[nH]c2cc(-c3cccnc3C#N)ccc21] | 3-[1-(2,2-dimethylpropyl)-2-oxo-2,3-dihydro-1H-benzimidazol-5-yl]pyridine-2-carbonitrile | LRMS m/z (M + H) 307.1 found, 307.4 required. |

Table 1 for Scheme 1

| Cmp | Structure | Name | LRMS m/z (M + H) |
|---|---|---|---|
| 1-101 | 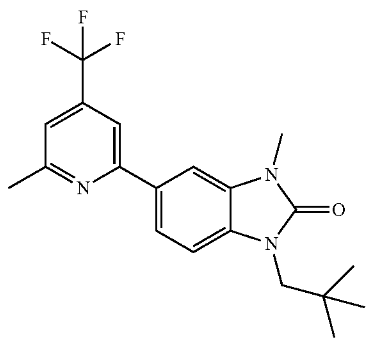 [SMILES: Cc1cc(C(F)(F)F)cc(-c2ccc3c(c2)n(C)c(=O)n3CC(C)(C)C)n1] | 1-(2,2-dimethylpropyl)-3-methyl-5-[6-methyl-4-(trifluoromethyl)pyridin-2-yl]-1,3-dihydro-2H-benzimidazol-2-one | LRMS m/z (M + H) 378.2 found, 378.4 required. |
| 1-102 | 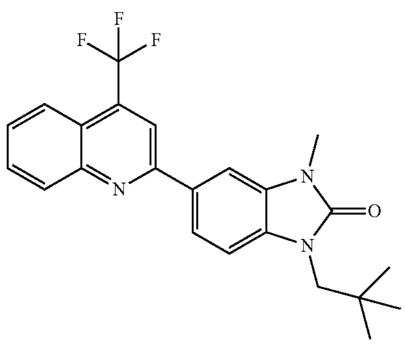 [SMILES: Cn1c(=O)n(CC(C)(C)C)c2ccc(-c3cc(C(F)(F)F)c4ccccc4n3)cc21] | 1-(2,2-dimethylpropyl)-3-methyl-5-[4-(trifluoromethyl)quinolin-2-yl]-1,3-dihydro-2H-benzimidazol-2-one | LRMS m/z (M + H) 414.2 found, 414.4 required. |
| 1-103 | 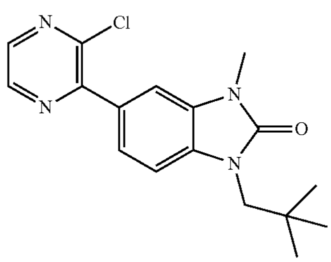 [SMILES: Cn1c(=O)n(CC(C)(C)C)c2ccc(-c3nccnc3Cl)cc21] | 5-(3-chloropyrazin-2-yl)-1-(2,2-dimethylpropyl)-3-methyl-1,3-dihydro-2H-benzimidazol-2-one | LRMS m/z (M + H) 331.1 found, 331.8 required. |
| 1-104 | 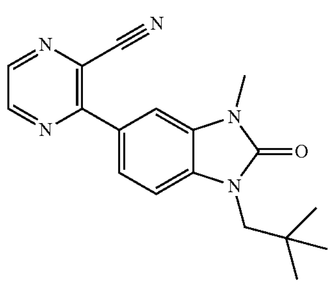 [SMILES: Cn1c(=O)n(CC(C)(C)C)c2ccc(-c3nccnc3C#N)cc21] | 3-[1-(2,2-dimethylpropyl)-3-methyl-2-oxo-2,3-dihydro-1H-benzimidazol-5-yl]pyrazine-2-carbonitrile | LRMS m/z (M + H) 322.2 found, 322.4 required. |
| 1-105 | 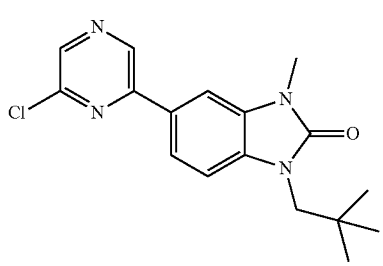 [SMILES: Cn1c(=O)n(CC(C)(C)C)c2ccc(-c3cncc(Cl)n3)cc21] | 5-(6-chloropyrazin-2-yl)-1-(2,2-dimethylpropyl)-3-methyl-1,3-dihydro-2H-benzimidazol-2-one | LRMS m/z (M + H) 331.1 found, 331.8 required. |

Table 1 for Scheme 1

| Cmp | Structure | Name | LRMS m/z (M + H) |
|---|---|---|---|
| 1-106 | 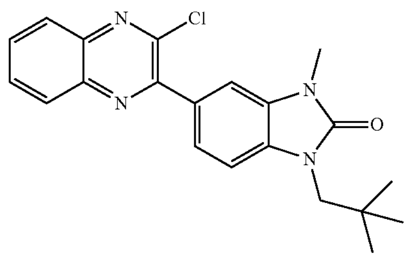 [SMILES: Cn1c(=O)n(CC(C)(C)C)c2ccc(-c3nc4ccccc4nc3Cl)cc21] | 5-(3-chloroquinoxalin-2-yl)-1-(2,2-dimethylpropyl)-3-methyl-1,3-dihydro-2H-benzimidazol-2-one | LRMS m/z (M + H) 381.2 found, 381.9 required. |
| 1-107 | 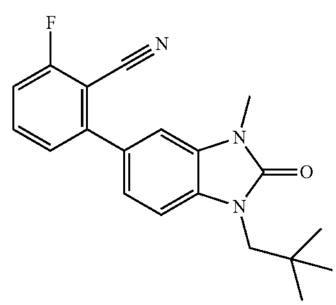 [SMILES: Cn1c(=O)n(CC(C)(C)C)c2ccc(-c3cccc(F)c3C#N)cc21] | 2-[1-(2,2-dimethylpropyl)-3-methyl-2-oxo-2,3-dihydro-1H-benzimidazol-5-yl]-6-fluorobenzonitrile | LRMS m/z (M + H) 338.2 found, 338.4 required. |
| 1-108 | 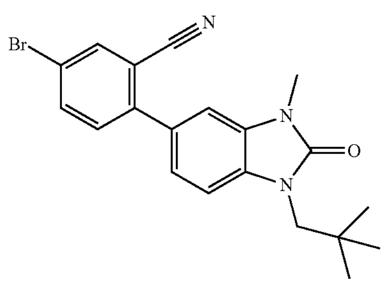 [SMILES: Cn1c(=O)n(CC(C)(C)C)c2ccc(-c3ccc(Br)cc3C#N)cc21] | 5-bromo-2-[1-(2,2-dimethylpropyl)-3-methyl-2-oxo-2,3-dihydro-1H-benzimidazol-5-yl]benzonitrile | LRMS m/z (M + H) 398.1 found, 399.3 required. |
| 1-109 | 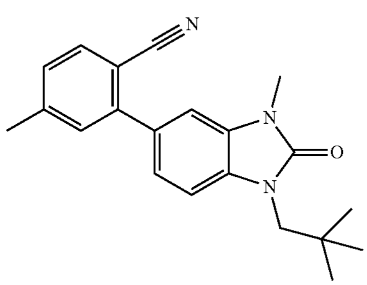 [SMILES: Cc1ccc(C#N)c(-c2ccc3c(c2)n(C)c(=O)n3CC(C)(C)C)c1] | 2-[1-(2,2-dimethylpropyl)-3-methyl-2-oxo-2,3-dihydro-1H-benzimidazol-5-yl]-4-methylbenzonitrile | LRMS m/z (M + H) 334.2 found, 334.4 required. |
| 1-110 | 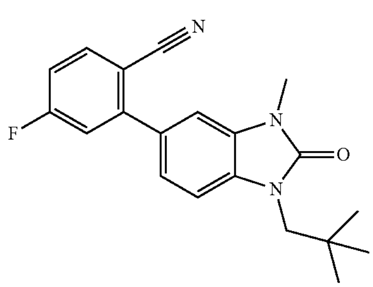 [SMILES: Cn1c(=O)n(CC(C)(C)C)c2ccc(-c3cc(F)ccc3C#N)cc21] | 2-[1-(2,2-dimethylpropyl)-3-methyl-2-oxo-2,3-dihydro-1H-bnzimidazol-5-yl]-4-fluorobenzonitrile | LRMS m/z (M + H) 338.2 found, 338.4 required. |

-continued

Table 1 for Scheme 1

| Cmp | Structure | Name | LRMS m/z (M + H) |
|---|---|---|---|
| 1-111 | 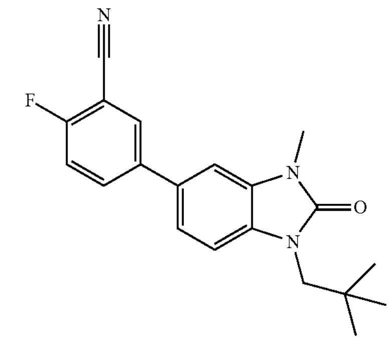 [SMILES: Cn1c(=O)n(CC(C)(C)C)c2ccc(-c3ccc(F)c(C#N)c3)cc21] | 5-[1-(2,2-dimethylpropyl)-3-methyl-2-oxo-2,3-dihydro-1H-benzimidazol-5-yl]-2-fluorobenzonitrile | LRMS m/z (M + H) 338.2 found, 338.4 required. |
| 1-112 | 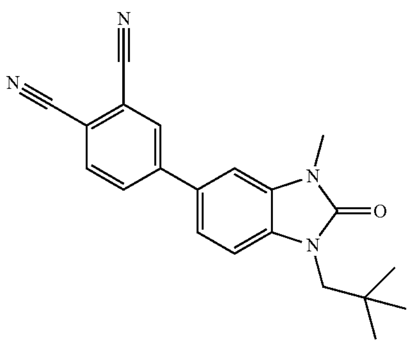 [SMILES: Cn1c(=O)n(CC(C)(C)C)c2ccc(-c3ccc(C#N)c(C#N)c3)cc21] | 4-[1-(2,2-dimethylpropyl)-3-methyl-2-oxo-2,3-dihydro-1H-benzimidazol-5-yl]phthalonitrile | LRMS m/z (M + H) 345.2 found, 345.4 required. |
| 1-113 | 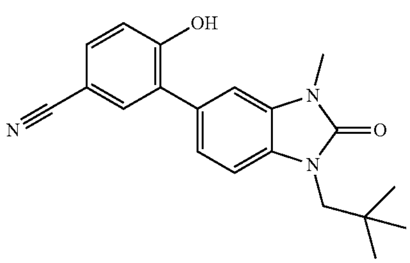 [SMILES: Cn1c(=O)n(CC(C)(C)C)c2ccc(-c3cc(C#N)ccc3O)cc21] | 3-[1-(2,2-dimethylpropyl)-3-methyl-2-oxo-2,3-dihydro-1H-benzimidazol-5-yl]-4-hydroxybenzonitrile | LRMS m/z (M + H) 336.2 found, 336.4 required. |
| 1-114 | 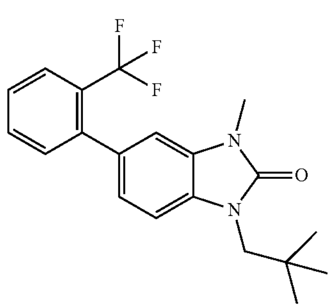 [SMILES: Cn1c(=O)n(CC(C)(C)C)c2ccc(-c3ccccc3C(F)(F)F)cc21] | 1-(2,2-dimethylpropyl)-3-methyl-5-[2-(trifluoromethyl)phenyl]-1,3-dihydro-2H-benzimidazol-2-one | LRMS m/z (M + H) 363.2 found, 363.4 required. |

Table 1 for Scheme 1

| Cmp | Structure | Name | LRMS m/z (M + H) |
|---|---|---|---|
| 1-115 | 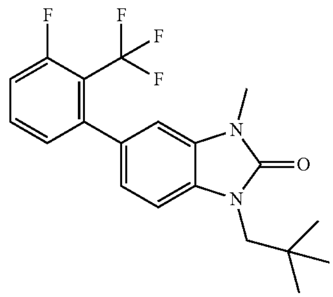 [SMILES: Cn1c(=O)n(CC(C)(C)C)c2ccc(-c3cccc(F)c3C(F)(F)F)cc21] | 1-(2,2-dimethylpropyl)-5-[3-fluoro-2-(trifluoromethyl)phenyl]-3-methyl-1,3-dihydro-2H-benzimidazol-2-one | LRMS m/z (M + H) 381.2 found, 381.4 required. |
| 1-116 | 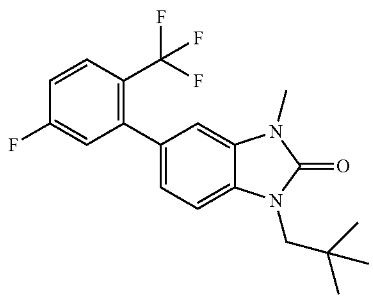 [SMILES: Cn1c(=O)n(CC(C)(C)C)c2ccc(-c3cc(F)ccc3C(F)(F)F)cc21] | 1-(2,2-dimethylpropyl)-5-[5-fluoro-2-(trifluoromethyl)phenyl]-3-methyl-1,3-dihydro-2H-benzimidazol-2-one | LRMS m/z (M + H) 381.2 found, 381.4 required. |
| 1-117 | 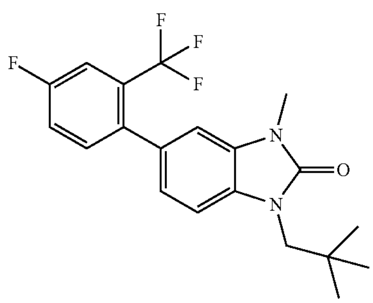 [SMILES: Cn1c(=O)n(CC(C)(C)C)c2ccc(-c3ccc(F)cc3C(F)(F)F)cc21] | 1-(2,2-dimethylpropyl)-5-[4-fluoro-2-(trifluoromethyl)phenyl]-3-methyl-1,3-dihydro-2H-benzimidazol-2-one | LRMS m/z (M + H) 381.2 found, 381.4 required. |
| 1-118 | 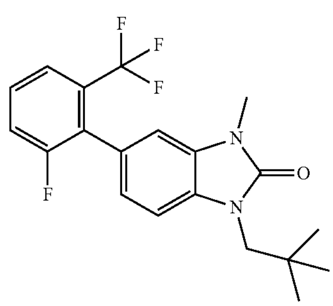 [SMILES: Cn1c(=O)n(CC(C)(C)C)c2ccc(-c3c(F)cccc3C(F)(F)F)cc21] | 1-(2,2-dimethylpropyl)-5-[2-fluoro-6-(trifluoromethyl)phenyl]-3-methyl-1,3-dihydro-2H-benzimidazol-2-one | LRMS m/z (M + H) 381.2 found, 381.4 required. |
| 1-119 | 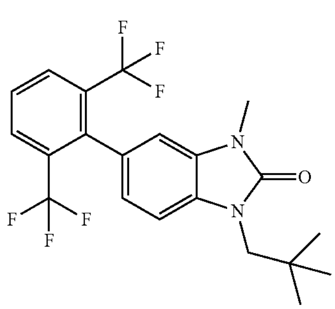 [SMILES: Cn1c(=O)n(CC(C)(C)C)c2ccc(-c3c(C(F)(F)F)cccc3C(F)(F)F)cc21] | 5-[2,6-bis(trifluoromethyl)phenyl]-1-(2,2-dimethylpropyl)-3-methyl-1,3-dihydro-2H-benzimidazol-2-one | LRMS m/z (M + H) 431.2 found, 431.4 required. |

Table 1 for Scheme 1

| Cmp | Structure | Name | LRMS m/z (M + H) |
|---|---|---|---|
| 1-120 | 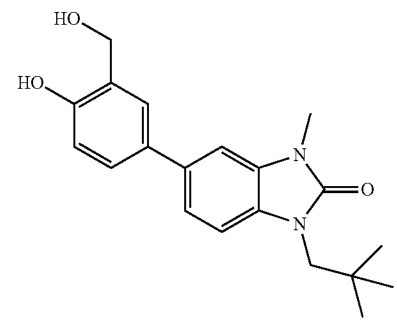 [SMILES: Cn1c(=O)n(CC(C)(C)C)c2ccc(-c3ccc(O)c(CO)c3)cc21] | 1-(2,2-dimethylpropyl)-5-[4-hydroxy-3-(hydroxymethyl)phenyl]-3-methyl-1,3-dihydro-2H-benzimidazol-2-one | LRMS m/z (M + H) 341.2 found, 341.4 required. |
| 1-121 | 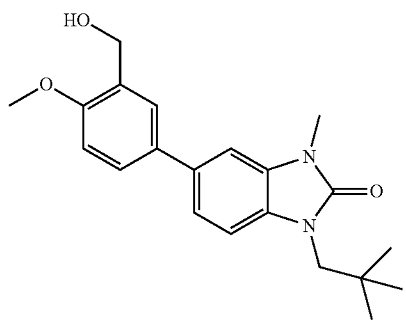 [SMILES: COc1ccc(-c2ccc3c(c2)n(C)c(=O)n3CC(C)(C)C)cc1CO] | 1-(2,2-dimethylpropyl)-5-[3-(hydroxymethyl)-4-methoxyphenyl]-3-methyl-1,3-dihydro-2H-benzimidazol-2-one | LRMS m/z (M + H) 355.2 found, 355.4 required. |
| 1-122 | 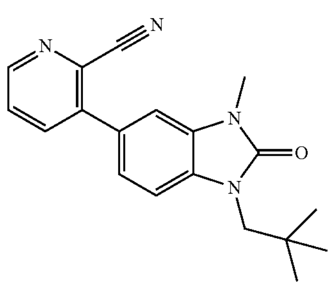 [SMILES: Cn1c(=O)n(CC(C)(C)C)c2ccc(-c3cccnc3C#N)cc21] | 3-[1-(2,2-dimethylpropyl)-3-methyl-2-oxo-2,3-dihydro-1H-benzimidazol-5-yl]pyridine-2-carbonitrile | LRMS m/z (M + H) 321.2 found, 321.4 required. |
| 1-123 | 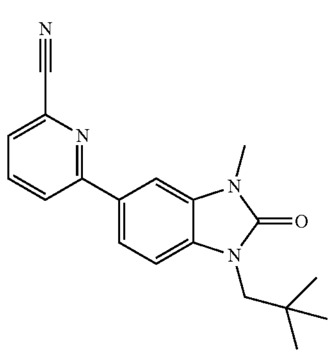 [SMILES: Cn1c(=O)n(CC(C)(C)C)c2ccc(-c3cccc(C#N)n3)cc21] | 6-[1-(2,2-dimethylpropyl)-3-methyl-2-oxo-2,3-dihydro-1H-benzimidazol-5-yl]pyridine-2-carbonitrile | LRMS m/z (M + H) 321.2 found, 321.4 required. |

-continued

Table 1 for Scheme 1

| Cmp | Structure | Name | LRMS m/z (M + H) |
|---|---|---|---|
| 1-124 | 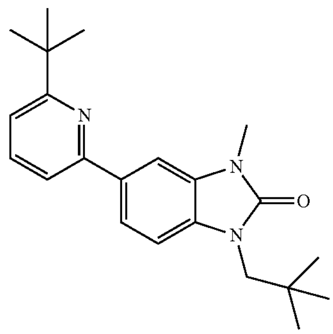 [SMILES: Cn1c(=O)n(CC(C)(C)C)c2ccc(-c3cccc(C(C)(C)C)n3)cc21] | 5-(6-tert-butylpyridin-2-yl)-1-(2,2-dimethylpropyl)-3-methyl-1,3-dihydro-2H-benzimidazol-2-one | LRMS m/z (M + H) 352.2 found, 352.5 required. |
| 1-125 | 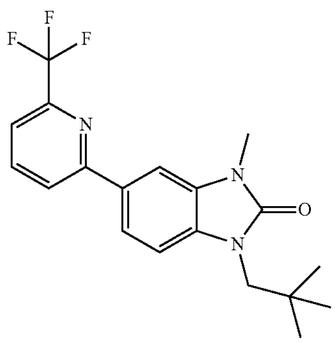 [SMILES: Cn1c(=O)n(CC(C)(C)C)c2ccc(-c3cccc(C(F)(F)F)n3)cc21] | 1-(2,2-dimethylpropyl)-3-methyl-5-[6-(trifluoromethyl)pyridin-2-yl]-1,3-dihydro-2H-benzimidazol-2-one | LRMS m/z (M + H) 364.2 found, 364.4 required. |
| 1-126 | 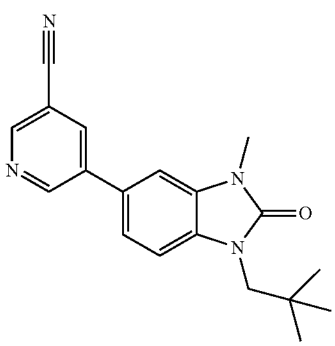 [SMILES: Cn1c(=O)n(CC(C)(C)C)c2ccc(-c3cncc(C#N)c3)cc21] | 5-[1-(2,2-dimethylpropyl)-3-methyl-2-oxo-2,3-dihydro-1H-benzimidazol-5-yl]nicotinonitrile | LRMS m/z (M + H) 321.2 found, 321.4 required. |
| 1-127 | 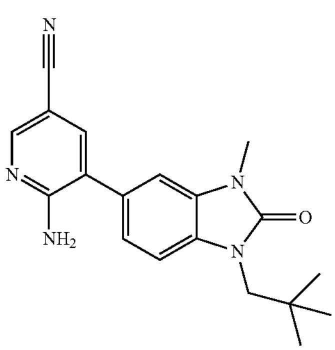 [SMILES: Cn1c(=O)n(CC(C)(C)C)c2ccc(-c3cc(C#N)cnc3N)cc21] | 6-amino-5-[1-(2,2-dimethylpropyl)-3-methyl-2-oxo-2,3-dihydro-1H-benzimidazol-5-yl]nicotinonitrile | LRMS m/z (M + H) 336.2 found, 336.4 required. |

-continued

Table 1 for Scheme 1

| Cmp | Structure | Name | LRMS m/z (M + H) |
|---|---|---|---|
| 1-128 | 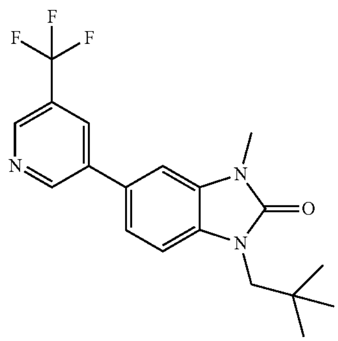 [SMILES: Cn1c(=O)n(CC(C)(C)C)c2ccc(-c3cncc(C(F)(F)F)c3)cc21] | 1-(2,2-dimethylpropyl)-3-methyl-5-[5-(trifluoromethyl)pyridin-3-yl]-1,3-dihydro-2H-benzimidazol-2-one | LRMS m/z (M + H) 364.2 found, 364.4 required. |
| 1-129 | 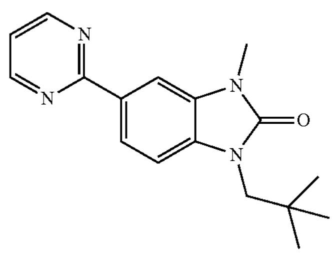 [SMILES: Cn1c(=O)n(CC(C)(C)C)c2ccc(-c3ncccn3)cc21] | 1-(2,2-dimethylpropyl)-3-methyl-5-pyrimidin-2-yl-1,3-dihydro-2H-benzimidazol-2-one | LRMS m/z (M + H) 297.2 found, 297.4 required. |
| 1-130 | 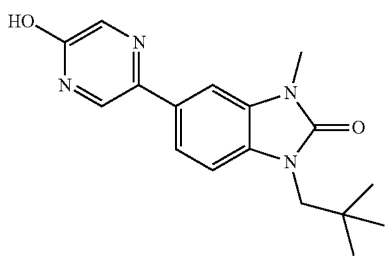 [SMILES: Cn1c(=O)n(CC(C)(C)C)c2ccc(-c3cnc(O)cn3)cc21] | 1-(2,2-dimethylpropyl)-5-(5-hydroxypyrazin-2-yl)-3-methyl-1,3-dihydro-2H-benzimidazol-2-one | LRMS m/z (M + H) 313.2 found, 313.4 required. |
| 1-131 | 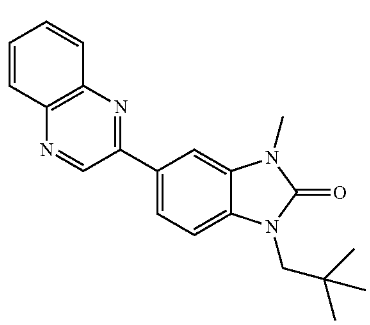 [SMILES: Cn1c(=O)n(CC(C)(C)C)c2ccc(-c3cnc4ccccc4n3)cc21] | 1-(2,2-dimethylpropyl)-3-methyl-5-quinoxalin-2-yl-1,3-dihydro-2H-benzimidazol-2-one | LRMS m/z (M + H) 347.2 found, 347.4 required. |

-continued

Table 1 for Scheme 1

| Cmp | Structure | Name | LRMS m/z (M + H) |
|---|---|---|---|
| 1-132 | 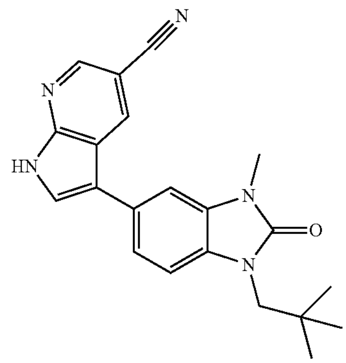 [SMILES: Cn1c(=O)n(CC(C)(C)C)c2ccc(-c3c[nH]c4ncc(C#N)cc34)cc21] | 3-[1-(2,2-dimethylpropyl)-3-methyl-2-oxo-2,3-dihydro-1H-benzimidazol-5-yl]-1H-pyrrolo[2,3-b]pyridine-5-carbonitrile | LRMS m/z (M + H) 360.2 found, 360.4 required. |
| 1-133 | 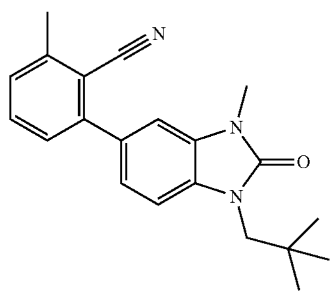 [SMILES: Cc1cccc(-c2ccc3c(c2)n(C)c(=O)n3CC(C)(C)C)c1C#N] | 2-[1-(2,2-dimethylpropyl)-3-methyl-2-oxo-2,3-dihydro-1H-benzimidazol-5-yl]-6-methylbenzonitrile | LRMS m/z (M + H) 334.2 found, 334.4 required. |
| 1-134 | 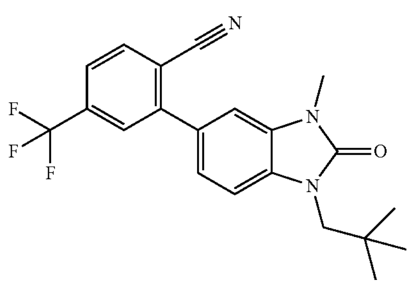 [SMILES: Cn1c(=O)n(CC(C)(C)C)c2ccc(-c3cc(C(F)(F)F)ccc3C#N)cc21] | 2-[1-(2,2-dimethylpropyl)-3-methyl-2-oxo-2,3-dihydro-1H-benzimidazol-5-yl]-4-(trifluoromethyl)benzonitrile | LRMS m/z (M + H) 388.2 found, 388.4 required. |
| 1-135 | 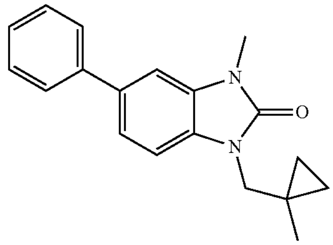 [SMILES: Cn1c(=O)n(CC2(C)CC2)c2ccc(-c3ccccc3)cc21] | 3-methyl-1-[(1-methylcyclopropyl)methyl]-5-phenyl-1,3-dihydro-2H-benzimidazol-2-one | LRMS m/z (M + H) 293.1 found, 293.4 required. |

Table 1 for Scheme 1 (continued)

| Cmp | Structure | Name | LRMS m/z (M + H) |
|---|---|---|---|
| 1-136 | 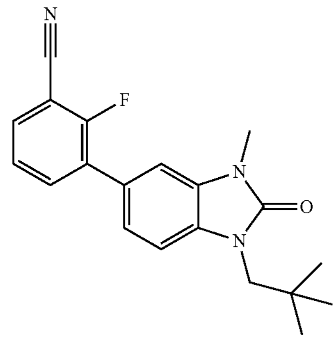 [SMILES: Cn1c(=O)n(CC(C)(C)C)c2ccc(-c3cccc(C#N)c3F)cc21] | 3-[1-(2,2-dimethylpropyl)-3-methyl-2-oxo-2,3-dihydro-1H-benzimidazol-5-yl]-2-fluorobenzonitrile | LRMS m/z (M + H) 338.1 found, 338.4 required. |
| 1-137 | 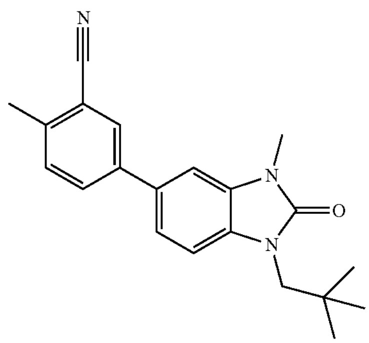 [SMILES: Cc1ccc(-c2ccc3c(c2)n(C)c(=O)n3CC(C)(C)C)cc1C#N] | 5-[1-(2,2-dimethylpropyl)-3-methyl-2-oxo-2,3-dihydro-1H-benzimidazol-5-yl]-2-methylbenzonitrile | LRMS m/z (M + H) 334.2 found, 334.4 required. |
| 1-138 | 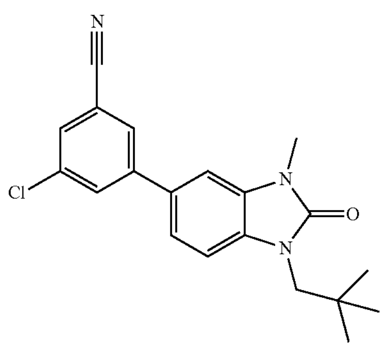 [SMILES: Cn1c(=O)n(CC(C)(C)C)c2ccc(-c3cc(Cl)cc(C#N)c3)cc21] | 3-chloro-5-[1-(2,2-dimethylpropyl)-3-methyl-2-oxo-2,3-dihydro-1H-benzimidazol-5-yl]benzonitrile | LRMS m/z (M + H) 354.1 found, 354.9 required. |
| 1-139 | 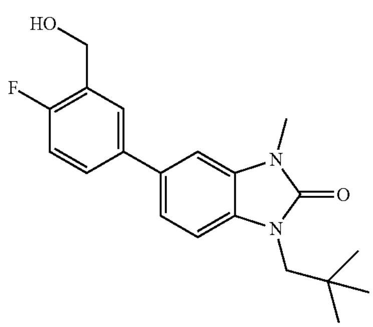 [SMILES: Cn1c(=O)n(CC(C)(C)C)c2ccc(-c3ccc(F)c(CO)c3)cc21] | 1-(2,2-dimethylpropyl)-5-[4-fluoro-3-(hydroxymethyl)phenyl]-3-methyl-1,3-dihydro-2H-benzimidazol-2-one | LRMS m/z (M + H) 343.2 found, 343.4 required. |

-continued

Table 1 for Scheme 1

| Cmp | Structure | Name | LRMS m/z (M + H) |
|---|---|---|---|
| 1-140 | 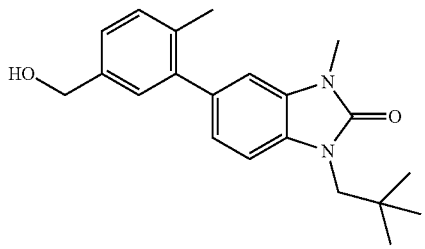 [SMILES: Cc1ccc(CO)cc1-c1ccc2c(c1)n(C)c(=O)n2CC(C)(C)C] | 1-(2,2-dimethylpropyl)-5-[5-(hydroxymethyl)-2-methylphenyl]-3-methyl-1,3-dihydro-2H-benzimidazol-2-one | LRMS m/z (M + H) 339.2 found, 339.5 required. |
| 1-141 | 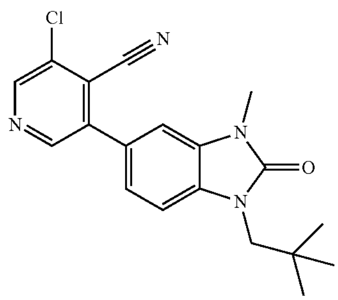 [SMILES: Cn1c(=O)n(CC(C)(C)C)c2ccc(-c3cncc(Cl)c3C#N)cc21] | 3-chloro-5-[1-(2,2-dimethylpropyl)-3-methyl-2-oxo-2,3-dihydro-1H-benzimidazol-5-yl]isonicotinonitrile | LRMS m/z (M + H) 355.1 found, 355.9 required. |
| 1-142 | 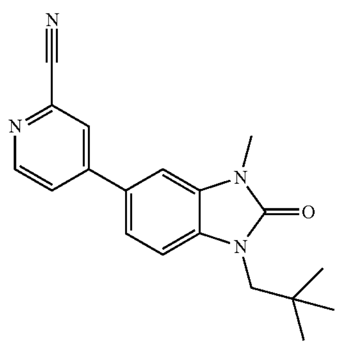 [SMILES: Cn1c(=O)n(CC(C)(C)C)c2ccc(-c3ccnc(C#N)c3)cc21] | 4-[1-(2,2-dimethylpropyl)-3-methyl-2-oxo-2,3-dihydro-1H-benzimidazol-5-yl]pyridine-2-carbonitrile | LRMS m/z (M + H) 321.2 found, 321.4 required. |
| 1-143 | 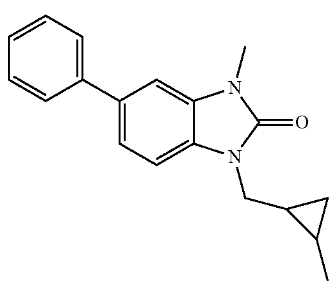 [SMILES: CC1CC1Cn1c(=O)n(C)c2cc(-c3ccccc3)ccc21] | 3-methyl-1-[(2-methylcyclopropyl)methyl]-5-phenyl-1,3-dihydro-2H-benzimidazol-2-one | LRMS m/z (M + H) 293.2 found, 293.4 required. |
| 1-144 | 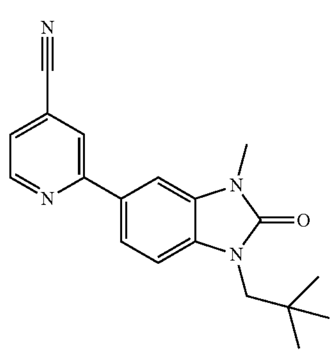 [SMILES: Cn1c(=O)n(CC(C)(C)C)c2ccc(-c3cc(C#N)ccn3)cc21] | 2-[1-(2,2-dimethylpropyl)-3-methyl-2-oxo-2,3-dihydro-1H-benzimidazol-5-yl]isonicotinonitrile | LRMS m/z (M + H) 321.2 found, 321.4 required. |

Table 1 for Scheme 1

| Cmp | Structure | Name | LRMS m/z (M + H) |
|---|---|---|---|
| 1-145 | 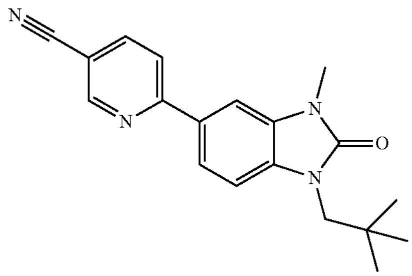 [SMILES: Cn1c(=O)n(CC(C)(C)C)c2ccc(-c3ccc(C#N)cn3)cc21] | 6-[1-(2,2-dimethylpropyl)-3-methyl-2-oxo-2,3-dihydro-1H-benzimidazol-5-yl]nicotinonitrile | LRMS m/z (M + H) 321.2 found, 321.4 required. |
| 1-146 | 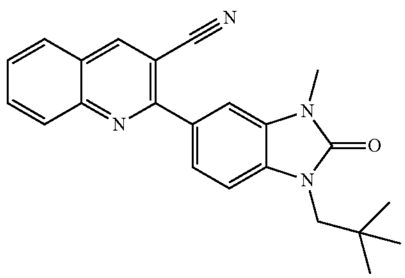 [SMILES: Cn1c(=O)n(CC(C)(C)C)c2ccc(-c3nc4ccccc4cc3C#N)cc21] | 2-[1-(2,2-dimethylpropyl)-3-methyl-2-oxo-2,3-dihydro-1H-benzimidazol-5-yl]quinoline-3-carbonitrile | LRMS m/z (M + H) 371.2 found, 371.5 required. |
| 1-147 | 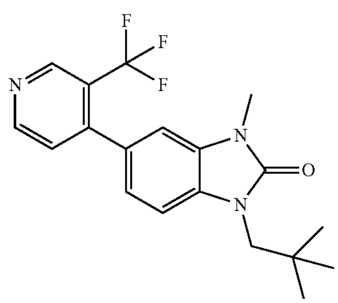 [SMILES: Cn1c(=O)n(CC(C)(C)C)c2ccc(-c3ccncc3C(F)(F)F)cc21] | 1-(2,2-dimethylpropyl)-3-methyl-5-[3-(trifluoromethyl)pyridin-4-yl]-1,3-dihydro-2H-benzimidazol-2-one | LRMS m/z (M + H) 364.2 found, 364.4 required. |
| 1-148 | 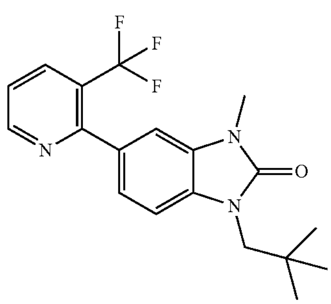 [SMILES: Cn1c(=O)n(CC(C)(C)C)c2ccc(-c3ncccc3C(F)(F)F)cc21] | 1-(2,2-dimethylpropyl)-3-methyl-5-[3-(trifluoromethyl)pyridin-2-yl]-1,3-dihydro-2H-benzimidazol-2-one | LRMS m/z (M + H) 364.2 found, 364.4 required. |
| 1-149 | 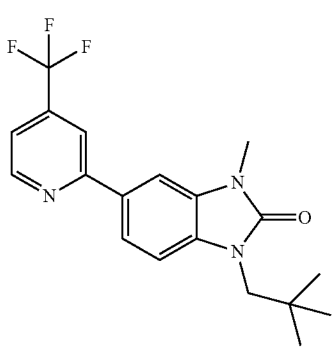 [SMILES: Cn1c(=O)n(CC(C)(C)C)c2ccc(-c3cc(C(F)(F)F)ccn3)cc21] | 1-(2,2-dimethylpropyl)-3-methyl-5-[4-(trifluoromethyl)pyridin-2-yl]-1,3-dihydro-2H-benzimidazol-2-one | LRMS m/z (M + H) 364.1 found, 364.4 required. |

-continued

Table 1 for Scheme 1

| Cmp | Structure | Name | LRMS m/z (M + H) |
|---|---|---|---|
| 1-150 | 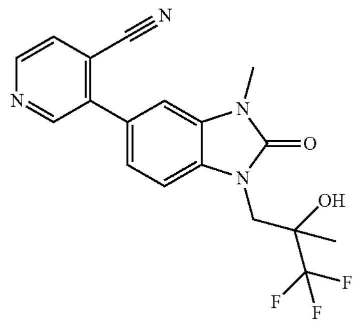 [SMILES: Cn1c(=O)n(CC(C)(O)C(F)(F)F)c2ccc(-c3cnccc3C#N)cc21] | 3-[3-methyl-2-oxo-1-(3,3,3-trifluoro-2-hydroxy-2-methylpropyl)-2,3-dihydro-1H-benzimidazol-5-yl]isonicotinonitrile | LRMS m/z (M + H) 377.2 found, 377.3 required. |
| 1-151 | 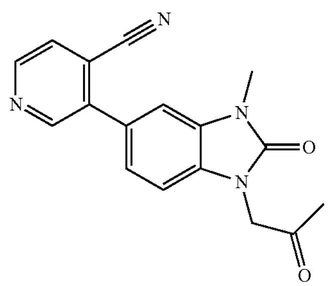 [SMILES: CC(=O)Cn1c(=O)n(C)c2cc(-c3cnccc3C#N)ccc21] | 3-[3-methyl-2-oxo-1-(2-oxopropyl)-2,3-dihydro-1H-benzimidazol-5-yl]isonicotinonitrile | LRMS m/z (M + H) 307.2 found, 307.3 required. |
| 1-152 | 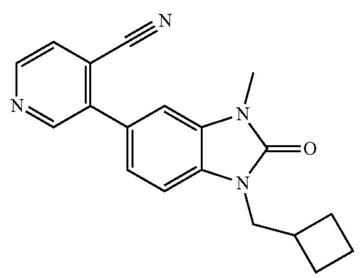 [SMILES: Cn1c(=O)n(CC2CCC2)c2ccc(-c3cnccc3C#N)cc21] | 3-[1-(cyclobutylmethyl)-3-methyl-2-oxo-2,3-dihydro-1H-benzimidazol-5-yl]isonicotinonitrile | LRMS m/z (M + H) 319.1 found, 319.4 required. |
| 1-153 | 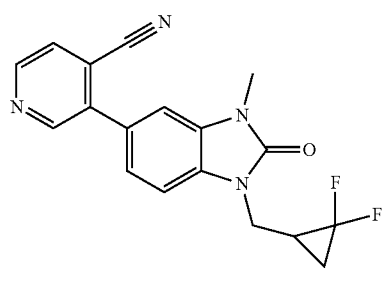 [SMILES: Cn1c(=O)n(CC2CC2(F)F)c2ccc(-c3cnccc3C#N)cc21] | 3-{1-[(2,2-difluorocyclopropyl)methyl]-3-methyl-2-oxo-2,3-dihydro-1H-benzimidazol-5-yl}isonicotinonitrile | LRMS m/z (M + H) 341.1 found, 341.3 required. |
| 1-154 | 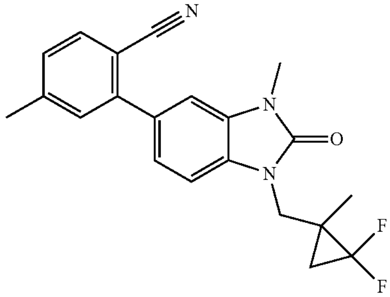 [SMILES: Cc1ccc(C#N)c(-c2ccc3c(c2)n(C)c(=O)n3CC2(C)CC2(F)F)c1] | 2-{1-[(2,2-difluoro-1-methylcyclopropyl)methyl]-3-methyl-2-oxo-2,3-dihyro-1H-benzimidazol-5-yl}-4-methylbenzonitrile | LRMS m/z (M + H) 368.3 found, 368.4 required. |

Table 1 for Scheme 1

| Cmp | Structure | Name | LRMS m/z (M + H) |
|---|---|---|---|
| 1-155 | 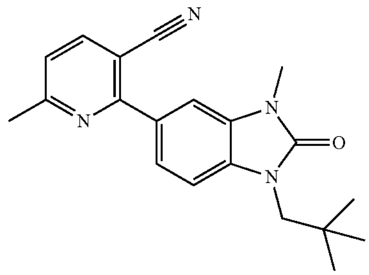 [SMILES: Cc1ccc(C#N)c(-c2ccc3c(c2)n(C)c(=O)n3CC(C)(C)C)n1] | 2-[1-(2,2-dimethylpropyl)-3-methyl-2-oxo-2,3-dihydro-1H-benzimidazol-5-yl]-6-methylnicotinonitrile | LRMS m/z (M + H) 335.1 found, 335.4 required. |
| 1-156 | 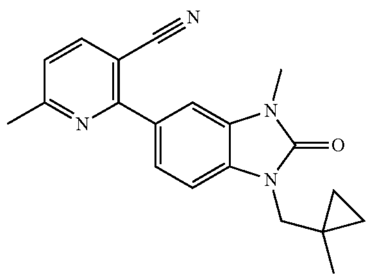 [SMILES: Cc1ccc(C#N)c(-c2ccc3c(c2)n(C)c(=O)n3CC2(C)CC2)n1] | 6-methyl-2-{3-methyl-1-[(1-methylcyclopropyl)methyl]-2-oxo-2,3-dihydro-1H-benzimidazol-5-yl}nicotinonitrile | LRMS m/z (M + H) 333.1 found, 333.4 required. |
| 1-157 | 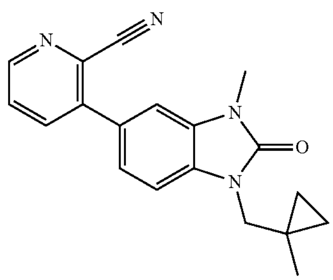 [SMILES: Cn1c(=O)n(CC2(C)CC2)c2ccc(-c3cccnc3C#N)cc21] | 3-{3-methyl-1-[(1-methylcyclopropyl)methyl]-2-oxo-2,3-dihydro-1H-benzimidazol-5-yl}pyridine-2-carbonitrile | LRMS m/z (M + H) 319.1 found, 319.4 required. |
| 1-158 | 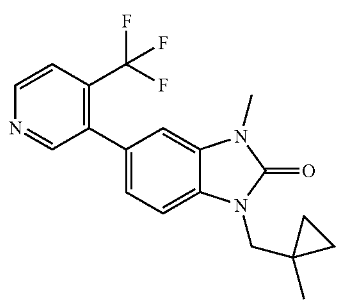 [SMILES: Cn1c(=O)n(CC2(C)CC2)c2ccc(-c3cnccc3C(F)(F)F)cc21] | 3-methyl-1-[(1-methylcyclopropyl)methyl]-5-[4-(trifluoromethyl)pyridin-3-yl]-1,3-dihydro-2H-benzimidazol-2-one | LRMS m/z (M + H) 362.1 found, 362.4 required. |
| 1-159 | 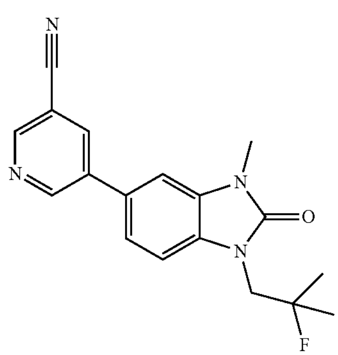 [SMILES: Cn1c(=O)n(CC(C)(C)F)c2ccc(-c3cncc(C#N)c3)cc21] | 5-[1-(2-fluoro-2-methylpropyl)-3-methyl-2-oxo-2,3-dihydro-1H-benzimidazol-5-yl]nicotinonitrile | LRMS m/z (M + H) 325.1 found, 325.4 required. |

Table 1 for Scheme 1

| Cmp | Structure | Name | LRMS m/z (M + H) |
|---|---|---|---|
| 1-160 | 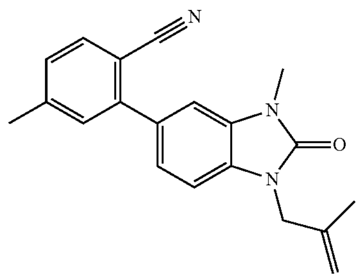 [SMILES: C=C(C)Cn1c(=O)n(C)c2cc(-c3cc(C)ccc3C#N)ccc21] | 4-methyl-2-[3-methyl-1-(2-methylprop-2-en-1-yl)-2-oxo-2,3-dihydro-1H-benzimidazol-5-yl]benzonitrile | LRMS m/z (M + H) 318.2 found, 318.4 required. |
| 1-161 | 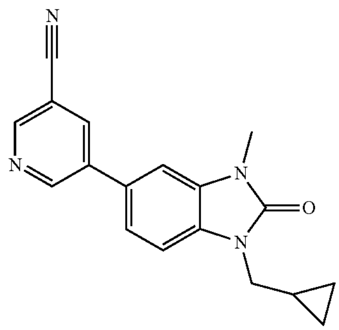 [SMILES: Cn1c(=O)n(CC2CC2)c2ccc(-c3cncc(C#N)c3)cc21] | 5-[1-(cyclopropylmethyl)-3-methyl-2-oxo-2,3-dihydro-1H-benzimidazol-5-yl]nicotinonitrile | LRMS m/z (M + H) 305.1 found, 305.4 required. |
| 1-162 | 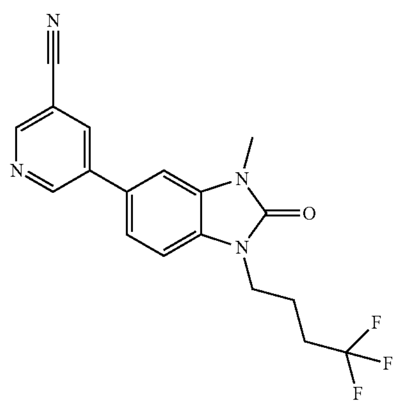 [SMILES: Cn1c(=O)n(CCCC(F)(F)F)c2ccc(-c3cncc(C#N)c3)cc21] | 5-[3-methyl-2-oxo-1-(4,4,4-trifluorobutyl)-2,3-dihydro-1H-benzimidazol-5-yl]nicotinonitrile | LRMS m/z (M + H) 361.1 found, 361.3 required. |
| 1-163 | 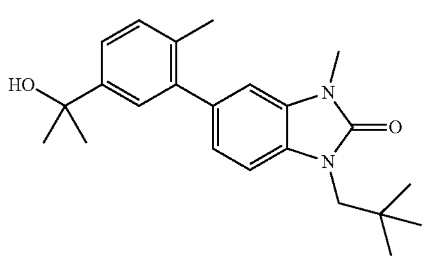 [SMILES: Cc1ccc(C(C)(C)O)cc1-c1ccc2c(c1)n(C)c(=O)n2CC(C)(C)C] | 1-(2,2-dimethylpropyl)-5-[5-(1-hydroxy-1-methylethyl)-2-methylphenyl]-3-methyl-1,3-dihydro-2H-benzimidazol-2-one | LRMS m/z (M + H) 367.2385 found, 367.2380 required. |

-continued

Table 1 for Scheme 1

| Cmp | Structure | Name | LRMS m/z (M + H) |
|---|---|---|---|
| 1-164 | 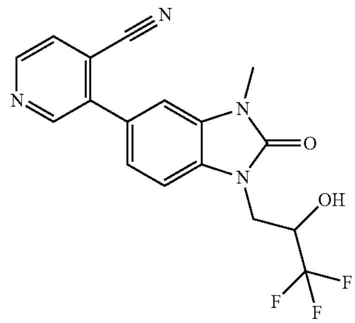 [SMILES: Cn1c(=O)n(CC(O)C(F)(F)F)c2ccc(-c3cnccc3C#N)cc21] | 3-[3-methyl-2-oxo-1-(3,3,3-trifluoro-2-hydroxypropyl)-2,3-dihydro-1H-benzimidazol-5-yl]isonicotinonitrile | LRMS m/z (M + H) 363.1 found, 363.3 required. |
| 1-165 | 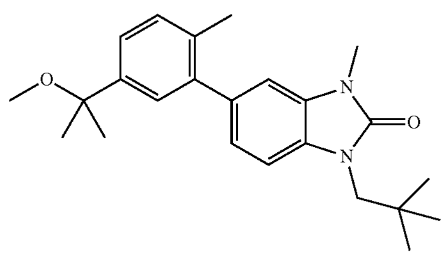 [SMILES: COC(C)(C)c1ccc(C)c(-c2ccc3c(c2)n(C)c(=O)n3CC(C)(C)C)c1] | 1-(2,2-dimethylpropyl)-5-[5-(1-methoxy-1-methylethyl)-2-methylphenyl]-3-methyl-1,3-dihydro-2H-benzimidazol-2-one | LRMS m/z (M + H) 381.2538 found, 381.2537 required. |
| 1-166 | 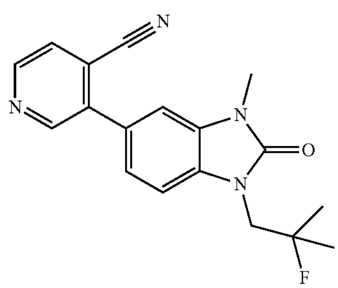 [SMILES: Cn1c(=O)n(CC(C)(C)F)c2ccc(-c3cnccc3C#N)cc21] | 3-[1-(2-fluoro-2-methylpropyl)-3-methyl-2-oxo-2,3-dihydro-1H-benzimidazol-5-yl]isonicotinonitrile | LRMS m/z (M + H) 325.1 found, 325.4 required. |
| 1-167 | 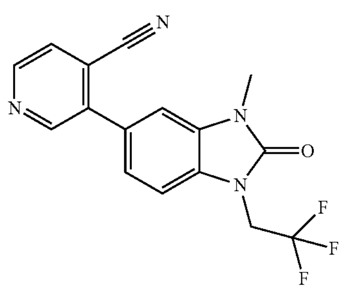 [SMILES: Cn1c(=O)n(CC(F)(F)F)c2ccc(-c3cnccc3C#N)cc21] | 3-[3-methyl-2-oxo-1-(2,2,2-trifluoroethyl)-2,3-dihydro-1H-benzimidazol-5-yl]isonicotinonitrile | LRMS m/z (M + H) 333.1 found, 333.3 required. |
| 1-168 | 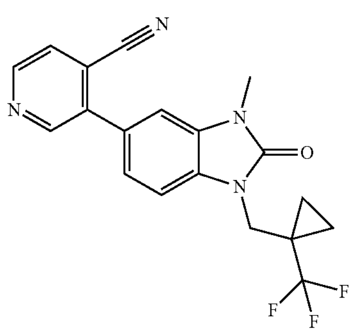 [SMILES: Cn1c(=O)n(CC2(C(F)(F)F)CC2)c2ccc(-c3cnccc3C#N)cc21] | 3-(3-methyl-2-oxo-1-{[1-(trifluoromethyl)cyclopropyl]methyl}-2,3-dihydro-1H-benzimidazol-5-yl)isonicotinonitrile | LRMS m/z (M + H) 373.1 found, 373.4 required. |

-continued

Table 1 for Scheme 1

| Cmp | Structure | Name | LRMS m/z (M + H) |
|---|---|---|---|
| 1-169 | 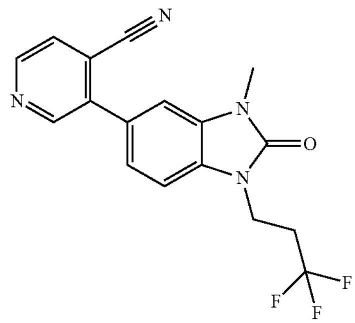 [SMILES: Cn1c(=O)n(CCC(F)(F)F)c2ccc(-c3cnccc3C#N)cc21] | 3-[3-methyl-2-oxo-1-(3,3,3-trifluoropropyl)-2,3-dihydro-1H-benzimidazol-5-yl]isonicotinonitrile | LRMS m/z (M + H) 347.1 found, 347.3 required. |
| 1-170 | 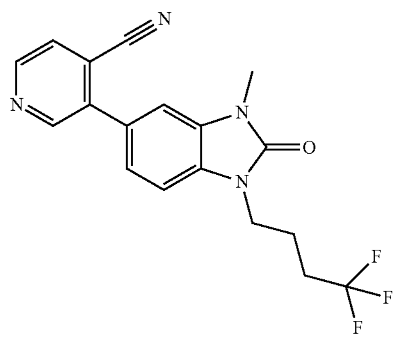 [SMILES: Cn1c(=O)n(CCCC(F)(F)F)c2ccc(-c3cnccc3C#N)cc21] | 3-[3-methyl-2-oxo-1-(4,4,4-trifluorobutyl)-2,3-dihydro-1H-benzimidazol-5-yl]isonicotinonitrile | LRMS m/z (M + H) 361.1 found, 361.3 required. |
| 1-171 | 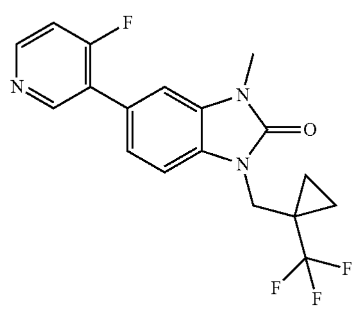 [SMILES: Cn1c(=O)n(CC2(C(F)(F)F)CC2)c2ccc(-c3cnccc3F)cc21] | 5-(4-fluoropyridin-3-yl)-3-methyl-1-{[1-(trifluoromethyl)cyclopropyl]methyl}-1,3-dihydro-2H-benzimidazol-2-one | LRMS m/z (M + H) 366.1 found, 366.3 required. |
| 1-172 | 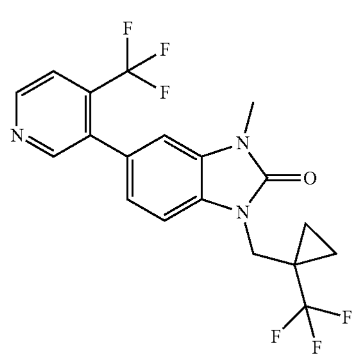 [SMILES: Cn1c(=O)n(CC2(C(F)(F)F)CC2)c2ccc(-c3cnccc3C(F)(F)F)cc21] | 3-methyl-1-{[1-(trifluoromethyl)cyclopropyl]methyl}-5-[4-(trifluoromethyl)pyridin-3-yl]-1,3-dihydro-2H-benzimidazol-2-one | LRMS m/z (M + H) 416.1 found, 416.3 required. |

-continued

Table 1 for Scheme 1

| Cmp | Structure | Name | LRMS m/z (M + H) |
|---|---|---|---|
| 1-173 | 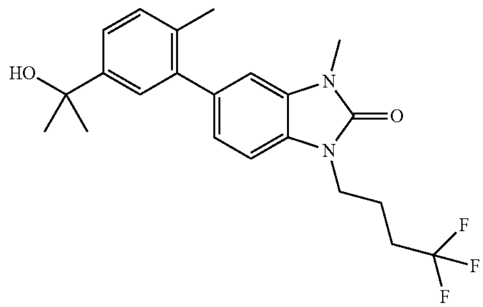 [SMILES: Cc1ccc(C(C)(C)O)cc1-c1ccc2c(c1)n(C)c(=O)n2CCCC(F)(F)F] | 5-[5-(1-hydroxy-1-methylethyl)-2-methylphenyl]-3-methyl-1-(4,4,4-trifluorobutyl)-1,3-dihydro-2H-benzimidazol-2-one | LRMS m/z (M + H) 407.1951 found, 407.1941 required. |
| 1-174 | 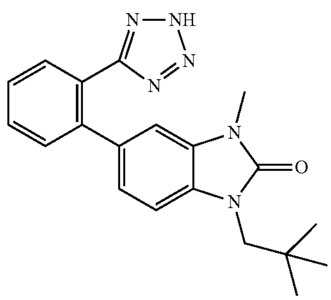 [SMILES: Cn1c(=O)n(CC(C)(C)C)c2ccc(-c3ccccc3-c3nn[nH]n3)cc21] | 1-(2,2-dimethylphenyl)-3-methyl-5-[2-(2H-tetrazol-5-yl)phenyl]-1,3-dihydro-2H-benzimidazol-2-one | LRMS m/z (M + H) 363.2 found, 362.4 required. |
| 1-175 | 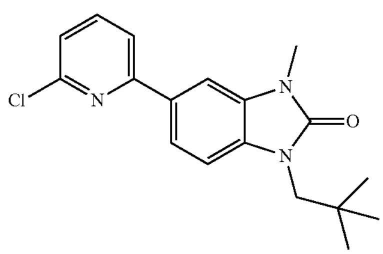 [SMILES: Cn1c(=O)n(CC(C)(C)C)c2ccc(-c3cccc(Cl)n3)cc21] | 5-(6-chloropyridin-2-yl)-1-(2,2-dimethylpropyl)-3-methyl-1,3-dihydro-2H-benzimidazol-2-one | LRMS m/z (M + H) 330.1 found, 330.8 required. |
| 1-176 | 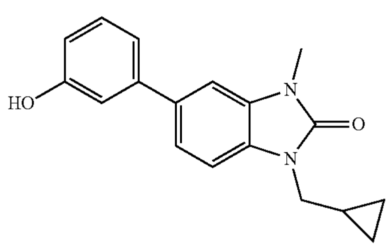 [SMILES: Cn1c(=O)n(CC2CC2)c2ccc(-c3cccc(O)c3)cc21] | 1-(cyclopropylmethyl)-5-(3-hydroxyphenyl)-3-methyl-1,3-dihydro-2H-benzimidazol-2-one | LRMS m/z (M + H) 295.0 found, 295.4 required. |
| 1-177 | 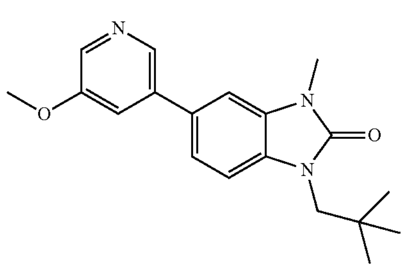 [SMILES: COc1cncc(-c2ccc3c(c2)n(C)c(=O)n3CC(C)(C)C)c1] | 1-(2,2-dimethylpropyl)-5-(5-methoxypyridin-3-yl)-3-methyl-1,3-dihydro-2H-benzimidazol-2-one | LRMS m/z (M + H) 326.1 found, 326.4 required. |

Table 1 for Scheme 1

| Cmp | Structure | Name | LRMS m/z (M + H) |
|---|---|---|---|
| 1-178 | 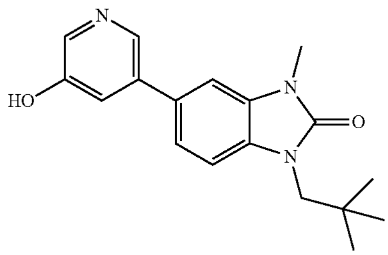 [SMILES: Cn1c(=O)n(CC(C)(C)C)c2ccc(-c3cncc(O)c3)cc21] | 1-(2,2-dimethylpropyl)-5-(5-hydroxypyridin-3-yl)-3-methyl-1,3-dihydro-2H-benzimidazol-2-one | LRMS m/z (M + H) 312.1 found, 312.4 required. |
| 1-179 | 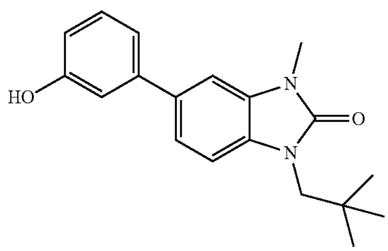 [SMILES: Cn1c(=O)n(CC(C)(C)C)c2ccc(-c3cccc(O)c3)cc21] | 1-(2,2-dimethylpropyl)-5-(3-hydroxyphenyl)-3-methyl-1,3-dihydro-2H-benzimidazol-2-one | LRMS m/z (M + H) 311.0 found, 331.4 required. |
| 1-180 | 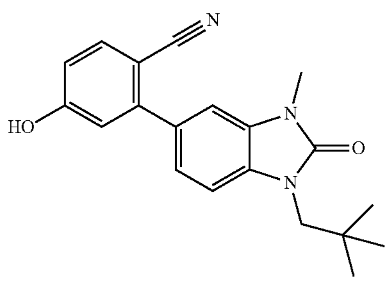 [SMILES: Cn1c(=O)n(CC(C)(C)C)c2ccc(-c3cc(O)ccc3C#N)cc21] | 2-[1-(2,2-dimethylpropyl)-3-methyl-2-oxo-2,3-dihydro-1H-benzimidazol-5-yl]-4-hydroxybenzonitrile | LRMS m/z (M + H) 336.0 found, 336.4 required. |
| 1-181 | 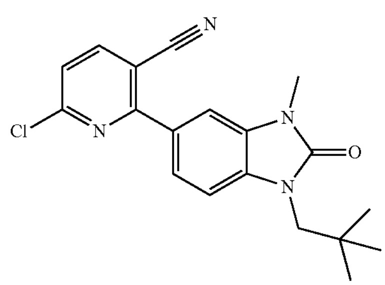 [SMILES: Cn1c(=O)n(CC(C)(C)C)c2ccc(-c3nc(Cl)ccc3C#N)cc21] | 6-chloro-2-[1-(2,2-dimethylpropyl)-3-methyl-2-oxo-2,3-dihydro-1H-benzimidazol-5-yl]nicotinonitrile | LRMS m/z (M + H) 355.0 found, 355.8 required. |
| 1-182 | 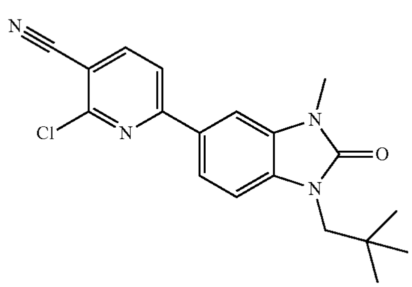 [SMILES: Cn1c(=O)n(CC(C)(C)C)c2ccc(-c3ccc(C#N)c(Cl)n3)cc21] | 2-chloro-6-[1-(2,2-dimethylpropyl)-3-methyl-2-oxo-2,3-dihydro-1H-benzimidazol-5-yl]nicotinitrile | LRMS m/z (M + H) 355.0 found, 355.8 required. |

-continued

Table 1 for Scheme 1

| Cmp | Structure | Name | LRMS m/z (M + H) |
|---|---|---|---|
| 1-183 | 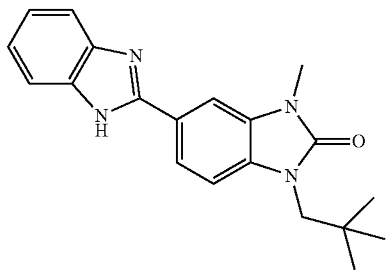 [SMILES: Cn1c(=O)n(CC(C)(C)C)c2ccc(-c3nc4ccccc4[nH]3)cc21] | 1'-(2,2-dimethylpropyl)-3'-methyl-1',3'-dihydro-1H-2'H-2,5'-bibenzimidazol-2'-one | LRMS m/z (M + H) 335.1 found, 335.4 required. |
| 1-184 | 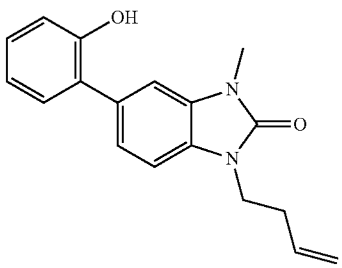 [SMILES: C=CCCn1c(=O)n(C)c2cc(-c3ccccc3O)ccc21] | 1-but-3-en-1-yl-5-(2-hydroxyphenyl)-3-methyl-1,3-dihydro-2H-benzimidazol-2-one | LRMS m/z (M + H) 295.0 found, 295.4 required. |
| 1-185 | 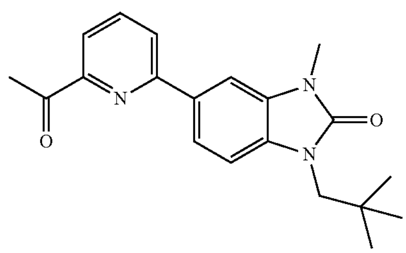 [SMILES: CC(=O)c1cccc(-c2ccc3c(c2)n(C)c(=O)n3CC(C)(C)C)n1] | 5-(6-acetylpyridin-2-yl)-1-(2,2-dimethylpropyl)-3-methyl-1,3-dihydro-2H-benzimidazol-2-one | LRMS m/z (M + H) 338.0 found, 338.4 required. |
| 1-186 | 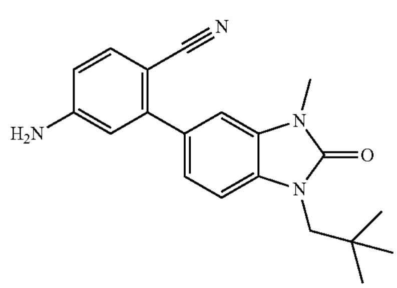 [SMILES: Cn1c(=O)n(CC(C)(C)C)c2ccc(-c3cc(N)ccc3C#N)cc21] | 4-amino-2-[1-(2,2-dimethylpropyl)-3-methyl-2-oxo-2,3-dihydro-1H-benzimidazol-5-yl]benzonitrile | LRMS m/z (M + H) 335.0 found, 335.4 required. |
| 1-187 | 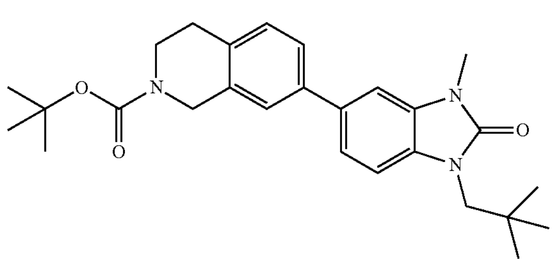 [SMILES: Cn1c(=O)n(CC(C)(C)C)c2ccc(-c3ccc4c(c3)CN(C(=O)OC(C)(C)C)CC4)cc21] | tert-butyl 7-[1-(2,2-dimethylpropyl)-3-methyl-2-oxo-2,3-dihydro-1H-benzimidazol-5-yl]-3,4-dihydroisoquinoline-2(1H)-carboxylate | LRMS m/z (M + H) 450.2756 found, 450.2751 required. |

-continued

Table 1 for Scheme 1

| Cmp | Structure | Name | LRMS m/z (M + H) |
|---|---|---|---|
| 1-188 | 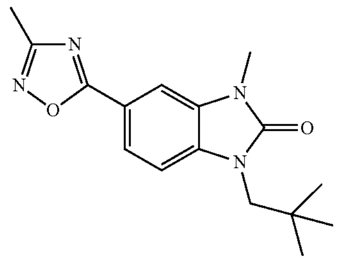 [SMILES: Cc1noc(-c2ccc3c(c2)n(C)c(=O)n3CC(C)(C)C)n1] | 1-(2,2-dimethylpropyl)-3-methyl-5-(3-methyl-1,2,4-oxadiazol-5-yl)-1,3-dihydro-2H-benzimidazol-2-one | LRMS m/z (M + H) 301.1661 found, 301.1659 required. |
| 1-189 | 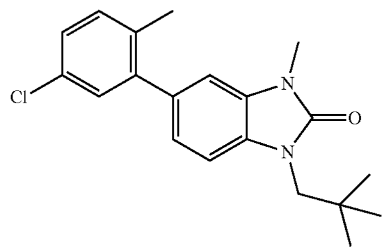 [SMILES: Cc1ccc(Cl)cc1-c1ccc2c(c1)n(C)c(=O)n2CC(C)(C)C] | 5-(5-chloro-2-methylphenyl)-1-(2,2-dimethylpropyl)-3-methyl-1,3-dihydro-2H-benzimidazol-2-one | LRMS m/z (M + H) 343.0 found, 343.9 required. |
| 1-190 | 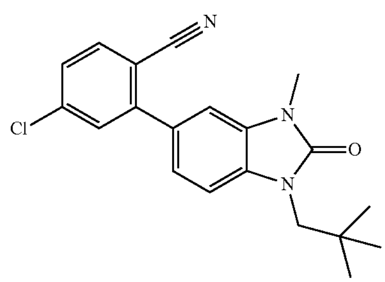 [SMILES: Cn1c(=O)n(CC(C)(C)C)c2ccc(-c3cc(Cl)ccc3C#N)cc21] | 4-chloro-2-[1-(2,2-dimethylpropyl)-3-methyl-2-oxo-2,3-dihydro-1H-benzimidazol-5-yl]benzonitrile | LRMS m/z (M + H) 354.0 found, 354.9 required. |
| 1-191 | 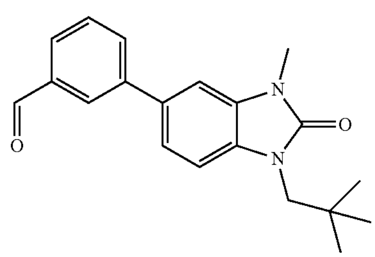 [SMILES: Cn1c(=O)n(CC(C)(C)C)c2ccc(-c3cccc(C=O)c3)cc21] | 3-[1-(2,2-dimethylpropyl)-3-methyl-2-oxo-2,3-dihydro-1H-benzimidazol-5-yl]benzaldehyde | LRMS m/z (M + H) 323.0 found, 323.4 required. |
| 1-192 | 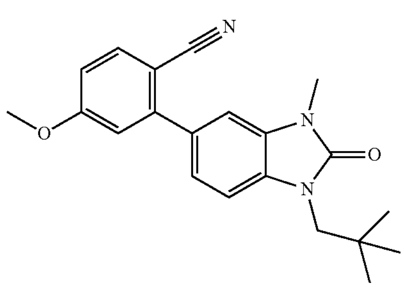 [SMILES: COc1ccc(C#N)c(-c2ccc3c(c2)n(C)c(=O)n3CC(C)(C)C)c1] | 2-[1-(2,2-dimethylpropyl)-3-methyl-2-oxo-2,3-dihydro-1H-benzimidazol-5-yl]-4-methoxybenzonitrile | LRMS m/z (M + H) 350.0 found, 350.4 required. |

-continued

Table 1 for Scheme 1

| Cmp | Structure | Name | LRMS m/z (M + H) |
|---|---|---|---|
| 1-193 | 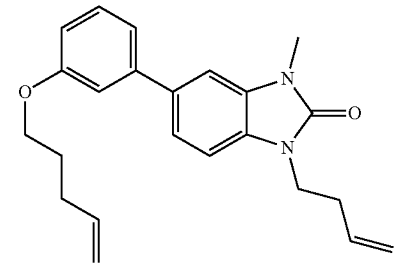 [SMILES: C=CCCCOc1cccc(-c2ccc3c(c2)n(C)c(=O)n3CCC=C)c1] | 1-but-3-en-1-yl-3-methyl-5-[3-(pent-4-en-1-yloxy)phenyl]-1,3-dihydro-2H-benzimidazol-2-one | LRMS m/z (M + H) 363.1 found, 363.5 required. |
| 1-194 | 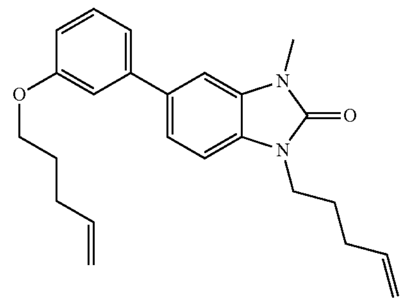 [SMILES: C=CCCCOc1cccc(-c2ccc3c(c2)n(C)c(=O)n3CCCC=C)c1] | 3-methyl-1-pent-4-en-1-yl-5-[3-(pent-4-en-1-yloxy)phenyl]-1,3-dihydro-2H-benzimidazol-2-one | LRMS m/z (M + H) 377.2 found, 377.5 required. |
| 1-195 | 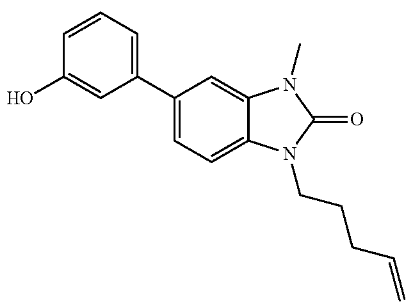 [SMILES: C=CCCCn1c(=O)n(C)c2cc(-c3cccc(O)c3)ccc21] | 5-(3-hydroxyphenyl)-3-methyl-1-pent-4-en-1-yl-1,3-dihydro-2H-benzimidazol-2-one | LRMS m/z (M + H) 309.1 found, 309.4 required. |
| 1-196 | 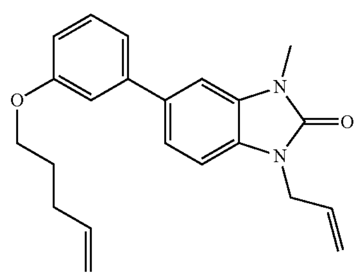 [SMILES: C=CCCCOc1cccc(-c2ccc3c(c2)n(C)c(=O)n3CC=C)c1] | 1-allyl-3-methyl-5-[3-(pent-4-en-1-yloxy)phenyl]-1,3-dihydro-2H-benzimidazol-2-one | LRMS m/z (M + H) 349.1 found, 349.5 required. |
| 1-197 | 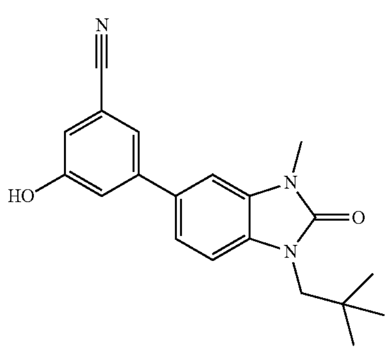 [SMILES: Cn1c(=O)n(CC(C)(C)C)c2ccc(-c3cc(O)cc(C#N)c3)cc21] | 3-[1-(2,2-dimethylpropyl)-3-methyl-2-oxo-2,3-dihydro-1H-benzimidazol-5-yl]-5-hydroxybenzonitrile | LRMS m/z (M + H) 336.1 found, 336.4 required. |

-continued

Table 1 for Scheme 1

| Cmp | Structure | Name | LRMS m/z (M + H) |
|---|---|---|---|
| 1-198 | 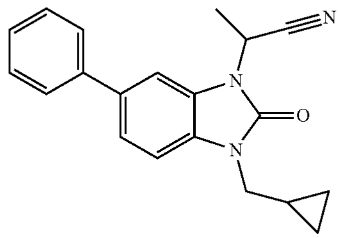 [SMILES: CC(C#N)n1c(=O)n(CC2CC2)c2ccc(-c3ccccc3)cc21] | 2-[3-(cyclopropylmethyl)-2-oxo-6-phenyl-2,3-dihydro-1H-benzimidazol-1-yl]propanenitrile | LRMS m/z (M + H) 318.1 found, 318.4 required. |
| 1-199 | 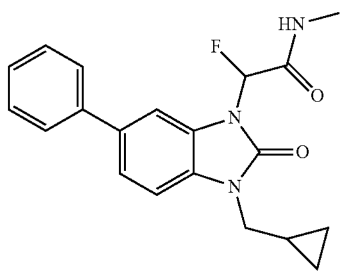 [SMILES: CNC(=O)C(F)n1c(=O)n(CC2CC2)c2ccc(-c3ccccc3)cc21] | 2-[3-(cyclopropylmethyl)-2-oxo-6-phenyl-2,3-dihydro-1H-benzimidazol-1-yl]-2-fluoro-N-methylacetamide | LRMS m/z (M + H) 354.1 found, 354.4 required. |
| 1-200 | 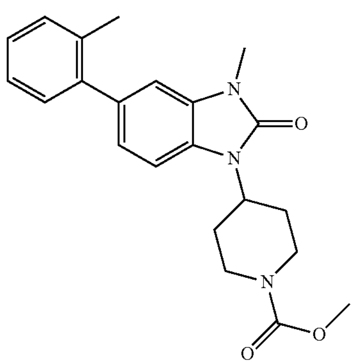 [SMILES: COC(=O)N1CCC(n2c(=O)n(C)c3cc(-c4ccccc4C)ccc32)CC1] | methyl-4-[3-methyl-5-(2-methylphenyl)-2-oxo-2,3-dihydro-1H-benzimidazol-1-yl]piperidine-1-carboxylate | LRMS m/z (M + H) 380.1967 found, 380.1969 required. |
| 1-201 | 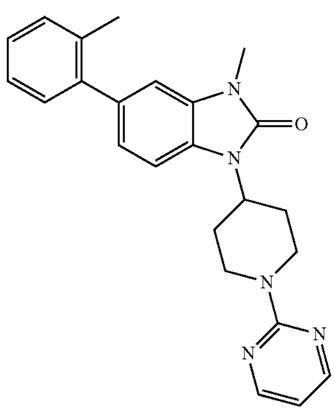 [SMILES: Cc1ccccc1-c1ccc2c(c1)n(C)c(=O)n2C1CCN(c2ncccn2)CC1] | 3-methyl-5-(2-methylphenyl)-1-(1-pyrimidin-2-ylpiperidin-4-yl)-1,3-dihydro-2H-benzimidazol-2-one | LRMS m/z (M + H) 400.3 found, 400.5 required. |

-continued

Table 1 for Scheme 1

| Cmp | Structure | Name | LRMS m/z (M + H) |
|---|---|---|---|
| 1-202 | 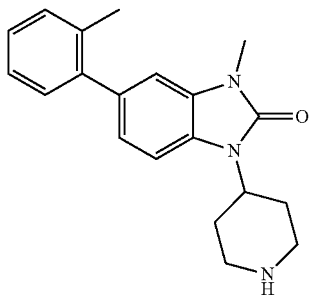 [SMILES: Cc1ccccc1-c1ccc2c(c1)n(C)c(=O)n2C1CCNCC1] | 3-methyl-5-(2-methylphenyl)-1-piperidin-4-yl-1,3-dihydro-2H-benzimidazol-2-one | LRMS m/z (M + H) 322.3 found, 322.4 required. |
| 1-203 | 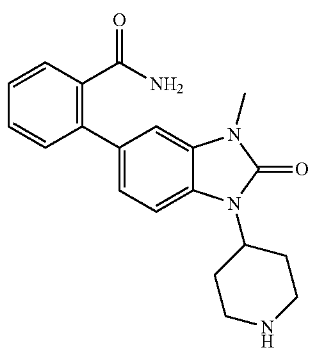 [SMILES: Cn1c(=O)n(C2CCNCC2)c2ccc(-c3ccccc3C(N)=O)cc21] | 2-(3-methyl-2-oxo-1-piperidin-4-yl-2,3-dihydro-1H-benzimidazol-5-yl)benzamide | LRMS m/z (M + H) 351.2 found, 351.4 required. |
| 1-204 | 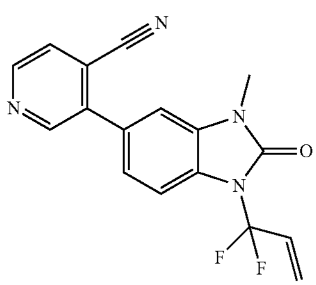 [SMILES: C=CC(F)(F)n1c(=O)n(C)c2cc(-c3cnccc3C#N)ccc21] | 3-[1-(1,1-difluoroprop-2-en-1-yl)-3-methyl-2-oxo-2,3-dihydro-1H-benzimidazol-5-yl]isonicotinonitrile | LRMS m/z (M + H) 327.1046 found, 327.1052 required. |
| 1-205 | 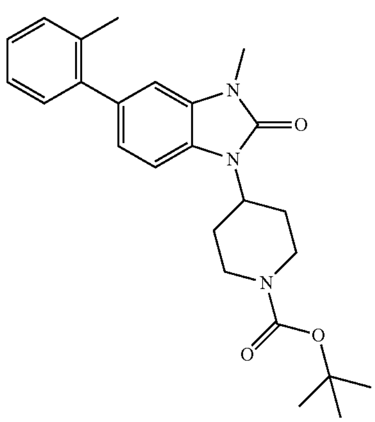 [SMILES: Cc1ccccc1-c1ccc2c(c1)n(C)c(=O)n2C1CCN(C(=O)OC(C)(C)C)CC1] | tert-butyl 4-[3-methyl-5-(2-methylphenyl)-2-oxo-2,3-dihydro-1H-benzimidazol-1-yl]piperidine-1-carboxylate | LRMS m/z (M − 56) 366.3 found, 366.5 required. |

-continued

Table 1 for Scheme 1

| Cmp | Structure | Name | LRMS m/z (M + H) |
|---|---|---|---|
| 1-206 | 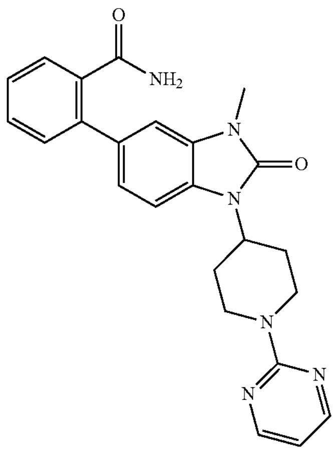 [SMILES: Cn1c(=O)n(C2CCN(c3ncccn3)CC2)c2ccc(-c3ccccc3C(N)=O)cc21] | 2-[3-methyl-2-oxo-1-(1-pyrimidin-2-ylpiperidin-4-yl)-2,3-dihydro-1H-benzimidazol-5-yl]benzamide | LRMS m/z (M + H) 429.3 found, 429.5 required. |

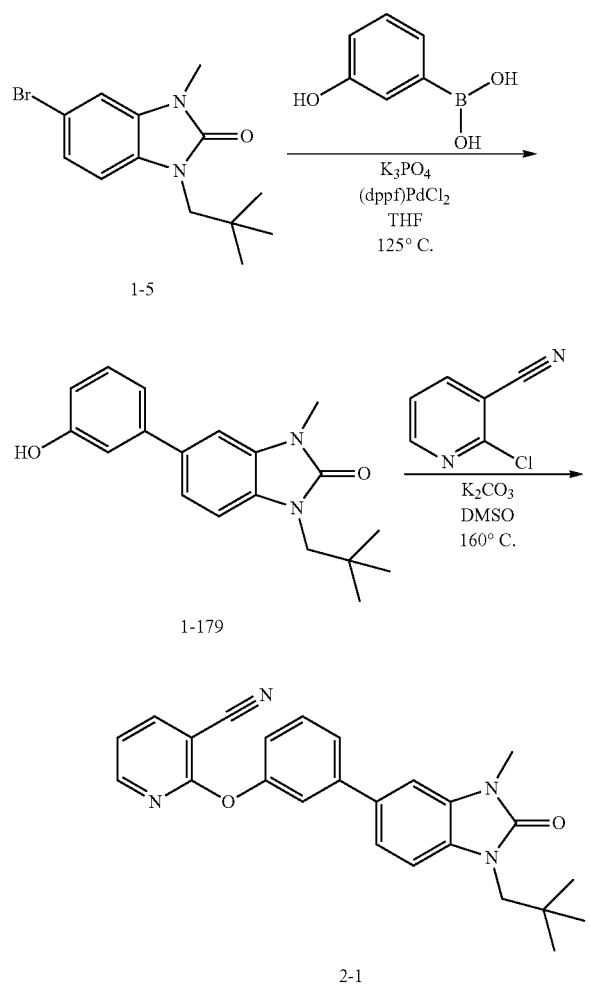

Scheme 2

1-5

1-179

2-1

1-(2,2-dimethylpropyl)-5-(3-hydroxyphenyl)-3-methyl-1,3-dihydro-2H-benzimidazol-2-one (1-179)

A solution of Cesium carbonate (3.66 g, 11.2 mmol, 3.0 eq) in Water (1 ml) was charged with a solution of 5-bromo-1-(2,2-dimethylpropyl)-3-methyl-1,3-dihydro-2H-benzimidazol-2-one (1-5, 1.37 g, 3.74 mmol) dissolved in anhydrous THF (19 ml). 3-Hydroxyphenyl boronic acid was introduced and the solution was deoxygenated. The 1,1'-Bis(diphenylphosphino) ferrocene-palladium(II)dichloride dichloromethane complex (153 mg, 0.19 mmol, 0.05 eq) was introduced and the mixture was irradiated in a microwave at 125 deg C. for 15 min. LC/MS analysis showed ~50% conversion, so more of each reagent was added and the reaction was irradiated again at 120 deg C. for 30 min. The completed reaction was partitioned between EtOAc (2×25 ml) and saturated aqueous $NaHCO_3$ (25 ml), and the combined organic layers were dried over $Na_2SO_4$ and concentrated. The crude product was purified via flash column chromatography ($SiO_2$: 100% Hex to 60:40 EtOAc/Hex), affording 1-(2,2-dimethylpropyl)-5-(3-hydroxyphenyl)-3-methyl-1,3-dihydro-2H-benzimidazol-2-one (1479) as a pink-orange solid. $^1$H NMR (500 MHz, $CDCl_3$) δ 7.34-7.29 (m, 2H), 7.21-7.15 (m, 2H), 7.11-7.06 (m, 2H), 6.81 (d, 1H, J=5.4 Hz), 3.68 (s, 2H), 3.47 (s, 3H), 1.07 (s, 9H). LRMS m/z: Calc'd for $C_{19}H_{22}N_2O_2$ (M+H) 311.4, found 311.1.

2-{3-[1-(2,2-dimethylpropyl)-3-methyl-2-oxo-2,3-dihydro-1H-benzimidazol-5-yl]phenoxy}nicotinonitrile (2-1)

A solution of 1-(2,2-dimethylpropyl)-5-(3-hydroxyphenyl)-3-methyl-1,3-dihydro-2H-benzimidazol-2-one (1-179, 23 mg, 0.07 mmol) in DMSO (2 ml) was charged with Potassium carbonate (20.5 mg, 0.15 mmol, 2.0 eq) and 2-Chloro-3-cyanopyridine (15.4 mg, 0.11 mmol, 1.5 eq). The mixture was irradiated in a microwave at 160 deg C. for 20 min. The resulting dark mixture was purified via reverse-phase HPLC (Acetonitrile/Water gradient with 0.1% TFA present), providing the title compound, 2-{3-[1-(2,2-dimethylpropyl)-3-methyl-2-oxo-2,3-dihydro-1H-benzimidazol-5-yl]phenoxy} nicotinonitrile (2-1), as a tan solid-oil. $^1$H NMR (400 MHz, CDCl$_3$) δ 8.34 (d, 1H, J=3.3 Hz), 8.03 (d, 1H, J=5.9 Hz), 7.51-7.50 (m, 2H), 7.42 (s, 1H), 7.32 (d, 1H, J=8.2 Hz), 7.20-7.17 (m, 2H), 7.13-7.09 (m, 2H), 3.70 (s, 2H), 3.49 (s, 3H), 1.06 (s, 9H). LRMS m/z: Calc'd for C$_{25}$H$_{24}$N$_4$O$_2$(M+H) 413.4, found 413.2.

Table 1 for Scheme 2

| Cmp | Structure | Name | LRMS m/z (M + H) |
|---|---|---|---|
| 2-2 | 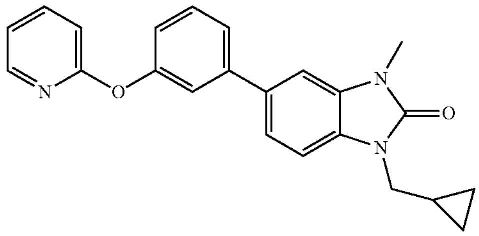 [SMILES: Cn1c(=O)n(CC2CC2)c2ccc(-c3cccc(Oc4ccccn4)c3)cc21] | 1-(cyclopropylmethyl)-3-methyl-5-[3-(pyridin-2-yloxy)phenyl]-1,3-dihydro-2H-benzimidazol-2-one | LRMS m/z (M + H) 372.2 found, 372.4 required. |
| 2-3 | 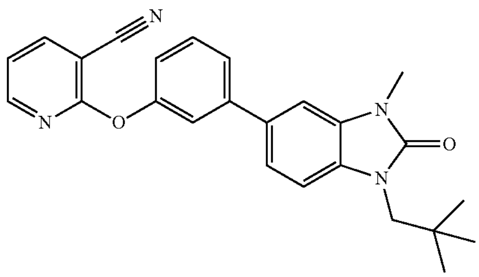 [SMILES: Cn1c(=O)n(CC(C)(C)C)c2ccc(-c3cccc(Oc4ncccc4C#N)c3)cc21] | 2-{3-[1-(2,2-dimethylpropyl)-3-methyl-2-oxo-2,3-dihydro-1H-benzimidazol-5-yl]phenoxy}nicotinonitrile | LRMS m/z (M + H) 413.2 found, 413.5 required. |
| 2-4 | 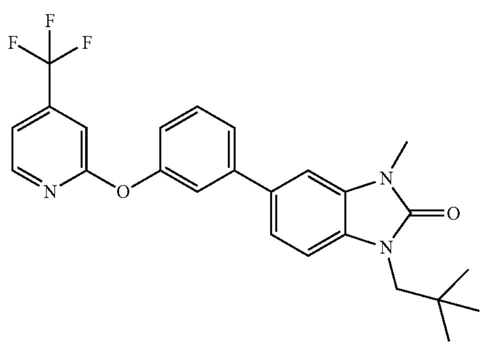 [SMILES: Cn1c(=O)n(CC(C)(C)C)c2ccc(-c3cccc(Oc4cc(C(F)(F)F)ccn4)c3)cc21] | 1-(2,2-dimethylpropyl)-3-methyl-5-(3-{[4-(trifluoromethyl)pyridin-2-yl]oxy}phenyl)-1,3-dihydro-2H-benzimidazol-2-one | LRMS m/z (M + H) 456.3 found, 456.5 required. |
| 2-5 | 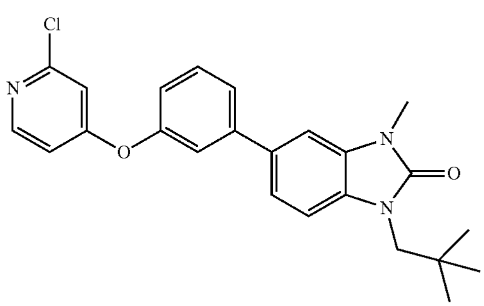 [SMILES: Cn1c(=O)n(CC(C)(C)C)c2ccc(-c3cccc(Oc4ccnc(Cl)c4)c3)cc21] | 5-(3-[(2-chloropyridin-4-yl)oxy]phenyl}-1-(2,2-dimethylpropyl)-3-methyl-1,3-dihydro-2H-benzimidazol-2-one | LRMS m/z (M + H) 422.2 found, 422.9 required. |
| 2-6 | 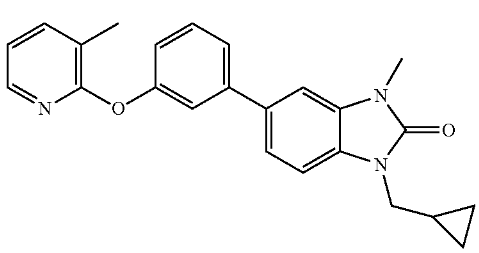 [SMILES: Cc1cccnc1Oc1cccc(-c2ccc3c(c2)n(C)c(=O)n3CC2CC2)c1] | 1-(cyclopropylmethyl)-3-methyl-5-{3-[(3-methylpyridin-2-yl)oxy]phenyl}-1,3-dihydro-2H-benzimidazol-2-one | LRMS m/z (M + H) 386.2 found, 386.5 required. |

-continued

Table 1 for Scheme 2

| Cmp | Structure | Name | LRMS m/z (M + H) |
|---|---|---|---|
| 2-7 | 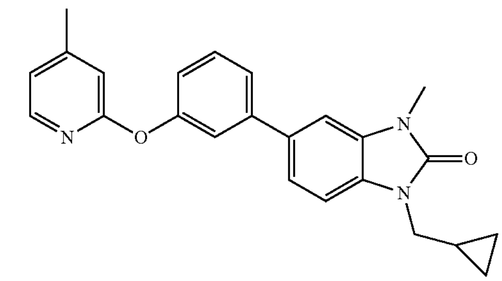 [SMILES: Cc1ccnc(Oc2cccc(-c3ccc4c(c3)n(C)c(=O)n4CC3CC3)c2)c1] | 1-(cyclopropylmethyl)-3-methyl-5-{3-[(4-methylpyridin-2-yl)oxy]phenyl}-1,3-dihydro-2H-benzimidazol-2-one | LRMS m/z (M + H) 386.2 found, 386.5 required. |
| 2-8 | 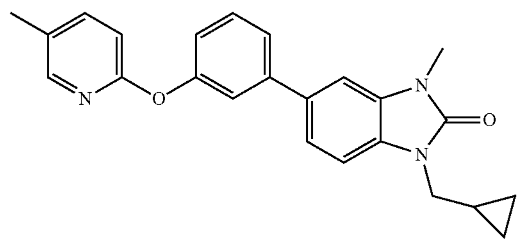 [SMILES: Cc1ccc(Oc2cccc(-c3ccc4c(c3)n(C)c(=O)n4CC3CC3)c2)nc1] | 1-(cyclopropylmethyl)-3-methyl-5-{3-[(5-methylpyridin-2-yl)oxy]phenyl}-1,3-dihydro-2H-benzimidazol-2-one | LRMS m/z (M + H) 386.2 found, 386.5 required. |
| 2-9 | 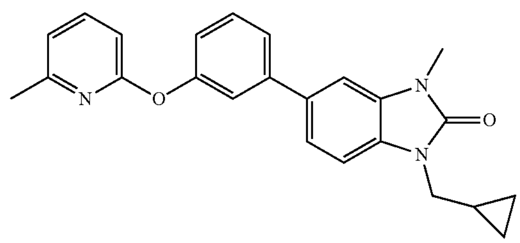 [SMILES: Cc1cccc(Oc2cccc(-c3ccc4c(c3)n(C)c(=O)n4CC3CC3)c2)n1] | 1-(cyclopropylmethyl)-3-methyl-5-{3-[(6-methylpyridin-2-yl)oxy]phenyl}-1,3-dihydro-2H-benzimidazol-2-one | LRMS m/z (M + H) 3862 found, 386.5 required. |
| 2-10 | 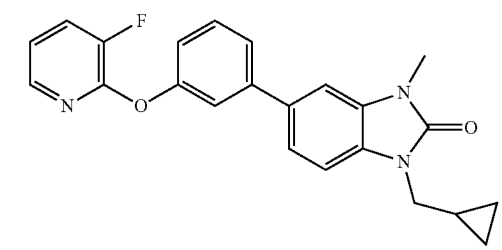 [SMILES: Cn1c(=O)n(CC2CC2)c2ccc(-c3cccc(Oc4ncccc4F)c3)cc21] | 1-(cyclopropylmethyl)-5-{3-[(3-fluoropyridin-2-yl)oxy]phenyl}-3-methyl-1,3-dihydro-2H-benzimidazol-2-one | LRMS m/z (M + H) 390.2 found, 390.4 required. |
| 2-11 | 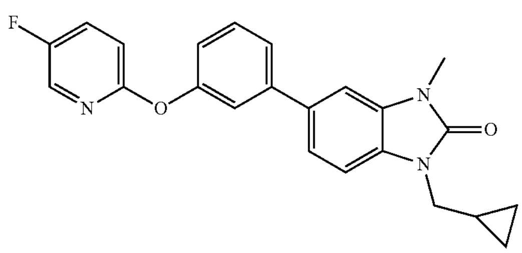 [SMILES: Cn1c(=O)n(CC2CC2)c2ccc(-c3cccc(Oc4ccc(F)cn4)c3)cc21] | 1-(cyclopropylmethyl)-5-{3-[(5-fluoropyridin-2-yl)oxy]phenyl}-3-methyl-1,3-dihydro-2H-benzimidazol-2-one | LRMS m/z (M + H) 390.1 found, 390.4 required. |
| 2-12 | 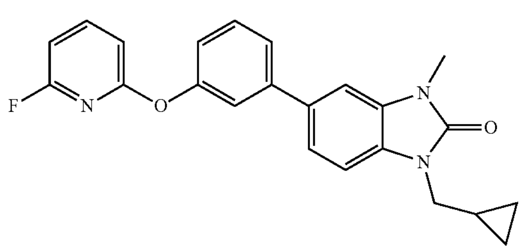 [SMILES: Cn1c(=O)n(CC2CC2)c2ccc(-c3cccc(Oc4cccc(F)n4)c3)cc21] | 1-(cyclopropylmethyl)-5-{3-[(6-fluoropyridin-2-yl)oxy]phenyl}-3-methyl-1,3-dihydro-2H-benzimidazol-2-one | LRMS m/z (M + H) 390.1 found, 390.4 required. |

-continued

Table 1 for Scheme 2

| Cmp | Structure | Name | LRMS m/z (M + H) |
| --- | --- | --- | --- |
| 2-13 | 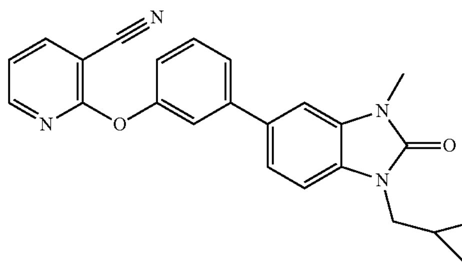 | 2-{3-[1-(cyclopropylmethyl)-3-methyl-2-oxo-2,3-dihydro-1H-benzimidazol-5-yl]phenoxy}nicotinonitrile | LRMS m/z (M + H) 397.2 found, 397.5 required. |
| 2-14 | 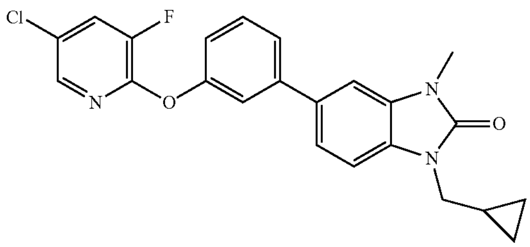 [SMILES: Cn1c(=O)n(CC2CC2)c2ccc(-c3cccc(Oc4ncc(Cl)cc4F)c3)cc21] | 5-{3-[(5-chloro-3-fluoropyridin-2-yl)oxy]phenyl}-1-(cyclopropylmethyl)-3-methyl-1,3-dihydro-2H-benzimidazol-2-one | LRMS m/z (M + H) 424.1 found, 424.9 required. |
| 2-15 | 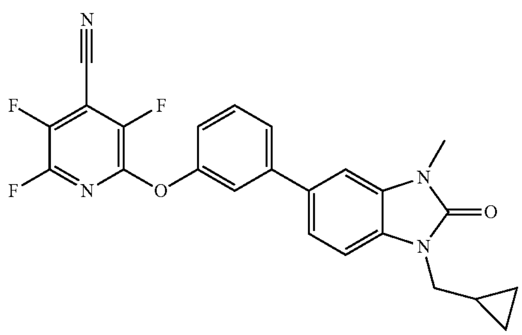 [SMILES: Cn1c(=O)n(CC2CC2)c2ccc(-c3cccc(Oc4nc(F)c(F)c(C#N)c4F)c3)cc21] | 2-{3-[1-(cyclopropylmethyl)-3-methyl-2-oxo-2,3-dihydro-1H-benzimidazol-5-yl]phenoxy}-3,5,6-trifluoroisonicotinonitrile | LRMS m/z (M + H) 451.1 found, 451.4 required. |
| 2-16 | 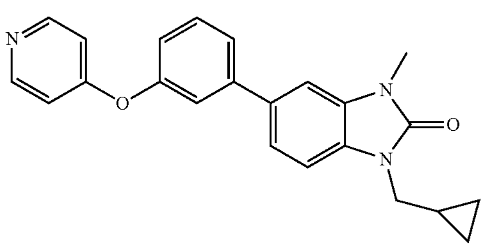 [SMILES: Cn1c(=O)n(CC2CC2)c2ccc(-c3cccc(Oc4ccncc4)c3)cc21] | 1-(cyclopropylmethyl)-3-methyl-5-[3-(pyridin-4-yloxy)phenyl]-1,3-dihydro-2H-benzimidazol-2-one | LRMS m/z (M + H) 371.2 found, 372.4 required. |
| 2-17 | 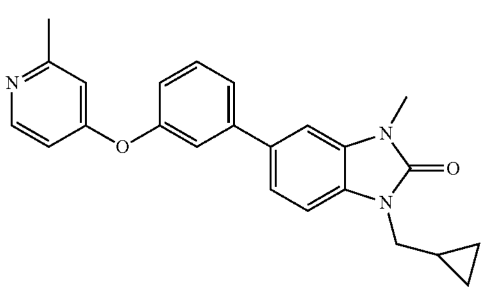 [SMILES: Cc1cc(Oc2cccc(-c3ccc4c(c3)n(C)c(=O)n4CC3CC3)c2)ccn1] | 1-(cyclopropylmethyl)-3-methyl-5-{3-[(2-methylpyridin-4-yl)oxy]phenyl}-1,3-dihydro-2H-benzimidazol-2-one | LRMS m/z (M + H) 386.2 found, 386.5 required. |

-continued

Table 1 for Scheme 2

| Cmp | Structure | Name | LRMS m/z (M + H) |
|---|---|---|---|
| 2-18 | 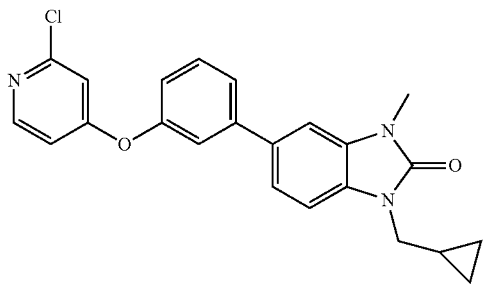 [SMILES: Cn1c(=O)n(CC2CC2)c2ccc(-c3cccc(Oc4ccnc(Cl)c4)c3)cc21] | 5-{3-[(2-chloropyridin-4-yl)oxy]phenyl}-1-(cyclopropylmethyl)-3-methyl-1,3-dihydro-2H-benzimidazol-2-one | LRMS m/z (M + H) 406.1 found, 406.5 required. |
| 2-19 | 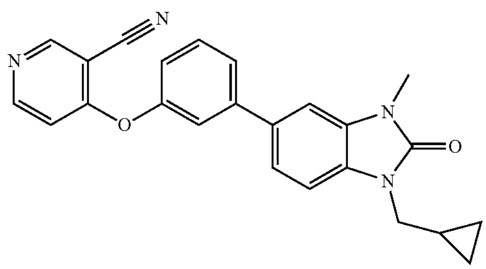 [SMILES: Cn1c(=O)n(CC2CC2)c2ccc(-c3cccc(Oc4ccncc4C#N)c3)cc21] | 4-{3-[1-(cyclopropylmethyl)-3-methyl-2-oxo-2,3-dihydro-1H-benzimidazol-5-yl]phenoxy}nicotinonitrile | LRMS m/z (M + H) 397.2 found, 397.5 required. |
| 2-20 | 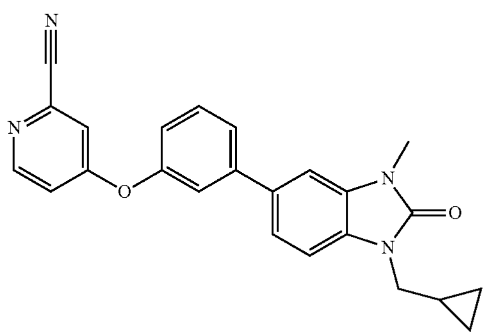 [SMILES: Cn1c(=O)n(CC2CC2)c2ccc(-c3cccc(Oc4ccnc(C#N)c4)c3)cc21] | 4-{3-[1-(cyclopropylmethyl)-3-methyl-2-oxo-2,3-dihydro-1H-benzimidazol-5-yl]phenoxy}pyridine-2-carbonitrile | LRMS m/z (M + H) 397.1 found, 397.5 required. |
| 2-21 | 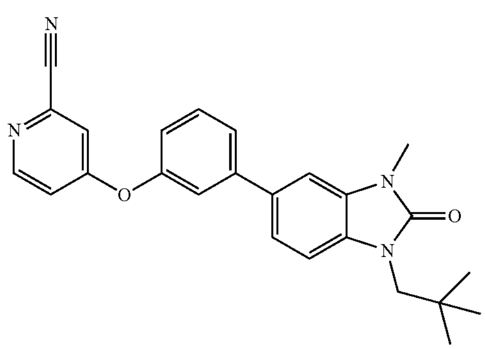 [SMILES: Cn1c(=O)n(CC(C)(C)C)c2ccc(-c3cccc(Oc4ccnc(C#N)c4)c3)cc21] | 4-{3-[1-(2,2-dimethylpropyl)-3-methyl-2-oxo-2,3-dihydro-1H-benzimidazol-5-yl]phenoxy}pyridine-2-carbonitrile | LRMS m/z (M + H) 413.2 found, 413.5 required. |
| 2-22 | 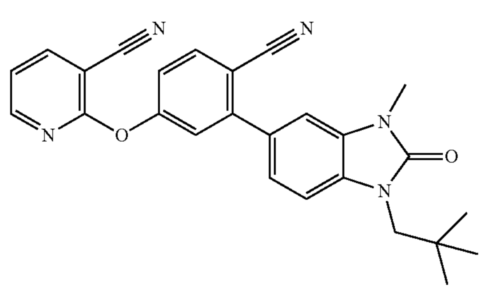 [SMILES: Cn1c(=O)n(CC(C)(C)C)c2ccc(-c3cc(Oc4ncccc4C#N)ccc3C#N)cc21] | 2-{4-cyano-3-[1-(2,2-dimethylpropyl)-3-methyl-2-oxo-2,3-dihydro-1H-benzimidazol-5-yl]phenoxy}nicotinonitrile | LRMS m/z (M + H) 438.1 found, 438.5 required. |

-continued

Table 1 for Scheme 2

| Cmp | Structure | Name | LRMS m/z (M + H) |
| --- | --- | --- | --- |
| 2-23 | 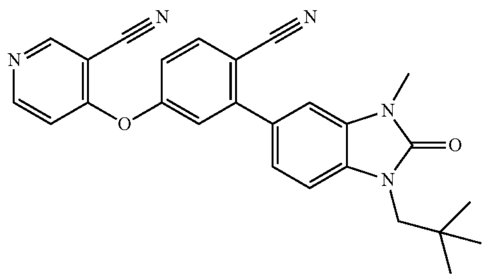 [SMILES: Cn1c(=O)n(CC(C)(C)C)c2ccc(-c3cc(Oc4ccncc4C#N)ccc3C#N)cc21] | 4-{4-cyano-3-[1-(2,2-dimethylpropyl)-3-methyl-2-oxo-2,3-dihydro-1H-benzimidazol-5-yl]phenoxy}nicotinonitrile | LRMS m/z (M + H) 438.1 found, 438.5 required. |
| 2-24 | 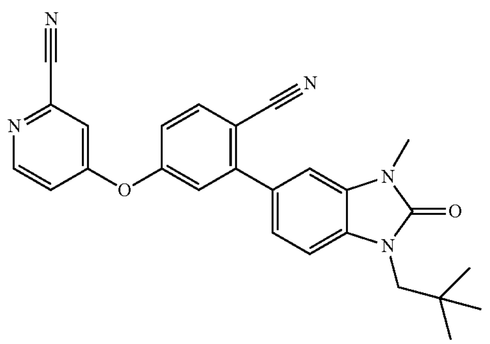 [SMILES: Cn1c(=O)n(CC(C)(C)C)c2ccc(-c3cc(Oc4ccnc(C#N)c4)ccc3C#N)cc21] | 4-{4-cyano-3-[1-(2,2-dimethylpropyl)-3-methyl-2-oxo-2,3-dihydro-1H-benzimidazol-5-yl]phenoxy}pyridine-2-carbonitrile | LRMS m/z (M + H) 438.1 found, 438.5 required. |
| 2-25 | 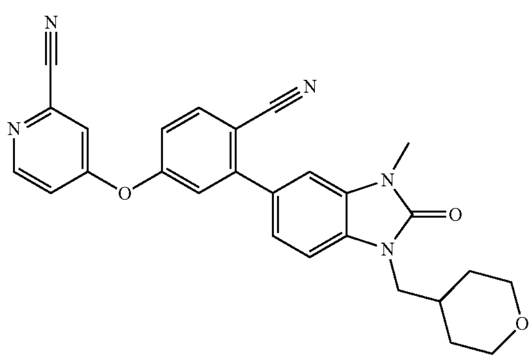 [SMILES: Cn1c(=O)n(CC2CCOCC2)c2ccc(-c3cc(Oc4ccnc(C#N)c4)ccc3C#N)cc21] | 4-{4-cyano-3-[3-methyl-2-oxo-1-(tetrahydro-2H-pyran-4-ylmethyl)-2,3-dihydro-1H-benzimidazol-5-yl]phenoxy}pyridine-2-carbonitrile | LRMS m/z (M + H) 466.2 found, 466.5 required. |
| 2-26 | 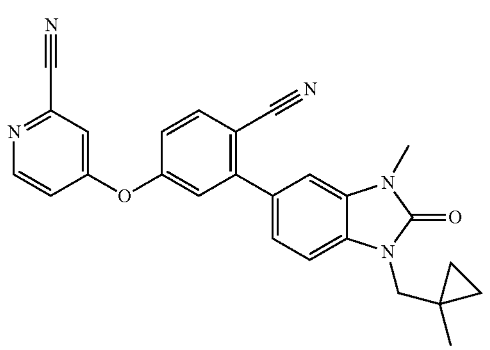 [SMILES: Cn1c(=O)n(CC2(C)CC2)c2ccc(-c3cc(Oc4ccnc(C#N)c4)ccc3C#N)cc21] | 4-(4-cyano-3-{3-methyl-1-[(1-methylcyclopropyl)methyl]-2-oxo-2,3-dihydro-1H-benzimidazol-5-yl}phenoxy)pyridine-2-carbonitrile | LRMS m/z (M + H) 436.2 found, 436.5 required. |

-continued

Table 1 for Scheme 2

| Cmp | Structure | Name | LRMS m/z (M + H) |
| --- | --- | --- | --- |
| 2-27 | 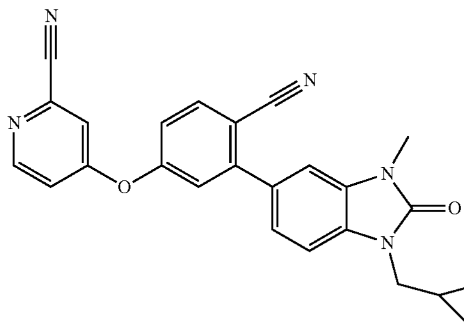 | 4-{4-cyano-3-[1-(cyclopropylmethyl)-3-methyl-2-oxo-2,3-dihydro-1H-benzimidazol-5-yl]phenoxy}pyridine-2-carbonitrile | LRMS m/z (M + H) 422.1 found, 422.5 required. |
| 2-28 | 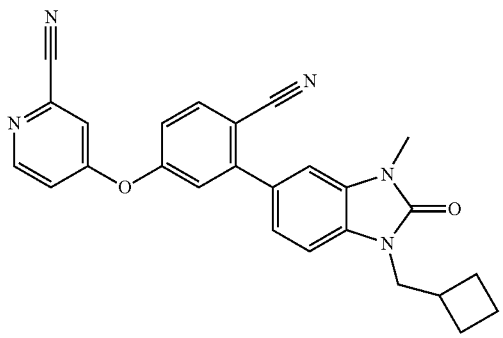 [SMILES: Cn1c(=O)n(CC2CCC2)c2ccc(-c3cc(Oc4ccnc(C#N)c4)ccc3C#N)cc21] | 4-{4-cyano-3-[1-(cyclobutylmethyl)-3-methyl-2-oxo-2,3-dihydro-1H-benzimidazol-5-yl]phenoxy}pyridine-2-carbonitrile | LRMS m/z (M + H) 436.2 found, 436.5 required. |
| 2-29 | 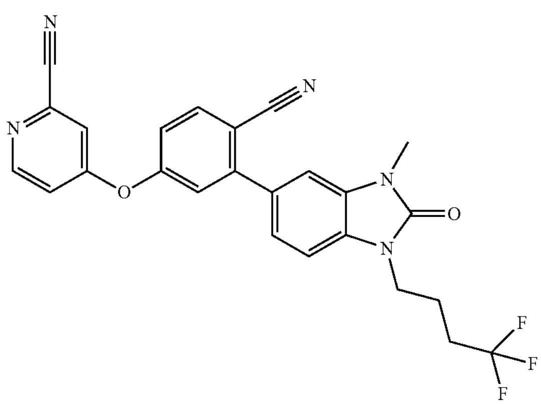 [SMILES: Cn1c(=O)n(CCCC(F)(F)F)c2ccc(-c3cc(Oc4ccnc(C#N)c4)ccc3C#N)cc21] | 4-{4-cyano-3-[3-methyl-2-oxo-1-(4,4,4-trifluorobutyl)-2,3-dihydro-1H-benzimidazol-5-yl]phenoxy}pyridine-2-carbonitrile | LRMS m/z (M + H) 478.1 found, 478.5 required. |
| 2-30 | 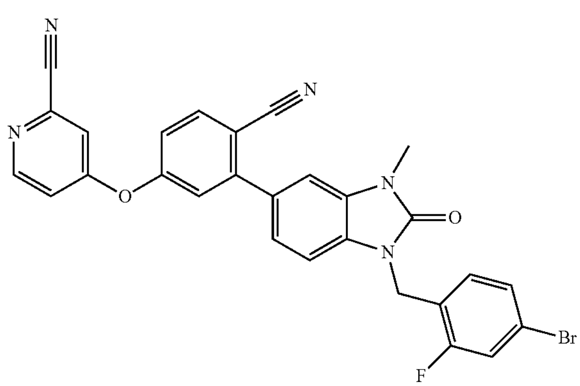 [SMILES: Cn1c(=O)n(Cc2ccc(Br)cc2F)c2ccc(-c3cc(Oc4ccnc(C#N)c4)ccc3C#N)cc21] | 4-{3-[1-(4-bromo-2-fluorobenzyl)-3-methyl-2-oxo-2,3-dihydro-1H-benzimidazol-5-yl]-4-cyanophenoxy}pyridine-2-carbonitrile | LRMS m/z (M + H) 555.1 found, 555.4 required. |

-continued

Table 1 for Scheme 2

| Cmp | Structure | Name | LRMS m/z (M + H) |
|---|---|---|---|
| 2-31 | 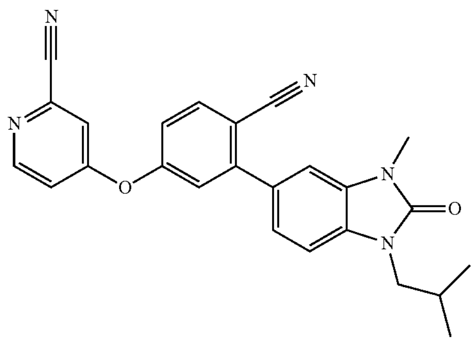 [SMILES: CC(C)Cn1c(=O)n(C)c2cc(-c3cc(Oc4ccnc(C#N)c4)ccc3C#N)ccc21] | 4-[4-cyano-3-(1-isobutyl-3-methyl-2-oxo-2,3-dihydro-1H-benzimidazol-5-yl)phenoxy]pyridine-2-carbonitrile | LRMS m/z (M + H) 424.2 found, 424.5 required. |
| 2-32 | 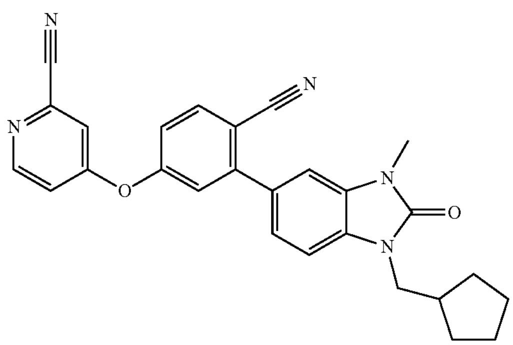 [SMILES: Cn1c(=O)n(CC2CCCC2)c2ccc(-c3cc(Oc4ccnc(C#N)c4)ccc3C#N)cc21] | 4-{4-cyano-3-[1-(cyclopentylmethyl)-3-methyl-2-oxo-2,3-dihydro-1H-benzimidazol-5-yl]phenoxy}pyridine-2-carbonitrile | LRMS m/z (M + H) 450.2 found, 450.5 required. |
| 2-33 | 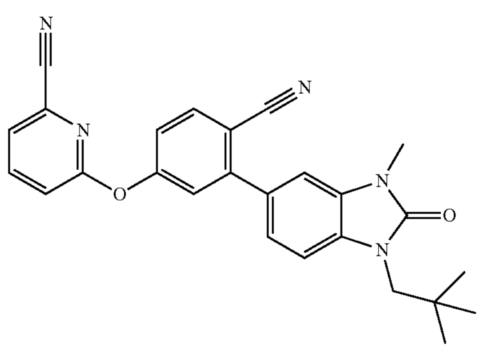 [SMILES: Cn1c(=O)n(CC(C)(C)C)c2ccc(-c3cc(Oc4cccc(C#N)n4)ccc3C#N)cc21] | 6-{4-cyano-3-[1-(2,2-dimethylpropyl)-3-methyl-2-oxo-2,3-dihydro-1H-benzimidazol-5-yl]phenoxy}pyridine-2-carbonitrile | LRMS m/z (M + H) 438.1 found, 438.5 required. |
| 2-34 | 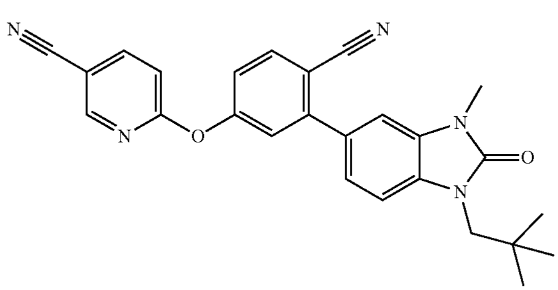 [SMILES: Cn1c(=O)n(CC(C)(C)C)c2ccc(-c3cc(Oc4ccc(C#N)cn4)ccc3C#N)cc21] | 6-{4-cyano-3-[1-(2,2-dimethylpropyl)-3-methyl-2-oxo-2,3-dihydro-1H-benzimidazol-5-yl]phenoxy}nicotinonitrile | LRMS m/z (M + H) 438.1 found, 438.5 required. |

-continued

Table 1 for Scheme 2

| Cmp | Structure | Name | LRMS m/z (M + H) |
| --- | --- | --- | --- |
| 2-35 | 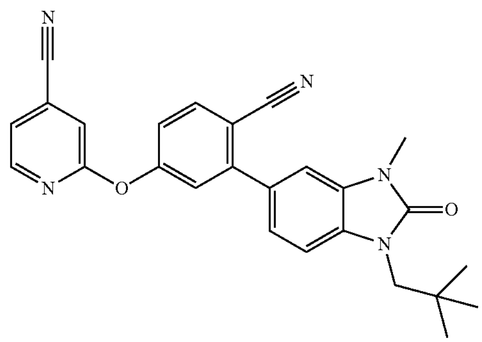 [SMILES: Cn1c(=O)n(CC(C)(C)C)c2ccc(-c3cc(Oc4cc(C#N)ccn4)ccc3C#N)cc21] | 2-{4-cyano-3-[1-(2,2-dimethylpropyl)-3-methyl-2-oxo-2,3-dihydro-1H-benzimidazol-5-yl]phenoxy}isonicotinonitrile | LRMS m/z (M + H) 438.1 found, 438.5 required. |
| 2-36 | 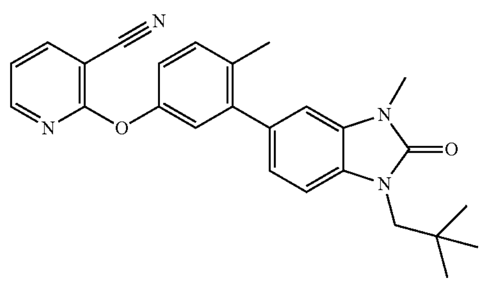 [SMILES: Cc1ccc(Oc2ncccc2C#N)cc1-c1ccc2c(c1)n(C)c(=O)n2CC(C)(C)C] | 2-{3-[1-(2,2-dimethylpropyl)-3-methyl-2-oxo-2,3-dihydro-1H-benzimidazol-5-yl]-4-methylphenoxy}nicotinonitrile | LRMS m/z (M + H) 427.1 found, 427.5 required. |
| 2-37 | 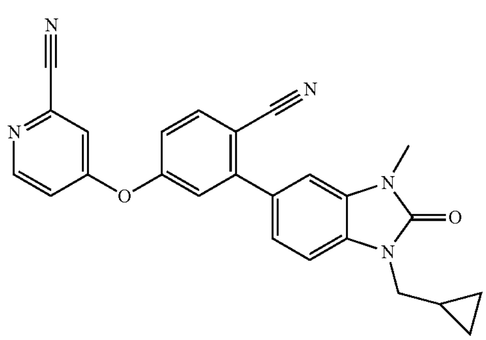 [SMILES: Cn1c(=O)n(CC2CC2)c2ccc(-c3cc(Oc4ccnc(C#N)c4)ccc3C#N)cc21] | 4-{4-cyano-3-[1-(cyclopropylmethyl)-3-methyl-2-oxo-2,3-dihydro-1H-benzimidazol-5-yl]phenoxy}pyridine-2-carbonitrile | LRMS m/z (M + H) 422.0 found, 422.5 required. |
| 2-38 | 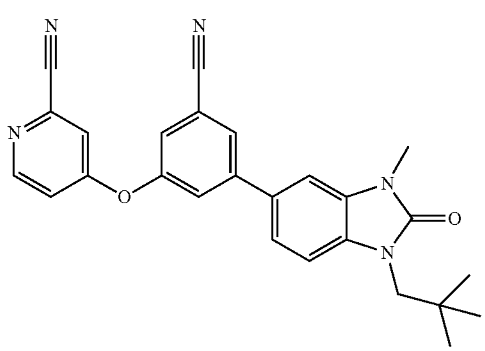 [SMILES: Cn1c(=O)n(CC(C)(C)C)c2ccc(-c3cc(C#N)cc(Oc4ccnc(C#N)c4)c3)cc21] | 4-{3-cyano-5-[1-(2,2-dimethylpropyl)-3-methyl-2-oxo-2,3-dihydro-1H-benzimidazol-5-yl]phenoxy}pyridine-2-carbonitrile | LRMS m/z (M + H) 438.2 found, 438.5 required. |

Scheme 3

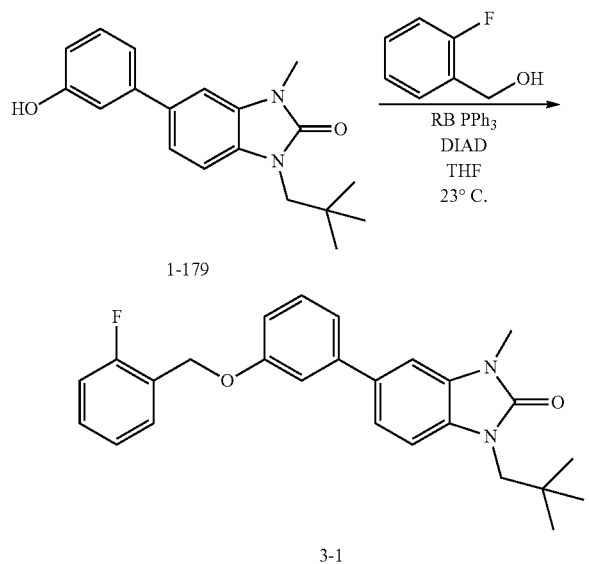

1-(2,2-dimethylpropyl)-5-{3-[(2-fluorobenzyl)oxy]phenyl}-3-methyl-1,3-dihydro-2H-benzimidazol-2-one (3-1)

An orange solution of 1-(2,2-dimethylpropyl)-5-(3-hydroxyphenyl)-3-methyl-1,3-dihydro-2H-benzimidazol-2-one (1-179, 70 mg, 0.23 mmol) in Dichloromethane (10 ml) was treated with polymer bound-Triphenylphosphine (177 mg, 0.68 mmol, 3.0 eq) and the 2-Fluorobenzyl alcohol (56.9 mg, 0.45 mmol, 2.0 eq). The mixture was charged, in portions, with Di-tert-butyl azodicarboxylate (104 mg, 0.45 mmol, 2.0 eq) and the resulting maroon-orange solution was stirred at 23 deg C. for 1 h. The reaction mixture was filtered through a frit and the filtrate was purified via flash column chromatography (SiO$_2$: 100% Hex to 75:25% Hex:EtOAc) to afford the title compound, 1-(2,2-dimethylpropyl)-5-{3-[(2-fluorobenzyl)oxy]phenyl}-3-methyl-1,3-dihydro-2H-benzimidazol-2-one (3-1), as an orange oil. $^1$H NMR (400 MHz, CDCl$_3$) δ 7.55 (t, 1H, J=7.0 Hz), 7.38-7.26 (m, 3H), 7.22-7.15 (m, 3H), 7.13-7.06 (m, 3H), 6.97 (d, 1H, J=7.1 Hz), 5.21 (s, 2H), 3.68 (s, 2H), 3.47 (s, 3H), 1.06 (s, 9H). LRMS m/z: Calc'd for C$_{26}$H$_{27}$FN$_2$O$_2$ (M+H) 419.2, found 419.3.

Table for Scheme 3

| Cmp | Structure | Name | LRMS m/z (M + H) |
| --- | --- | --- | --- |
| 3-2 | 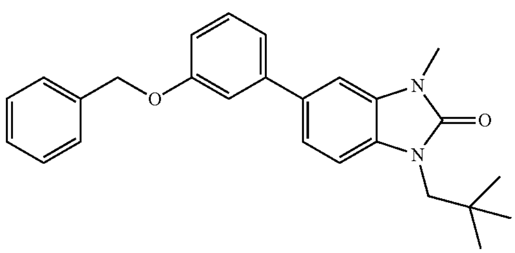 [SMILES: Cn1c(=O)n(CC(C)(C)C)c2ccc(-c3cccc(OCc4ccccc4)c3)cc21] | 5-[3-(benzyloxy)phenyl]-1-(2,2-dimethylpropyl)-3-methyl-1,3-dihydro-2H-benzimidazol-2-one | LRMS m/z (M + H) 401.3 found, 401.5 required. |
| 3-3 | 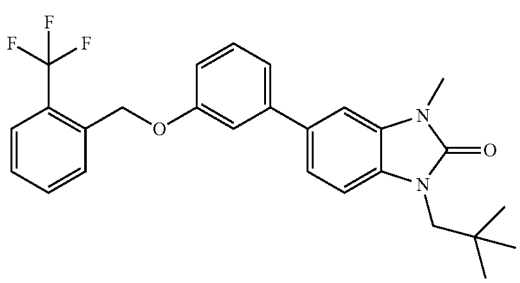 [SMILES: Cn1c(=O)n(CC(C)(C)C)c2ccc(-c3cccc(OCc4ccccc4C(F)(F)F)c3)cc21] | 1-(2,2-dimethylpropyl)-3-methyl-5-(3-{[2-(trifluoromethyl)benzyl]oxy}phenyl)-1,3-dihydro-2H-benzimidazol-2-one | LRMS m/z (M + H) 469.3 found, 469.5 required. |
| 3-4 | 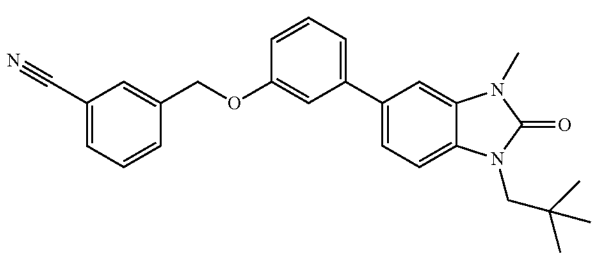 [SMILES: Cn1c(=O)n(CC(C)(C)C)c2ccc(-c3cccc(OCc4cccc(C#N)c4)c3)cc21] | 3-({3-[1-(2,2-dimethylpropyl)-3-methyl-2-oxo-2,3-dihydro-1H-benzimidazol-5-yl]phenoxy}methyl)benzonitrile | LRMS m/z (M + H) 426.3 found, 426.5 required. |

Table for Scheme 3

| Cmp | Structure | Name | LRMS m/z (M + H) |
|---|---|---|---|
| 3-5 | 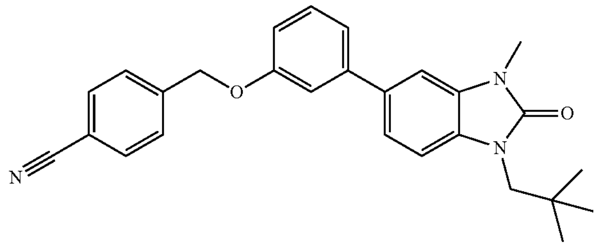 [SMILES: Cn1c(=O)n(CC(C)(C)C)c2ccc(-c3cccc(OCc4ccc(C#N)cc4)c3)cc21] | 4-({3-[1-(2,2-dimethylpropyl)-3-methyl-2-oxo-2,3-dihydro-1H-benzimidazol-5-yl]phenoxy}methyl)benzonitrile | LRMS m/z (M + H) 426.3 found, 426.5 required. |

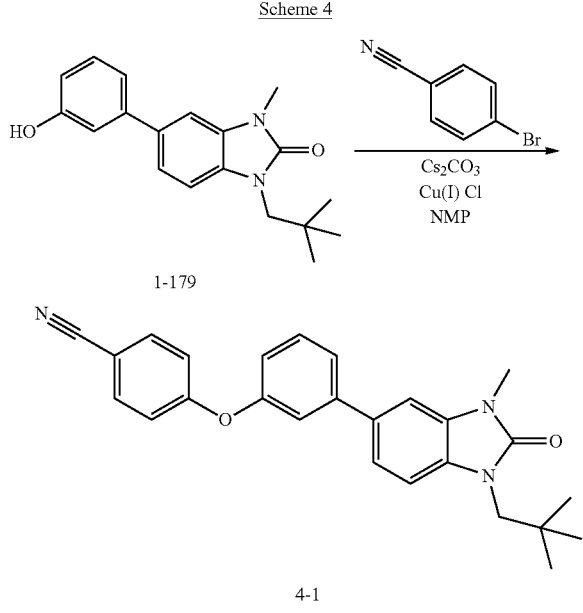

Scheme 4

4-{3-[1-(2,2-dimethylpropyl)-3-methyl-2-oxo-2,3-dihydro-1H-benzimidazol-5-yl]henoxy}benzonitrile (4-1)

A solution of 1-(2,2-dimethylpropyl)-5-(3-hydroxyphenyl)-3-methyl-1,3-dihydro-2H-benzimidazol-2-one (1-179, 70 mg, 0.23 mmol) and Cesium carbonate (73.5 mg, 0.23 mmol, 1.0 eq) in N-Methylpyrrolidine (1 ml) was stirred at 23 deg C. for 45 min. 4-Bromobenzonitrile and Copper (I) Chloride were added and the resulting mixture was irradiated in a microwave at 150 deg C. for 5 min. LC/MS analysis showed very little conversion, so the reaction was capped and heated in an oil bath at 175 deg C. for 16 h. The resulting crude, dark mixture was run through a filter disk, then purified via reverse-phase HPLC (Acetonitrile/Water gradient with 0.1% TFA present), providing 4-{3-[1-(2,2-dimethylpropyl)-3-methyl-2-oxo-2,3-dihydro-1H-benzimidazol-5-yl]phenoxy}benzonitrile (4-1) as a tan solid-oil. $^1$H NMR (400 MHz, CDCl$_3$) δ 7.62 (d, 2H, J=8.7 Hz), 7.48-7.47 (m, 2H), 7.30-7.28 (m, 2H), 7.08 (s, 1H), 7.08-7.02 (m, 4H), 3.69 (s, 2H), 3.47 (s, 3H), 1.06 (s, 9H). LRMS m/z: Calc'd for C$_{26}$H$_{25}$N$_3$O$_2$(M+H) 412.5, found 412.3.

Table 1 for Scheme 4

| Cmp | Structure | Name | LRMS m/z (M + H) |
|---|---|---|---|
| 4-2 | 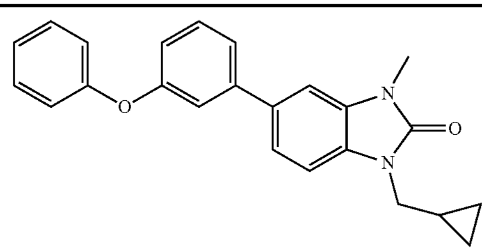 | 1-(cyclopropylmethyl)-3-methyl-5-(3-phenoxyphenyl)-1,3-dihydro-2H-benzimidazol-2-one | LRMS m/z (M + H) 371.2 found, 371.5 required. |
| 4-3 | 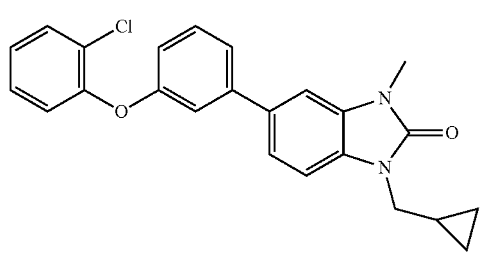 [SMILES: Cn1c(=O)n(CC2CC2)c2ccc(-c3cccc(Oc4ccccc4Cl)c3)cc21] | 5-[3-(2-chlorophenoxy)phenyl]-1-(cyclopropylmethyl)-3-methyl-1,3-dihydro-2H-benzimidazol-2-one | LRMS m/z (M + H) 405.1 found, 405.9 required. |

-continued

Table 1 for Scheme 4

| Cmp | Structure | Name | LRMS m/z (M + H) |
|---|---|---|---|
| 4-4 | 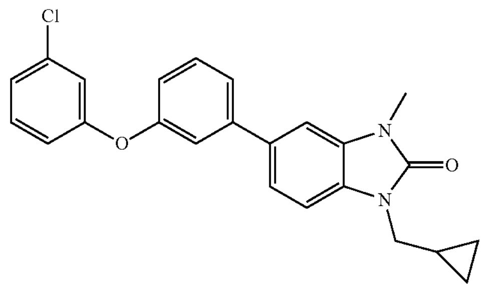 [SMILES: Cn1c(=O)n(CC2CC2)c2ccc(-c3cccc(Oc4cccc(Cl)c4)c3)cc21] | 5-[3-(3-chlorophenoxy)phenyl]-1-(cyclopropylmethyl)-3-methyl-1,3-dihydro-2H-benzimidazol-2-one | LRMS m/z (M + H) 405.1 found, 405.9 required. |
| 4-5 | 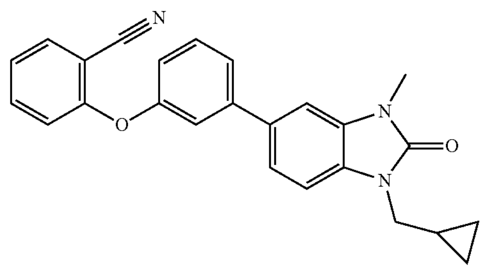 [SMILES: Cn1c(=O)n(CC2CC2)c2ccc(-c3cccc(Oc4ccccc4C#N)c3)cc21] | 2-{3-[1-(cyclopropylmethyl)-3-methyl-2-oxo-2,3-dihydro-1H-benzimidazol-5-yl]phenoxy}benzonitrile | LRMS m/z (M + H) 396.2 found, 396.5 required. |
| 4-6 | 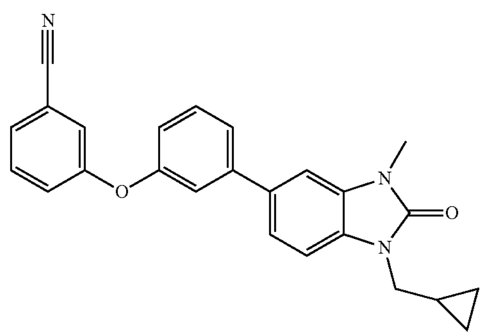 [SMILES: Cn1c(=O)n(CC2CC2)c2ccc(-c3cccc(Oc4cccc(C#N)c4)c3)cc21] | 3-{3-[1-(cyclopropylmethyl)-3-methyl-2-oxo-2,3-dihydro-1H-benzimidazol-5-yl]phenoxy}benzonitrile | LRMS m/z (M + H) 396.2 found, 396.5 required. |
| 4-7 | 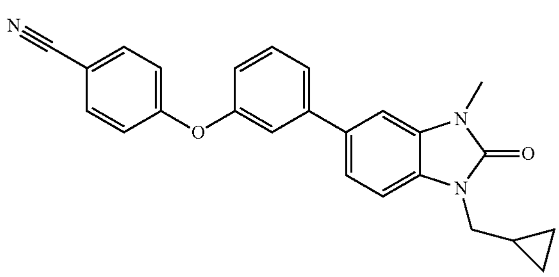 [SMILES: Cn1c(=O)n(CC2CC2)c2ccc(-c3cccc(Oc4ccc(C#N)cc4)c3)cc21] | 4-{3-[1-(cyclopropylmethyl)-3-methyl-2-oxo-2,3-dihydro-1H-benzimidazol-5-yl]phenoxy}benzonitrile | LRMS m/z (M + H) 396.1 found, 396.5 required. |
| 4-8 | 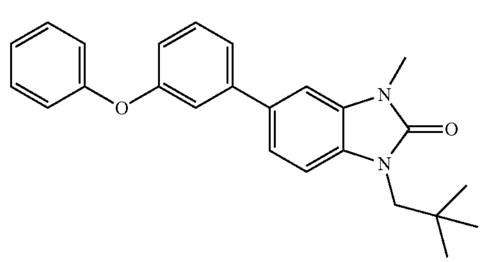 [SMILES: Cn1c(=O)n(CC(C)(C)C)c2ccc(-c3cccc(Oc4ccccc4)c3)cc21] | 1-(2,2-dimethylpropyl)-3-methyl-5-(3-phenoxyphenyl)-1,3-dihydro-2H-benzimidazol-2-one | LRMS m/z (M + H) 387.2 found, 387.5 required. |

Table 1 for Scheme 4

| Cmp | Structure | Name | LRMS m/z (M + H) |
|---|---|---|---|
| 4-9 | 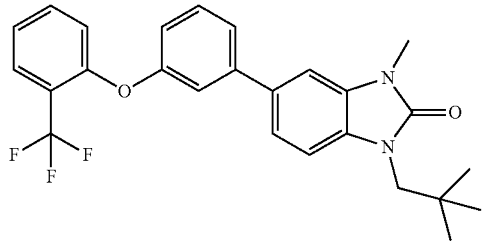 [SMILES: Cn1c(=O)n(CC(C)(C)C)c2ccc(-c3cccc(Oc4ccccc4C(F)(F)F)c3)cc21] | 1-(2,2-dimethylpropyl)-3-methyl-5-{3-[2-(trifluoromethyl)phenoxy]phenyl}-1,3-dihydro-2H-benzimidazol-2-one | LRMS m/z (M + H) 455.3 found, 455.5 required. |

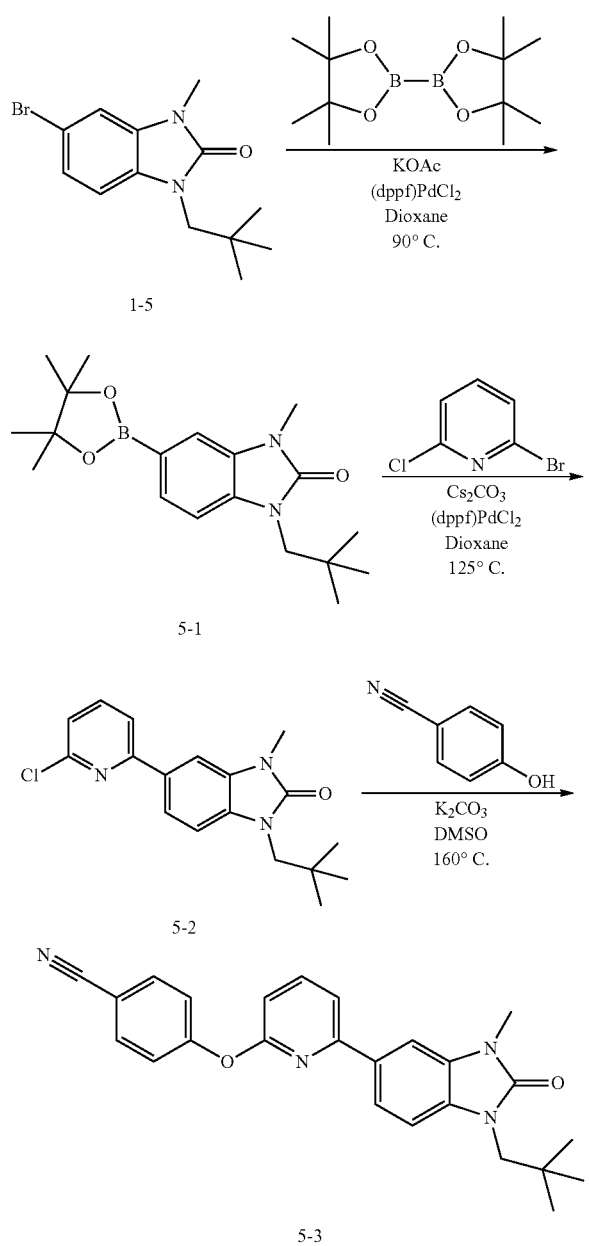

Scheme 5

5-1

5-2

5-3

1-(2,2-dimethylpropyl)-3-methyl-5-(4,4,5,5-tetramethyl-1,3,2-dioxaborolan-2-yl)-1,3-dihydro-2,1-benzimidazol-2-one (5-1)

A solution of 5-bromo-1-(2,2-dimethylpropyl)-3-methyl-1,3-dihydro-2H-benzimidazol-2-one (1-5, 300 mg, 1.01 mmol), Bis(pinacolato)diboron (308 mg, 1.21 mmol, 1.2 eq), and Potassium acetate (297 mg, 3.03 mmol, 3.0 eq) in Dioxane (10 ml) was deoxygenated, then treated with 1,1'-Bis(diphenylphosphino) ferrocene-palladium(II)dichloride dichloromethane complex (41.2 mg, 0.05 mmol, 0.05 eq). The resulting mixture was heated to 90 deg C. and stirred for 15 h. The reaction was partially complete, so an additional amount of bis(pinacoloto)diboron (308 mg, 1.21 mmol, 1.2 eq) and Pd catalyst (41.2 mg, 0.05 mmol, 0.05 eq) was added and the reaction was stirred at 90 deg C. for 16 h. The reaction was diluted with water (70 ml) and the resulting gray solid was filtered and washed with water (25 ml). The solid was then dissolved in EtOAc (70 ml) and the insoluble material was removed by filtration. The resulting orange filtrate was concentrated in vacuo, affording the title compound, 1-(2,2-dimethylpropyl)-3-methyl-5-(4,4,5,5-tetramethyl-1,3,2-dioxaborolan-2-yl)-1,3-dihydro-2H-benzimidazol-2-one (5-1), as a maroon-orange oil. LRMS m/z: Calc'd for $C_{19}H_{29}BN_2O_3$ (M+H) 345.3, found 345.2.

5-(6-chloropyridin-2-yl)-4-(2,2-dimethylpropyl)-3-methyl-1,3-dihydro-2H-benzimidazol-2-one (5-2)

Cesium carbonate (852 mg, 2.61 mmol, 3.0 eq) was added to a solution of 1-(2,2-dimethylpropyl)-3-methyl-5-(4,4,5,5-tetramethyl-1,3,2-dioxaborolan-2-yl)-1,3-dihydro-2H-benzimidazol-2-one (5-1, 300 mg, 0.87 mmol) dissolved in anhydrous Dioxane (5 ml). 2-Chloro-4-hydroxybenzonitrile (335 mg, 1.74 mmol, 2.0 eq) was introduced followed by 1,1'-Bis(diphenylphosphino) ferrocene-palladium(II)dichloride dichloromethane complex (35.6 mg, 0.04 mmol, 0.05 eq). The reaction mixture was irradiated at 125 deg C. for 15 min. The reaction not complete, so more 2-Chloro-4-hydroxybenzonitrile (335 mg, 1.74 mmol, 2.0 eq) and Pd catalyst (35.6 mg, 0.04 mmol, 0.05 eq) was added and the reaction was irradiated again at 150 deg C. for 30 min. The reaction was partitioned between EtOAc (2×100 ml) and saturated aqueous $NaHCO_3$ (90 ml). The combined organic layers were dried over $Na_2SO_4$ and concentrated, and the crude product was purified via flash column chromatography ($SiO_2$: 100% Hex to 60:40 Hex/EtOAc), providing 5-(6-chloropyridin-2-yl)-1-(2,2-dimethylpropyl)-3-methyl-1,3-dihydro-2H-benzimidazol-2-one (5-2) as a yellow. $^1$H NMR (500 MHz, $CDCl_3$) δ 7.70-7.63 (m, 4H), 7.22 (d, 2H, J=6.8 Hz), 7.07 (d, 1H, J=8.3 Hz), 3.69 (s, 2H), 3.50 (s, 3H), 1.05 (s, 9H). LRMS m/z: Calc'd for $C_{18}H_{20}ClN_3O$ (M+H) 330.8, found 330.1.

4-({6-[1-(2,2-dimethylpropyl)-3-methyl-2-oxo-2,3-dihydro-1H-benzimidazol-5-yl]pyridin-2-yl}oxy)benzonitrile (5-3)

A solution of 5-(6-chloropyridin-2-yl)-1-(2,2-dimethylpropyl)-3-methyl-1,3-dihydro-2H-benzimidazol-2-one (5-2, 55 mg, 0.17 mmol) in DMSO (1 ml), was charged with Potassium carbonate (34.6 mg, 0.25 mmol, 1.5 eq) and 4-Cyanophenol (39.7 mg, 0.33 nmol, 2.0 eq), then irradiated in a microwave at 160 deg C. for 20 min. A second addition of Potassium carbonate (34.6 mg, 0.25 mmol, 1.5 eq) and 4-Cyanophenol (39.7 mg, 0.33 mmol, 2.0 eq) was necessary, then the reaction was irradiated again at 160 deg C. for 20 min. The crude, dark mixture was filtered through a fritted disk, then purified via reverse-phase HPLC (Acetonitrile/Water gradient with 0.1% TFA present) to afford the title compound, 4-({6-[1-(2,2-dimethylpropyl)-3-methyl-2-oxo-2,3-dihydro-1H-benzimidazol-5-yl]pyridin-2-yl}oxy)benzonitrile (5-3), as an orange oil. $^1$H NMR (500 MHz, CDCl$_3$) δ 7.80 (t, 1H, J=Hz), 7.71 (d, 2H, J=9.0 Hz), 7.62 (d, 1H, J=7.1 Hz), 7.55 (d, 1H, J=7.3 Hz), 7.51 (s, 1H), 7.34-7.31 (m, 2H), 7.06-7.04 (d, 2H, 8.3 Hz), 6.87 (d, 1H, J=8.1 Hz), 3.68 (s, 2H), 3.44 (s, 3H), 1.04 (s, 9H). LRMS m/z: Calcd for $C_{25}H_{25}N_4O_2$ (M+H) 414.2, found 414.3.

Table 1 for Scheme 5

| Cmp | Structure | Name | LRMS m/z (M + H) |
|---|---|---|---|
| 5-4 | 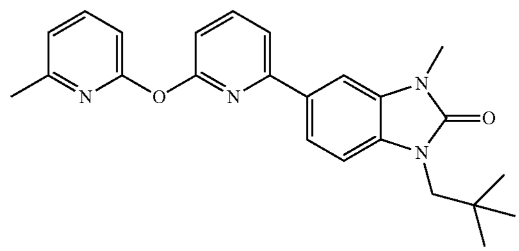 [SMILES: Cc1cccc(Oc2cccc(-c3ccc4c(c3)n(C)c(=O)n4CC(C)(C)C)n2)n1] | 1-(2,2-dimethylpropyl)-3-methyl-5-{6-[(6-methylpyridin-2-yl)oxy]pyridin-2-yl}-1,3-dihydro-2H-benzimidazol-2-one | LRMS m/z (M + H) 403.2 found, 403.5 required. |
| 5-5 | 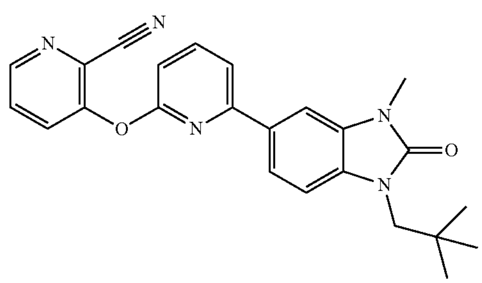 [SMILES: Cn1c(=O)n(CC(C)(C)C)c2ccc(-c3cccc(Oc4cccnc4C#N)n3)cc21] | 3-({6-[1-(2,2-dimethylpropyl)-3-methyl-2-oxo-2,3-dihydro-1H-benzimidazol-5-yl]pyridin-2-yl}oxy)pyridine-2-carbonitrile | LRMS m/z (M + H) 414.2 found, 414.5 required. |
| 5-6 | 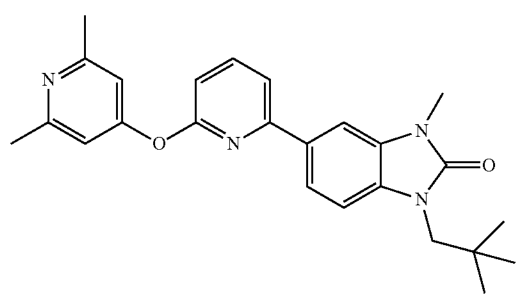 [SMILES: Cc1cc(Oc2cccc(-c3ccc4c(c3)n(C)c(=O)n4CC(C)(C)C)n2)cc(C)n1] | 1-(2,2-dimethylpropyl)-5-{6-[(2,6-dimethylpyridin-4-yl)oxy]pyridin-2-yl}-3-methyl-1,3-dihydro-2H-benzimidazol-2-one | LRMS m/z (M + H) 417.2 found, 417.5 required. |
| 5-7 | 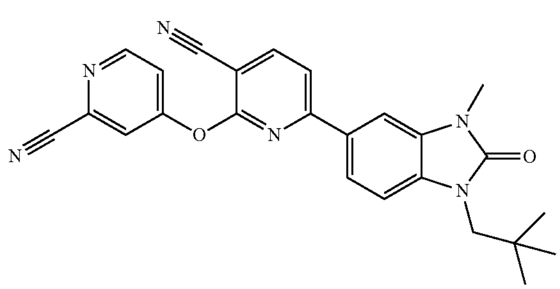 [SMILES: Cn1c(=O)n(CC(C)(C)C)c2ccc(-c3ccc(C#N)c(Oc4ccnc(C#N)c4)n3)cc21] | 4-({3-cyano-6-[1-(2,2-dimethylpropyl)-3-methyl-2-oxo-2,3-dihydro-1H-benzimidazol-5-yl]pyridin-2-yl}oxy)pyridine-2-carbonitrile | LRMS m/z (M + H) 439.1 found, 439.5 required. |

-continued

Table 1 for Scheme 5

| Cmp | Structure | Name | LRMS m/z (M + H) |
| --- | --- | --- | --- |
| 5-8 | 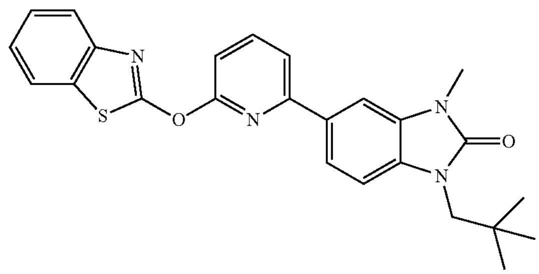 [SMILES: Cn1c(=O)n(CC(C)(C)C)c2ccc(-c3cccc(Oc4nc5ccccc5s4)n3)cc21] | 5-[6-(1,3-benzothiazol-2-yloxy)pyridin-2-yl]-1-(2,2-dimethylpropyl)-3-methyl-1,3-dihydro-2H-benzimidazol-2-one | LRMS m/z (M + H) 445.1 found, 445.6 required. |
| 5-9 | 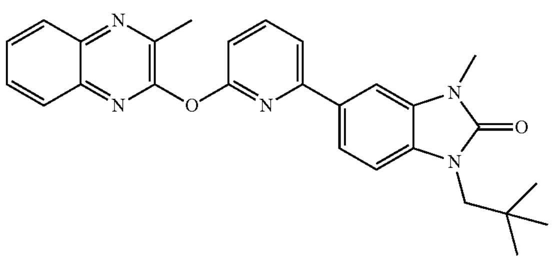 [SMILES: Cc1nc2ccccc2nc1Oc1cccc(-c2ccc3c(c2)n(C)c(=O)n3CC(C)(C)C)n1] | 1-(2,2-dimethylpropyl)-3-methyl-5-{6-[(3-methylquinoxalin-2-yl)oxy]pyridin-2-yl}-1,3-dihydro-2H-benzimidazol-2-one | LRMS m/z (M + H) 454.2 found, 454.5 required. |
| 5-10 | 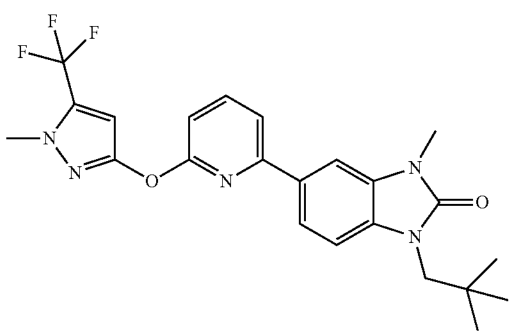 [SMILES: Cn1nc(Oc2cccc(-c3ccc4c(c3)n(C)c(=O)n4CC(C)(C)C)n2)cc1C(F)(F)F] | 1-(2,2-dimethylpropyl)-3-methyl-5-(6-{[1-methyl-5-(trifluoromethyl)-1H-pyrazol-3-yl]oxy}pyridin-2-yl)-1,3-dihydro-2H-benzimidazol-2-one | LRMS m/z (M + H) 460.1 found, 460.5 required. |
| 5-11 | 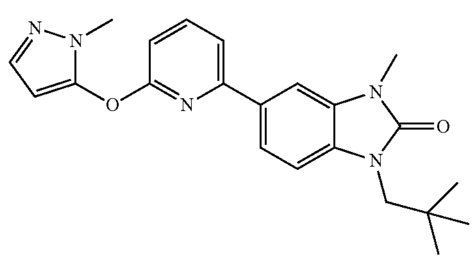 [SMILES: Cn1nccc1Oc1cccc(-c2ccc3c(c2)n(C)c(=O)n3CC(C)(C)C)n1] | 1-(2,2-dimethylpropyl)-3-methyl-5-{6-[(1-methyl-1H-pyrazol-5-yl)oxy]pyridin-2-yl}-1,3-dihydro-2H-benzimidazol-2-one | LRMS m/z (M + H) 392.1 found, 392.5 required. |
| 5-12 | 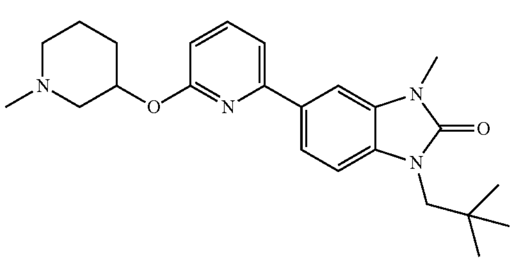 [SMILES: CN1CCCC(Oc2cccc(-c3ccc4c(c3)n(C)c(=O)n4CC(C)(C)C)n2)C1] | 1-(2,2-dimethylpropyl)-3-methyl-5-{6-[(1-methylpiperidin-3-yl)oxy]pyridin-2-yl}-1,3-dihydro-2H-benzimidazol-2-one | LRMS m/z (M + H) 409.1 found, 409.5 required. |

Table 1 for Scheme 5

| Cmp | Structure | Name | LRMS m/z (M + H) |
|---|---|---|---|
| 5-13 | 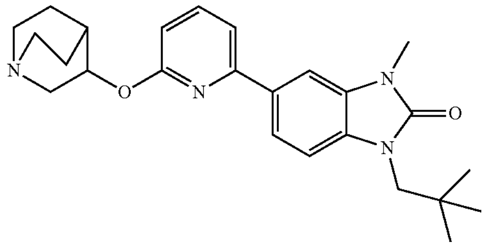 [SMILES: Cn1c(=O)n(CC(C)(C)C)c2ccc(-c3cccc(OC4CN5CCC4CC5)n3)cc21] | 5-[6-(1-azabicyclo[2.2.2]oct-3-yloxy)pyridin-2-yl]-1-(2,2-dimethylpropyl)-3-methyl-1,3-dihydro-2H-benzimidazol-2-one | LRMS m/z (M + H) 421.2 found, 421.6 required. |
| 5-14 | 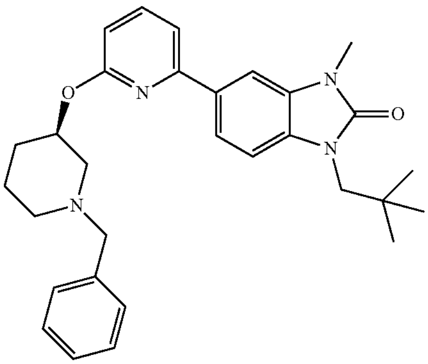 [SMILES: Cn1c(=O)n(CC(C)(C)C)c2ccc(-c3cccc(O[C@@H]4CCCN(Cc5ccccc5)C4)n3)cc21] | 5-(6-{[(3R)-1-benzylpiperidin-3-yl]oxy}pyridin-2-yl)-1-(2,2-dimethylpropyl)-3-methyl-1,3-dihydro-2H-benzimidazol-2-one | LRMS m/z (M + H) 485.2 found, 485.6 required. |
| 5-15 | 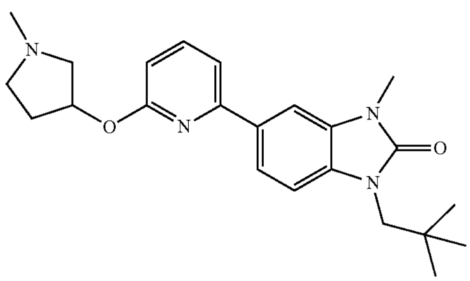 [SMILES: CN1CCC(Oc2cccc(-c3ccc4c(c3)n(C)c(=O)n4CC(C)(C)C)n2)C1] | 1-(2,2-dimethylpropyl)-3-methyl-5-{6-[(1-methylpyrrolidin-3-yl)oxy]pyridin-2-yl}-1,3-dihydro-2H-benzimidazol-2-one | LRMS m/z (M + H) 395.1 found, 395.5 required. |
| 5-16 | 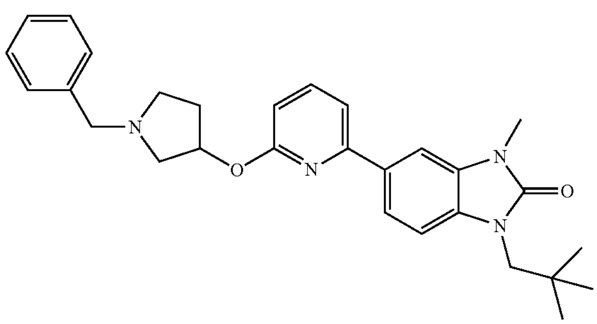 [SMILES: Cn1c(=O)n(CC(C)(C)C)c2ccc(-c3cccc(OC4CCN(Cc5ccccc5)C4)n3)cc21] | 5-{6-[(1-benzylpyrrolidin-3-yl)oxy]pyridin-2-yl}-1-(2,2-dimethylpropyl)-3-methyl-1,3-dihydro-2H-benzimidazol-2-one | LRMS m/z (M + H) 471.2 found, 471.6 required. |
| 5-17 | 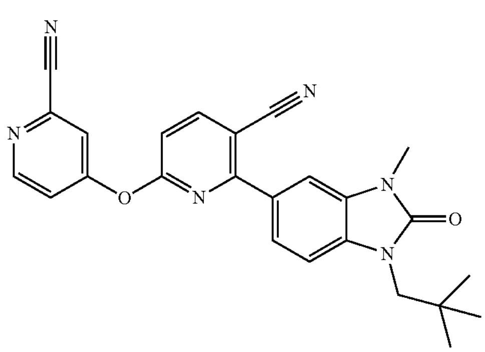 [SMILES: Cn1c(=O)n(CC(C)(C)C)c2ccc(-c3nc(Oc4ccnc(C#N)c4)ccc3C#N)cc21] | 4-({5-cyano-6-[1-(2,2-dimethylpropyl)-3-methyl-2-oxo-2,3-dihydro-1H-benzimidazol-5-yl]pyridin-2-yl}oxy)pyridine-2-carbonitrile | LRMS m/z (M + H) 439.1 found, 439.5 required. |

-continued

Table 1 for Scheme 5

| Cmp | Structure | Name | LRMS m/z (M + H) |
|---|---|---|---|
| 5-18 | 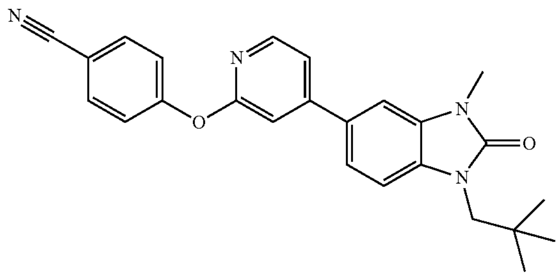 [SMILES: Cn1c(=O)n(CC(C)(C)C)c2ccc(-c3ccnc(Oc4ccc(C#N)cc4)c3)cc21] | 4-({4-[1-(2,2-dimethylpropyl)-3-methyl-2-oxo-2,3-dihydro-1H-benzimidazol-5-yl]pyridin-2-yl}oxy)benzonitrile | LRMS m/z (M + H) 413.2 found, 413.5 required. |
| 5-19 | 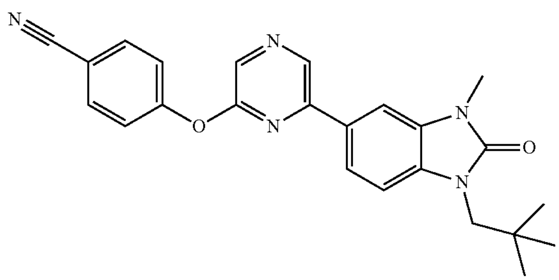 [SMILES: Cn1c(=O)n(CC(C)(C)C)c2ccc(-c3cncc(Oc4ccc(C#N)cc4)n3)cc21] | 4-({6-[1-(2,2-dimethylpropyl)-3-methyl-2-oxo-2,3-dihydro-1H-benzimidazol-5-yl]pyrazin-2-yl}oxy)benzonitrile | LRMS m/z (M + H) 414.2 found, 414.5 required. |
| 5-20 | 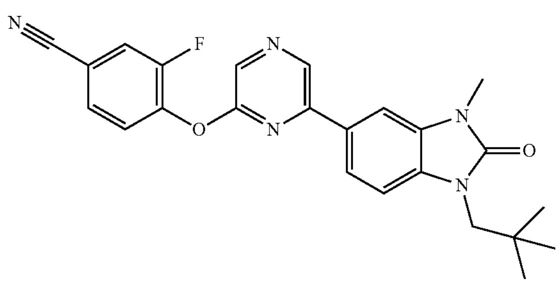 [SMILES: Cn1c(=O)n(CC(C)(C)C)c2ccc(-c3cncc(Oc4ccc(C#N)cc4F)n3)cc21] | 4-({6-[1-(2,2-dimethylpropyl)-3-methyl-2-oxo-2,3-dihydro-1H-benzimidazol-5-yl]pyrazin-2-yl}oxy)-3-fluorobenzonitrile | LRMS m/z (M + H) 432.2 found, 432.5 required. |
| 5-21 | 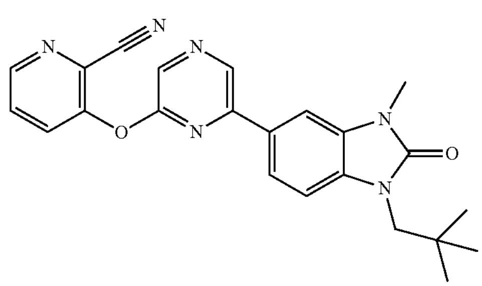 [SMILES: Cn1c(=O)n(CC(C)(C)C)c2ccc(-c3cncc(Oc4cccnc4C#N)n3)cc21] | 3-({6-[1-(2,2-dimethylpropyl)-3-methyl-2-oxo-2,3-dihydro-1H-benzimidazol-5-yl]pyrazin-2-yl}oxy)pyridine-2-carbonitrile | LRMS m/z (M + H) 415.2 found, 415.5 required. |
| 5-22 | 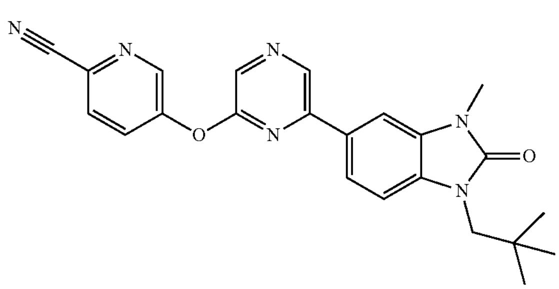 [SMILES: Cn1c(=O)n(CC(C)(C)C)c2ccc(-c3cncc(Oc4ccc(C#N)nc4)n3)cc21] | 5-({6-[1-(2,2-dimethylpropyl)-3-methyl-2-oxo-2,3-dihydro-1H-benzimidazol-5-yl]pyrazin-2-yl}oxy)pyridine-2-carbonitrile | LRMS m/z (M + H) 415.2 found, 415.5 required. |

Table 1 for Scheme 5

| Cmp | Structure | Name | LRMS m/z (M + H) |
|---|---|---|---|
| 5-23 | 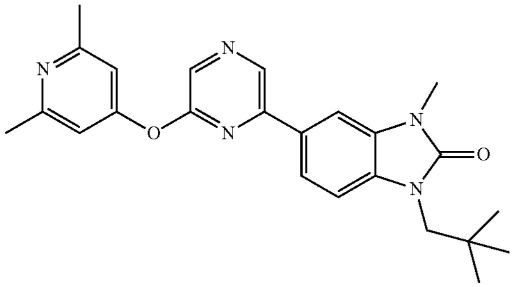 [SMILES: Cc1cc(Oc2cncc(-c3ccc4c(c3)n(C)c(=O)n4CC(C)(C)C)n2)cc(C)n1] | 1-(2,2-dimethylpropyl)-5-{6-[(2,6-dimethylpyridin-4-yl)oxy]pyrazin-2-yl}-3-methyl-1,3-dihydro-2H-benzimidazol-2-one | LRMS m/z (M + H) 418.2 found, 418.5 required. |

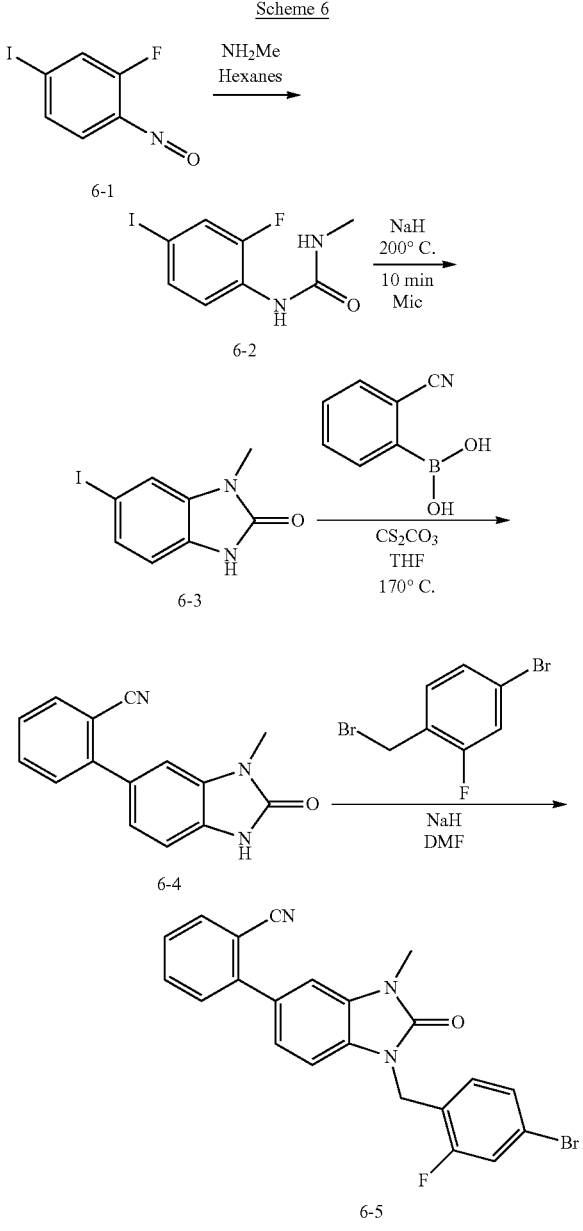

Scheme 6

N-(2-fluoro-4-iodophenyl)-N'-methylurea (6-2)

A solution of 4-Iodo-2-fluorophenyl isocyanate (6-1, 5.15 g, 19.6 mmol) in Hexanes (80 ml) was treated with a solution of Methylamine (2M in THF, 9.8 mL, 19.6 mmol, 1.0 eq). A white precipitate formed as the mixture stirred at 23 deg C. for 30 min. The precipitate was collected via filtration and air dried, affording the title compound, N-(2-fluoro-4-iodophenyl)-N'-methylurea (6-2), as a white solid. $^1$H NMR (500 MHz, CDCl$_3$) δ 7.89 (t, 2H, J=8.6 Hz), 7.47-7.38 (m, 2H), 6.31 (bs, 1H), 4.58 (bs, 1H), 2.88 (d, 3H, J-4.9 Hz). LRMS m/z: Calc'd for C$_8$H$_8$FIN$_2$O (M+H) 295.1, found 294.9.

6-iodo-1-methyl-1,3-dihydro-2H-benzimidazol-2-one (6-3)

A solution of N-(2-fluoro-4-iodophenyl)-N'-methylurea (6-2, 2.9 g, 9.86 mmol) in DMF (12 ml) were treated with Sodium Hydride (308 mg, 12.8 mmol, 1.3 eq). The reaction mixture was irradiated in a microwave at 200 deg C. for 10 min. The starting material was consumed, so it was partitioned between EtOAc (2×75 ml) and water (85 ml), and the combined organic layers were dried over Na$_2$SO$_4$ and concentrated. The residual crude maroon oil was purified via flash column chromatography (SiO$_2$: 100% Hex to 50:50 Hex/EtOAc), which afforded the title compound, 6-iodo-1-methyl-1,3-dihydro-2H-benzimidazol-2-one (6-3), as a tan solid. $^1$H NMR (500 MHz, CDCl$_3$) δ 9.64 (bs, 1H), 7.39 (d, 1H, J=6.6 Hz), 7.30 (s, 1H), 6.87 (d, 1H, J=8.1 Hz), 3.39 (s, 3H). LRMS m/z: Calc'd for C$_8$H$_7$IN$_2$O (M+H) 275.1, found 274.9.

2-(3-methyl-2-oxo-2,3-dihydro-1H-benzimidazol-5-yl)benzonitrile (6-4)

A solution of Cesium carbonate (1100 mg, 3.38 mmol, 5.0 eq) was treated with a solution of 6-iodo-1-methyl-1,3-dihydro-2H-benzimidazol-2-one (6-3, 185 mg, 0.68 mmol) and 2-Cyanophenylboronic acid (198 mg, 1.35 mmol, 2.0 eq). The 1,1'-Bis(diphenylphosphino)ferrocene-palladium(II) dichloride dichloromethane complex (27.6 mg, 0.03 mmol, 0.05 eq) was introduced and the mixture was irradiated in a microwave at 140 deg C. for 15 min. The product was worked up by partitioning between EtOAc (2×85 ml) and saturated aqueous NaHCO$_3$ (95 ml), and the combined organic layers were dried over Na$_2$SO$_4$ and concentrated. Afforded 2-(3-methyl-2-oxo-2,3-dihydro-1H-benzimidazol-5-yl)benzonitrile (6-4), as a maroon-orange solid.

LRMS m/z: Calc'd for $C_{15}H_{11}N_3O$ (M+H) 250.3, found 250.0.

2-[1-(4-bromo-2-fluorobenzyl)-3-methyl-2-oxo-2,3-dihydro-1H-benzimidazol-5-yl]benzonitrile (6-5)

A solution of 2-(3-methyl-2-oxo-2,3-dihydro-1H-benzimidazol-5-yl)benzonitrile (6-4, 20 mg, 0.08 mmol) in anhydrous DMF (1 ml) was charged with Sodium Hydride (6.42 mg, 0.16 mmol, 2.0 eq) and 4-Bromo-2-fluorobenzyl bromide (42.5 mg, 0.16 mmol, 2.0 eq). The resulting dark mixture was irradiated in a microwave at 200 deg C. for 15 min, then quenched with water, filtered and purified via reverse-phase HPLC (Acetonitrile/Water gradient with 0.1% TFA present) to afford the title compound, 2-[1-(4-bromo-2-fluorobenzyl)-3-methyl-2-oxo-2,3-dihydro-1H-benzimidazol-5-yl]benzonitrile (6-5), as an orange-tan solid-oil. LRMS m/z: Calc'd for $C_{22}H_{15}BrFN_3O$ (M+H) 436.0, found 435.9.

Table 1 for Scheme 6

| Cmp | Structure | Name | LRMS m/z (M + H) |
|---|---|---|---|
| 6-6 | 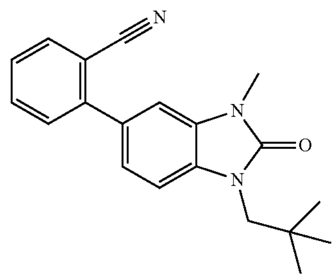 [SMILES: Cn1c(=O)n(CC(C)(C)C)c2ccc(-c3ccccc3C#N)cc21] | 2-[1-(2,2-dimethylpropyl)-3-methyl-2-oxo-2,3-dihydro-1H-benzimidazol-5-yl]benzonitrile | LRMS m/z (M + H) 320.1 found, 320.4 required. |
| 6-7 | 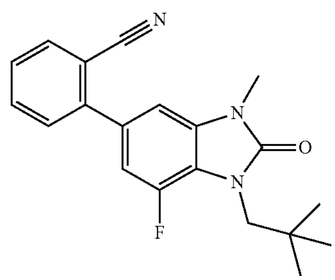 [SMILES: Cn1c(=O)n(CC(C)(C)C)c2c(F)cc(-c3ccccc3C#N)cc21] | 2-[1-(2,2-dimethylpropyl)-7-fluoro-3-methyl-2-oxo-2,3-dihydro-1H-benzimidazol-5-yl]benzonitrile | LRMS m/z (M + H) 338.0 found, 338.4 required. |
| 6-8 | 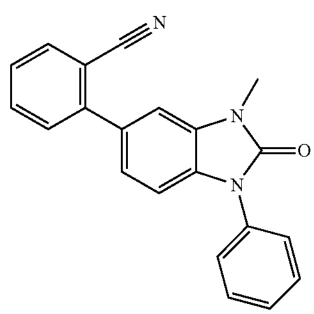 [SMILES: Cn1c(=O)n(-c2ccccc2)c2ccc(-c3ccccc3C#N)cc21] | 2-(3-methyl-2-oxo-1-phenyl-2,3-dihydro-1H-benzimidazol-5-yl)benzonitrile | LRMS m/z (M + H) 326.0 found, 326.1 required. |
| 6-9 | 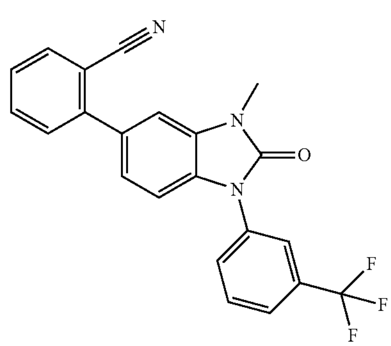 [SMILES: Cn1c(=O)n(-c2cccc(C(F)(F)F)c2)c2ccc(-c3ccccc3C#N)cc21] | 2-{3-methyl-2-oxo-1-[3-(trifluoromethyl)phenyl]-2,3-dihydro-1H-benzimidazol-5-yl}benzonitrile | LRMS m/z (M + H) 394.1 found, 394.1 required. |

-continued

Table 1 for Scheme 6

| Cmp | Structure | Name | LRMS m/z (M + H) |
|---|---|---|---|
| 6-10 | 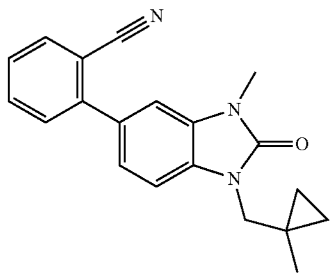 [SMILES: Cn1c(=O)n(CC2(C)CC2)c2ccc(-c3ccccc3C#N)cc21] | 2-{3-methyl-1-[(1-methylcyclopropyl)methyl]-2-oxo-2,3-dihydro-1H-benzimidazol-5-yl}benzonitrile | LRMS m/z (M + H) 318.0 found, 318.4 required. |
| 6-11 | 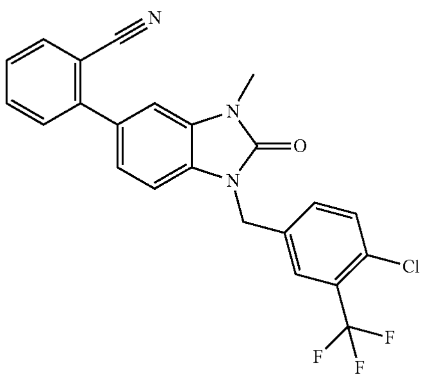 [SMILES: Cn1c(=O)n(Cc2ccc(Cl)c(C(F)(F)F)c2)c2ccc(-c3ccccc3C#N)cc21] | 2-{1-[4-chloro-3-(trifluoromethyl)benzyl]-3-methyl-2-oxo-2,3-dihydro-1H-benzimidazol-5-yl}benzonitrile | LRMS m/z (M + H) 442.0 found, 442.8 required. |
| 6-12 | 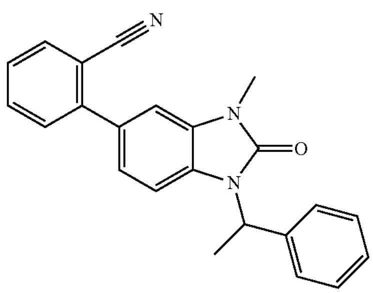 [SMILES: CC(c1ccccc1)n1c(=O)n(C)c2cc(-c3ccccc3C#N)ccc21] | 2-[3-methyl-2-oxo-1-(1-phenylethyl)-2,3-dihydro-1H-benzimidazol-5-yl]benzonitrile | LRMS m/z (M + H) 354.1 found, 354.4 required. |
| 6-13 | 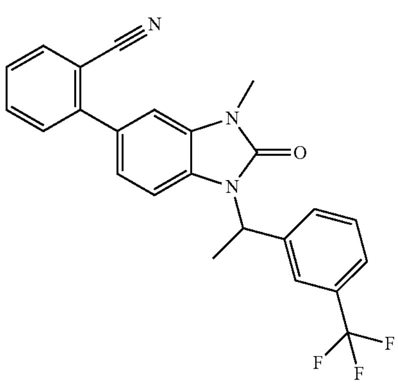 [SMILES: CC(c1cccc(C(F)(F)F)c1)n1c(=O)n(C)c2cc(-c3ccccc3C#N)ccc21] | 2-(3-methyl-2-oxo-1-{1-[3-(trifluoromethyl)phenyl]ethyl}-2,3-dihydro-1H-benzimidazol-5-yl)benzonitrile | LRMS m/z (M + H) 422.1 found, 422.4 required. |
| 6-14 | 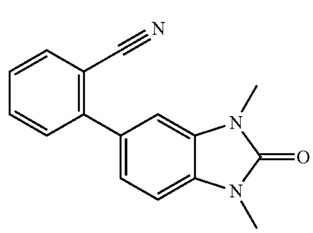 [SMILES: Cn1c(=O)n(C)c2cc(-c3ccccc3C#N)ccc21] | 2-(1,3-dimethyl-2-oxo-2,3-dihydro-1H-benzimidazol-5-yl)benzonitrile | LRMS m/z (M + H) 264.1 found, 264.3 required. |

Table 1 for Scheme 6

| Cmp | Structure | Name | LRMS m/z (M + H) |
|---|---|---|---|
| 6-15 | 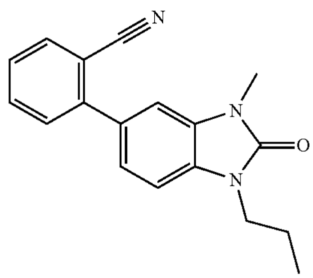 [SMILES: CCCn1c(=O)n(C)c2cc(-c3ccccc3C#N)ccc21] | 2-(3-methyl-2-oxo-1-propyl-2,3-dihydro-1H-benzimidazol-5-yl)benzonitrile | LRMS m/z (M + H) 292.1 found, 292.4 required. |
| 6-16 | 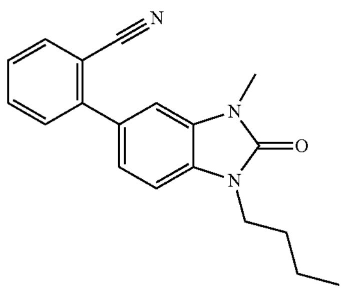 [SMILES: CCCCn1c(=O)n(C)c2cc(-c3ccccc3C#N)ccc21] | 2-(1-butyl-3-methyl-2-oxo-2,3-dihydro-1H-benzimidazol-5-yl)benzonitrile | LRMS m/z (M + H) 306.1 found, 306.4 required. |
| 6-17 | 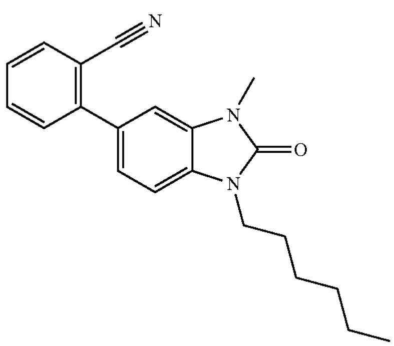 [SMILES: CCCCCCn1c(=O)n(C)c2cc(-c3ccccc3C#N)ccc21] | 2-(1-hexyl-3-methyl-2-oxo-2,3-dihydro-1H-benzimidazol-5-yl)benzonitrile | LRMS m/z (M + H) 334.2 found, 334.4 required. |
| 6-18 | 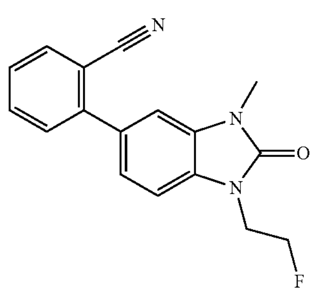 [SMILES: Cn1c(=O)n(CCF)c2ccc(-c3ccccc3C#N)cc21] | 2-[1-(2-fluoroethyl)-3-methyl-2-oxo-2,3-dihydro-1H-benzimidazol-5-yl]benzonitrile | LRMS m/z (M + H) 296.1 found, 296.4 required. |
| 6-19 | 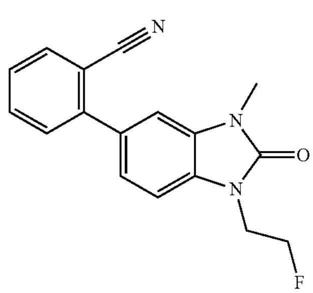 | 2-[1-(2-cyanoethyl)-3-methyl-2-oxo-2,3-dihydro-1H-benzimidazol-5-yl]benzonitrile | LRMS m/z (M + H) 303.2 found, 303.3 required. |

Table 1 for Scheme 6

| Cmp | Structure | Name | LRMS m/z (M + H) |
|---|---|---|---|
| 6-20 | 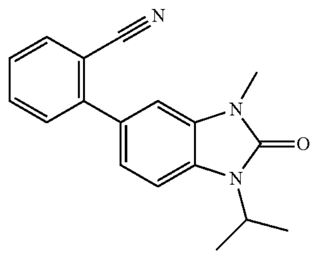 [SMILES: CC(C)n1c(=O)n(C)c2cc(-c3ccccc3C#N)ccc21] | 2-(1-isopropyl-3-methyl-2-oxo-2,3-dihydro-1H-benzimidazol-5-yl)benzonitrile | LRMS m/z (M + H) 292.1 found, 292.4 required. |
| 6-21 | 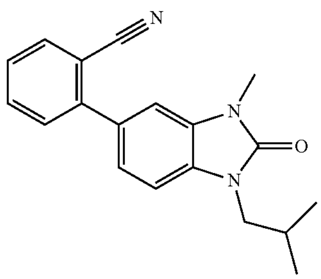 [SMILES: CC(C)Cn1c(=O)n(C)c2cc(-c3ccccc3C#N)ccc21] | 2-(1-isobutyl-3-methyl-2-oxo-2,3-dihydro-1H-benzimidazol-5-yl)benzonitrile | LRMS m/z (M + H) 306.2 found, 306.4 required. |
| 6-22 | 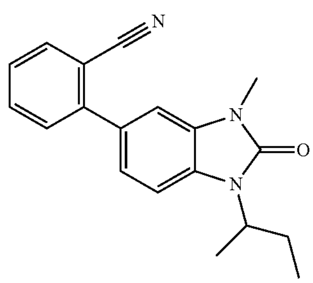 [SMILES: CCC(C)n1c(=O)n(C)c2cc(-c3ccccc3C#N)ccc21] | 2-(1-sec-butyl-3-methyl-2-oxo-2,3-dihydro-1H-benzimidazol-5-yl)benzonitrile | LRMS m/z (M + H) 306.2 found, 306.4 required. |
| 6-23 | 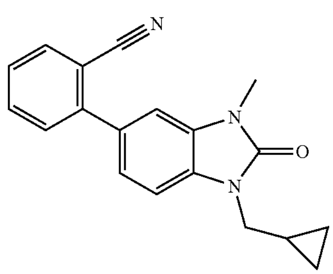 [SMILES: Cn1c(=O)n(CC2CC2)c2ccc(-c3ccccc3C#N)cc21] | 2-[1-(cyclopropylmethyl)-3-methyl-2-oxo-2,3-dihydro-1H-benzimidazol-5-yl]benzonitrile | LRMS m/z (M + H) 304.1 found, 304.4 required. |
| 6-24 | 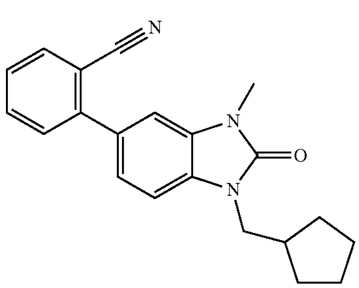 [SMILES: Cn1c(=O)n(CC2CCCC2)c2ccc(-c3ccccc3C#N)cc21] | 2-[1-(cyclopentylmethyl)-3-methyl-2-oxo-2,3-dihydro-1H-benzimidazol-5-yl]benzonitrile | LRMS m/z (M + H) 332.2 found, 332.4 required. |

Table 1 for Scheme 6

| Cmp | Structure | Name | LRMS m/z (M + H) |
|---|---|---|---|
| 6-25 | 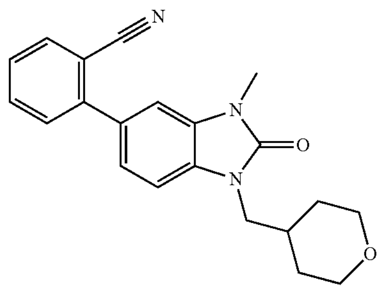 [SMILES: Cn1c(=O)n(CC2CCOCC2)c2ccc(-c3ccccc3C#N)cc21] | 2-[3-methyl-2-oxo-1-(tetrahydro-2H-pyran-4-ylmethyl)-2,3-dihydro-1H-benzimidazol-5-yl]benzonitrile | LRMS m/z (M + H) 348.1 found, 348.4 required. |
| 6-26 | 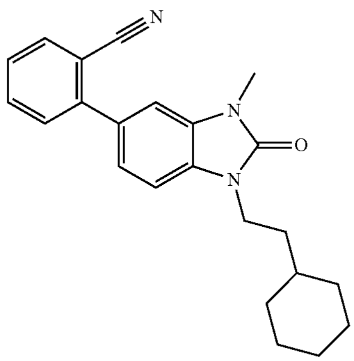 [SMILES: Cn1c(=O)n(CCC2CCCCC2)c2ccc(-c3ccccc3C#N)cc21] | 2-[1-(2-cyclohexylethyl)-3-methyl-2-oxo-2,3-dihydro-1H-benzimidazol-5-yl]benzonitrile | LRMS m/z (M + H) 360.1 found, 360.5 required. |
| 6-27 | 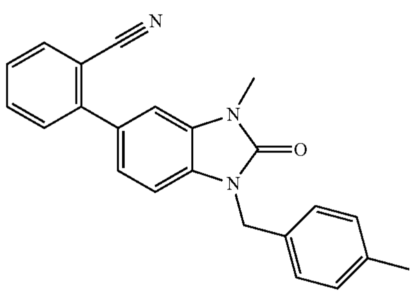 [SMILES: Cc1ccc(Cn2c(=O)n(C)c3cc(-c4ccccc4C#N)ccc32)cc1] | 2-[3-methyl-1-(4-methylbenzyl)-2-oxo-2,3-dihydro-1H-benzimidazol-5-yl]benzonitrile | LRMS m/z (M + H) 354.1 found, 354.4 required. |
| 6-28 | 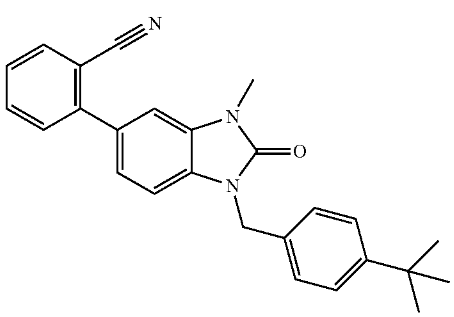 [SMILES: Cn1c(=O)n(Cc2ccc(C(C)(C)C)cc2)c2ccc(-c3ccccc3C#N)cc21] | 2-[1-(4-tert-butylbenzyl)-3-methyl-2-oxo-2,3-dihydro-1H-benzimidazol-5-yl]benzonitrile | LRMS m/z (M + H) 396.1 found, 396.5 required. |
| 6-29 | 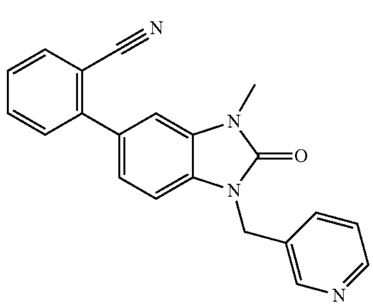 [SMILES: Cn1c(=O)n(Cc2cccnc2)c2ccc(-c3ccccc3C#N)cc21] | 2-[3-methyl-2-oxo-1-(pyridin-3-ylmethyl)-2,3-dihydro-1H-benzimidazol-5-yl]benzonitrile | LRMS m/z (M + H) 341.0 found, 341.4 required. |

-continued

Table 1 for Scheme 6

| Cmp | Structure | Name | LRMS m/z (M + H) |
|---|---|---|---|
| 6-30 | 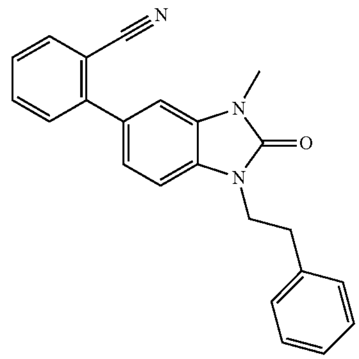 [SMILES: Cn1c(=O)n(CCc2ccccc2)c2ccc(-c3ccccc3C#N)cc21] | 2-[3-methyl-2-oxo-1-(2-phenylethyl)-2,3-dihydro-1H-benzimidazol-5-yl]benzonitrile | LRMS m/z (M + H) 354.1 found, 354.4 required. |
| 6-31 | 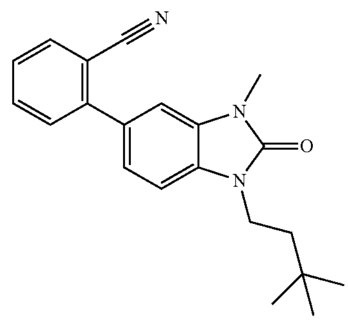 [SMILES: Cn1c(=O)n(CCC(C)(C)C)c2ccc(-c3ccccc3C#N)cc21] | 2-[1-(3,3-dimethylbutyl)-3-methyl-2-oxo-2,3-dihydro-1H-benzimidazol-5-yl]benzonitrile | LRMS m/z (M + H) 334.2 found, 334.4 required. |
| 6-32 | 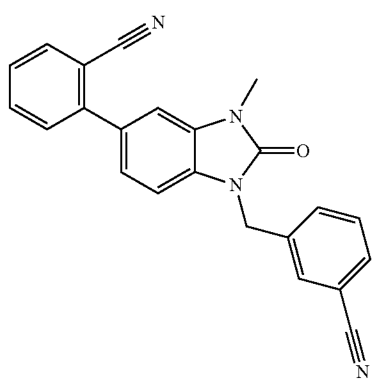 [SMILES: Cn1c(=O)n(Cc2cccc(C#N)c2)c2ccc(-c3ccccc3C#N)cc21] | 2-[1-(3-cyanobenzyl)-3-methyl-2-oxo-2,3-dihydro-1H-benzimidazol-5-yl]benzonitrile | LRMS m/z (M + H) 365.1 found, 365.4 required. |
| 6-33 | 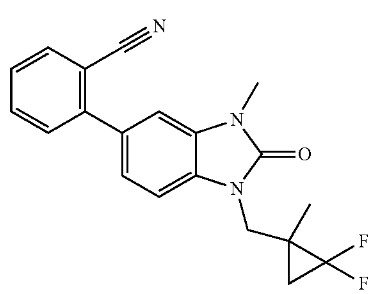 [SMILES: Cn1c(=O)n(CC2(C)CC2(F)F)c2ccc(-c3ccccc3C#N)cc21] | 2-{1-[(2,2-difluoro-1-methylcyclopropyl)methyl]-3-methyl-2-oxo-2,3-dihydro-1H-benzimidazol-5-yl}benzonitrile | LRMS m/z (M + H) 354.3 found, 354.4 required. |

Table 1 for Scheme 6
| Cmp | Structure | Name | LRMS m/z (M + H) |
|---|---|---|---|
| 6-34 | 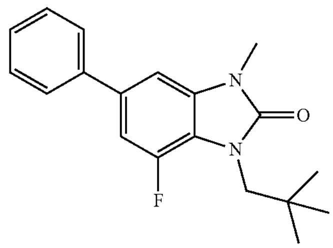 [SMILES: Cn1c(=O)n(CC(C)(C)C)c2c(F)cc(-c3ccccc3)cc21] | 3-(2,2-dimethylpropyl)-4-fluoro-1-methyl-6-phenyl-1,3-dihydro-2H-benzimidazol-2-one | LRMS m/z (M + H) 313.0 found, 313.4 required. |
| 6-35 | 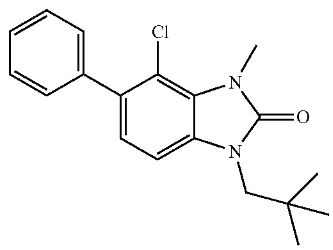 [SMILES: Cn1c(=O)n(CC(C)(C)C)c2ccc(-c3ccccc3)c(Cl)c21] | 4-chloro-1-(2,2-dimethylpropyl)-3-methyl-5-phenyl-1,3-dihydro-2H-benzimidazol-2-one | LRMS m/z (M + H) 329.0 found, 329.9 required. |
REACTION SCHEME 7
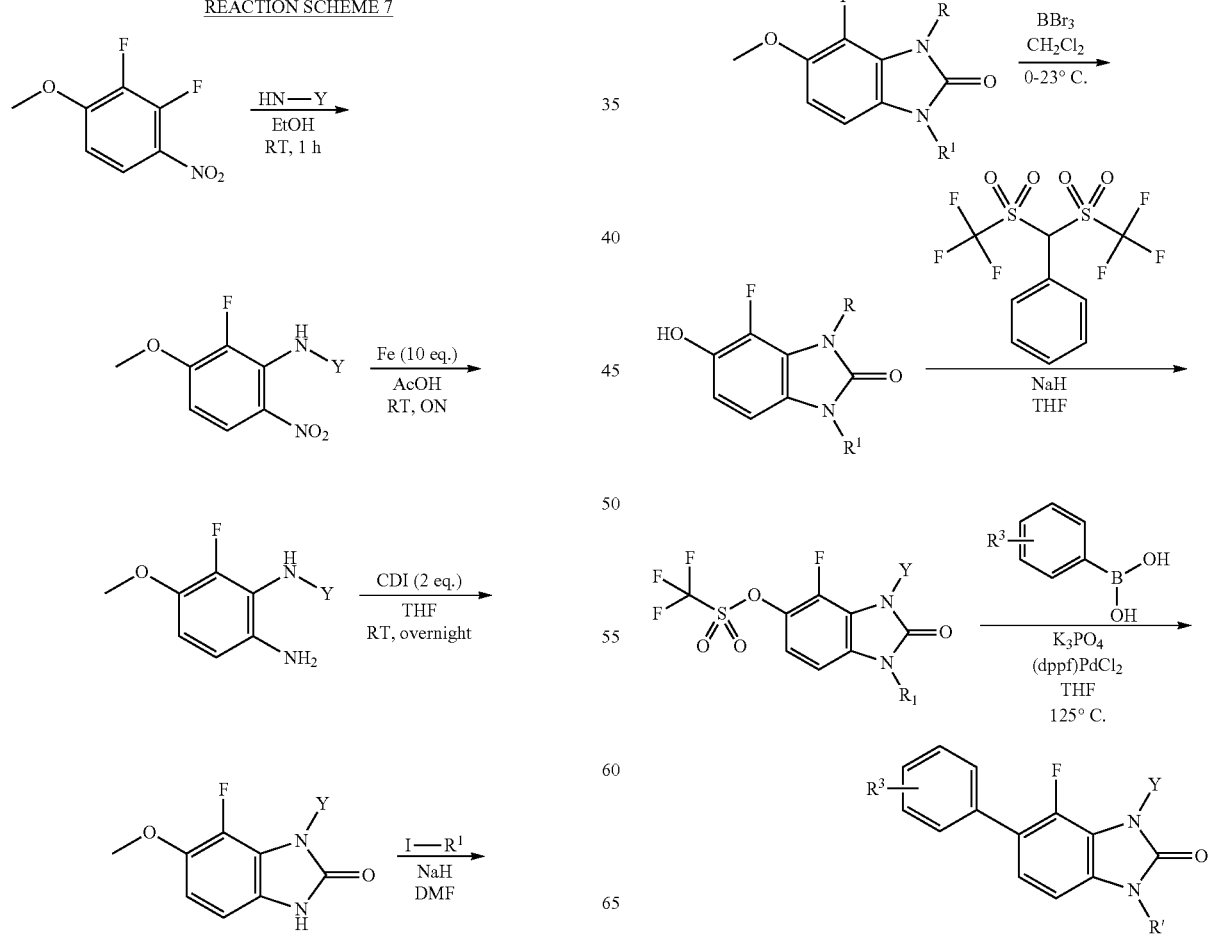

Scheme 7

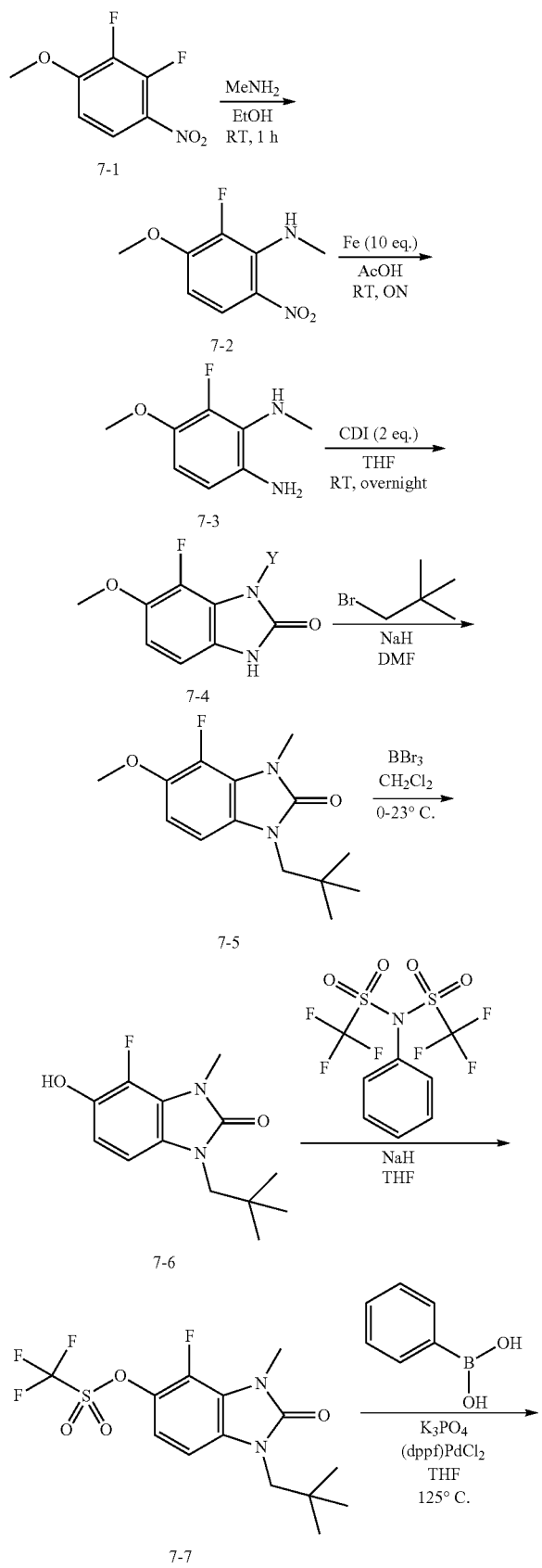

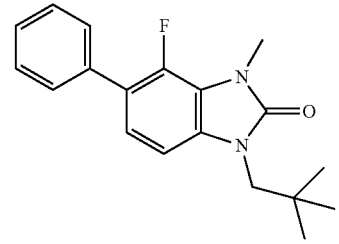

2-fluoro-3-methoxy-N-methyl-6-nitroaniline (7-2)

A solution of 2,3-Difluoro-4-nitroanisole (7-1, 1.0 g, 5.29 mmol) in EtOH (20 ml) was treated with Methylamine (2M in THF, 3.17 ml, 6.35 mmol, 1.2 eq) and the resulting yellow solution was stirred at 23 deg C. for 1 h. The reaction was complete by LC/MS, but allowed to stir at 23 deg C. for an additional 17 h. The residual bright orange-yellow solution was concentrated in vacuo, then partitioned between EtOAc (2×80 ml) and water (90 ml). The combined organic layers were dried over $Na_2SO_4$ and concentrated, leaving the title compound, 2-fluoro-3-methoxy-N-methyl-6-nitroaniline (7-2), as an orange solid with >90% purity. $^1$H NMR (500 MHz, $CDCl_3$) δ 8.01 (d, 1H, J=1.9 Hz), 7.84 (bs, 1H), 6.81-6.83 (m, 1H), 3.95 (s, 3H), 3.24 (m, 3H). LRMS m/z: Calc'd for $C_8H_9FN_2O_3$ (M+H) 201.2, found 200.9.

3-fluoro-4-methoxy-$N^2$-methylbenzene-1,2-diamine (7-3)

A solution of 2-fluoro-3-methoxy-N-methyl-6-nitroaniline (7-2, 1.04 g, 5.20 mmol) in Acetic acid (25 ml) was charged with Iron (powder). The resulting mixture was stirred at 23 deg C. for 22 h. The reduced material concentrated in vacuo, and the residual oil was taken up in Methylene Chloride and filtered through Celite. The filtrate was again concentrated in vacuo, leaving the title compound, 3-fluoro-4-methoxy-$N^2$-methylbenzene-1,2-diamine (7-3), as a maroon oil with >80% purity. LRMS m/z: Calc'd for $C_8H_{11}FN_2O$ (M+H) 171.2, found 170.9.

7-fluoro-6-methoxy-1-methyl-1,3-dihydro-2H-benzimidazol-2-one (7-4)

3-fluoro-4-methoxy-$N^2$-methylbenzene-1,2-diamine (7-3, 1.09 g, 6.40 mmol) was dissolved in anhydrous THF (15 ml) and treated with CDI (1.25 g, 7.69 mmol, 1.2 eq). The resulting orange solution was stirred at reflux for 6 h, then cooled to 23 deg C. The remaining dark reaction mixture was partitioned between EtOAc (2×40 ml) and water (45 ml). The combined organic layers were dried over $Na_2SO_4$ and concentrated. The crude mixture was purified via flash column chromatography ($SiO_2$: 100% Hex to 50:50 Hex:EtOAc), affording the title compound, 7-fluoro-6-methoxy-1-methyl-1,3-dihydro-2H-benzimidazol-2-one (7-4), as a maroon oil. $^1$H NMR (500 MHz, $CDCl_3$) δ 7.11 (s, 1H), 6.68-6.74 (m, 2H), 3.89 (s, 3H), 3.60 (s, 3H). LRMS m/z: Calc'd for $C_9H_9FN_2O_2$ (M+H) 197.2, found 196.9.

1-(2,2-dimethylpropyl)-4-fluoro-5-methoxy-3-methyl-1,3-dihydro-2H-benzimidazol-2-one (7-5)

A solution of 7-fluoro-6-methoxy-1-methyl-1,3-dihydro-2H-benzimidazol-2-one (7-4, 250 mg, 1.27 mmol) in anhydrous DMF (1.5 ml) was treated with NaH and 1-Bromo-2,2-dimethylpropane. The reaction was then irradiated in a microwave at 175 deg C. for 25 min. The reaction was partitioned between EtOAc (2×60 ml) and water (75 ml). The combined organic layers were dried over Na₂SO₄ and concentrated, affording the title compound, 1-(2,2-dimethylpropyl)-4-fluoro-5-methoxy-3-methyl-1,3-dihydro-2H-benzimidazol-2-one (7-5), as an orange oil. ¹H NMR (300 MHz, CDCl₃) δ 6.65-6.70 (m, 2H), 3.88 (s, 3H), 3.60 (m, 5H), 1.03 (s, 9H). LRMS m/z: Calc'd for C₁₄H₁₉FN₂O₂(M+H) 267.3, found 267.0.

1-(2,2-dimethylpropyl)-4-fluoro-5-hydroxy-3-methyl-1,3-dihydro-2,1-benzimidazol-2-one (7-6)

A solution of 1-(2,2-dimethylpropyl)-4-fluoro-5-methoxy-3-methyl-1,3-dihydro-2H-benzimidazol-2-one (7-5, 193 mg, 0.73 mmol) in anhydrous Dichloromethane (10 ml) was cooled to −78 deg C. (Acetone/dry ice) and treated with Boron tribromide (1M in DCM, 1.45 ml, 1.45 mmol, 2 eq). The resulting mixture was allowed to slowly warm to 23 deg C. over 15 h. The reaction was only ~75% complete by LC/MS, so it was treated with more BBr₃ (360 ml, 0.36 mmol, 0.5 eq). The reaction was stirred at 23 deg C. for 1 h, then was carefully quenched by pouring directly into a solution of saturated aqueous NaHCO₃ cooled to 0 deg C. The aqueous mixture was extracted with Methylene Chloride (2×200 ml), and the combined organic layers were dried over Na₂SO₄ and concentrated, thereby providing the title compound, 1-(2,2-dimethylpropyl)-4-fluoro-5-hydroxy-3-methyl-1,3-dihydro-2H-benzimidazol-2-one (7-6), as a green-tan solid. ¹H NMR (500 MHz, CDCl₃) δ 6.65-6.73 (m, 2H), 3.61 (m, 5H), 1.02 (s, 9H). LRMS m/z: Calc'd for C₁₃H₁₇FN₂O₂ (M+H) 253.3, found 253.0.

1-(2,2-dimethylpropyl)-4-fluoro-3-methyl-2-oxo-2,3-dihydro-1H-benzimidazol-5-yl trifluoromethanesulfonate (7-7)

1-(2,2-dimethylpropyl)-4-fluoro-5-hydroxy-3-methyl-1,3-dihydro-2H-benzimidazol-2-one (7-6, 125 mg, 0.50 mmol) was dissolved in anhydrous THF (8 ml) and cooled to 0 deg C. (water/wet ice). The resulting maroon solution was treated with NaH (27.7 mg, 0.69 mmol, 1.4 eq) causing it to become dark green-black. The mixture then became maroon-orange again upon addition of N-Phenylbis (trifluoromethanesulfonimide) (266 mg, 0.74 mmol, 1.5 eq). The reaction mixture was allowed to slowly warm to 23 deg C. over 16 h. The reaction mixture was then partitioned between EtOAc (2×55 ml) and water (65 ml). The residual maroon-orange oil containing the title compound, 1-(2,2-dimethylpropyl)-4-fluoro-3-methyl-2-oxo-2,3-dihydro-1H-benzimidazol-5-yl trifluoromethanesulfonate (7-7), was used crude. LRMS m/z: Calc'd for C₁₄H₁₆F₄N₂O₄S (M+H) 385.3, found 385.1.

1-(2,2-dimethylpropyl)-4-fluoro-3-methyl-5-phenyl-1,3-dihydro-2H-benzimidazol-2-one (7-8)

A solution of Cesium carbonate was treated with a solution of 1-(2,2-dimethylpropyl)-4-fluoro-3-methyl-2-oxo-2,3-dihydro-1H-benzimidazol-5-yl trifluoromethanesulfonate (7-7, 80 mg, 0.21 mmol) and Phenylboronic acid (50.8 mg, 0.42 mmol, 2.0 eq) in anhydrous THF (5 ml). The mixture was deoxygenated, and 1,1'-Bis(diphenylphosphino)ferrocene-palladium(II)dichloride dichloromethane complex was introduced (8.5 mg, 10.4 μmol, 0.05 eq) and the mixture was irradiated in a microwave at 140 deg C. for 15 min. The reaction was not complete, so more Phenylboronic acid (26 mg, 0.24 mmol, 1.0 eq) and catalyst (8.5 mg, 10.4 μmol, 0.05 eq) was added and the reaction was irradiated again at 170 deg C. for 25 min. LC/MS showed complete conversion, so the crude maroon oil was partitioned between EtOAc (2×45 ml) and aqueous saturated NaHCO₃ (55 ml), the combined organic layers were dried over Na₂SO₄ and concentrated, then purified via reverse-phase HPLC (Acetonitrile/Water gradient with 0.1% TFA present). The title compound, 1-(2,2-dimethylpropyl)-4-fluoro-3-methyl-5-phenyl-1,3-dihydro-2H-benzimidazol-2-one (7-8), was obtained as a brown oil with >95% purity. ¹H NMR (500 MHz, CDCl₃) δ 7.54-7.52 (m, 2H), 7.45 (t, 2H, J=5.86 Hz), 7.38-7.35 (m, 1H), 7.09 (t, 1H, J=5.38 Hz), 6.89 (d, 1H, J=6.35 Hz), 3.69 (s, 2H), 3.66 (s, 3H), 1.06 (s, 9H). LRMS m/z: Calc'd for C₁₉H₂₁FN₂O (M+H) 313.4, found 313.1.

Table 1 for Scheme 7

| Cmp | Structure | Name | LRMS m/z (M + H) |
| --- | --- | --- | --- |
| 7-9 | 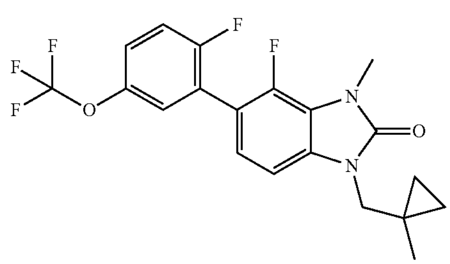 [SMILES: Cn1c(=O)n(CC2(C)CC2)c2ccc(-c3cc(OC(F)(F)F)ccc3F)c(F)c21] | 4-fluoro-5-[2-fluoro-5-(trifluoromethoxy)phenyl]-3-methyl-1-[(1-methylcyclopropyl)methyl]-1,3-dihydro-2H-benzimidazol-2-one | LRMS m/z (M + H) 413.1 found, 413.4 required. |
| 7-10 | 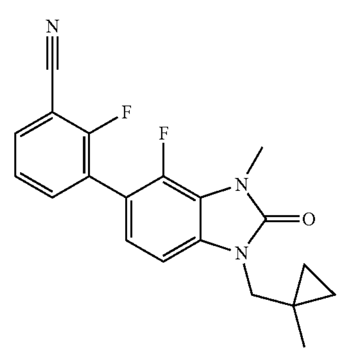 [SMILES: Cn1c(=O)n(CC2(C)CC2)c2ccc(-c3cccc(C#N)c3F)c(F)c21] | 2-fluoro-3-{4-fluoro-3-methyl-1-[(1-methylcyclopropyl)methyl]-2-oxo-2,3-dihydro-1H-benzimidazol-5-yl}benzonitrile | LRMS m/z (M + H) 354.1 found, 354.4 required. |

-continued

Table 1 for Scheme 7

| Cmp | Structure | Name | LRMS m/z (M + H) |
|---|---|---|---|
| 7-11 | 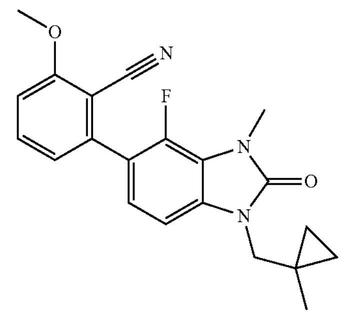 [SMILES: COc1cccc(-c2ccc3c(c2F)n(C)c(=O)n3CC2(C)CC2)c1C#N] | 2-{4-fluoro-3-methyl-1-[(1-methylcyclopropyl)methyl]-2-oxo-2,3-dihydro-1H-benzimidazol-5-yl}-6-methoxybenzonitrile | LRMS m/z (M + H) 366.1 found, 366.4 required. |
| 7-12 | 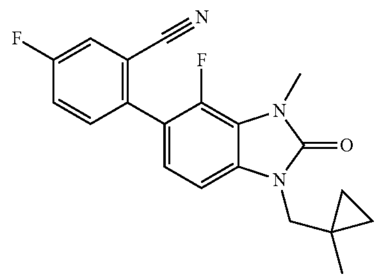 [SMILES: Cn1c(=O)n(CC2(C)CC2)c2ccc(-c3ccc(F)cc3C#N)c(F)c21] | 5-fluoro-2-{4-fluoro-3-methyl-1-[(1-methylcyclopropyl)methyl]-2-oxo-2,3-dihydro-1H-benzimidazol-5-yl}benzonitrile | LRMS m/z (M + H) 354.1 found, 354.4 required. |
| 7-13 | 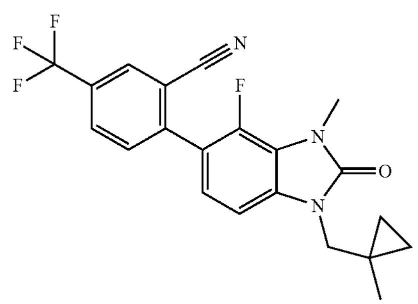 [SMILES: Cn1c(=O)n(CC2(C)CC2)c2ccc(-c3ccc(C(F)(F)F)cc3C#N)c(F)c21] | 2-{4-fluoro-3-methyl-1-[(1-methylcyclopropyl)methyl]-2-oxo-2,3-dihydro-1H-benzimidazol-5-yl}-5-(trifluoromethyl)benzonitrile | LRMS m/z (M + H) 404.1 found, 404.4 required. |
| 7-14 | 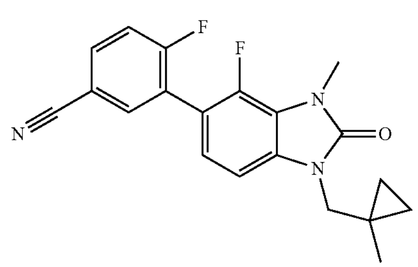 [SMILES: Cn1c(=O)n(CC2(C)CC2)c2ccc(-c3cc(C#N)ccc3F)c(F)c21] | 4-fluoro-3-{4-fluoro-3-methyl-1-[(1-methylcyclopropyl)methyl]-2-oxo-2,3-dihydro-1H-benzimidazol-5-yl}benzonitrile | LRMS m/z (M + H) 354.2 found, 354.5 required. |
| 7-15 | 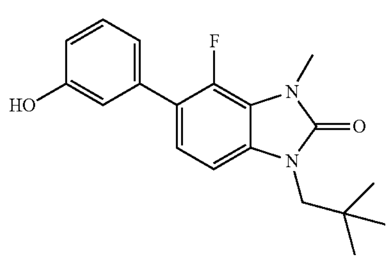 [SMILES: Cn1c(=O)n(CC(C)(C)C)c2ccc(-c3cccc(O)c3)c(F)c21] | 1-(2,2-dimethylpropyl)-4-fluoro-5-(3-hydroxyphenyl)-3-methyl-1,3-dihydro-2H-benzimidazol-2-one | LRMS m/z (M + H) 329.1 found, 329.4 required. |

Table 1 for Scheme 7

| Cmp | Structure | Name | LRMS m/z (M + H) |
|---|---|---|---|
| 7-16 | 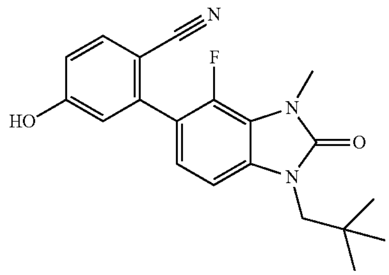 [SMILES: Cn1c(=O)n(CC(C)(C)C)c2ccc(-c3cc(O)ccc3C#N)c(F)c21] | 2-[1-(2,2-dimethylpropyl)-4-fluoro-3-methyl-2-oxo-2,3-dihydro-1H-benzimidazol-5-yl]-4-hydroxybenzonitrile | LRMS m/z (M + H) 353.8 found, 354.4 required. |
| 7-17 | 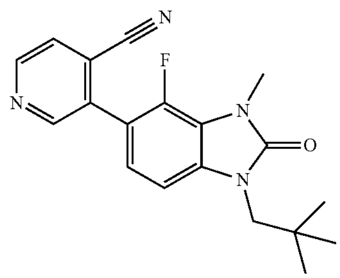 [SMILES: Cn1c(=O)n(CC(C)(C)C)c2ccc(-c3cnccc3C#N)c(F)c21] | 3-[1-(2,2-dimethylpropyl)-4-fluoro-3-methyl-2-oxo-2,3-dihydro-1H-benzimidazol-5-yl]isonicotinonitrile | LRMS m/z (M + H) 339.1 found, 339.4 required. |
| 7-18 | 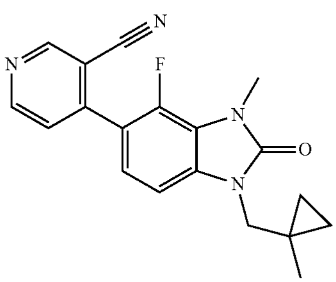 [SMILES: Cn1c(=O)n(CC2(C)CC2)c2ccc(-c3ccncc3C#N)c(F)c21] | 4-{4-fluoro-3-methyl-1-[(1-methylcyclopropyl)methyl]-2-oxo-2,3-dihydro-1H-benzimidazol-5-yl}nicotinonitrile | LRMS m/z (M + H) 337.1 found, 337.4 required. |
| 7-19 | 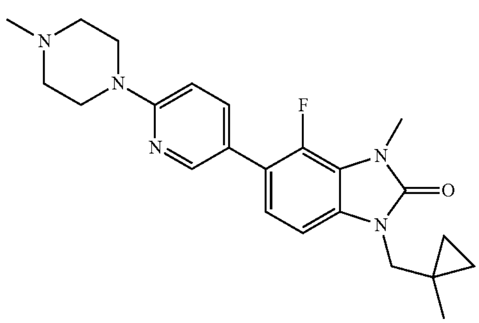 [SMILES: CN1CCN(c2ccc(-c3ccc4c(c3F)n(C)c(=O)n4CC3(C)CC3)cn2)CC1] | 4-fluoro-3-methyl-1-[(1-methylcyclopropyl)methyl]-5-[6-(4-methylpiperazin-1-yl)pyridin-3-yl]-1,3-dihydro-2H-benzimidazol-2-one | LRMS m/z (M + H) 410.2 found, 410.5 required. |
| 7-20 | 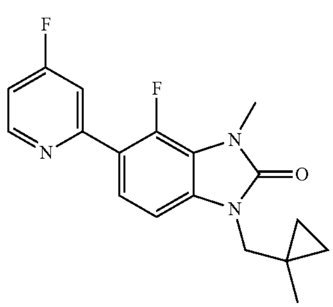 [SMILES: Cn1c(=O)n(CC2(C)CC2)c2ccc(-c3cc(F)ccn3)c(F)c21] | 4-fluoro-5-(4-fluoropyridin-2-yl)-3-methyl-1-[(1-methylcyclopropyl)methyl]-1,3-dihydro-2H-benzimidazol-2-one | LRMS m/z (M + H) 330.1 found, 330.4 required. |

Table 1 for Scheme 7

| Cmp | Structure | Name | LRMS m/z (M + H) |
|---|---|---|---|
| 7-21 | 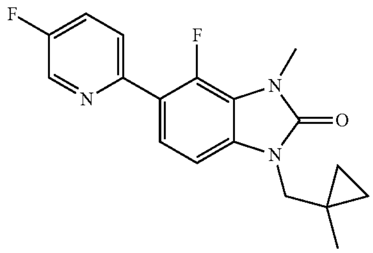 [SMILES: Cn1c(=O)n(CC2(C)CC2)c2ccc(-c3ccc(F)cn3)c(F)c21] | 4-fluoro-5-(5-fluoropyridin-2-yl)-3-methyl-1-[(1-methylcyclopropyl)methyl]-1,3-dihydro-2H-benzimidazol-2-one | LRMS m/z (M + H) 330.1 found, 330.4 required. |
| 7-22 | 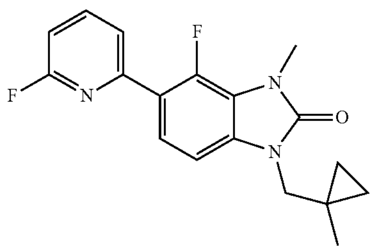 [SMILES: Cn1c(=O)n(CC2(C)CC2)c2ccc(-c3cccc(F)n3)c(F)c21] | 4-fluoro-5-(6-fluoropyridin-2-yl)-3-methyl-1-[(1-methylcyclopropyl)methyl]-1,3-dihydro-2H-benzimidazol-2-one | LRMS m/z (M + H) 330.1 found, 330.4 required. |
| 7-23 | 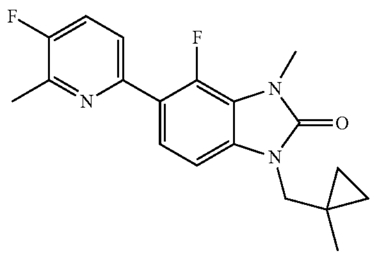 | 4-fluoro-5-(5-fluoro-6-methylpyridin-2-yl)-3-methyl-1-[(1-methylcyclopropyl)methyl]-1,3-dihydro-2H-benzimidazol-2-one | LRMS m/z (M + H) 344.1 found, 344.4 required. |
| 7-24 | 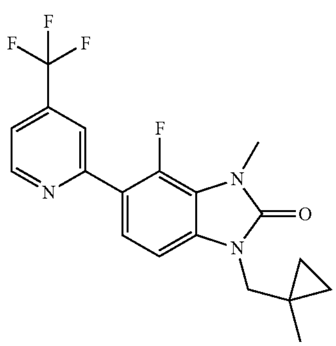 [SMILES: Cn1c(=O)n(CC2(C)CC2)c2ccc(-c3cc(C(F)(F)F)ccn3)c(F)c21] | 4-fluoro-3-methyl-1-[(1-methylcyclopropyl)methyl]-5-[4-(trifluoromethyl)pyridin-2-yl]-1,3-dihydro-2H-benzimidazol-2-one | LRMS m/z (M + H) 380.1 found, 380.4 required. |
| 7-25 | 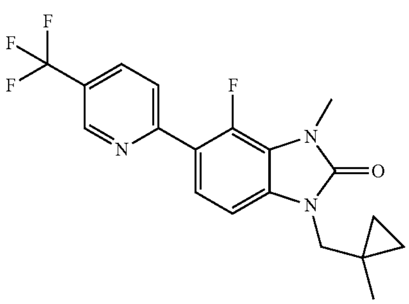 [SMILES: Cn1c(=O)n(CC2(C)CC2)c2ccc(-c3ccc(C(F)(F)F)cn3)c(F)c21] | 4-fluoro-3-methyl-1-[(1-methylcyclopropyl)methyl]-5-[5-(trifluoromethyl)pyridin-2-yl]-1,3-dihydro-2H-benzimidazol-2-one | LRMS m/z (M + H) 380.1 found, 380.4 required. |

-continued

Table 1 for Scheme 7

| Cmp | Structure | Name | LRMS m/z (M + H) |
| --- | --- | --- | --- |
| 7-26 | 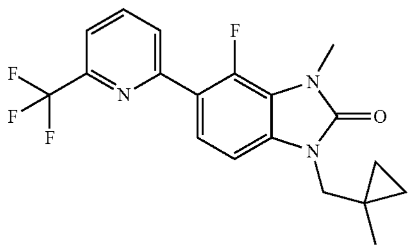 [SMILES: Cn1c(=O)n(CC2(C)CC2)c2ccc(-c3cccc(C(F)(F)F)n3)c(F)c21] | 4-fluoro-3-methyl-1-[(1-methylcyclopropyl)methyl]-5-[6-(trifluoromethyl)pyridin-2-yl]-1,3-dihydro-2H-benzimidazol-2-one | LRMS m/z (M + H) 380.1 found, 380.4 required. |
| 7-27 | 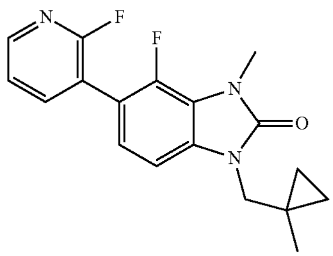 [SMILES: Cn1c(=O)n(CC2(C)CC2)c2ccc(-c3cccnc3F)c(F)c21] | 4-fluoro-5-(2-fluoropyridin-3-yl)-3-methyl-1-[(1-methylcyclopropyl)methyl]-1,3-dihydro-2H-benzimidazol-2-one | LRMS m/z (M + H) 330.1 found, 330.4 required. |
| 7-28 | 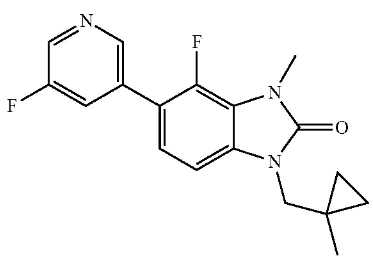 [SMILES: Cn1c(=O)n(CC2(C)CC2)c2ccc(-c3cncc(F)c3)c(F)c21] | 4-fluoro-5-(5-fluoropyridin-3-yl)-3-methyl-1-[(1-methylcyclopropyl)methyl]-1,3-dihydro-2H-benzimidazol-2-one | LRMS m/z (M + H) 330.2 found, 330.5 required. |
| 7-29 | 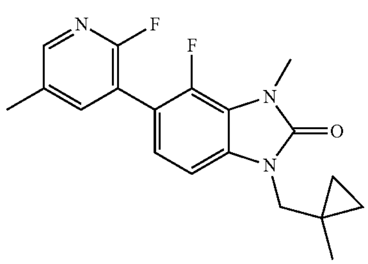 [SMILES: Cc1cnc(F)c(-c2ccc3c(c2F)n(C)c(=O)n3CC2(C)CC2)c1] | 4-fluoro-5-(2-fluoro-5-methylpyridin-3-yl)-3-methyl-1-[(1-methylcyclopropyl)methyl]-1,3-dihydro-2H-benzimidazol-2-one | LRMS m/z (M + H) 344.1 found, 344.4 required. |
| 7-30 | 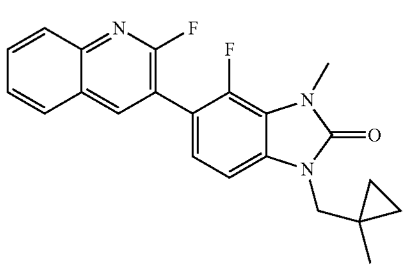 [SMILES: Cn1c(=O)n(CC2(C)CC2)c2ccc(-c3cc4ccccc4nc3F)c(F)c21] | 4-fluoro-5-(2-fluoroquinolin-3-yl)-3-methyl-1-[(1-methylcyclopropyl)methyl]-1,3-dihydro-2H-benzimidazol-2-one | LRMS m/z (M + H) 380.1 found, 380.4 required. |

-continued

Table 1 for Scheme 7

| Cmp | Structure | Name | LRMS m/z (M + H) |
|---|---|---|---|
| 7-31 | 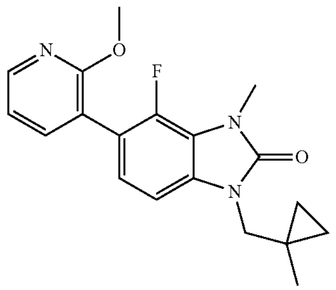 [SMILES: COc1ncccc1-c1ccc2c(c1F)n(C)c(=O)n2CC1(C)CC1] | 4-fluoro-5-(2-methoxypyridin-3-yl)-3-methyl-1-[(1-methylcyclopropyl)methyl]-1,3-dihydro-2H-benzimidazol-2-one | LRMS m/z (M + H) 342.1 found, 342.4 required. |
| 7-32 | 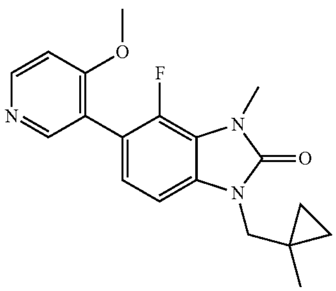 [SMILES: COc1ccncc1-c1ccc2c(c1F)n(C)c(=O)n2CC1(C)CC1] | 4-fluoro-5-(4-methoxypyridin-3-yl)-3-methyl-1-[(1-methylcyclopropyl)methyl]-1,3-dihydro-2H-benzimidazol-2-one | LRMS m/z (M + H) 342.1 found, 342.4 required. |
| 7-33 | 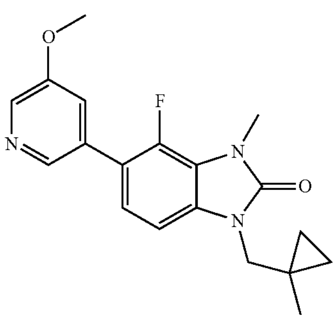 [SMILES: COc1cncc(-c2ccc3c(c2F)n(C)c(=O)n3CC2(C)CC2)c1] | 4-fluoro-5-(5-methoxypyridin-3-yl)-3-methyl-1-[(1-methylcyclopropyl)methyl]-1,3-dihydro-2H-benzimidazol-2-one | LRMS m/z (M + H) 342.1 found, 342.4 required. |
| 7-34 | 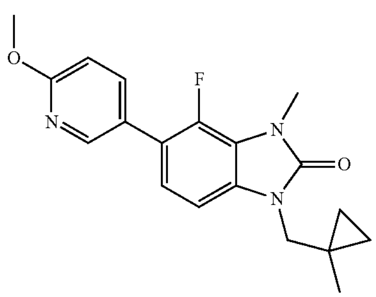 [SMILES: COc1ccc(-c2ccc3c(c2F)n(C)c(=O)n3CC2(C)CC2)cn1] | 4-fluoro-5-(6-methoxypyridin-3-yl)-3-methyl-1-[(1-methylcyclopropyl)methyl]-1,3-dihydro-2H-benzimidazol-2-one | LRMS m/z (M + H) 342.2 found, 342.2 required. |
| 7-35 | 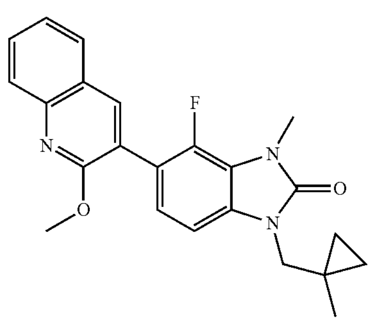 [SMILES: COc1nc2ccccc2cc1-c1ccc2c(c1F)n(C)c(=O)n2CC1(C)CC1] | 4-fluoro-5-(2-methoxyquinolin-3-yl)-3-methyl-1-[(1-methylcyclopropyl)methyl]-1,3-dihydro-2H-benzimidazol-2-one | LRMS m/z (M + H) 392.2 found, 392.4 required. |

-continued

Table 1 for Scheme 7

| Cmp | Structure | Name | LRMS m/z (M + H) |
|---|---|---|---|
| 7-36 | 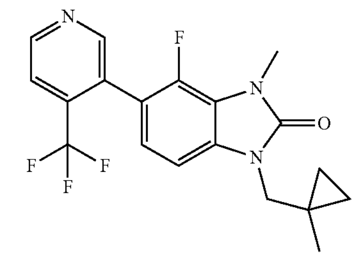 [SMILES: Cn1c(=O)n(CC2(C)CC2)c2ccc(-c3cnccc3C(F)(F)F)c(F)c21] | 4-fluoro-3-methyl-1-[(1-methylcyclopropyl)methyl]-5-[4-(trifluoromethyl)pyridin-3-yl]-1,3-dihydro-2H-benzimidazol-2-one | LRMS m/z (M + H) 380.1 found, 380.4 required. |
| 7-37 | 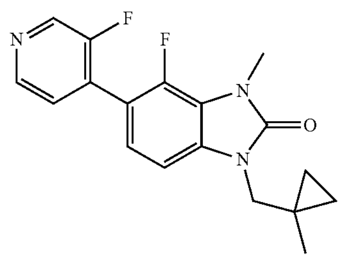 [SMILES: Cn1c(=O)n(CC2(C)CC2)c2ccc(-c3ccncc3F)c(F)c21] | 4-fluoro-5-(3-fluoropyridin-4-yl)-3-methyl-1-[(1-methylcyclopropyl)methyl]-1,3-dihydro-2H-benzimidazol-2-one | LRMS m/z (M + H) 330.1 found, 330.4 required. |
| 7-38 | 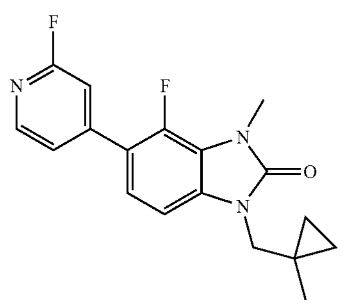 [SMILES: Cn1c(=O)n(CC2(C)CC2)c2ccc(-c3ccnc(F)c3)c(F)c21] | 4-fluoro-5-(2-fluoropyridin-4-yl)-3-methyl-1-[(1-methylcyclopropyl)methyl]-1,3-dihydro-2H-benzimidazol-2-one | LRMS m/z (M + H) 330.1 found, 330.4 required. |
| 7-39 | 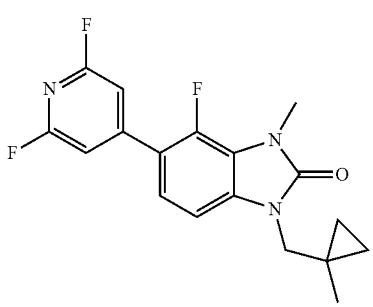 [SMILES: Cn1c(=O)n(CC2(C)CC2)c2ccc(-c3cc(F)nc(F)c3)c(F)c21] | 5-(2,6-difluoropyridin-4-yl)-4-fluoro-3-methyl-1-[(1-methylcyclopropyl)methyl]-1,3-dihydro-2H-benzimidazol-2-one | LRMS m/z (M + H) 348.1 found, 348.4 required. |
| 7-40 | 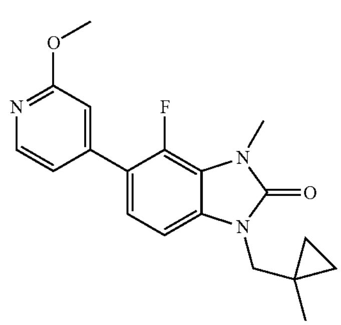 [SMILES: COc1cc(-c2ccc3c(c2F)n(C)c(=O)n3CC2(C)CC2)ccn1] | 4-fluoro-5-(2-methoxypyridin-4-yl)-3-methyl-1-[(1-methylcyclopropyl)methyl]-1,3-dihydro-2H-benzimidazol-2-one | LRMS m/z (M + H) 342.1 found, 342.4 required. |

Table 1 for Scheme 7

| Cmp | Structure | Name | LRMS m/z (M + H) |
|---|---|---|---|
| 7-41 | 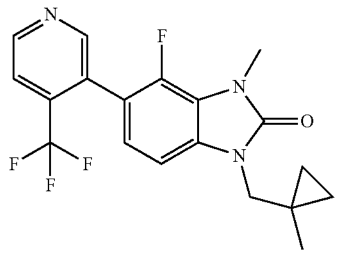 [SMILES: Cn1c(=O)n(CC2(C)CC2)c2ccc(-c3cnccc3C(F)(F)F)c(F)c21] | 4-fluoro-3-methyl-1-[(1-methylcyclopropyl)methyl]-5-[4-(trifluoromethyl)pyridin-3-yl]-1,3-dihydro-2H-benzimidazol-2-one | LRMS m/z (M + H) 380.1 found, 380.4 required. |
| 7-42 | 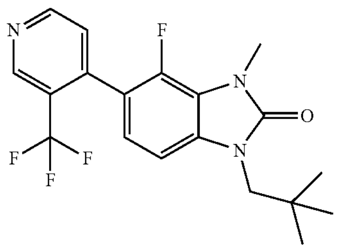 [SMILES: Cn1c(=O)n(CC(C)(C)C)c2ccc(-c3ccncc3C(F)(F)F)c(F)c21] | 1-(2,2-dimethylpropyl)-4-fluoro-3-methyl-5-[3-(trifluoromethyl)pyridin-4-yl]-1,3-dihydro-2H-benzimidazol-2-one | LRMS m/z (M + H) 382.1 found, 382.4 required. |
| 7-43 | 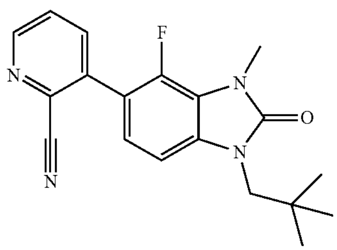 [SMILES: Cn1c(=O)n(CC(C)(C)C)c2ccc(-c3cccnc3C#N)c(F)c21] | 3-[1-(2,2-dimethylpropyl)-4-fluoro-3-methyl-2-oxo-2,3-dihydro-1H-benzimidazol-5-yl]pyridine-2-carbonitrile | LRMS m/z (M + H) 339.1 found, 339.4 required. |
| 7-44 | 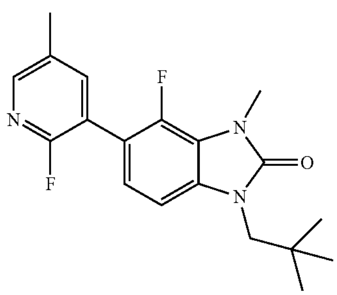 [SMILES: Cc1cnc(F)c(-c2ccc3c(c2F)n(C)c(=O)n3CC(C)(C)C)c1] | 1-(2,2-dimethylpropyl)-4-fluoro-5-(2-fluoro-5-methylpyridin-3-yl)-3-methyl-1,3-dihydro-2H-benzimidazol-2-one | LRMS m/z (M + H) 346.1 found, 346.4 required. |
| 7-45 | 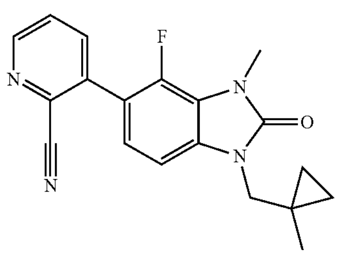 [SMILES: Cn1c(=O)n(CC2(C)CC2)c2ccc(-c3cccnc3C#N)c(F)c21] | 3-{4-fluoro-3-methyl-1-[(1-methylcyclopropyl)methyl]-2-oxo-2,3-dihydro-1H-benzimidazol-5-yl}pyridine-2-carbonitrile | LRMS m/z (M + H) 337.1 found, 337.4 required. |
| 7-46 | 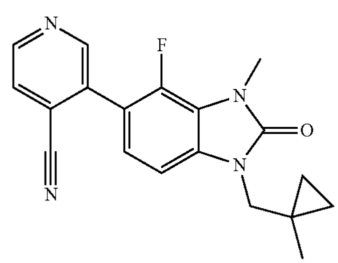 [SMILES: Cn1c(=O)n(CC2(C)CC2)c2ccc(-c3cnccc3C#N)c(F)c21] | 4-fluoro-5-(2-methoxyquinolin-3-yl)-3-methyl-1-[(1-methylcyclopropyl)methyl]-1,3-dihydro-2H-benzimidazol-2-one | LRMS m/z (M + H) 337.1 found, 337.4 required. |

-continued

Table 1 for Scheme 7

| Cmp | Structure | Name | LRMS m/z (M + H) |
|---|---|---|---|
| 7-47 | 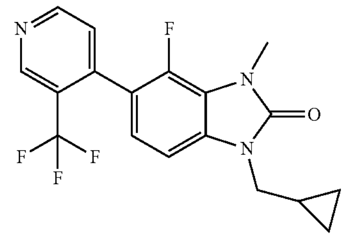 [SMILES: Cn1c(=O)n(CC2CC2)c2ccc(-c3ccncc3C(F)(F)F)c(F)c21] | 1-(cyclopropylmethyl)-4-fluoro-3-methyl-5-[3-(trifluoromethyl)pyridin-4-yl]-1,3-dihydro-2H-benzimidazol-2-one | LRMS m/z (M + H) 366.1 found, 366.3 required. |
| 7-48 | 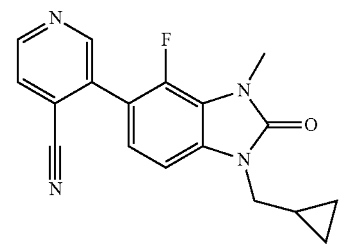 [SMILES: Cn1c(=O)n(CC2CC2)c2ccc(-c3cnccc3C#N)c(F)c21] | 3-[1-(cyclopropylmethyl)-4-fluoro-3-methyl-2-oxo-2,3-dihydro-1H-benzimidazol-5-yl]isonicotinonitrile | LRMS m/z (M + H) 323.1 found, 323.3 required. |

REACTION SCHEME 8

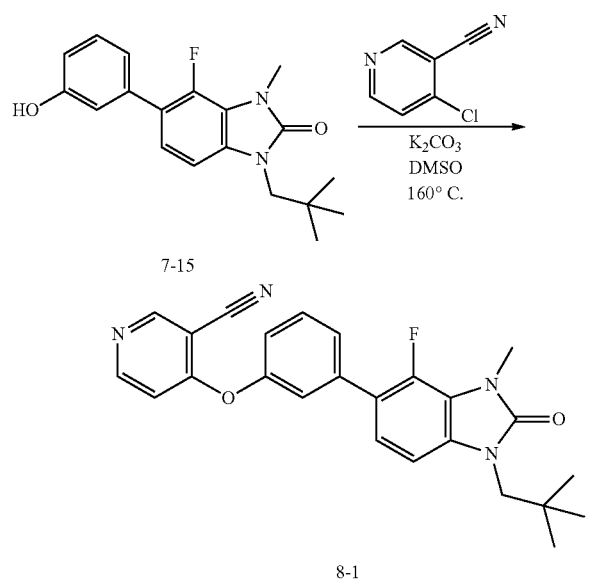

4-{3-[1-(2,2-dimethylpropyl)-4-fluoro-3-methyl-2-oxo-2,3-dihydro-1H-benzimidazol-5-yl]phenoxy}nicotinonitrile (8-1)

A solution of 1-(2,2-dimethylpropyl)-4-fluoro-5-(3-hydroxyphenyl)-3-methyl-1,3-dihydro-2H-benzimidazol-2-one (7-15, 55 mg, 0.17 mmol) in DMSO (1 ml) was charged with Potassium carbonate (46.3 mg, 0.34 mmol, 2.0 eq) and 4-Chloro-3-cyanopyridine (34.8 mg, 0.25 mmol, 1.5 eq). The mixture was irradiated in a microwave at 160 deg C. for 20 min, then purified via reverse-phase HPLC (Acetonitrile/Water gradient with 0.1% TFA present) providing 4-{3-[1-(2,2-dimethylpropyl)-4-fluoro-3-methyl-2-oxo-2,3-dihydro-1H-benzimidazol-5-yl]phenoxy}nicotinonitrile (8-1) as a tan solid-oil. $^1$H NMR (400 MHz, CDCl$_3$) δ 8.81 (bs, 1H), 7.60-7.53 (m, 2H), 7.35 (s, 1H), 7.27 (s, 1H), 7.17-7.14 (m, 1H), 7.11-7.07 (m, 1H), 6.91 (d, 2H, J=8.24 Hz), 3.69 (s, 2H), 3.66 (s, 3H), 1.10 (s, 9H). LRMS m/z: Calc'd for $C_{25}H_{23}FN_4O_2$ (M+H) 431.4, found 431.5.

Table 1 for Scheme 8

| Cmp | Structure | Name | LRMS m/z (M + H) |
|---|---|---|---|
| 8-2 | 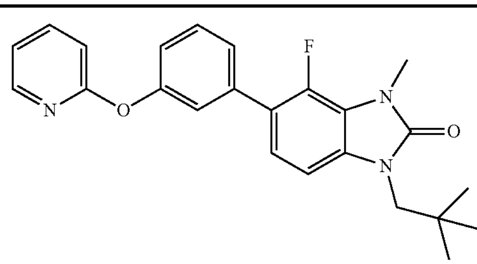 | 1-(2,2-dimethylpropyl)-4-fluoro-3-methyl-5-[3-(pyridin-2-yloxy)phenyl]-1,3-dihydro-2H-benzimidazol-2-one | LRMS m/z (M + H) 406.2 found, 406.5 required. |

Table 1 for Scheme 8

| Cmp | Structure | Name | LRMS m/z (M + H) |
|---|---|---|---|
| 8-3 | 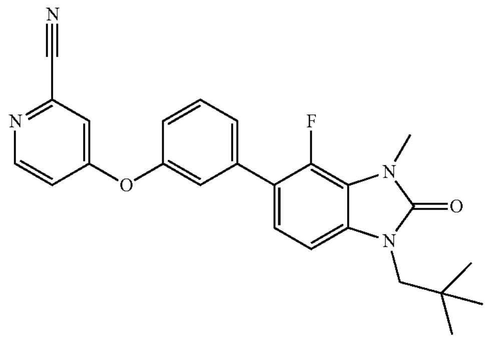 [SMILES: Cn1c(=O)n(CC(C)(C)C)c2ccc(-c3cccc(Oc4ccnc(C#N)c4)c3)c(F)c21] | 4-{3-[1-(2,2-dimethylpropyl)-4-fluoro-3-methyl-2-oxo-2,3-dihydro-1H-benzimidazol-5-yl]phenoxy}pyridine-2-carbonitrile | LRMS m/z (M + H) 431.2 found, 431.5 required. |
| 8-4 | 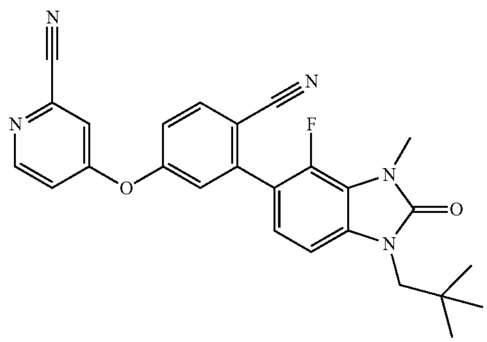 [SMILES: Cn1c(=O)n(CC(C)(C)C)c2ccc(-c3cc(Oc4ccnc(C#N)c4)ccc3C#N)c(F)c21] | 4-{4-cyano-3-[1-(2,2-dimethylpropyl)-4-fluoro-3-methyl-2-oxo-2,3-dihydro-1H-benzimidazol-5-yl]phenoxy}pyridine-2-carbonitrile | LRMS m/z (M + H) 456.0 found, 456.5 required. |
| 8-5 | 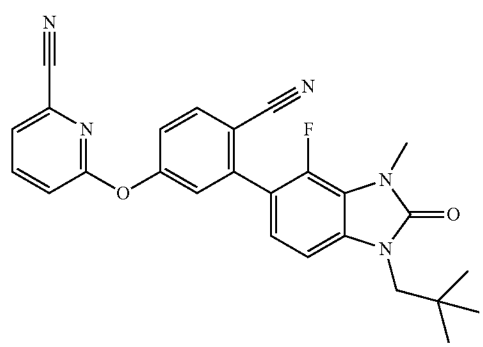 [SMILES: Cn1c(=O)n(CC(C)(C)C)c2ccc(-c3cc(Oc4cccc(C#N)n4)ccc3C#N)c(F)c21] | 6-{4-cyano-3-[1-(2,2-dimethylpropyl)-4-fluoro-3-methyl-2-oxo-2,3-dihydro-1H-benzimidazol-5-yl]phenoxy}pyridine-2-carbonitrile | LRMS m/z (M + H) 456.0 found, 456.5 required. |

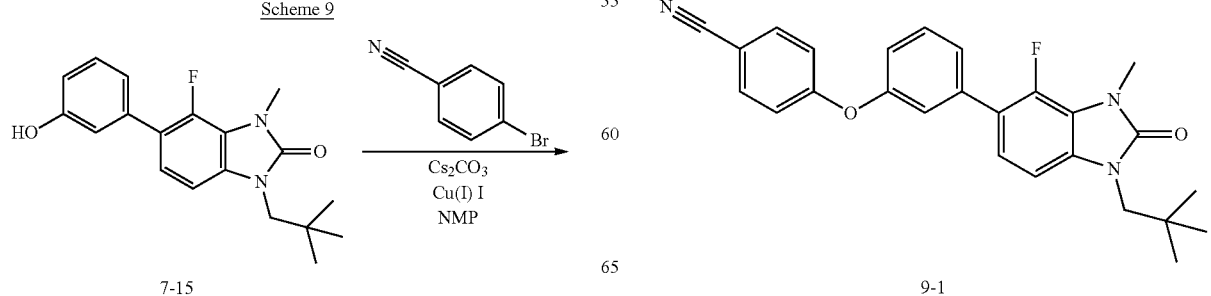

Scheme 9

4-{3-[1-(2,2-dimethylpropyl)-4-fluoro-3-methyl-2-oxo-2,3-dihydro-1H-benzimidazol-5-yl]phenoxy}benzonitrile (9-1)

A solution of 1-(2,2-dimethylpropyl)-4-fluoro-5-(3-hydroxyphenyl)-3-methyl-1,3-dihydro-2H-benzimidazol-2-one (7-15, 55 mg, 0.17 mmol) in NMP (1 ml) was sequentially charged with 4-Bromobenzonitrile (61.0 mg, 0.34 mmol, 2.0 eq), Cesium carbonate (109 mg, 0.34 mmol, 2.0 eq) and Copper(I) iodide (31.9 mg, 0.17 mmol, 1.0 eq). The resulting mixture was irradiated in a microwave at 195 deg C. for 2 h. LC/MS analysis showed only partial conversion, therefore additional amounts of 4-Bromobenzonitrile (61.0 mg, 0.34 mmol, 2.0 eq) and Cu(I)I (31.9 mg, 0.17 mmol, 1.0 eq) were added and the reaction was irradiated again at 195 deg C. for 1 h. The completed reaction was filtered and the filtrate purified via reverse-phase HPLC (Acetonitrile/Water gradient with 0.1% TFA present) to afford the title compound, 4-{3-[1-(2,2-dimethylpropyl)-4-fluoro-3-methyl-2-oxo-2,3-dihydro-1H-benzimidazol-5-yl]phenoxy}benzonitrile (9-1), as a tan solid-oil. $^1$H NMR (400 MHz, CDCl$_3$) δ 7.62 (d, 2H, J=8.9 Hz), 7.50-7.46 (m, 1H), 7.39 (m, 1H), 7.25 (s, 1H), 7.09-7.04 (m, 4H), 6.87 (d, 1H, J=8.2 Hz), 3.67 (s, 2H), 3.64 (s, 3H), 1.05 (s, 9H). LRMS m/z: Calc'd for C$_{26}$H$_{24}$FN$_3$O$_2$ (M+H) 430.2, found 430.5.

Scheme 10

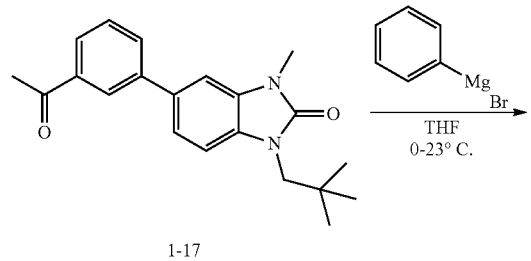

1-17

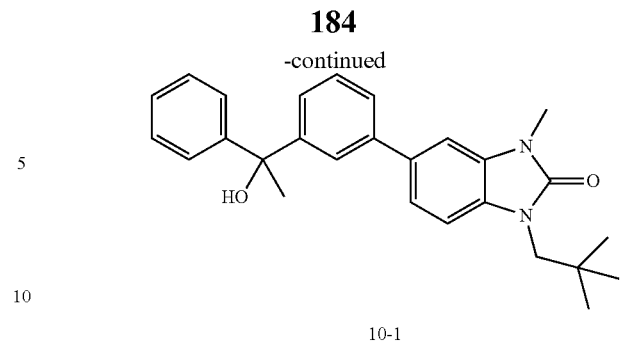

10-1

1-(2,2-dimethylpropyl)-5-[3-(1-hydroxy-1-phenylethyl)phenyl]-3-methyl-1,3-dihydro-2H-benzimidazol-2-one (10-1)

A solution of 5-(3-acetylphenyl)-1-(2,2-dimethylpropyl)-3-methyl-1,3-dihydro-2H-benzimidazol-2-one (1-17, 170 mg, 0.51 mmol) in anhydrous THF (5 ml) was cooled to −78 deg C. and treated with Phenyl magnesium chloride (1.8 M in THF, 365 μL, 0.66 mmol, 1.3 eq). The reaction mixture was warmed to 0 deg C. and stirred for 1 h. The reaction was only ~30% complete, so more of the Grignard reagent (1.8 M in THF, 365 μL, 0.66 mmol, 1.3 eq) was added at 0 deg C. and the reaction was maintained there for 30 min. The completed reaction was partitioned between EtOAc (50 ml) and water (55 ml) and the cloudy, white precipitate present which was removed via filtration. The filtrate was separated in a separatory funnel and the aqueous layer was re-extracted with EtOAc (50 ml). The combined organic layers were dried over Na$_2$SO$_4$, concentrated, then purified via flash column chromatography (SiO$_2$: 100% Hex to 50:50 Hex/EtOAc), affording the title compound, 1-(2,2-dimethylpropyl)-5-[3-(1-hydroxy-1-phenylethyl)phenyl]-3-methyl-1,3-dihydro-2H-benzimidazol-2-one (10-1) as a colorless oil. $^1$H NMR (400 MHz, CDCl$_3$) δ 7.70 (s, 1H), 7.48-7.45 (m, 3H), 7.40-7.31 (m, 4H), 7.27-7.24 (m, 2H), 7.12 (s, 1H), 7.05 (d, 1H, J=8.15 Hz), 3.67 (s, 2H), 3.45 (s, 3H), 2.02 (s, 3H), 1.05 (s, 9H). LRMS m/z: Calc'd for C$_{27}$H$_{30}$N$_2$O$_2$(M+H) 415.2, found 415.5.

Table 1 for Scheme 10

| Cmp | Structure | Name | LRMS m/z (M + H) |
| --- | --- | --- | --- |
| 10-2 | 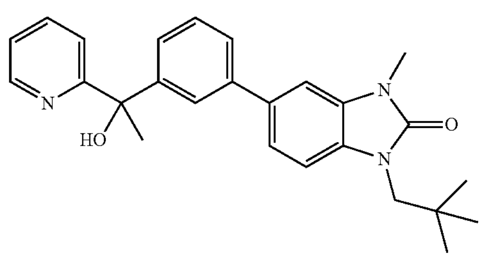 [SMILES: Cn1c(=O)n(CC(C)(C)C)c2ccc(-c3cccc(C(C)(O)c4ccccn4)c3)cc21] | 1-(2,2-dimethylpropyl)-5-[3-(1-hydroxy-1-pyridin-2-ylethyl)phenyl]-3-methyl-1,3-dihydro-2H-benzimidazol-2-one | LRMS m/z (M + H) 416.1 found, 416.5 required. |
| 10-3 | 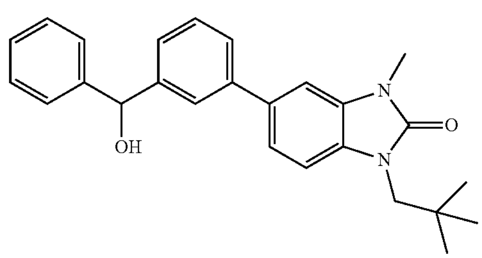 [SMILES: Cn1c(=O)n(CC(C)(C)C)c2ccc(-c3cccc(C(O)c4ccccc4)c3)cc21] | 1-(2,2-dimethylpropyl)-5-{3-[hydroxy(phenyl)methyl]phenyl}-3-methyl-1,3-dihydro-2H-benzimidazol-2-one | LRMS m/z (M + H) 401.1 found, 401.5 required. |

Table 1 for Scheme 10

| Cmp | Structure | Name | LRMS m/z (M + H) |
|---|---|---|---|
| 10-4 | 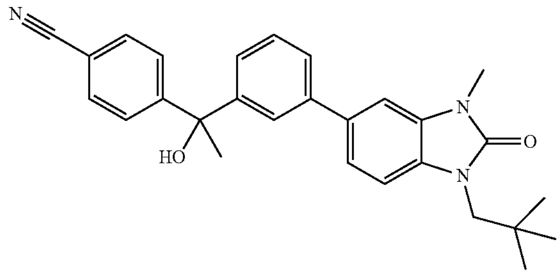 [SMILES: Cn1c(=O)n(CC(C)(C)C)c2ccc(-c3cccc(C(C)(O)c4ccc(C#N)cc4)c3)cc21] | 4-(1-{3-[1-(2,2-dimethylpropyl)-3-methyl-2-oxo-2,3-dihydro-1H-benzimidazol-5-yl]phenyl}-1-hydroxyethyl)benzonitrile | LRMS m/z (M + H) 440.1 found, 440.6 required. |
| 10-5 | 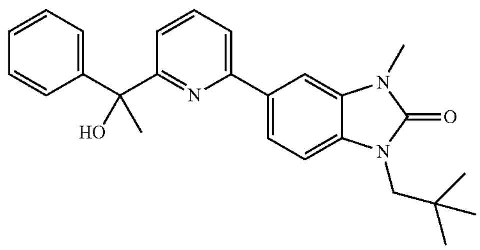 [SMILES: Cn1c(=O)n(CC(C)(C)C)c2ccc(-c3cccc(C(C)(O)c4ccccc4)n3)cc21] | 1-(2,2-dimethylpropyl)-5-[6-(1-hydroxy-1-phenylethyl)pyridin-2-yl]-3-methyl-1,3-dihydro-2H-benzimidazol-2-one | LRMS m/z (M + H) 416.1 found, 416.5 required. |

What is claimed is:

1. A compound according Formula Ic

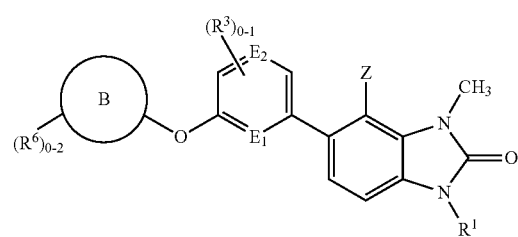

or a pharmaceutically acceptable salt thereof, wherein
$E_1$ and $E_2$ are independently C or N;
ring B is phenyl or heteroaryl,
$R^3$ is CN, halo or $C_{1-4}$alkyl, optionally substituted with 1-5 halo atoms, and
each $R^6$ is independently selected from the group consisting of: CN, halo, $R^5$, —O—$R^5$, —N(R)—$R^5$, —N(R)C(O)—$R^5$, —N(R)S(O)_2—$R^5$, —N(R)—C(O)—O—$R^5$, —C(O)—N(R)—$R^5$, —C(O)—O—$R^5$, —C(O)—$R^5$, —C(O)—C($R^4$)_2—$R^5$, —C(O)—C($R^4$)_2—S(O)_2—$R^5$, —C($R^4$)_2—N(R)—$R^5$, —SO_2—N(R)—$R^5$, —Si(CH_3)_2($R^5$), —C($R^4$)_2—$R^5$ and —SO_2—$R^5$;
each R is independently selected from the group consisting of: H and $C_{1-4}$alkyl;
each $R^4$ is independently selected from the group consisting of: H, OH and $C_{1-4}$alkyl;
each $R^5$ is independently selected from the group consisting of: H, $C_{1-4}$alkyl, $C_{2-4}$alkenyl, $C_{2-4}$alkynyl, $C_{3-6}$cycloalkyl, phenyl, benzyl, heterocycle and heteroaryl, wherein each member of the group excluding hydrogen is optionally substituted with 1 to 3 substituents independently selected from: halogen, cyano, hydroxy and methyl;
Z is selected from H, halo, hydroxy, methyl, methoxy or CN;

$R^1$ is selected from the group consisting of:
(1) $C_{2-8}$alkyl,
(2) $C_{2-8}$alkenyl,
(3) $C_{2-8}$alkynyl,
(4) $C_{3-6}$cycloalkyl-(CH_2)_p—,
(5) aryl-(CH_2)_p—,
(6) heteroaryl-(CH_2)_p—, and
(7) heterocycle-(CH_2)_p—,
wherein p is 0, 1, 2, 3 or 4, and groups (1) to (7) above are optionally substituted with 1 to 4 $R^2$ groups; and
each $R^2$ is independently selected from the group consisting of: halo, OH, —CN, $C_{1-4}$alkyl, $C_{1-4}$alkoxy, CF_3, —OCF_3, —C(O)—O—$C_{1-4}$alkyl, —N(R)_2, pyrimidinyl and —CN.

2. The compound according to claim 1 wherein ring B is phenyl.

3. The compound according to claim 1 wherein ring B is pyridyl.

4. The compound according to claim 1 wherein $E_1$ is C and $E_2$ is C.

5. The compound according to claim 1 wherein $E_1$ is N and $E_2$ is C.

6. The compound according to claim 1 wherein $E_1$ is C and $E_2$ is N.

7. A compound of Formula Id

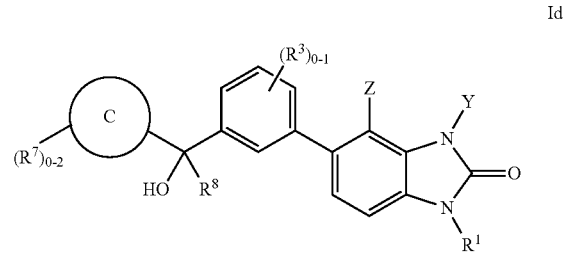

or a pharmaceutically acceptable salt thereof, wherein
ring C is phenyl or heteroaryl,
$R^3$ is CN, halo or $C_{1-4}$alkyl, optionally substituted with 1-5 halo atoms, and each R⁷ is independently selected from the group consisting of: CN, halo, R⁵, —O—R⁵, —N(R)—R⁵, —N(R)C(O)—R⁵, —N(R)S(O)₂—R⁵, —N(R)—C(O)—O—R⁵, —C(O)—N(R)—R⁵, —C(O)—O—R⁵, —C(O)—R⁵, —C(O)—C(R⁴)₂—R⁵, —C(O)—C(R⁴)₂—S(O)₂—R⁵, —C(R⁴)₂—N(R)—R⁵, —SO₂—N(R)—R⁵, —Si(CH₃)₂(R⁵), —C(R⁴)₂—R⁵ and —SO₂—R⁵;
R⁸ is H or methyl;
each R is independently selected from the group consisting of: H and C₁₋₄alkyl;
each R⁴ is independently selected from the group consisting of: H, OH and C₁₋₄alkyl;
each R⁵ is independently selected from the group consisting of: H, C₁₋₄alkyl, C₂₋₄alkenyl, C₂₋₄alkynyl, C₃₋₆cycloalkyl, phenyl, benzyl, heterocycle and heteroaryl, wherein each member of the group excluding hydrogen is optionally substituted with 1 to 3 substituents independently selected from: halogen, cyano, hydroxy and methyl;
Z is selected from H, halo, hydroxy, methyl, methoxy or CN;
Y is cyano, benzyl, C₁₋₆alkyl or C₂₋₆alkenyl, said C₁₋₆alkyl and C₂₋₆alkenyl optionally substituted with cyano;
R¹ is selected from the group consisting of:
 (1) C₂₋₈alkyl,
 (2) C₂₋₈alkenyl,
 (3) C₂₋₈alkynyl,
 (4) C₃₋₆cycloalkyl-(CH₂)ₚ—,
 (5) aryl-(CH₂)ₚ—,
 (6) heteroaryl-(CH₂)ₚ—, and
 (7) heterocycle-(CH₂)ₚ—,
wherein wherein p is 0, 1, 2, 3 or 4, and groups (1) to (7) above are optionally substituted with 1 to 4 R² groups; and
each R² is independently selected from the group consisting of: halo, OH, —CN, C₁₋₄alkyl, C₁₋₄alkoxy, CF₃, —OCF₃, —C(O)—O—C₁₋₄alkyl, —N(R)₂, pyrimidinyl and —CN.

8. A compound selected from the following group consisting of:
1-(2,2-dimethylpropyl)-3-methyl-5-phenyl-1,3-dihydro-2H-benzimidazol-2-one;
1-(cyclopropylmethyl)-3-ethyl-5-phenyl-1,3-dihydro-2H-benzimidazol-2-one;
1-(cyclopropylmethyl)-5-phenyl-3-propyl-1,3-dihydro-2H-benzimidazol-2-one;
[3-(cyclopropylmethyl)-2-oxo-6-phenyl-2,3-dihydro-1H-benzimidazol-1-yl]acetonitrile;
3-benzyl-1-(cyclopropylmethyl)-5-phenyl-1,3-dihydro-2H-benzimidazol-2-one;
2-[1-(2,2-dimethylpropyl)-2-oxo-2,3-dihydro-1H-benzimidazol-5-yl]benzonitrile;
1-(2,2-dimethylpropyl)-5-phenyl-1,3-dihydro-2H-benzimidazol-2-one;
5-(3-chlorophenyl)-1-(2,2-dimethylpropyl)-3-methyl-1,3-dihydro-2H-benzimidazol-2-one;
1-(2,2-dimethylpropyl)-5-(3-isopropylphenyl)-3-methyl-1,3-dihydro-2H-benzimidazol-2-one;
1-(2,2-dimethylpropyl)-3-methyl-5-[3-(trifluoromethyl)phenyl]-1,3-dihydro-2H-benzimidazol-2-one;
1-(2,2-dimethylpropyl)-5-[3-(hydroxymethyl)phenyl]-3-methyl-1,3-dihydro-2H-benzimidazol-2-one;
5-(3-acetylphenyl)-1-(2,2-dimethylpropyl)-3-methyl-1,3-dihydro-2H-benzimidazol-2-one;
3-[1-(2,2-dimethylpropyl)-3-methyl-2-oxo-2,3-dihydro-1H-benzimidazol-5-yl]-N,N-dimethylbenzamide;
3-[1-(2,2-dimethylpropyl)-3-methyl-2-oxo-2,3-dihydro-1H-benzimidazol-5-yl]-N-phenylbenzamide;
1-(2,2-dimethylpropyl)-5-(2-fluorophenyl)-3-methyl-1,3-dihydro-2H-benzimidazol-2-one;
N-(tert-butyl)-2-[1-(2,2-dimethylpropyl)-3-methyl-2-oxo-2,3-dihydro-1H-benzimidazol-5-yl]benzenesulfonamide;
1-(2,2-dimethylpropyl)-3-methyl-5-(3-methylphenyl)-1,3-dihydro-2H-benzimidazol-2-one;
1-(2,2-dimethylpropyl)-5-(3-fluorophenyl)-3-methyl-1,3-dihydro-2H-benzimidazol-2-one;
{3-[1-(2,2-dimethylpropyl)-3-methyl-2-oxo-2,3-dihydro-1H-benzimidazol-5-yl]phenyl}acetic acid;
5-biphenyl-3-yl-1-(2,2-dimethylpropyl)-3-methyl-1,3-dihydro-2H-benzimidazol-2-one;
3-(2,2-dimethylpropyl)-1-methyl-5-phenyl-1,3dihydro-2H-benzimidazol-2-one;
3-(cyclopropylmethyl)-2-oxo-6-phenyl-2,3-dihydro-1H-benzimidazole-1-carbonitrile;
1-(2,2-dimethylpropyl)-3-methyl-5-(2-thienyl)-1,3-dihydro-2H-benzimidazol-2-one;
1-(2,2-dimethylpropyl)-3-methyl-5-(3-thienyl)-1,3-dihydro-2H-benzimidazol-2-one;
5-(1-benzothien-3-yl)-1-(2,2-dimethylpropyl)-3-methyl-1,3-dihydro-2H-benzimidazol-2-one;
5-(1-benzofuran-2-yl)-1-(2,2-dimethylpropyl)-3-methyl-1,3-dihydro-2H-benzimidazol-2-one;
1-(2,2-dimethylpropyl)-5-(3-furyl)-3-methyl-1,3-dihydro-2H-benzimidazol-2-one;
5-(1-benzofuran-3-yl)-1-(2,2-dimethylpropyl)-3-methyl-1,3-dihydro-2H-benzimidazol-2-one;
5-(3,5-dimethylisoxazol-4-yl)-1-(2,2-dimethylpropyl)-3-methyl-1,3-dihydro-2H-benzimidazol-2-one;
1-(2,2-dimethylpropyl)-3-methyl-5-(5-methyl-3-phenylisoxazol-4-yl)-1,3-dihydro-2H-benzimidazol-2-one;
1-(2,2-dimethylpropyl)-3-methyl-5-(1H-pyrazol-3-yl)-1,3-dihydro-2H-benzimidazol-2-one;
1-(2,2-dimethylpropyl)-3-methyl-5-(1H-pyrazol-4-yl)-1,3-dihydro-2H-benzimidazol-2-one;
1-(2,2-dimethylpropyl)-5-(3,5-dimethyl-1H-pyrazol-4-yl)-3-methyl-1,3-dihydro-2H-benzimidazol-2-one;
1-(2,2-dimethylpropyl)-3-methyl-5-[6-(1H-pyrazol-1-yl)pyridin-2-yl]-1,3-dihydro-2H-benzimidazol-2-one;
1-(2,2-dimethylpropyl)-5-(2-fluoropyridin-3-yl)-3-methyl-1,3-dihydro-2H-benzimidazol-2-one;
1-(2,2-dimethylpropyl)-5-(6-fluoropyridin-3-yl)-3-methyl-1,3-dihydro-2H-benzimidazol-2-one;
1-(2,2-dimethylpropyl)-3-methyl-5-quinolin-3-yl-1,3-dihydro-2H-benzimidazol-2-one;
1-(2,2-dimethylpropyl)-3-methyl-5-pyridin-4-yl-1,3-dihydro-2H-benzimidazol-2-one;
1-(2,2-dimethylpropyl)-5-(2-fluoropyridin-4-yl)-3-methyl-1,3-dihydro-2H-benzimidazol-2-one;
1-(2,2-dimethylpropyl)-5-(2-methoxypyridin-4-yl)-3-methyl-1,3-dihydro-2H-benzimidazol-2-one;
1-(2,2-dimethylpropyl)-5-(3-fluoropyridin-4-yl)-3-methyl-1,3-dihydro-2H-benzimidazol-2-one;
5-(5-chloro-2-fluoropyridin-4-yl)-1-(2,2-dimethylpropyl)-3-methyl-1,3-dihydro-2H-benzimidazol-2-one;
5-(2,6-difluoropyridin-4-yl)-1-(2,2-dimethylpropyl)-3-methyl-1,3-dihydro-2H-benzimidazol-2-one;
5-(3-chlorophenyl)-1-(2,2-dimethylpropyl)-3-methyl-1,3-dihydro-2H-benzimidazol-2-one;
1-(2,2-dimethylpropyl)-5-(1-isobutyl-1H-pyrazol-4-yl)-3-methyl-1,3-dihydro-2H-benzimidazol-2-one;

1-(2,2-dimethylpropyl)-3-methyl-5-[1-(2-morpholin-4-ylethyl)-1H-pyrazol-4-yl]-1,3-dihydro-2H-benzimidazol-2-one;
1-(2,2-dimethylpropyl)-3-methyl-5-(4,5,6,7-tetrahydropyrazolo[1,5-a]pyridin-3-yl)-1,3-dihydro-2H-benzimidazol-2-one;
5-(1-benzyl-1H-pyrazol-5-yl)-1-(2,2-dimethylpropyl)-3-methyl-1,3-dihydro-2H-benzimidazol-2-one;
1-(2,2-dimethylpropyl)-3-methyl-5-[1-methyl-3-(trifluoromethyl)-1H-pyrazol-5-yl]-1,3-dihydro-2H-benzimidazol-2-one;
1-(2,2-dimethylpropyl)-5-(2-fluoroquinolin-3-yl)-3-methyl-1,3-dihydro-2H-benzimidazol-2-one;
1-(2,2-dimethylpropyl)-3-methyl-5-(6-morpholin-4-ylpyridin-3-yl)-1,3-dihydro-2H-benzimidazol-2-one;
1-(2,2-dimethylpropyl)-3-methyl-5-(5-methylpyridin-3-yl)-1,3-dihydro-2H-benzimidazol-2-one;
1-(2,2-dimethylpropyl)-5-[5-(hydroxymethyl)pyridin-3-yl]-3-methyl-1,3-dihydro-2H-benzimidazol-2-one;
5-(2,6-difluoropyridin-3-yl)-1-(2,2-dimethylpropyl)-3-methyl-1,3-dihydro-2H-benzimidazol-2-one;
1-(2,2-dimethylpropyl)-3-methyl-5-[4-(trifluoromethyl)pyridin-3-yl]-1,3-dihydro-2H-benzimidazol-2-one;
1-(2,2-dimethylpropyl)-3-methyl-5-pyrimidin-5-yl-1,3-dihydro-2H-benzimidazol-2-one;
5-(2,4-dimethoxypyrimidin-5-yl)-1-(2,2-dimethylpropyl)-3-methyl-1,3-dihydro-2H-benzimidazol-2-one;
1-(2,2-dimethylpropyl)-5-(2-fluorophenyl)-3-methyl-1,3-dihydro-2H-benzimidazol-2-one;
1-(2,2-dimethylpropyl)-3-methyl-5-[3-(1H-pyrazol-1-yl)phenyl]-1,3-dihydro-2H-benzimidazol-2-one;
1-(2,2-dimethylpropyl)-3-methyl-5-(4-methylphenyl)-1,3-dihydro-2H-benzimidazol-2-one;
1-(2,2-dimethylpropyl)-5-(4-fluorophenyl)-3-methyl-1,3-dihydro-2H-benzimidazol-2-one;
1-(2,2-dimethylpropyl)-3-methyl-5-[4-(trifluoromethoxy)phenyl]-1,3-dihydro-2H-benzimidazol-2-one;
5-(2,4-difluorophenyl)-1-(2,2-dimethylpropyl)-3-methyl-1,3-dihydro-2H-benzimidazol-2-one;
1-(2,2-dimethylpropyl)-5-(5-fluoro-2-methylphenyl)-3-methyl-1,3-dihydro-2H-benzimidazol-2-one;
1-(2,2-dimethylpropyl)-5-[4-hydroxy-2-(trifluoromethyl)phenyl]-3-methyl-1,3-dihydro-2H-benzimidazol-2-one;
1-(2,2-dimethylpropyl)-5-[2-fluoro-5-(trifluoromethyl)phenyl]-3-methyl-1,3-dihydro-2H-benzimidazol-2-one;
5-(3,4-difluorophenyl)-1-(2,2-dimethylpropyl)-3-methyl-1,3-dihydro-2H-benzimidazol-2-one;
5-[1-(2,2-dimethylpropyl)-3-methyl-2-oxo-2,3-dihydro-1H-benzimidazol-5-yl]-2-fluorobenzoic acid;
5-(3-chloro-4-ethoxyphenyl)-1-(2,2-dimethylpropyl)-3-methyl-1,3-dihydro-2H-benzimidazol-2-one;
5-(2,3-dihydro-1-benzofuran-5-yl)-1-(2,2-dimethylpropyl)-3-methyl-1,3-dihydro-2H-benzimidazol-2-one;
1-(2,2-dimethylpropyl)-5-(1H-indol-5-yl)-3-methyl-1,3-dihydro-2H-benzimidazol-2-one;
1-(2,2-dimethylpropyl)-5-(1H-indazol-5-yl)-3-methyl-1,3-dihydro-2H-benzimidazol-2-one;
1-(2,2-dimethylpropyl)-5-(1H-indazol-6-yl)-3-methyl-1,3-dihydro-2H-benzimidazol-2-one;
1-(2,2-dimethylpropyl)-3-methyl-5-phenyl-1,3-dihydro-2H-benzimidazol-2-one;
1-(2,2-dimethylpropyl)-3-methyl-5-(1-methyl-1H-pyrazol-4-yl)-1,3-dihydro-2H-benzimidazol-2-one;
1-(2,2-dimethylpropyl)-3-methyl-5-(5-methyl-1-phenyl-1H-pyrazol-4-yl)-1,3-dihydro-2H-benzimidazol-2-one;
1-(2,2-dimethylpropyl)-5-(2-methoxypyrimidin-5-yl)-3-methyl-1,3-dihydro-2H-benzimidazol-2-one;
3-[1-(2,2-dimethylpropyl)-3-methyl-2-oxo-2,3-dihydro-1H-benzimidazol-5-yl]benzonitrile;
6-[1-(2,2-dimethylpropyl)-3-methyl-2-oxo-2,3-dihydro-1H-benzimidazol-5-yl]-4-(trifluoromethyl)nicotinic acid;
1-(2,2-dimethylpropyl)-5-[4-(1-hydroxy-1-methylethyl)phenyl]-3-methyl-1,3-dihydro-2H-benzimidazol-2-one;
1-(2,2-dimethylpropyl)-5-[3-(1-hydroxy-1-methylethyl)phenyl]-3-methyl-1,3-dihydro-2H-benzimidazol-2-one;
1-(2,2-dimethylpropyl)-3-methyl-5-(2-piperidin-1-yl-1,3-thiazol-4-yl)-1,3-dihydro-2H-benzimidazol-2-one;
4-[1-(2,2-dimethylpropyl)-3-methyl-2-oxo-2,3-dihydro-1H-benzimidazol-5-yl]benzonitrile;
2-[1-(2,2-dimethylpropyl)-3-methyl-2-oxo-2,3-dihydro-1H-benzimidazol-5-yl]-3-methoxybenzonitrile;
2-[1-(2,2-dimethylpropyl)-3-methyl-2-oxo-2,3-dihydro-1H-benzimidazol-5-yl]-5-(trifluoromethyl)benzonitrile;
2-chloro-6-[1-(2,2-dimethylpropyl)-3-methyl-2-oxo-2,3-dihydro-1H-benzimidazol-5-yl]benzonitrile;
2-[1-(2,2-dimethylpropyl)-3-methyl-2-oxo-2,3-dihydro-1H-benzimidazol-5-yl]-6-(trifluoromethyl)benzonitrile;
2-[1-(2,2-dimethylpropyl)-3-methyl-2-oxo-2,3-dihydro-1H-benzimidazol-5-yl]-6-methoxybenzonitrile;
2-[1-(2,2-dimethylpropyl)-3-methyl-2-oxo-2,3-dihydro-1H-benzimidazol-5-yl]-5-fluorobenzonitrile;
2-[1-(2,2-dimethylpropyl)-3-methyl-2-oxo-2,3-dihydro-1H-benzimidazol-5-yl]-5-methylbenzonitrile;
3-[1-(2,2-dimethylpropyl)-3-methyl-2-oxo-2,3-dihydro-1H-benzimidazol-5-yl]isonicotinonitrile;
5-{3-methyl-1-[(1-methylcyclopropyl)methyl]-2-oxo-2,3-dihydro-1H-benzimidazol-5-yl}nicotinonitrile;
1-(cyclopropylmethyl)-3,5-diphenyl-1,3-dihydro-2H-benzimidazol-2-one;
1-(cyclopropylmethyl)-3-methyl-5-phenyl-1,3-dihydro-2H-benzimidazol-2-one;
3-[1-(2,2-dimethylpropyl)-2-oxo-2,3-dihydro-1H-benzimidazol-5-yl]isonicotinonitrile;
3-[1-(2,2-dimethylpropyl)-2-oxo-2,3-dihydro-1H-benzimidazol-5-yl]pyridine-2-carbonitrile;
1-(2,2-dimethylpropyl)-3-methyl-5-[6-methyl-4-(trifluoromethyl)pyridin-2-yl]-1,3-dihydro-2H-benzimidazol-2-one;
1-(2,2-dimethylpropyl)-3-methyl-5-[4-(trifluoromethyl)quinolin-2-yl]-1,3-dihydro-2H-benzimidazol-2-one;
5-(3-chloropyrazin-2-yl)-1-(2,2-dimethylpropyl)-3-methyl-1,3-dihydro-2H-benzimidazol-2-one;
3-[1-(2,2-dimethylpropyl)-3-methyl-2-oxo-2,3-dihydro-1H-benzimidazol-5-yl]pyrazine-2-carbonitrile;
5-(6-chloropyrazin-2-yl)-1-(2,2-dimethylpropyl)-3-methyl-1,3-dihydro-2H-benzimidazol-2-one;
5-(3-chloroquinoxalin-2-yl)-1-(2,2-dimethylpropyl)-3-methyl-1,3-dihydro-2H-benzimidazol-2-one;
2-[1-(2,2-dimethylpropyl)-3-methyl-2-oxo-2,3-dihydro-1H-benzimidazol-5-yl]-6-fluorobenzonitrile;
5-bromo-2-[1-(2,2-dimethylpropyl)-3-methyl-2-oxo-2,3-dihydro-1H-benzimidazol-5-yl]benzonitrile;
2-[1-(2,2-dimethylpropyl)-3-methyl-2-oxo-2,3-dihydro-1H-benzimidazol-5-yl]-4-methylbenzonitrile;

2-[1-(2,2-dimethylpropyl)-3-methyl-2-oxo-2,3-dihydro-1H-benzimidazol-5-yl]-4-fluorobenzonitrile;
5-[1-(2,2-dimethylpropyl)-3-methyl-2-oxo-2,3-dihydro-1H-benzimidazol-5-yl]-2-fluorobenzonitrile;
4-[1-(2,2-dimethylpropyl)-3-methyl-2-oxo-2,3-dihydro-1H-benzimidazol-5-yl]phthalonitrile;
3-[1-(2,2-dimethylpropyl)-3-methyl-2-oxo-2,3-dihydro-1H-benzimidazol-5-yl]-4-hydroxybenzonitrile;
1-(2,2-dimethylpropyl)-3-methyl-5-[2-(trifluoromethyl)phenyl]-1,3-dihydro-2H-benzimidazol-2-one;
1-(2,2-dimethylpropyl)-5-[3-fluoro-2-(trifluoromethyl)phenyl]-3-methyl-1,3-dihydro-2H-benzimidazol-2-one;
1-(2,2-dimethylpropyl)-5-[5-fluoro-2-(trifluoromethyl)phenyl]-3-methyl-1,3-dihydro-2H-benzimidazol-2-one;
1-(2,2-dimethylpropyl)-5-[4-fluoro-2-(trifluoromethyl)phenyl]-3-methyl-1,3-dihydro-2H-benzimidazol-2-one;
1-(2,2-dimethylpropyl)-5-[2-fluoro-6-(trifluoromethyl)phenyl]-3-methyl-1,3-dihydro-2H-benzimidazol-2-one;
5-[2,6-bis(trifluoromethyl)phenyl]-1-(2,2-dimethylpropyl)-3-methyl-1,3-dihydro-2H-benzimidazol-2-one;
1-(2,2-dimethylpropyl)-5-[4-hydroxy-3-(hydroxymethyl)phenyl]-3-methyl-1,3-dihydro-2H-benzimidazol-2-one;
1-(2,2-dimethylpropyl)-5-[3-(hydroxymethyl)-4-methoxyphenyl]-3-methyl-1,3-dihydro-2H-benzimidazol-2-one;
3-[1-(2,2-dimethylpropyl)-3-methyl-2-oxo-2,3-dihydro-1H-benzimidazol-5-yl]pyridine-2-carbonitrile;
6-[1-(2,2-dimethylpropyl)-3-methyl-2-oxo-2,3-dihydro-1H-benzimidazol-5-yl]pyridine-2-carbonitrile;
5-(6-tert-butylpyridin-2-yl)-1-(2,2-dimethylpropyl)-3-methyl-1,3-dihydro-2H-benzimidazol-2-one;
1-(2,2-dimethylpropyl)-3-methyl-5-[6-(trifluoromethyl)pyridin-2-yl]-1,3-dihydro-2H-benzimidazol-2-one;
5-[1-(2,2-dimethylpropyl)-3-methyl-2-oxo-2,3-dihydro-1H-benzimidazol-5-yl]nicotinonitrile;
6-amino-5-[1-(2,2-dimethylpropyl)-3-methyl-2-oxo-2,3-dihydro-1H-benzimidazol-5-yl]nicotinonitrile;
1-(2,2-dimethylpropyl)-3-methyl-5-[5-(trifluoromethyl)pyridin-3-yl]-1,3-dihydro-2H-benzimidazol-2-one;
1-(2,2-dimethylpropyl)-3-methyl-5-pyrimidin-2-yl-1,3-dihydro-2H-benzimidazol-2-one;
1-(2,2-dimethylpropyl)-5-(5-hydroxypyrazin-2-yl)-3-methyl-1,3-dihydro-2H-benzimidazol-2-one;
1-(2,2-dimethylpropyl)-3-methyl-5-quinoxalin-2-yl-1,3-dihydro-2H-benzimidazol-2-one;
3-[1-(2,2-dimethylpropyl)-3-methyl-2-oxo-2,3-dihydro-1H-benzimidazol-5-yl]-1H-pyrrolo[2,3-b]pyridine-5-carbonitrile;
2-[1-(2,2-dimethylpropyl)-3-methyl-2-oxo-2,3-dihydro-1H-benzimidazol-5-yl]-6-methylbenzonitrile;
2-[1-(2,2-dimethylpropyl)-3-methyl-2-oxo-2,3-dihydro-1H-benzimidazol-5-yl]-4-(trifluoromethyl)benzonitrile;
3-methyl-1-[(1-methylcyclopropyl)methyl]-5-phenyl-1,3-dihydro-2H-benzimidazol-2-one;
3-[1-(2,2-dimethylpropyl)-3-methyl-2-oxo-2,3-dihydro-1H-benzimidazol-5-yl]-2-fluorobenzonitrile;
5-[1-(2,2-dimethylpropyl)-3-methyl-2-oxo-2,3-dihydro-1H-benzimidazol-5-yl]-2-methylbenzonitrile;
3-chloro-5-[1-(2,2-dimethylpropyl)-3-methyl-2-oxo-2,3-dihydro-1H-benzimidazol-5-yl]benzonitrile;
1-(2,2-dimethylpropyl)-5-[4-fluoro-3-(hydroxymethyl)phenyl]-3-methyl-1,3-dihydro-2H-benzimidazol-2-one;
1-(2,2-dimethylpropyl)-5-[5-(hydroxymethyl)-2-methylphenyl]-3-methyl-1,3-dihydro-2H-benzimidazol-2-one;
3-chloro-5-[1-(2,2-dimethylpropyl)-3-methyl-2-oxo-2,3-dihydro-1H-benzimidazol-5-yl]isonicotinonitrile;
4-[1-(2,2-dimethylpropyl)-3-methyl-2-oxo-2,3-dihydro-1H-benzimidazol-5-yl]pyridine-2-carbonitrile;
3-methyl-1-[(2-methylcyclopropyl)methyl]-5-phenyl-1,3-dihydro-2H-benzimidazol-2-one;
2-[1-(2,2-dimethylpropyl)-3-methyl-2-oxo-2,3-dihydro-1H-benzimidazol-5-yl]isonicotinonitrile;
6-[1-(2,2-dimethylpropyl)-3-methyl-2-oxo-2,3-dihydro-1H-benzimidazol-5-yl]nicotinonitrile;
2-[1-(2,2-dimethylpropyl)-3-methyl-2-oxo-2,3-dihydro-1H-benzimidazol-5-yl]quinoline-3-carbonitrile;
1-(2,2-dimethylpropyl)-3-methyl-5-[3-(trifluoromethyl)pyridin-4-yl]-1,3-dihydro-2H-benzimidazol-2-one;
1-(2,2-dimethylpropyl)-3-methyl-5-[3-(trifluoromethyl)pyridin-2-yl]-1,3-dihydro-2H-benzimidazol-2-one;
1-(2,2-dimethylpropyl)-3-methyl-5-[4-(trifluoromethyl)pyridin-2-yl]-1,3-dihydro-2H-benzimidazol-2-one;
3-[3-methyl-2-oxo-1-(3,3,3-trifluoro-2-hydroxy-2-methylpropyl)-2,3-dihydro-1H-benzimidazol-5-yl]isonicotinonitrile;
3-[3-methyl-2-oxo-1-(2-oxopropyl)-2,3-dihydro-1H-benzimidazol-5-yl]isonicotinonitrile;
3-[1-(cyclobutylmethyl)-3-methyl-2-oxo-2,3-dihydro-1H-benzimidazol-5-yl]isonicotinonitrile;
3-{1-[(2,2-difluorocyclopropyl)methyl]-3-methyl-2-oxo-2,3-dihydro-1H-benzimidazol-5-yl}isonicotinonitrile;
2-{1-[(2,2-difluoro-1-methylcyclopropyl)methyl]-3-methyl-2-oxo-2,3-dihyro-1H-benzimidazol-5-yl}-4-methylbenzonitrile;
2-[1-(2,2-dimethylpropyl)-3-methyl-2-oxo-2,3-dihydro-1H-benzimidazol-5-yl]-6-methylnicotinonitrile;
6-methyl-2-{3-methyl-1-[(1-methylcyclopropyl)methyl]-2-oxo-2,3-dihydro-1H-benzimidazol-5-yl}nicotinonitrile;
3-{3-methyl-1-[(1-methylcyclopropyl)methyl]-2-oxo-2,3-dihydro-1H-benzimidazol-5-yl}pyridine-2-carbonitrile;
3-methyl-1-[(1-methylcyclopropyl)methyl]-5-[4-(trifluoromethyl)pyridin-3-yl]-1,3-dihydro-2H-benzimidazol-2-one;
5-[1-(2-fluoro-2-methylpropyl)-3-methyl-2-oxo-2,3-dihydro-1H-benzimidazol-5-yl]nicotinonitrile;
4-methyl-2-[3-methyl-1-(2-methylprop-2-en-1-yl)-2-oxo-2,3-dihydro-1H-benzimidazol-5-yl]benzonitrile;
5-[1-(cyclopropylmethyl)-3-methyl-2-oxo-2,3-dihydro-1H-benzimidazol-5-yl]nicotinonitrile;
5-[3-methyl-2-oxo-1-(4,4,4-trifluorobutyl)-2,3-dihydro-1H-benzimidazol-5-yl]nicotinonitrile;
1-(2,2-dimethylpropyl)-5-[5-(1-hydroxy-1-methylethyl)-2-methylphenyl]-3-methyl-1,3-dihydro-2H-benzimidazol-2-one;
3-[3-methyl-2-oxo-1-(3,3,3-trifluoro-2-hydroxypropyl)-2,3-dihydro-1H-benzimidazol-5-yl]isonicotinonitrile;
1-(2,2-dimethylpropyl)-5-[5-(1-methoxy-1-methylethyl)-2-methylphenyl]-3-methyl-1,3-dihydro-2H-benzimidazol-2-one;
3-[1-(2-fluoro-2-methylpropyl)-3-methyl-2-oxo-2,3-dihydro-1H-benzimidazol-5-yl]isonicotinonitrile;
3-[3-methyl-2-oxo-1-(2,2,2-trifluoroethyl)-2,3-dihydro-1H-benzimidazol-5-yl]isonicotinonitrile;

3-(3-methyl-2-oxo-1-{[1-(trifluoromethyl)cyclopropyl]methyl}-2,3-dihydro-1H-benzimidazol-5-yl)isonicotinonitrile;
3-[3-methyl-2-oxo-1-(3,3,3-trifluoropropyl)-2,3-dihydro-1H-benzimidazol-5-yl]isonicotinonitrile;
3-[3-methyl-2-oxo-1-(4,4,4-trifluorobutyl)-2,3-dihydro-1H-benzimidazol-5-yl]isonicotinonitrile;
5-(4-fluoropyridin-3-yl)-3-methyl-1-{[1-(trifluoromethyl)cyclopropyl]methyl}-1,3-dihydro-2H-benzimidazol-2-one;
3-methyl-1-{[1-(trifluoromethyl)cyclopropyl]methyl}-5-[4-(trifluoromethyl)pyridin-3-yl]-1,3-dihydro-2H-benzimidazol-2-one;
5-[5-(1-hydroxy-1-methylethyl)-2-methylphenyl]-3-methyl-1-(4,4,4-trifluorobutyl)-1,3-dihydro-2H-benzimidazol-2-one;
1-(2,2-dimethylpropyl)-3-methyl-5-[2-(2H-tetrazol-5-yl)phenyl]-1,3-dihydro-2H-benzimidazol-2-one;
5-(6-chloropyridin-2-yl)-1-(2,2-dimethylpropyl)-3-methyl-1,3-dihydro-2H-benzimidazol-2-one;
1-(cyclopropylmethyl)-5-(3-hydroxyphenyl)-3-methyl-1,3-dihydro-2H-benzimidazol-2-one;
1-(2,2-dimethylpropyl)-5-(5-methoxypyridin-3-yl)-3-methyl-1,3-dihydro-2H-benzimidazol-2-one;
1-(2,2-dimethylpropyl)-5-(5-hydroxypyridin-3-yl)-3-methyl-1,3-dihydro-2H-benzimidazol-2-one;
1-(2,2-dimethylpropyl)-5-(3-hydroxyphenyl)-3-methyl-1,3-dihydro-2H-benzimidazol-2-one;
2-[1-(2,2-dimethylpropyl)-3-methyl-2-oxo-2,3-dihydro-1H-benzimidazol-5-yl]-4-hydroxybenzonitrile;
6-chloro-2-[1-(2,2-dimethylpropyl)-3-methyl-2-oxo-2,3-dihydro-1H-benzimidazol-5-yl]nicotinonitrile;
2-chloro-6-[1-(2,2-dimethylpropyl)-3-methyl-2-oxo-2,3-dihydro-1H-benzimidazol-5-yl]nicotinonitrile;
1'-(2,2-dimethylpropyl)-3'-methyl-1',3'-dihydro-1H-2'H-2,5'-bibenzimidazol-2'-one;
1-but-3-en-1-yl-5-(2-hydroxyphenyl)-3-methyl-1,3-dihydro-2H-benzimidazol-2-one;
5-(6-acetylpyridin-2-yl)-1-(2,2-dimethylpropyl)-3-methyl-1,3-dihydro-2H-benzimidazol-2-one;
4-amino-2-[1-(2,2-dimethylpropyl)-3-methyl-2-oxo-2,3-dihydro-1H-benzimidazol-5-yl]benzonitrile;
tert-butyl 7-[1-(2,2-dimethylpropyl)-3-methyl-2-oxo-2,3-dihydro-1H-benzimidazol-5-yl]-3,4-dihydroisoquinoline-2(1H)-carboxylate;
1-(2,2-dimethylpropyl)-3-methyl-5-(3-methyl-1,2,4-oxadiazol-5-yl)-1,3-dihydro-2H-benzimidazol-2-one;
5-(5-chloro-2-methylphenyl)-1-(2,2-dimethylpropyl)-3-methyl-1,3-dihydro-2H-benzimidazol-2-one;
4-chloro-2-[1-(2,2-dimethylpropyl)-3-methyl-2-oxo-2,3-dihydro-1H-benzimidazol-5-yl]benzonitrile;
3-[1-(2,2-dimethylpropyl)-3-methyl-2-oxo-2,3-dihydro-1H-benzimidazol-5-yl]benzaldehyde;
2-[1-(2,2-dimethylpropyl)-3-methyl-2-oxo-2,3-dihydro-1H-benzimidazol-5-yl]-4-methoxybenzonitrile;
1-but-3-en-1-yl-3-methyl-5-[3-(pent-4-en-1-yloxy)phenyl]-1,3-dihydro-2H-benzimidazol-2-one;
3-methyl-1-pent-4-en-1-yl-5-[3-(pent-4-en-1-yloxy)phenyl]-1,3-dihydro-2H-benzimidazol-2-one;
5-(3-hydroxyphenyl)-3-methyl-1-pent-4-en-1-yl-1,3-dihydro-2H-benzimidazol-2-one;
1-allyl-3-methyl-5-[3-(pent-4-en-1-yloxy)phenyl]-1,3-dihydro-2H-benzimidazol-2-one;
3-[1-(2,2-dimethylpropyl)-3-methyl-2-oxo-2,3-dihydro-1H-benzimidazol-5-yl]-5-hydroxybenzonitrile;
2-[3-(cyclopropylmethyl)-2-oxo-6-phenyl-2,3-dihydro-1H-benzimidazol-1-yl]propanenitrile;
2-[3-(cyclopropylmethyl)-2-oxo-6-phenyl-2,3-dihydro-1H-benzimidazol-1-yl]-2-fluoro-N-methylacetamide;
methyl-4-[3-methyl-5-(2-methylphenyl)-2-oxo-2,3-dihydro-1H-benzimidazol-1-yl]piperidine-1-carboxylate;
3-[1-(1,1-difluoroprop-2-en-1-yl)-3-methyl-2-oxo-2,3-dihydro-1H-benzimidazol-5-yl]isonicotinonitrile;
2-{3-[1-(2,2-dimethylpropyl)-3-methyl-2-oxo-2,3-dihydro-1H-benzimidazol-5-yl]phenoxy}nicotinonitrile;
1-(cyclopropylmethyl)-3-methyl-5-[3-(pyridin-2-yloxy)phenyl]-1,3-dihydro-2H-benzimidazol-2-one;
2-{3-[1-(2,2-dimethylpropyl)-3-methyl-2-oxo-2,3-dihydro-1H-benzimidazol-5-yl]phenoxy}nicotinonitrile;
1-(2,2-dimethylpropyl)-3-methyl-5-(3-{[4-(trifluoromethyl)pyridin-2-yl]oxy}phenyl)-1,3-dihydro-2H-benzimidazol-2-one;
5-{3-[(2-chloropyridin-4-yl)oxy]phenyl}-1-(2,2-dimethylpropyl)-3-methyl-1,3-dihydro-2H-benzimidazol-2-one;
1-(cyclopropylmethyl)-3-methyl-5-{3-[(3-methylpyridin-2-yl)oxy]phenyl}-1,3-dihydro-2H-benzimidazol-2-one;
1-(cyclopropylmethyl)-3-methyl-5-{3-[(4-methylpyridin-2-yl)oxy]phenyl}-1,3-dihydro-2H-benzimidazol-2-one;
1-(cyclopropylmethyl)-3-methyl-5-{3-[(5-methylpyridin-2-yl)oxy]phenyl}-1,3-dihydro-2H-benzimidazol-2-one;
1-(cyclopropylmethyl)-3-methyl-5-{3-[(6-methylpyridin-2-yl)oxy]phenyl}-1,3-dihydro-2H-benzimidazol-2-one;
1-(cyclopropylmethyl)-5-{3-[(3-fluoropyridin-2-yl)oxy]phenyl}-3-methyl-1,3-dihydro-2H-benzimidazol-2-one;
1-(cyclopropylmethyl)-5-{3-[(5-fluoropyridin-2-yl)oxy]phenyl}-3-methyl-1,3-dihydro-2H-benzimidazol-2-one;
1-(cyclopropylmethyl)-5-{3-[(6-fluoropyridin-2-yl)oxy]phenyl}-3-methyl-1,3-dihydro-2H-benzimidazol-2-one;
2-{3-[1-(cyclopropylmethyl)-3-methyl-2-oxo-2,3-dihydro-1H-benzimidazol-5-yl]phenoxy}nicotinonitrile;
5-{3-[(5-chloro-3-fluoropyridin-2-yl)oxy]phenyl}-1-(cyclopropylmethyl)-3-methyl-1,3-dihydro-2H-benzimidazol-2-one;
2-{3-[1-(cyclopropylmethyl)-3-methyl-2-oxo-2,3-dihydro-1H-benzimidazol-5-yl]phenoxy}-3,5,6-trifluoroisonicotinonitrile;
1-(cyclopropylmethyl)-3-methyl-5-[3-(pyridin-4-yloxy)phenyl]-1,3-dihydro-2H-benzimidazol-2-one;
1-(cyclopropylmethyl)-3-methyl-5-{3-[(2-methylpyridin-4-yl)oxy]phenyl}-1,3-dihydro-2H-benzimidazol-2-one;
5-{3-[(2-chloropyridin-4-yl)oxy]phenyl}-1-(cyclopropylmethyl)-3-methyl-1,3-dihydro-2H-benzimidazol-2-one;
4-{3-[1-(cyclopropylmethyl)-3-methyl-2-oxo-2,3-dihydro-1H-benzimidazol-5-yl]phenoxy}nicotinonitrile;
4-{3-[1-(cyclopropylmethyl)-3-methyl-2-oxo-2,3-dihydro-1H-benzimidazol-5-yl]phenoxy}pyridine-2-carbonitrile;
4-{3-[1-(2,2-dimethylpropyl)-3-methyl-2-oxo-2,3-dihydro-1H-benzimidazol-5-yl]phenoxy}pyridine-2-carbonitrile;
2-{4-cyano-3-[1-(2,2-dimethylpropyl)-3-methyl-2-oxo-2,3-dihydro-1H-benzimidazol-5-yl]phenoxy}nicotinonitrile;

4-{4-cyano-3-[1-(2,2-dimethylpropyl)-3-methyl-2-oxo-2,3-dihydro-1H-benzimidazol-5-yl]phenoxy}nicotinonitrile;
4-{4-cyano-3-[1-(2,2-dimethylpropyl)-3-methyl-2-oxo-2,3-dihydro-1H-benzimidazol-5-yl]phenoxy}pyridine-2-carbonitrile;
4-{4-cyano-3-[3-methyl-2-oxo-1-(tetrahydro-2H-pyran-4-ylmethyl)-2,3-dihydro-1H-benzimidazol-5-yl]phenoxy}pyridine-2-carbonitrile;
4-(4-cyano-3-{3-methyl-1-[(1-methylcyclopropyl)methyl]-2-oxo-2,3-dihydro-1H-benzimidazol-5-yl}phenoxy)pyridine-2-carbonitrile;
4-{4-cyano-3-[1-(cyclopropylmethyl)-3-methyl-2-oxo-2,3-dihydro-1H-benzimidazol-5-yl]phenoxy}pyridine-2-carbonitrile;
4-{4-cyano-3-[1-(cyclobutylmethyl)-3-methyl-2-oxo-2,3-dihydro-1H-benzimidazol-5-yl]phenoxy}pyridine-2-carbonitrile;
4-{4-cyano-3-[3-methyl-2-oxo-1-(4,4,4-trifluorobutyl)-2,3-dihydro-1H-benzimidazol-5-yl]phenoxy}pyridine-2-carbonitrile;
4-{3-[1-(4-bromo-2-fluorobenzyl)-3-methyl-2-oxo-2,3-dihydro-1H-benzimidazol-5-yl]-4-cyanophenoxy}pyridine-2-carbonitrile;
4-[4-cyano-3-(1-isobutyl-3-methyl-2-oxo-2,3-dihydro-1H-benzimidazol-5-yl)phenoxy]pyridine-2-carbonitrile;
4-{4-cyano-3-[1-(cyclopentylmethyl)-3-methyl-2-oxo-2,3-dihydro-1H-benzimidazol-5-yl]phenoxy}pyridine-2-carbonitrile;
6-{4-cyano-3-[1-(2,2-dimethylpropyl)-3-methyl-2-oxo-2,3-dihydro-1H-benzimidazol-5-yl]phenoxy}pyridine-2-carbonitrile;
6-{4-cyano-3-[1-(2,2-dimethylpropyl)-3-methyl-2-oxo-2,3-dihydro-1H-benzimidazol-5-yl]phenoxy}nicotinonitrile;
2-{4-cyano-3-[1-(2,2-dimethylpropyl)-3-methyl-2-oxo-2,3-dihydro-1H-benzimidazol-5-yl]phenoxy}isonicotinonitrile;
2-{3-[1-(2,2-dimethylpropyl)-3-methyl-2-oxo-2,3-dihydro-1H-benzimidazol-5-yl]-4-methylphenoxy}nicotinonitrile;
4-{4-cyano-3-[1-(cyclopropylmethyl)-3-methyl-2-oxo-2,3-dihydro-1H-benzimidazol-5-yl]phenoxy}pyridine-2-carbonitrile;
4-{3-cyano-5-[1-(2,2-dimethylpropyl)-3-methyl-2-oxo-2,3-dihydro-1H-benzimidazol-5-yl]phenoxy}pyridine-2-carbonitrile;
1-(2,2-dimethylpropyl)-5-{3-[(2-fluorobenzyl)oxy]phenyl}-3-methyl-1,3-dihydro-2H-benzimidazol-2-one;
5-[3-(benzyloxy)phenyl]-1-(2,2-dimethylpropyl)-3-methyl-1,3-dihydro-2H-benzimidazol-2-one;
1-(2,2-dimethylpropyl)-3-methyl-5-(3-{[2-(trifluoromethyl)benzyl]oxy}phenyl)-1,3-dihydro-2H-benzimidazol-2-one;
3-({3-[1-(2,2-dimethylpropyl)-3-methyl-2-oxo-2,3-dihydro-1H-benzimidazol-5-yl]phenoxy}methyl)benzonitrile;
4-({3-[1-(2,2-dimethylpropyl)-3-methyl-2-oxo-2,3-dihydro-1H-benzimidazol-5-yl]phenoxy}methyl)benzonitrile;
4-{3-[1-(2,2-dimethylpropyl)-3-methyl-2-oxo-2,3-dihydro-1H-benzimidazol-5-yl]phenoxy}benzonitrile;
1-(cyclopropylmethyl)-3-methyl-5-(3-phenoxyphenyl)-1,3-dihydro-2H-benzimidazol-2-one;
5-[3-(2-chlorophenoxy)phenyl]-1-(cyclopropylmethyl)-3-methyl-1,3-dihydro-2H-benzimidazol-2-one;
5-[3-(3-chlorophenoxy)phenyl]-1-(cyclopropylmethyl)-3-methyl-1,3-dihydro-2H-benzimidazol-2-one;
2-{3-[1-(cyclopropylmethyl)-3-methyl-2-oxo-2,3-dihydro-1H-benzimidazol-5-yl]phenoxy}benzonitrile;
3-{3-[1-(cyclopropylmethyl)-3-methyl-2-oxo-2,3-dihydro-1H-benzimidazol-5-yl]phenoxy}benzonitrile;
4-{3-[1-(cyclopropylmethyl)-3-methyl-2-oxo-2,3-dihydro-1H-benzimidazol-5-yl]phenoxy}benzonitrile;
1-(2,2-dimethylpropyl)-3-methyl-5-(3-phenoxyphenyl)-1,3-dihydro-2H-benzimidazol-2-one;
1-(2,2-dimethylpropyl)-3-methyl-5-{3-[2-(trifluoromethyl)phenoxy]phenyl}-1,3-dihydro-2H-benzimidazol-2-one;
4-({6-[1-(2,2-dimethylpropyl)-3-methyl-2-oxo-2,3-dihydro-1H-benzimidazol-5-yl]pyridin-2-yl}oxy)benzonitrile;
1-(2,2-dimethylpropyl)-3-methyl-5-{6-[(6-methylpyridin-2-yl)oxy]pyridin-2-yl}-1,3-dihydro-2H-benzimidazol-2-one;
3-({6-[1-(2,2-dimethylpropyl)-3-methyl-2-oxo-2,3-dihydro-1H-benzimidazol-5-yl]pyridin-2-yl}oxy)pyridine-2-carbonitrile;
1-(2,2-dimethylpropyl)-5-{6-[(2,6-dimethylpyridin-4-yl)oxy]pyridin-2-yl}-3-methyl-1,3-dihydro-2H-benzimidazol-2-one;
4-({3-cyano-6-[1-(2,2-dimethylpropyl)-3-methyl-2-oxo-2,3-dihydro-1H-benzimidazol-5-yl]pyridin-2-yl}oxy)pyridine-2-carbonitrile;
5-[6-(1,3-benzothiazol-2-yloxy)pyridin-2-yl]-1-(2,2-dimethylpropyl)-3-methyl-1,3-dihydro-2H-benzimidazol-2-one;
1-(2,2-dimethylpropyl)-3-methyl-5-{6-[(3-methylquinoxalin-2-yl)oxy]pyridin-2-yl}-1,3-dihydro-2H-benzimidazol-2-one;
1-(2,2-dimethylpropyl)-3-methyl-5-(6-{[1-methyl-5-(trifluoromethyl)-1H-pyrazol-3-yl]oxy}pyridin-2-yl)-1,3-dihydro-2H-benzimidazol-2-one;
1-(2,2-dimethylpropyl)-3-methyl-5-{6-[(1-methyl-1H-pyrazol-5-yl)oxy]pyridin-2-yl}-1,3-dihydro-2H-benzimidazol-2-one;
1-(2,2-dimethylpropyl)-3-methyl-5-{6-[(1-methylpiperidin-3-yl)oxy]pyridin-2-yl}-1,3-dihydro-2H-benzimidazol-2-one;
5-[6-(1-azabicyclo[2.2.2]oct-3-yloxy)pyridin-2-yl]-1-(2,2-dimethylpropyl)-3-methyl-1,3-dihydro-2H-benzimidazol-2-one;
5-(6-{[(3R)-1-benzylpiperidin-3-yl]oxy}pyridin-2-yl)-1-(2,2-dimethylpropyl)-3-methyl-1,3-dihydro-2H-benzimidazol-2-one;
1-(2,2-dimethylpropyl)-3-methyl-5-{6-[(1-methylpyrrolidin-3-yl)oxy]pyridin-2-yl}-1,3-dihydro-2H-benzimidazol-2-one;
5-{6-[(1-benzylpyrrolidin-3-yl)oxy]pyridin-2-yl}-1-(2,2-dimethylpropyl)-3-methyl-1,3-dihydro-2H-benzimidazol-2-one;
4-({5-cyano-6-[1-(2,2-dimethylpropyl)-3-methyl-2-oxo-2,3-dihydro-1H-benzimidazol-5-yl]pyridin-2-yl}oxy)pyridine-2-carbonitrile;
4-({4-[1-(2,2-dimethylpropyl)-3-methyl-2-oxo-2,3-dihydro-1H-benzimidazol-5-yl]pyridin-2-yl}oxy)benzonitrile;
4-({6-[1-(2,2-dimethylpropyl)-3-methyl-2-oxo-2,3-dihydro-1H-benzimidazol-5-yl]pyrazin-2-yl}oxy)benzonitrile;
4-({6-[1-(2,2-dimethylpropyl)-3-methyl-2-oxo-2,3-dihydro-1H-benzimidazol-5-yl]pyrazin-2-yl}oxy)-3-fluorobenzonitrile;

3-({6-[1-(2,2-dimethylpropyl)-3-methyl-2-oxo-2,3-dihydro-1H-benzimidazol-5-yl]pyrazin-2-yl}oxy)pyridine-2-carbonitrile;

5-({6-[1-(2,2-dimethylpropyl)-3-methyl-2-oxo-2,3-dihydro-1H-benzimidazol-5-yl]pyrazin-2-yl}oxy)pyridine-2-carbonitrile;

1-(2,2-dimethylpropyl)-5-{6-[(2,6-dimethylpyridin-4-yl)oxy]pyrazin-2-y}-3-methyl-1,3-dihydro-2H-benzimidazol-2-one;

2-[1-(4-bromo-2-fluorobenzyl)-3-methyl-2-oxo-2,3-dihydro-1H-benzimidazol-5-yl]benzonitrile;

2-[1-(2,2-dimethylpropyl)-3-methyl-2-oxo-2,3-dihydro-1H-benzimidazol-5-yl]benzonitrile;

2-[1-(2,2-dimethylpropyl)-7-fluoro-3-methyl-2-oxo-2,3-dihydro-1H-benzimidazol-5-yl]benzonitrile;

2-(3-methyl-2-oxo-1-phenyl-2,3-dihydro-1H-benzimidazol-5-yl)benzonitrile;

2-{3-methyl-2-oxo-1-[3-(trifluoromethyl)phenyl]-2,3-dihydro-1H-benzimidazol-5-yl}benzonitrile;

2-{3-methyl-1-[(1-methylcyclopropyl)methyl]-2-oxo-2,3-dihydro-1H-benzimidazol-5-yl}benzonitrile;

2-{1-[4-chloro-3-(trifluoromethyl)benzyl]-3-methyl-2-oxo-2,3-dihydro-1H-benzimidazol-5-yl}benzonitrile;

2-[3-methyl-2-oxo-1-(1-phenylethyl)-2,3-dihydro-1H-benzimidazol-5-yl]benzonitrile;

2-(3-methyl-2-oxo-1-{1-[3-(trifluoromethyl)phenyl]ethyl}-2,3-dihydro-1H-benzimidazol-5-yl)benzonitrile;

2-(1,3-dimethyl-2-oxo-2,3-dihydro-1H-benzimidazol-5-yl)benzonitrile;

2-(3-methyl-2-oxo-1-propyl-2,3-dihydro-1H-benzimidazol-5-yl)benzonitrile;

2-(1-butyl-3-methyl-2-oxo-2,3-dihydro-1H-benzimidazol-5-yl)benzonitrile;

2-(1-hexyl-3-methyl-2-oxo-2,3-dihydro-1H-benzimidazol-5-yl)benzonitrile;

2-[1-(2-fluoroethyl)-3-methyl-2-oxo-2,3-dihydro-1H-benzimidazol-5-yl]benzonitrile;

2-[1-(2-cyanoethyl)-3-methyl-2-oxo-2,3-dihydro-1H-benzimidazol-5-yl]benzonitrile;

2-(1-isopropyl-3-methyl-2-oxo-2,3-dihydro-1H-benzimidazol-5-yl)benzonitrile;

2-(1-isobutyl-3-methyl-2-oxo-2,3-dihydro-1H-benzimidazol-5-yl)benzonitrile;

2-(1-sec-butyl-3-methyl-2-oxo-2,3-dihydro-1H-benzimidazol-5-yl)benzonitrile;

2-[1-(cyclopropylmethyl)-3-methyl-2-oxo-2,3-dihydro-1H-benzimidazol-5-yl]benzonitrile;

2-[1-(cyclopentylmethyl)-3-methyl-2-oxo-2,3-dihydro-1H-benzimidazol-5-yl]benzonitrile;

2-[3-methyl-2-oxo-1-(tetrahydro-2H-pyran-4-ylmethyl)-2,3-dihydro-1H-benzimidazol-5-yl]benzonitrile;

2-[1-(2-cyclohexylethyl)-3-methyl-2-oxo-2,3-dihydro-1H-benzimidazol-5-yl]benzonitrile;

2-[3-methyl-1-(4-methylbenzyl)-2-oxo-2,3-dihydro-1H-benzimidazol-5-yl]benzonitrile;

2-[1-(4-tert-butylbenzyl)-3-methyl-2-oxo-2,3-dihydro-1H-benzimidazol-5-yl]benzonitrile;

2-[3-methyl-2-oxo-1-(pyridin-3-ylmethyl)-2,3-dihydro-1H-benzimidazol-5-yl]benzonitrile;

2-[3-methyl-2-oxo-1-(2-phenylethyl)-2,3-dihydro-1H-benzimidazol-5-yl]benzonitrile;

2-[1-(3,3-dimethylbutyl)-3-methyl-2-oxo-2,3-dihydro-1H-benzimidazol-5-yl]benzonitrile;

2-[1-(3-cyanobenzyl)-3-methyl-2-oxo-2,3-dihydro-1H-benzimidazol-5-yl]benzonitrile;

2-{1-[(2,2-difluoro-1-methylcyclopropyl)methyl]-3-methyl-2-oxo-2,3-dihydro-1H-benzimidazol-5-yl}benzonitrile;

3-(2,2-dimethylpropyl)-4-fluoro-1-methyl-6-phenyl-1,3-dihydro-2H-benzimidazol-2-one;

4-chloro-1-(2,2-dimethylpropyl)-3-methyl-5-phenyl-1,3-dihydro-2H-benzimidazol-2-one;

1-(2,2-dimethylpropyl)-4-fluoro-3-methyl-5-phenyl-1,3-dihydro-2H-benzimidazol-2-one;

4-fluoro-5-[2-fluoro-5-(trifluoromethoxy)phenyl]-3-methyl-1-[(1-methylcyclopropyl)methyl]-1,3-dihydro-2H-benzimidazol-2-one;

2-fluoro-3-{4-fluoro-3-methyl-1-[(1-methylcyclopropyl)methyl]-2-oxo-2,3-dihydro-1H-benzimidazol-5-yl}benzonitrile;

2-{4-fluoro-3-methyl-1-[(1-methylcyclopropyl)methyl]-2-oxo-2,3-dihydro-1H-benzimidazol-5-yl}-6-methoxybenzonitrile;

5-fluoro-2-{4-fluoro-3-methyl-1-[(1-methylcyclopropyl)methyl]-2-oxo-2,3-dihydro-1H-benzimidazol-5-yl}benzonitrile;

2-{4-fluoro-3-methyl-1-[(1-methylcyclopropyl)methyl]-2-oxo-2,3-dihydro-1H-benzimidazol-5-yl}-5-(trifluoromethyl)benzonitrile;

4-fluoro-3-{4-fluoro-3-methyl-1-[(1-methylcyclopropyl)methyl]-2-oxo-2,3-dihydro-1H-benzimidazol-5-yl}benzonitrile;

1-(2,2-dimethylpropyl)-4-fluoro-5-(3-hydroxyphenyl)-3-methyl-1,3-dihydro-2H-benzimidazol-2-one;

2-[1-(2,2-dimethylpropyl)-4-fluoro-3-methyl-2-oxo-2,3-dihydro-1H-benzimidazol-5-yl]-4-hydroxybenzonitrile;

3-[1-(2,2-dimethylpropyl)-4-fluoro-3-methyl-2-oxo-2,3-dihydro-1H-benzimidazol-5-yl]isonicotinonitrile;

4-{4-fluoro-3-methyl-1-[(1-methylcyclopropyl)methyl]-2-oxo-2,3-dihydro-1H-benzimidazol-5-yl}nicotinonitrile;

4-fluoro-3-methyl-1-[(1-methylcyclopropyl)methyl]-5-[6-(4-methylpiperazin-1-yl)pyridin-3-yl]-1,3-dihydro-2H-benzimidazol-2-one;

4-fluoro-5-(4-fluoropyridin-2-yl)-3-methyl-1-[(1-methylcyclopropyl)methyl]-1,3-dihydro-2H-benzimidazol-2-one;

4-fluoro-5-(5-fluoropyridin-2-yl)-3-methyl-1-[(1-methylcyclopropyl)methyl]-1,3-dihydro-2H-benzimidazol-2-one;

4-fluoro-5-(6-fluoropyridin-2-yl)-3-methyl-1-[(1-methylcyclopropyl)methyl]-1,3-dihydro-2H-benzimidazol-2-one;

4-fluoro-5-(5-fluoro-6-methylpyridin-2-yl)-3-methyl-1-[(1-methylcyclopropyl)methyl]-1,3-dihydro-2H-benzimidazol-2-one;

4-fluoro-3-methyl-1-[(1-methylcyclopropyl)methyl]-5-[4-(trifluoromethyl)pyridin-2-yl]-1,3-dihydro-2H-benzimidazol-2-one;

4-fluoro-3-methyl-1-[(1-methylcyclopropyl)methyl]-5-[5-(trifluoromethyl)pyridin-2-yl]-1,3-dihydro-2H-benzimidazol-2-one;

4-fluoro-3-methyl-1-[(1-methylcyclopropyl)methyl]-5-[6-(trifluoromethyl)pyridin-2-yl]-1,3-dihydro-2H-benzimidazol-2-one;

4-fluoro-5-(2-fluoropyridin-3-yl)-3-methyl-1-[(1-methylcyclopropyl)methyl]-1,3-dihydro-2H-benzimidazol-2-one;

4-fluoro-5-(5-fluoropyridin-3-yl)-3-methyl-1-[(1-methylcyclopropyl)methyl]-1,3-dihydro-2H-benzimidazol-2-one;

4-fluoro-5-(2-fluoro-5-methylpyridin-3-yl)-3-methyl-1-[(1-methylcyclopropyl)methyl]-1,3-dihydro-2H-benzimidazol-2-one;

4-fluoro-5-(2-fluoroquinolin-3-yl)-3-methyl-1-[(1-methylcyclopropyl)methyl]-1,3-dihydro-2H-benzimidazol-2-one;

4-fluoro-5-(2-methoxypyridin-3-yl)-3-methyl-1-[(1-methylcyclopropyl)methyl]-1,3-dihydro-2H-benzimidazol-2-one;

4-fluoro-5-(4-methoxypyridin-3-yl)-3-methyl-1-[(1-methylcyclopropyl)methyl]-1,3-dihydro-2H-benzimidazol-2-one;

4-fluoro-5-(5-methoxypyridin-3-yl)-3-methyl-1-[(1-methylcyclopropyl)methyl]-1,3-dihydro-2H-benzimidazol-2-one;

4-fluoro-5-(6-methoxypyridin-3-yl)-3-methyl-1-[(1-methylcyclopropyl)methyl]-1,3-dihydro-2H-benzimidazol-2-one;

4-fluoro-5-(2-methoxyquinolin-3-yl)-3-methyl-1-[(1-methylcyclopropyl)methyl]-1,3-dihydro-2H-benzimidazol-2-one;

4-fluoro-3-methyl-1-[(1-methylcyclopropyl)methyl]-5-[4-(trifluoromethyl)pyridin-3-yl]-1,3-dihydro-2H-benzimidazol-2-one;

4-fluoro-5-(3-fluoropyridin-4-yl)-3-methyl-1-[(1-methylcyclopropyl)methyl]-1,3-dihydro-2H-benzimidazol-2-one;

4-fluoro-5-(2-fluoropyridin-4-yl)-3-methyl-1-[(1-methylcyclopropyl)methyl]-1,3-dihydro-2H-benzimidazol-2-one;

5-(2,6-difluoropyridin-4-yl)-4-fluoro-3-methyl-1-[(1-methylcyclopropyl)methyl]-1,3-dihydro-2H-benzimidazol-2-one;

4-fluoro-5-(2-methoxypyridin-4-yl)-3-methyl-1-[(1-methylcyclopropyl)methyl]-1,3-dihydro-2H-benzimidazol-2-one;

4-fluoro-3-methyl-1-[(1-methylcyclopropyl)methyl]-5-[4-(trifluoromethyl)pyridin-3-yl]-1,3-dihydro-2H-benzimidazol-2-one;

1-(2,2-dimethylpropyl)-4-fluoro-3-methyl-5-[3-(trifluoromethyl)pyridin-4-yl]-1,3-dihydro-2H-benzimidazol-2-one;

3-[1-(2,2-dimethylpropyl)-4-fluoro-3-methyl-2-oxo-2,3-dihydro-1H-benzimidazol-5-yl]pyridine-2-carbonitrile;

1-(2,2-dimethylpropyl)-4-fluoro-5-(2-fluoro-5-methylpyridin-3-yl)-3-methyl-1,3-dihydro-2H-benzimidazol-2-one;

3-{4-fluoro-3-methyl-1-[(1-methylcyclopropyl)methyl]-2-oxo-2,3-dihydro-1H-benzimidazol-5-yl}pyridine-2-carbonitrile;

4-fluoro-5-(2-methoxyquinolin-3-yl)-3-methyl-1-[(1-methylcyclopropyl)methyl]-1,3-dihydro-2H-benzimidazol-2-one;

1-(cyclopropylmethyl)-4-fluoro-3-methyl-5-[3-(trifluoromethyl)pyridin-4-yl]-1,3-dihydro-2H-benzimidazol-2-one;

3-[1-(cyclopropylmethyl)-4-fluoro-3-methyl-2-oxo-2,3-dihydro-1H-benzimidazol-5-yl]isonicotinonitrile;

4-{3-[1-(2,2-dimethylpropyl)-4-fluoro-3-methyl-2-oxo-2,3-dihydro-1H-benzimidazol-5-yl]phenoxy}nicotinonitrile;

1-(2,2-dimethylpropyl)-4-fluoro-3-methyl-5-[3-(pyridin-2-yloxy)phenyl]-1,3-dihydro-2H-benzimidazol-2-one;

4-{3-[1-(2,2-dimethylpropyl)-4-fluoro-3-methyl-2-oxo-2,3-dihydro-1H-benzimidazol-5-yl]phenoxy}pyridine-2-carbonitrile;

4-{4-cyano-3-[1-(2,2-dimethylpropyl)-4-fluoro-3-methyl-2-oxo-2,3-dihydro-1H-benzimidazol-5-yl]phenoxy}pyridine-2-carbonitrile;

6-{4-cyano-3-[1-(2,2-dimethylpropyl)-4-fluoro-3-methyl-2-oxo-2,3-dihydro-1H-benzimidazol-5-yl]phenoxy}pyridine-2-carbonitrile;

4-{3-[1-(2,2-dimethylpropyl)-4-fluoro-3-methyl-2-oxo-2,3-dihydro-1H-benzimidazol-5-yl]phenoxy}benzonitrile;

1-(2,2-dimethylpropyl)-5-[3-(1-hydroxy-1-phenylethyl)phenyl]-3-methyl-1,3-dihydro-2H-benzimidazol-2-one;

1-(2,2-dimethylpropyl)-5-[3-(1-hydroxy-1-pyridin-2-ylethyl)phenyl]-3-methyl-1,3-dihydro-2H-benzimidazol-2-one;

1-(2,2-dimethylpropyl)-5-{3-[hydroxy(phenyl)methyl]phenyl}-3-methyl-1,3-dihydro-2H-benzimidazol-2-one;

4-(1-{3-[1-(2,2-dimethylpropyl)-3-methyl-2-oxo-2,3-dihydro-1H-benzimidazol-5-yl]phenyl}-1-hydroxyethyl)benzonitrile; and 1-(2,2-dimethylpropyl)-5-[6-(1-hydroxy-1-phenylethyl)pyridin-2-yl]-3-methyl-1,3-dihydro-2H-benzimidazol-2-one; or a pharmaceutically acceptable salt thereof.

9. A pharmaceutical composition comprising a compound according to claim 8 in combination with a pharmaceutically acceptable carrier.

* * * * *